(12) United States Patent
Moss et al.

(10) Patent No.: US 9,119,853 B2
(45) Date of Patent: Sep. 1, 2015

(54) SANGLIFEHRIN BASED COMPOUNDS

(75) Inventors: Steven James Moss, Cambridge (GB);
Matthew Alan Gregory, Cambridge (GB); Barrie Wilkinson, Cambridge (GB); Christine Janet Martin, Cambridge (GB)

(73) Assignee: Neurovive Pharmaceutical AB, Lund (SE)

( * ) Notice: Subject to any disclaimer, the term of this patent is extended or adjusted under 35 U.S.C. 154(b) by 429 days.

(21) Appl. No.: 13/575,212

(22) PCT Filed: Feb. 9, 2011

(86) PCT No.: PCT/GB2011/050236
§ 371 (c)(1),
(2), (4) Date: Jul. 25, 2012

(87) PCT Pub. No.: WO2011/098809
PCT Pub. Date: Aug. 18, 2011

(65) Prior Publication Data
US 2012/0295841 A1 Nov. 22, 2012

(30) Foreign Application Priority Data

Feb. 9, 2010 (GB) .................................. 1002097.2
Apr. 13, 2010 (GB) .................................. 1006128.1
Jan. 21, 2011 (GB) .................................. 1101085.7

(51) Int. Cl.
*C07D 498/08* (2006.01)
*C07D 413/12* (2006.01)
*A61K 31/50* (2006.01)

(52) U.S. Cl.
CPC .............. *A61K 31/50* (2013.01); *C07D 498/08* (2013.01)

(58) Field of Classification Search
None
See application file for complete search history.

(56) References Cited

U.S. PATENT DOCUMENTS

2011/0229941 A1  9/2011  Liu et al.
2012/0251581 A1  10/2012  Gregory et al.

FOREIGN PATENT DOCUMENTS

WO  2006/138507  12/2006

OTHER PUBLICATIONS

Sedrani, R., et al. "Sanglifehrin-cyclophilin interaction: degradation work, synthetic macrocyclic analogues, X-ray crystal structure, and binding data." J Am Chem Soc. Apr. 2, 2003;125(13):3849-59.
Sedrani, R., et al. "Sanglifehrin-cyclophilin interaction: degradation work, synthetic macrocyclic analogues, X-ray crystal structure, and binding data." J Am Chem Soc. Apr. 2, 2003;S1-S40. Retrieved from the Internet [Apr. 12, 2011]: <http://pubs.acs.org/doi/suppl/10.1021/ja021327y/supp_file/ja021327y_s.pdf>.
Ou, Chunyan, "Review of Bioisosteres and Their Use in New Drug Design", Journal of Zhanjiang Ocean University, 2004, 24(4):82-86.

*Primary Examiner* — Noble Jarrell
(74) *Attorney, Agent, or Firm* — Robert C. Netter, Jr.; Kathleen D. Rigaut; Dann, Dorfman, Herrell & Skillman

(57) ABSTRACT

There are provided inter alia compounds of formula (I)

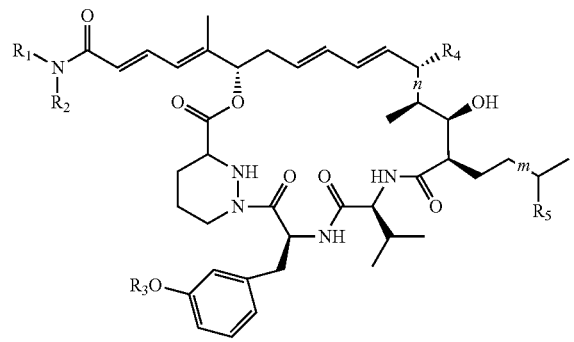

Figure 1:
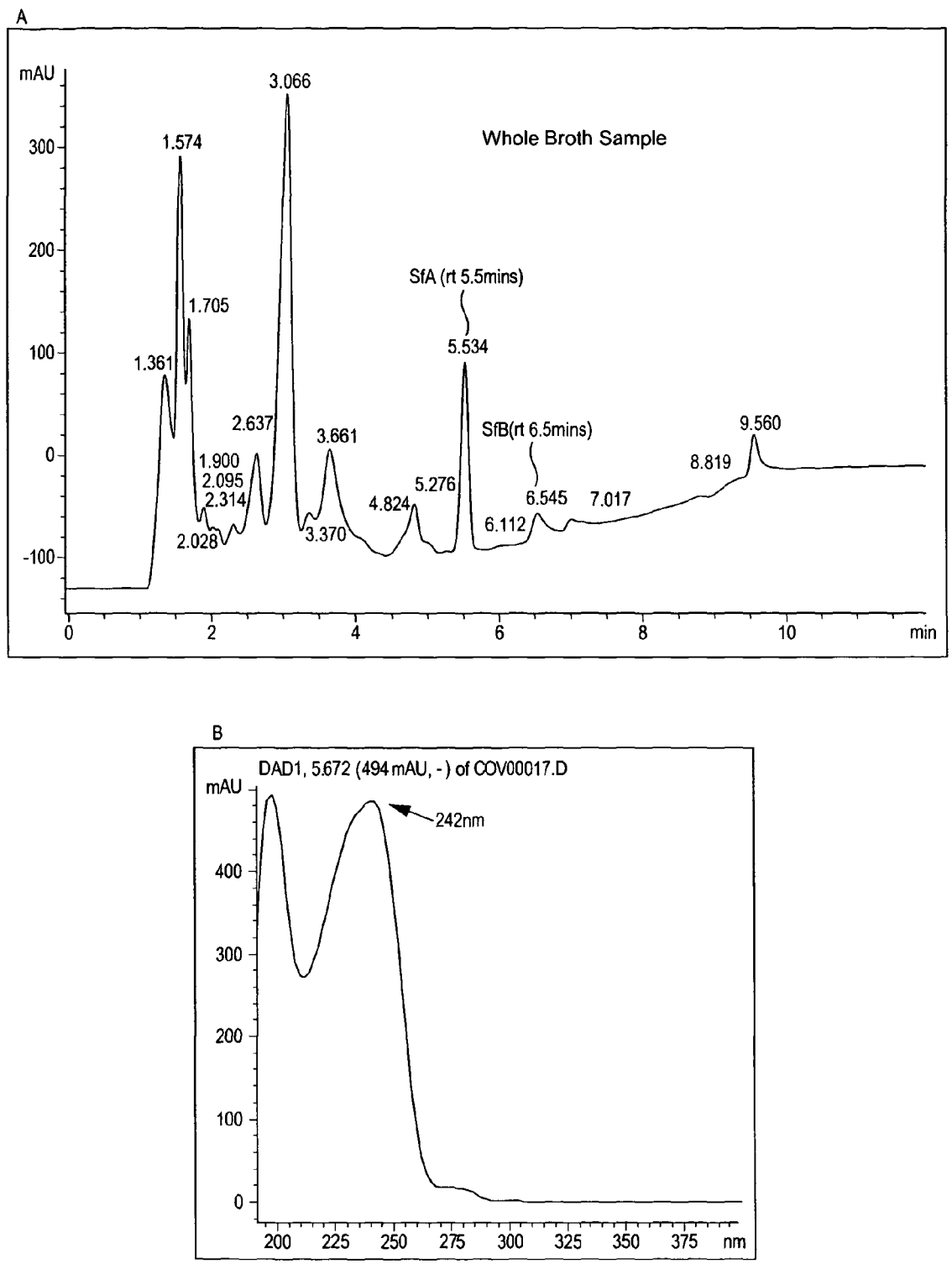

useful as cyclophilin inhibitors.

16 Claims, 18 Drawing Sheets

```
GCCGAATTCCGCTGCAAGTCCTACTCCGCCGAGGCCGACGGCACCGGCTGGTCCGAGGGCGT
CGGCATGCTCCTCGTCGAACGGCTCGGCGACGCCGAACGGCTCGGCCACCCCGTCCTCGCCG
TGCTGCGCGGCTCAGCGGTCAACCAGGACGGTGCCAGCAGCGGCCTCACCACCCCAACGGG
CCGGCCCAGCAGCGCGTCATCCGGCAGGCGCTCGCCGACGCCCGGCTCACCCCCGCCGACCT
GGACCTCGTGGAGGGCCACGGCACCGGCACCCCGCTCGGCGACCCGATCGAGGTGCAGGCCC
TGCTCGCCACCTACGGCCAGGACGCGCCGAACCGCTCTGGCTGGGCTCGGTGAAGTCCAAC
ATCGGCCACACCCAGGCCGCCGCCGGCGTCGCCGGAGTCATCAAGGCCGTCCTGGCCCTCCG
GCACGGTGTACTGCCCGGCACCGCCCACCTGACCGAGCCGACCCCGCAGGTCGACTGGACCG
CCGGCGCCGTGGAACCGCTGCGGGAGACGCGCGCCTGGCCCGAGACCGGCAGGCCGCGCCGC
GCGGCCGTGTCCTCGTTCGGCATCAGCGGCACCAACGCCCACATCGTCCTGGAACAGGCCCC
CGCCCCCGCGGCGCCGCAGGCGGCCGGAGCCCAGGCGCCCGCGGCGCCGCGGCCCGTCGGGA
ACCAGGCCACCGCCGCGCCGAGGTCCATGGAGGACCGGACCGCCGCCGCGCCTAGCGCCGGC
GGAGACCCGACCCTCACCGCGCCGGCCCCCTCCGCGCCCCGCCCCGCCCCGCCGCCCTCCC
CGTCCCGCTGTCCGCCGCGACCGAGCCCGGTGTCCGTGCCCAGGCCCTCCGGCTGGCCGCCC
ACCTCACCGAGCACCCCGAACTCGCCCCGCAGGACATCGCGTTCAGCGCCGCCACCACGCGC
GCCGCGCTGGCGTCCCGGGCCGTCGTGCTCGCCGACGACCGGGCCGGGCTGCTGGACGCCCT
CACCGCGCTGGCCGAGGGACGGCCCGGCCCCGCCGTCGTCACCGGCGCCGCCGCGGCCGGCG
CGCGCCGGATCACCTTCGTCTTCCCCGGCCAGGGCGCCCAGTGGGCCGGCATGGCCGTACCC
CTGCTGGAGACCTCGCCGGTGTTCGCGGCGAAGTGGGCCGAATGCGCCCGCGTGCTCGCCCC
CTGGGTGGACTGGTCGCCCGACGAGGCGCTGCGCTCACCGCAGGCACTGGAACGGGTCGACG
TCGTCCAGCCCGTGCTGTGGGCCGTCATGGTCAGCCTCGCCGAGCTGTGGCGGGCGGCGGGC
GTACGGCCCGACGCCGTACTCGGCCATTCGCAGGGCGAGATCGCCGCCGCCTGCGTCGCCGG
CGCCCTGTCCCTGGAGGACGGCGCCAAGGTCGTCGCGCTGCGCGCCAAGGCCCTGCTCGCGC
TCGCCGGCCGCGGCGGCATGCTCTCCGTCCCGCTGCCCGAGGCGGAGGTCCGCGCCCGGCTC
GACAGCCGGCCCGGCCTCGGCATCGCCGCCGTCAACGGGCCCGCCACCGTGGTGGTCTCCGG
CGAGACGGCCGCCCTCGACGAGGCCCAGGCCGCCTGGGAGGCCGAGGGCGTCCGGGTGCGCC
GCATCCCGTCGACTACGCCTCCCACTCCCCGCACGTCGCCGAGGTGCAGGACCGCCTCGCC
GCCGACCTCGCCGGCATCGCCCCGCGCCCGGCCGAGGTGACCTTCCTGTCCACGCTCACCGG
GGAACCCTTCGACACCACCGGACTCGACGCCGGCTACTGGTACCGCAACCTGCGCGAGCAGG
TCCGCTTCGAGGCGGCCACCCGGCGCGCCCTGGAGCAGGGCCACCGCGTGTTCATCGAGGTC
GGCCCGCACCCCGTGCTCACGCTCGGCGTCCAGCAGACGCCGAGGCCATGGACGTGCCCGC
CGAGGCGATCGCCACCCTCCGCCGCGACCAGGGCGACCTGCTCCGCTTCCGCACCGCGCTCG
CCGAGGCCGCCGTCCTCGGCGCCCCGTCGACTGGGCCGCCGAACTCGCCCCGTACGCGCCC
CGCCGGGTAGATCTGCCCTCGAGCGC
```

FIG. 16

GCTCTCGAGGCGGCTAGCCTCCCTGCCCGAGGCCGGCCGCCGGCGGGCCGTCACCGAACTGG
TCCGCGAGCACGCCGCCGCCGTCCTCGGCCACGACTCGCCCGCCGCGCTCCCCGCCGACCGC
GCCTTCCGGGACGTCGGCTTCGACTCCATCACCGCGGTCGAGCTGCGCAACCGGCTCCGCTC
GGCCACCGGCCTGGCCCTGCCCGCCACCCTCGTCTTCGACCACCCGTCGCCCACCGCGCTGG
CCGGCCACCTGCTCGCGCTCGCCTTCGACACCGCCGCGGCGGACCTCGCCGCGCCCGCCGCC
CGCGCCGCCGACGATGACGACGACCCGATCGCCGTCGTCGGCCTCAGCTGCCGCTACGCCGG
CGGCGTCGCCTCCCCGGACGAGCTGTGGCGGCTCGTCGTGGCCGGTCAGGACGCGGTGGGCG
CCCTGCCCACCGACCGTGGCTGGGACCTCGACTCGCTCTACGACTCCGACCCCGACGCCCGC
GGTCGCAGCTACGTCCGCCAAGGGGCCTTCCTCACCGACCCCGCCGGCTTCGACGCCGCCTT
CTTCGGCATCGCCCCGGCGGAGGCCCGGGCCACCGACCCGCAGCAGCGGCTGCTCCTGGAAG
CCGCCTGGGAGGCGTTCGAGCACGCCGGCATCGACGCCACCGGCCTGCGCGGCTCGCGCGTC
GGCGTCTTCGCCGGCGCCAACGTCGGCGACTACGCCTCCAGCCGCGGCCCTGGCGCCGGCGG
CTCCGACGGACAGCTGCTCACCGGCAACGTCCCCAGTGTGATCTCCGGCCGGATCTCCTACA
CCTTCGGTTTCGAGGGGCCGGCCGTCACCGTGGACACCGCCTGCTCGTCCGCCCTGGTCGCC
CTCCACCTGGCCTGCCGGTCGGTGCGCGGCGGCGAGAGCGACATGGCCCTGGCCGGCGGCGT
CGCGCTCATGTCCAGCCCGGCCGCCCTGATCGGCTTCTCCGCGCAGCGCGGCCTGTCCGGCG
ACGGCCGCTGCAAGGCCTTCGCCGACGCCGCCGACGGCACCGGTCTCGCCGAGGGCGTCGGA
CTGCTGCTGGTGGAACGCCTCTCCCGGGCCCGCGCCCAGGGCCACCGCGTCCTCGCCCTCGT
ACGCGGCTCGGCGATCAACCAGGACGGCGCCTCCAACGGACTCACCGCCCCAGCGGACCCG
CCCAGCAGCGCGTCATCACCGCCGCGCTCGCCGACGCCGGGCTGCGGCCCGCCGACGTCGAC
GCCGTGGAGGCCCATGGCACCGGCACCCGCCTCGGCGACCCGATCGAGGCCCAGGCCCTGCT
CGCCACCTACGGACAGGACCGCGCCGAACCGCTCTGGCTCGGCTCGGTGAAGTCCAACATCG
GCCACTCCCAGGCCGCGTCCGGCGCGGCCGGCGTGATCAAGACCGTGCAGGCGCTGCGGCAC
GGCCTGCTGCCCGCCACGCTCCACGTGGACCGGCCACCACCCAGGTCGACTGGACCGCCGG
CGCCGTCGAGGTGCTGACCGAGGCCCGGGACTGGCCGGCCGTGGACCGGCCTCGGCGGGCCG
CCGTGTCGGCGTTCGGCCTGTCCGGCACCAACGCGCACGTGATCCTCGAACAGGCCCCCGCC
GAAGACGCCCACCCGGCCCCGAACCGGCCCGGGCGAGGACTCCCACCCGACCCCCGAAAC
GGCCCCAGGCGAGGACGCCCCGCGGACCGCGCCCGAGCCCGCGCGGCCCGTGGTGTGGCCGG
TGCACGGCCGTACCCGGGACGCCCTGCGCGCCCAGGCGGCGCGGCTGCGCACCCACCTGGAG
ACCCGCCCCGACGCCCGCCCGGCCGACGTCGGCTGGACCCTCGCGGCCGGTCGGGCCGTGTT
CGACCACCGCGCCGTGGTGCTCGGCGCCGACCGCGCCGAGCTGCTGCGCGGACTCGACGCCG
TCGCCGCCGGCACCCCCGACCCCGCGGTCGCCGACGGCGCGGCCCAGGGCGCCGAGCCGGGC
CGAAGCTTTCT

FIG. 17

SANGLIFEHRIN BASED COMPOUNDS

The present application is §371 application of PCT/GB2011/050236, filed Feb. 9, 2011, which claims priority to GB Application No. 1002097.2, filed Feb. 9, 2010; GB Application No. 1006128.1, filed Apr. 13, 2010; and GB Application No. 1101085.7, filed Jan. 21, 2011. The entire disclosure of each of the foregoing applications is incorporated by reference herein.

INTRODUCTION

The present invention relates to sanglifehrin analogues, that are useful as cyclophilin inhibitors, e.g. in the treatment of viral infection by viruses such as Hepatitis C Virus (HCV), Hepatitis B Virus (HBV) and Human Immunodeficiency Virus (HIV). The present invention also provides methods for their use in medicine, in particular for the treatment of HCV, HBV and HIV infection, and in diseases where inhibition of the Mitochondrial Permeability Transition Pore (mPTP) is useful such as muscular dystrophy.

BACKGROUND OF THE INVENTION

Hepatitis C

Hepatitis C virus (HCV) is a positive strand RNA virus, and infection is a leading cause of post-transfusional hepatitis. HCV is the most common chronic blood borne infection, and the leading cause of death from liver disease in United States. The World Health Organization estimates that there are more than 170 million chronic carriers of HCV infection, which is about 3% of the world population. Among the untreated HCV-infected patients, about 70%-85% develop chronic HCV infection, and are therefore at high risk to develop liver cirrhosis and hepatocellular carcinoma. In developed countries, 50-76% of all cases of liver cancer and two-thirds of all liver transplants are due to chronic HCV infection (Manns et al, 2007).

In addition to liver diseases, chronically infected patients may also develop other chronic HCV-related diseases, and serve as a source of transmission to others. HCV infection causes non-liver complications such as arthralgias (joint pain), skin rash, and internal organ damage predominantly to the kidney. HCV infection represents an important global health-care burden, and currently there is no vaccine available for hepatitis C (Strader et al., 2004; Jacobson et al. 2007; Manns et al., 2007 Pawlotsky, 2005; Zeuzem & Hermann, 2002).

Treatment of HCV

The current standard of care (SoC) is subcutaneous injections of pegylated interferon-α (pIFNα) and oral dosing of the antiviral drug ribavirin for a period of 24-48 weeks. Success in treatment is defined by sustained virologic response (SVR), which is defined by absence of HCV RNA in serum at the end of treatment period and 6 months later. Overall response rates to SoC depend mainly on genotype and pre-treatment HCV RNA levels. Patients with genotype 2 and 3 are more likely to respond to SoC than patients infected with genotype 1 (Melnikova, 2008; Jacobson et al., 2007).

A significant number of HCV patients do not respond adequately to the SoC treatment, or cannot tolerate the therapy due to side effects, leading to frequent issues with completion of the full course. The overall clinical SVR rate of SoC is only around 50% (Melnikova, 2008). Development of resistance is another underlying factor for failure of treatment (Jacobson et al. et al. 2007). SoC is also contraindicated in some patients who are not considered candidates for treatment, such as patients with past significant episodes of depression or cardiac disease. Side effects of the SoC, which frequently lead to discontinuation of treatment include a flu-like illness, fever, fatigue, haematological disease, anaemia, leucopaenia, thrombocytopaenia, alopecia and depression (Manns et al., 2007).

Considering the side effects associated with the lengthy treatments using SoC, development of resistance, and suboptimum overall rate of success, more efficacious and safer new treatments are urgently needed for treatment of HCV infection. The objectives of new treatments include improved potency, improved toxicity profile, improved resistance profile, improved quality of life and the resulting improvement in patient compliance. HCV has a short life cycle and therefore development of drug resistance during drug therapy is common.

Novel, specifically targeted antiviral therapy for hepatitis C (STAT-C) drugs are being developed that target viral proteins such as viral RNA polymerase NS5B or viral protease NS3 (Jacobson et al, 2007; Parfieniuk et al., 2007). In addition, novel compounds also are being developed that target human proteins (e.g. cyclophilins) rather than viral targets, which might be expected to lead to a reduction in incidence of resistance during drug therapy (Manns et al., 2007; Pockros, 2008; Pawlotsky J-M, 2005).

Cyclophilin Inhibitors

Cyclophilins (CyP) are a family of cellular proteins that display peptidyl-prolyl cis-trans isomerase activity facilitating protein conformation changes and folding. CyPs are involved in cellular processes such as transcriptional regulation, immune response, protein secretion, and mitochondrial function. HCV virus recruits CyPs for its life cycle during human infection. Originally, it was thought that CyPs stimulate the RNA binding activity of the HCV non-structural protein NS5B RNA polymerase that promotes RNA replication, although several alternative hypotheses have been proposed including a requirement for CyP PPlase activity. Various isoforms of CyPs, including A and B, are believed to be involved in the HCV life cycle (Yang et al., 2008; Appel et al., 2006; Chatterji et al., 2009; Gaither et al., 2010). The ability to generate knockouts in mice (Colgan et al., 2000) and human T cells (Braaten and Luban, 2001) indicates that CyPA is optional for cell growth and survival. Similar results have been observed with disruption of CyPA homologues in bacteria (Herrler et al., 1994), *Neurospora* (Tropschug et al., 1989) and *Saccharomyces cerevisiae* (Dolinski et al. 1997). Therefore, inhibiting CyPs represent a novel and attractive host target for treating HCV infection, and a new potential addition to current SoC or STAT-C drugs, with the aim of increasing SVR, preventing emergence of resistance and lowering treatment side effects.

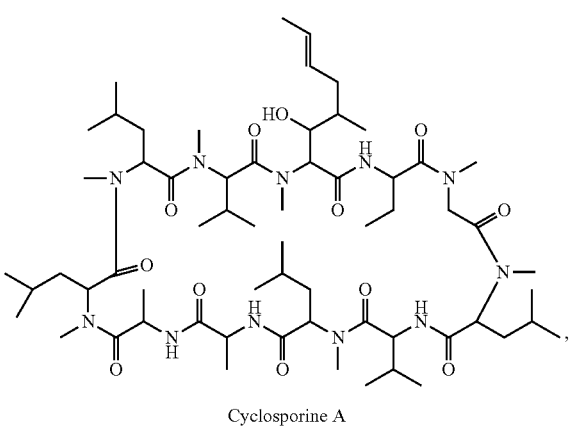

Cyclosporine A

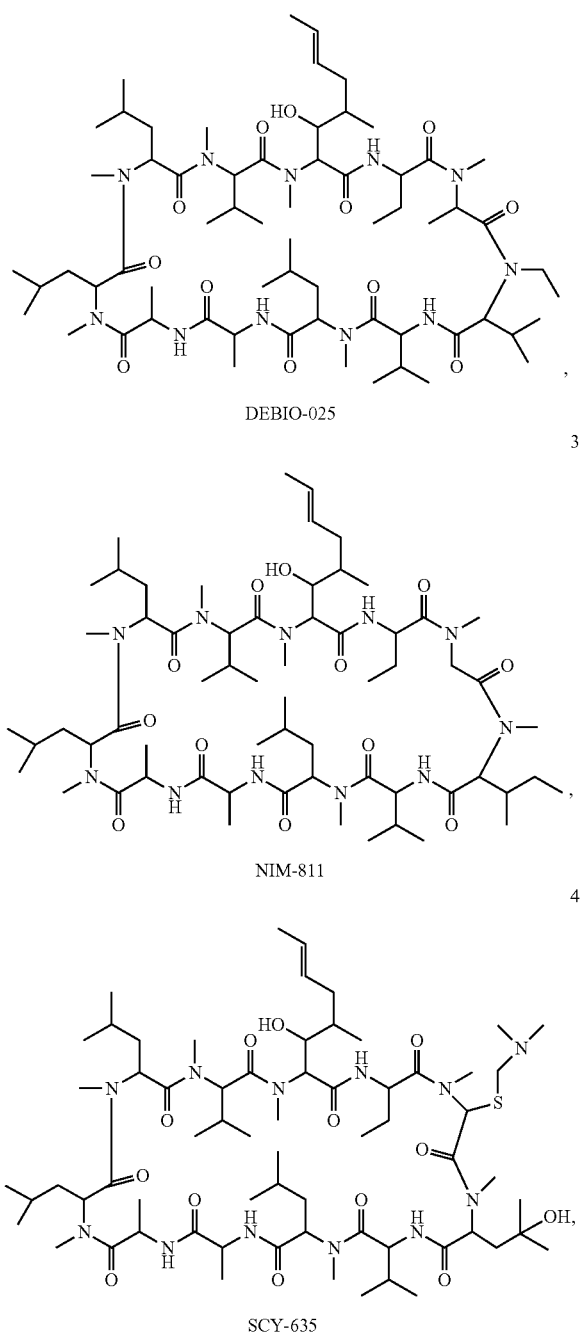

have suggested an essential role for cyclophilin A in HCV replication (Chatterji et al. 2009; Yang et al., 2008). Considering that mutations in NS5A viral protein are also associated with CsA resistance and that NS5A interacts with both CyPA and CypB for their specific peptidyl-prolyl cis/trans isomerase (PPlase) activity, a role for both cyclophilins in viral life cycle is further suggested (Hanoulle et al., 2009).

The anti-HCV effect of cyclosporine analogues is independent of the immunosuppressive property, which is dependent on calcineurin. This indicated that the essential requirement for HCV activity is CyP binding and calcineurin binding is not needed. DEBIO-025, the most clinically advanced cyclophilin inhibitor for the treatment of HCV, has shown in vitro and in vivo potency against the four most prevalent HCV genotypes (genotypes 1, 2, 3, and 4). Resistance studies showed that mutations conferring resistance to DEBIO-025 were different from those reported for polymerase and protease inhibitors, and that there was no cross resistance with STAT-C resistant viral replicons. More importantly, DEBIO-025 also prevented the development of escape mutations that confer resistance to both protease and polymerase inhibitors (Crabbe et al., 2009).

However, the CsA-based cyclophilin inhibitors in clinical development have a number of issues, which are thought to be related to their shared structural class, including: certain adverse events that can lead to a withdrawal of therapy and have limited the clinical dose levels; variable pharmacokinetics that can lead to variable efficacy; and an increased risk of drug-drug interactions that can lead to dosing issues.

The most frequently occurring adverse events (AEs) in patients who received DEB10-025 included jaundice, abdominal pain, vomiting, fatigue, and pyrexia. The most clinically important AEs were hyperbilirubinemia and reduction in platelet count (thrombocytopaenia). Peg-IFN can cause profound thrombocytopaenia and combination with DEBIO-025 could represent a significant clinical problem. Both an increase in bilirubin and decrease in platelets have also been described in early clinical studies with NIM-811 (Ke et al., 2009). Although the hyperbilirubinemia observed during DEBIO-025 clinical studies was reversed after treatment cessation, it was the cause for discontinuation of treatment in 4 out of 16 patients, and a reduction in dose levels for future trials. As the anti-viral effect of cyclophilin inhibitors in HCV is dose related, a reduction in dose has led to a reduction in anti-viral effect, and a number of later trials with CsA-based cyclophilin inhibitors have shown no or poor reductions in HCV viral load when dosed as a monotherapy (Lawitz et al., 2009; Hopkins et al., 2009; Nelson et al., 2009). DEBIO-025 and cyclosporine A are known to be inhibitors of biliary transporters such as bile salt export pumps and other hepatic transporters (especially MRP2/cMOAT/ABCC2) (Crabbe et al., 2009). It has been suggested that the interaction with biliary transporters, in particular MRP2, may be the cause of the hyperbilirubinaemia seen at high dose levels of DEBIO-025 (Nelson et al., 2009).

Moreover, DEBIO-025 and cyclosporine A are substrates for metabolism by cytochrome P450 (especially CYP3A4), and are known to be substrates and inhibitors of human P-glycoprotein (MDR1) (Crabbe et al., 2009). Cyclosporine A has also been shown to be an inhibitor of CYP3A4 in vitro (Niwa et al., 2007). This indicates that there could be an increased risk of drug-drug interactions with other drugs that are CYP3A4 substrates, inducers or inhibitors such as for Cyclosporine A (Inoue et al. 2003) ("CsA") and its closely structurally related non-immunosuppressive clinical analogues DEBIO-025 (Paeshuyse et al. 2006; Flisiak et al. 2008), NIM811 (Mathy et al. 2008) and SCY-635 (Hopkins et al., 2009) are known to bind to cyclophilins, and as cyclophilin inhibitors have shown in vitro and clinical efficacy in the treatment of HCV infection (Crabbe et al., 2009; Flisiak et al. 2008; Mathy et al. 2008; Inoue et al., 2007; Ishii et al., 2006; Paeshuyse et al., 2006). Although earlier resistance studies on CsA showed mutations in HCV NS5B RNA polymerase and suggested that only cyclophilin B would be involved in the HCV replication process (Robida et al., 2007), recent studies example ketoconazole, cimetidine and rifampicin. In addition, interactions are also expected with drugs that are subject to transport by P-glycoprotein (e.g. digoxin), which could cause severe drug-drug interactions in HCV patients receiving medical treatments for other concomitant diseases (Crabbe et al. 2009). CsA is also known to have highly variable pharmacokinetics, with early formulations showing oral bioavailability from 1-89% (Kapurtzak et al., 2004). Without expensive monitoring of patient blood levels, this can lead to increased prevalence of side effects due to increased plasma levels, or reduced clinical response due to lowered plasma levels.

Considering that inhibition of cyclophilins represent a promising new approach for treatment of HCV, there is a need for discovery and development of more potent and safer CyP inhibitors for use in combination therapy against HCV infection.

Sanglifehrins

Sanglifehrin A (SfA) and its natural congeners belong to a class of mixed non-ribosomal peptide/polyketides, produced by *Streptomyces* sp. A92-308110 (also known as DSM 9954) (see WO 97/02285), which were originally discovered on the basis of their high affinity to cyclophilin A (CyPA). SfA is the most abundant component in fermentation broths and exhibits approximately 20-fold higher affinity for CyPA compared to CsA. This has led to the suggestion that sanglifehrins could be useful for the treatment of HCV (WO2006/138507). Sanglifehrins have also been shown to exhibit a lower immunosuppressive activity than CsA when tested in vitro (Sanglier et al., 1999; Fehr et al., 1999). SfA binds with high affinity to the CsA binding site of CyPA (Kallen et al., 2005).

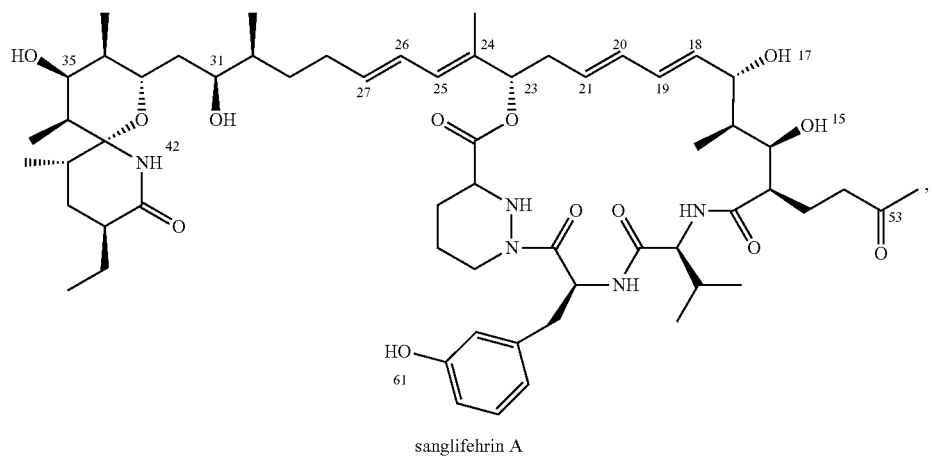

sanglifehrin A

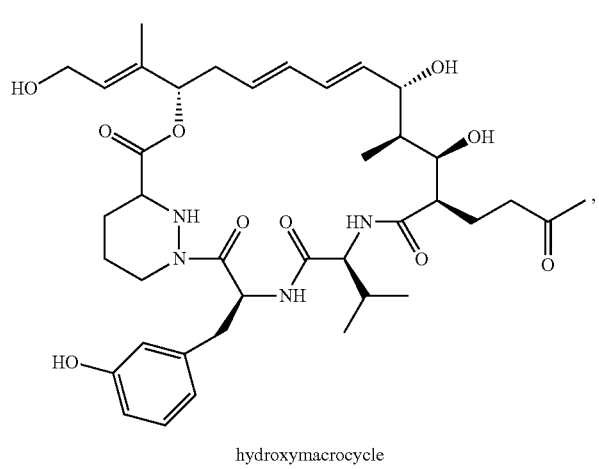

hydroxymacrocycle

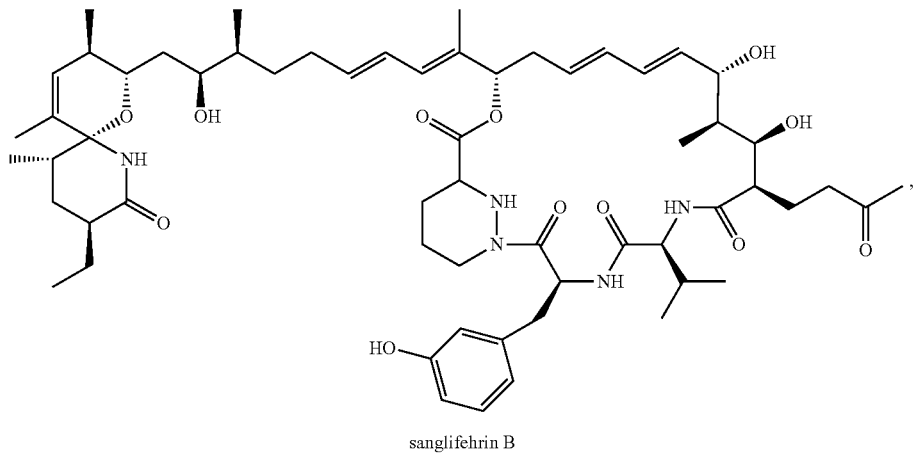

sanglifehrin B

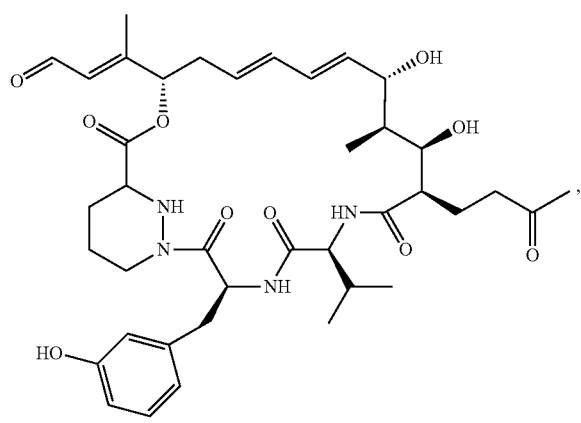

aldehydic macrocycle

The immunosuppressive mechanism of action of SfA is different to that of other known immunophilin-binding immunosuppressive drugs such as CsA, FK506 and rapamycin. SfA does not inhibit the phosphatase activity of calcineurin, the target of CsA (Zenke et al. 2001), instead its immunosuppressive activity has been attributed to the inhibition of interleukin-6 (Hartel et al., 2005), interleukin-12 (Steinschulte et al., 2003) and inhibition of interleukin-2-dependent T cell proliferation (Zhang & Liu, 2001). However, the molecular target and mechanism through which SfA exerts its immunosuppressive effect is hitherto unknown.

The molecular structure of SfA is complex and its interaction with CyPA is thought to be mediated largely by the macrocyclic portion of the molecule. In fact, a macrocyclic compound (hydroxymacrocycle) derived from oxidative cleavage of SfA has shown strong affinity for CyPA (Sedrani et al., 2003). X-ray crystal structure data has shown that the hydroxymacrocycle binds to the same active site of CyPA as CsA. Analogues based on the macrocycle moiety of SfA have also been shown to be devoid of immunosuppressive properties (Sedrani et al., 2003), providing opportunity for design of non-immunosuppressive CyP inhibitors for potential use in HCV therapy.

One of the issues in drug development of compounds such as sanglifehrins are the low solubilities if these highly lipophilic molecules. This can lead to issues with poor bioavailability, an increased chance of food effect, more frequent incomplete release from the dosage form and higher interpatient variability. Poorly soluble molecules also present many formulation issues, such as severely limited choices of delivery technologies and increasingly complex dissolution testing, with limited or poor correlation to in vivo absorption. These issues are often sufficiently formidable to halt development of many compounds (Hite et al., 2003).

Other Therapeutic Uses of Cyclophilin Inhibitors
Human Immunodeficiency Virus (HIV)

Cyclophilin inhibitors, such as CsA and DEBIO-025 have also shown potential utility in inhibition of HIV replication. The cyclophilin inhibitors are thought to interfere with function of CyPA during progression/completion of HIV reverse transcription (Ptak et al., 2008). However, when tested clinically, DEBIO-025 only reduced HIV-1 RNA levels ≥0.5 and >1 $\log_{10}$ copies/mL in nine and two patients respectively, whilst 27 of the treated patients showed no reduction in HIV-1 RNA levels (Steyn et al., 2006). Following this, DEBIO-025 was trialled in HCV/HIV coinfected patients, and showed better efficacy against HCV, and the HIV clinical trials were discontinued (see Watashi et al., 2010).

Treatment of HIV

More than 30 million people are infected by HIV-1 worldwide, with 3 million new cases each year. Treatment options have improved dramatically with the introduction of highly active antiretroviral therapy (HAART) (Schopman et al., 2010), By 2008, nearly 25 antiretroviral drugs had been licensed for treatment of HIV-1, including nine nucleoside reverse transcriptase inhibitors (NRTI), four non-nucleoside reverse transcriptase inhibitors (NNRTI), nine protease inhibitors (PI), one fusion inhibitor, one CCR5 inhibitor and one integrase inhibitor (Shafer and Schapiro, 2008). However, none of these current regimens lead to complete viral clearance, they can lead to severe side effects and antiviral resistance is still a major concern. Therefore, there still remains a need for new antiviral therapies, especially in mechanism of action classes where there are no approved drugs, such as is the case for cyclophilin inhibitors.

Hepatitis B Virus

Hepatitis B is a DNA virus of the family hepadnaviridae, and is the causative agent of Hepatitis B. As opposed to the cases with HCV and HIV, there have been very few published accounts of activity of cyclophilin inhibitors against Hepatitis B virus. Ptak et al. 2008 have described weak activity of Debio-025 against HBV ($IC_{50}$ of 4.1 µM), whilst Xie et al., 2007 described some activity of CsA against HBV (IC50>1.3 µg/mL). This is in contrast to HIV and HCV, where there are numerous reports of nanomolar antiviral activity of cyclophilin inhibitors.

Treatment of HBV

HBV infects up to 400 million people worldwide and is a major cause of chronic viral hepatitis and hepatocellular carcinoma. As of 2008, there were six drugs licensed for the treatment of HBV; interferon alpha and pegylated interferon alpha, three nucleoside analogues (lamivudine, entecavir and telbivudine) and one nucleotide analogue (adefovir dipivoxil). However, due to high rates of resistance, poor tolerability and possible side effects, new therapeutic options are needed (Ferir et al., 2008).

Inhibition of the Mitochondrial Permeability Transition Pore (mPTP)

Opening of the high conductance permeability transition pores in mitochondria initiates onset of the mitochondrial permeability transition (MPT). This is a causative event, leading to necrosis and apoptosis in hepatocytes after oxidative stress, $Ca^{2+}$ toxicity, and ischaemia/reperfusion. Inhibition of Cyclophilin D (also known as Cyclophilin F) by cyclophilin inhibitors has been shown to block opening of permeability transition pores and protects cell death after these stresses. Cyclophilin D inhibitors may therefore be useful in indications where the mPTP opening has been implicated, such as muscular dystrophy, in particular Ullrich congenital muscular dystrophy and Bethlem myopathy (Millay et al., 2008, WO2008/084368, Palma et al., 2009), multiple sclerosis (Forte et al., 2009), diabetes (Fujimoto et al., 2010), amyotrophic lateral sclerosis (Martin 2009), bipolar disorder (Kubota et al., 2010), Alzheimer's disease (Du and Yan, 2010), Huntington's disease (Perry et al., 2010), recovery after myocardial infarction (Gomez et al., 2007) and chronic alchohol consumption (King et al., 2010).

Further Therapeutic Uses

Cyclophilin inhibitors have potential activity against and therefore in the treatment of infections of other viruses, such as Varicella-zoster virus (Ptak et al., 2008), Influenza A virus (Liu et al., 2009), Severe acute respiratory syndrome coronavirus and other human and feline coronaviruses (Chen et al., 2005, Ptak et al., 2008), Dengue virus (Kaul et al., 2009), Yellow fever virus (Qing et al., 2009), West Nile virus (Qing et al., 2009), Western equine encephalitis virus (Qing et al., 2009), Cytomegalovirus (Kawasaki et al., 2007) and Vaccinia virus (Castro et al., 2003).

There are also reports of utility of cyclophilin inhibitors and cyclophilin inhibition in other therapeutic areas, such as in cancer (Han et al., 2009).

Therefore there remains a need to identify novel cyclophilin inhibitors, which may have utility, particularly in the treatment of HCV infection, but also in the treatment of other disease areas where inhibition of cyclophilins may be useful, such as virus infection, in particular HIV infection and HBV infection, muscular dystrophy, Ullrich congenital muscular dystrophy, Bethlem myopathy, multiple sclerosis, diabetes, amyotrophic lateral sclerosis, bipolar disorder, Alzheimer's disease, Huntington's disease, myocardial infarction and chronic alcohol consumption. Preferably, such cyclophilin inhibitors have improved properties over the currently available cyclophilin inhibitors, including one or more of the following properties: improved water solubility, improved antiviral potency against HCV, HIV or HBV or other viruses, reduced toxicity (including hepatotoxicity), improved pharmacological profile, such as high exposure to target organ (e.g. liver in the case of HCV) and/or long half life (enabling less frequent dosing), reduced drug-drug interactions, such as via reduced levels of CYP3A4 metabolism and inhibition and reduced (Pgp) inhibition (enabling easier multi-drug combinations) and improved side-effect profile, such as low binding to MRP2, leading to a reduced chance of hyperbilirubinaemia, lower immunosuppressive effect, such as might be shown by a mixed lymphocyte reaction (MLR) study, improved activity against resistant virus species, in particular CsA and CsA analogue (e.g DEBIO-025) resistant virus species and higher therapeutic (and/or selectivity) index. The present invention discloses novel sanglifehrin analogues which may have one or more of the above properties. In particular, the present invention discloses novel amide derivatives, which are anticipated to have one or more of the following beneficial properties: improved solubility, and therefore improved formulation, reduced immunosuppression and increased potency against certain virus types, including HCV, HIV and HBV.

SUMMARY OF THE INVENTION

The present invention provides novel macrocyclic sanglifehrin analogues, which have been generated by semisynthetic modification of native sanglifehrins. These analogues may be generated by dihydroxylation of a sanglifehrin, such as SfA, followed by cleavage to generate the aldehydic macrocycle, followed by further chemistry, including Horner-Emmons type reactions, to generate molecules with a variety of substituents to replace the aldehyde. As a result, the present invention provides macrocylic amide analogues of SfA, methods for the preparation of these compounds, and methods for the use of these compounds in medicine or as intermediates in the production of further compounds.

Therefore, in a first aspect, the present invention provides macrocyclic amides and derivatives thereof according to formula (I) below, or a pharmaceutically acceptable salt thereof:

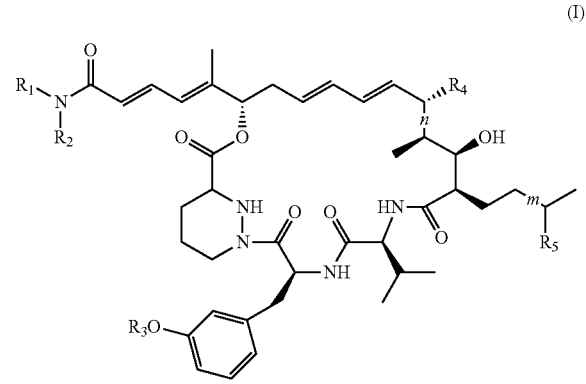

(I)

wherein:

$R_1$ or $R_2$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;

or $R_1$ and/or $R_2$ represents hydrogen;

and wherein one or more carbon atoms of $R_1$ and/or $R_2$ not being part of an aryl or heteroaryl group are optionally replaced by a heteroatom selected from O, N and $S(O)_p$ in which p represents 0, 1 or 2 and wherein one or more carbon atoms of $R_1$ and/or $R_2$ are optionally replaced by carbonyl;

or $R_1$ and $R_2$ are joined to form a saturated or unsaturated heterocyclic ring containing the nitrogen atom shown and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;

including a methanol adduct thereof in which a ketal is formed by the combination of the C-53 keto (if present) and the C-15 hydroxyl group and methanol.

The above structure shows a representative tautomer and the invention embraces all tautomers of the compounds of formula (I) for example keto compounds where enol compounds are illustrated and vice versa.

Specific tautomers that are included within the definition of formula (I) are those in which (i) the C-53 keto group forms a hemiketal with the C-15 hydroxyl, or (ii) the C-15 and C-17 hydroxyl can combine with the C-53 keto to form a ketal. All numberings use the system for the parent sanglifehrin A structure.

In another aspect, the present invention provides sanglifehrin analogues and derivatives thereof according to formula (III) or formula (IV) below, or a pharmaceutically acceptable salt thereof:

(III)

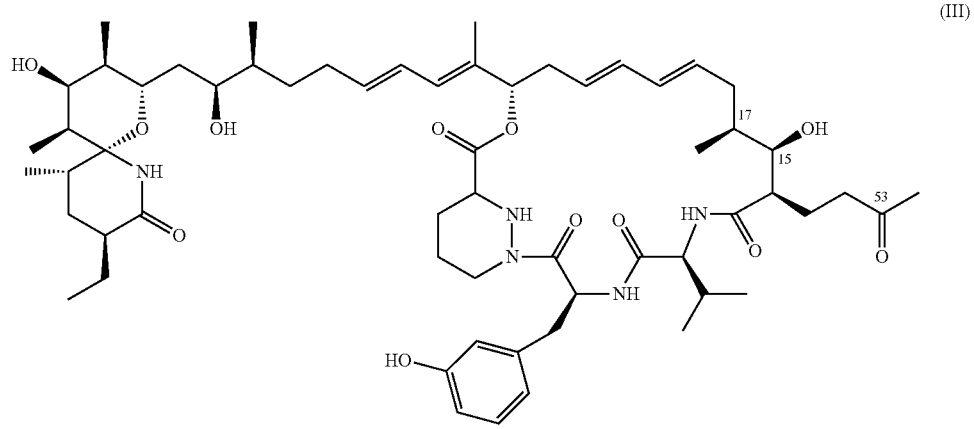

(IV)

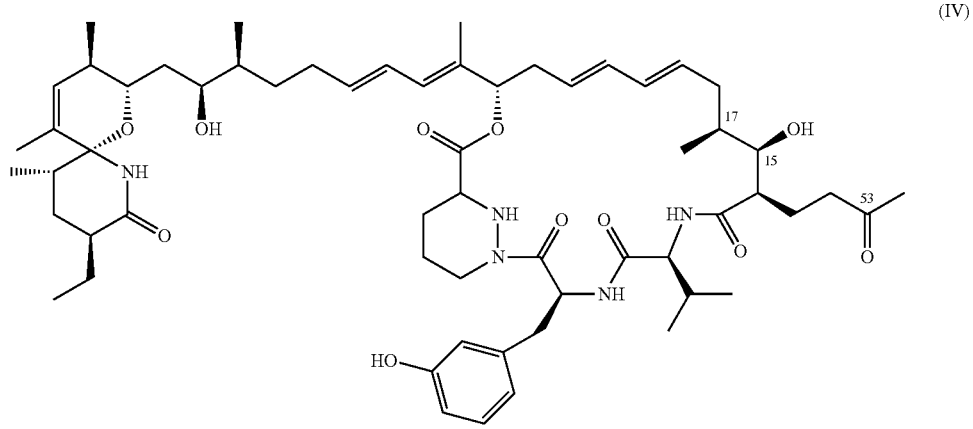

and wherein one or more carbon atoms of an $R_1$ and/or $R_2$ group may optionally be substituted by one or more halogen atoms;

$R_3$ represents H, $-(CO)_x$alkyl;

$R_4$ represents H or OH;

$R_5$ represents H, OH or =O;

n represents a single or double bond save that when n represents a double bond $R_4$ represents H; and m represents a single or double bond save that when m represents a double bond $R_5$ represents H;

x represents 0 or 1;

including any tautomer thereof; or an isomer thereof in which the C26, 27 C=C bond shown as trans is cis; and including any tautomer thereof; and including a methanol adduct thereof in which a ketal is formed by the combination of the C-53 keto and the C-15 hydroxyl group and methanol.

The above structure shows a representative tautomer and the invention embraces all tautomers of the compounds of formula (III) or (IV) for example keto compounds where enol compounds are illustrated and vice versa.

Specific tautomers that are included within the definition of formula (III) or (IV) are those in which (i) the C-53 keto group forms a hemiketal with the C-15 hydroxyl. All numberings use the system for the parent sanglifehrin A structure.

The compounds of formula (III) and (IV) are novel intermediates useful for the synthesis of certain compounds described herein. They may also have useful sanglifehrin like biological activity in their own right and as such may be useful as pharmaceuticals.

Definitions

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "sanglifehrin(s)" refers to chemical compounds that are structurally similar to sanglifehrin A but which differ slightly in composition (as in the replacement of one atom by another or in the presence or absence of a particular functional group), in particular those generated by fermentation of *Streptomyces* sp. A92-308110. Examples include the sanglifehrin-like compounds discussed in WO97/02285 and WO98/07743, such as sanglifehrin B.

As used herein, the term "HCV" refers to Hepatitis C Virus, a single stranded, RNA, enveloped virus in the viral family Flaviviridae.

As used herein, the term "HIV" refers to Human Immunodeficiency Virus, the causative agent of Human Acquired Immune Deficiency Syndrome.

As used herein, the term "HBV" refers to Hepatitis B Virus, a circular DNA, enveloped virus in the viral family Hepadnaviridae, and the causative agent of Hepatitis B.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Egorin et al. 2002).

The term "water solubility" as used in this application refers to solubility in aqueous media, e.g. phosphate buffered saline (PBS) at pH 7.4, or in 5% glucose solution. Tests for water solubility are given below in the Examples as "water solubility assay".

As used herein, the term "macrocyclic amide" refers to an amide referred to above as representing the invention in its broadest aspect, for example a compound according to formula (I) above, or a pharmaceutically acceptable salt thereof. These compounds are also referred to as "compounds of the invention" or "derivatives of sanglifehrin" or "sanglifehrin analogues" and these terms are used interchangeably in the present application.

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Hydrochloric acid salts are of particular interest. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts.

As used herein, the term "alkyl" represents a straight chain or branched alkyl group, containing typically 1-10 carbon atoms, for example a $C_{1-6}$ alkyl group. "Alkenyl" refers to an alkyl group containing two or more carbons (for example 2-10 carbons e.g. 2-6 carbons) which is unsaturated with one or more double bonds.

Examples of alkyl groups include $C_{1-4}$ alkyl groups such as methyl, ethyl, n-propyl, i-propyl, and n-butyl. Examples of alkenyl groups include $C_{2-4}$alkenyl groups such as —CH=$CH_2$ and —$CH_2$CH=$CH_2$.

As used herein, the term "cycloalkyl" represents a cyclic alkyl group, containing typically 3-10 carbon atoms, optionally branched, for example cyclobutyl, cyclopentyl, cyclohexyl or cycloheptyl. A branched example is 2-methylcyclopentyl. "Cycloalkenyl" refers to a cyclic alkenyl group containing typically 5-10 carbon atoms, for example cyclopentyl, cyclohexenyl or cycloheptenyl. Cycloalkyl and cycloalkenyl groups may for example be monocyclic or bicyclic (including spirocyclic) but are suitably monocyclic.

As used herein, the term "heterocyclyl" represents a cycloalkyl group in which one or more one or more ring carbon atoms (e.g. 1, 2 or 3 ring carbon atoms such as 1 or 2 e.g. 1) are replaced by heteroatoms selected from O, N and S. Examples include morpholinyl, piperidinyl, pyrrolidinyl, piperazinyl and N-methyl piperazinyl.

As used herein, the term "heterocyclenyl" represents a cycloalkenyl group in which one or more one or more ring carbon atoms (e.g. 1, 2 or 3 ring carbon atoms such as 1 or 2 e.g. 1) are replaced by heteroatoms selected from O, N and S.

Examples of aryl groups include (except where indicated) monocyclic groups i.e. phenyl and bicyclic rings (e.g. 9 and 10 membered rings) which are aromatic or (in the case of bicyclic rings contain at least one aromatic ring). For example a bicyclic ring may be fully aromatic e.g. naphthyl or may be partially aromatic (e.g. containing one aromatic ring), such as tetraline, indene or indane. Preferred aryl is phenyl. Aryl groups may optionally be substituted e.g. with one or more (e.g. 1, 2 or 3) substituents e.g. selected from alkyl (eg $C_{1-4}$alkyl), hydroxyl, $CF_3$, halogen, alkoxy (e.g. $C_{1-4}$alkoxy), nitro, —$SO_2$Me, cyano and —$CONH_2$.

Examples of heteroaryl groups include (except where indicated) monocyclic groups (e.g. 5 and 6 membered rings) and bicyclic rings (e.g. 9 and 10 membered rings) which are aromatic or (in the case of bicyclic rings contain at least one aromatic ring) and contain one or more heteroatoms (e.g. 1, 2, 3 or 4) heteroatoms selected from N, O and S. Examples of 5 membered heteroaryl rings include pyrrole, furan, thiophene, oxazole, oxadiazole, thiazole and triazole. Examples of 6 membered heteroaryl rings include pyridine, pyrimidine and pyrazine. Examples of bicyclic rings include fully aromatic rings such as quinoline, quinazoline, isoquinoline, indole, cinnoline, benzthiazole, benzimidazole, purine and quinoxaline and partially aromatic rings such as chromene, chromane, tetrahydroquinoline, dihydroquinoline, isoindoline and indoline. Monocyclic heteroaryl groups are preferred.

The aforementioned heteroaryl groups may be optionally substituted as described above for aryl groups.

When bicyclic aryl and heteroaryl groups are partially aromatic, the connection to the remainder of the molecule may be through the aromatic portion or through the non-aromatic portion.

The term "treatment" includes prophylactic as well as therapeutic treatment.

FIGURE LEGEND

FIG. 1: A: HPLC Profile of Harvest Whole Broth Sample of sanglifehrin A, 5 & sanglifehrin B, 7, (monitored at 240 nm) B: UV spectrum of sanglifehrin A, 5

Figure 2:
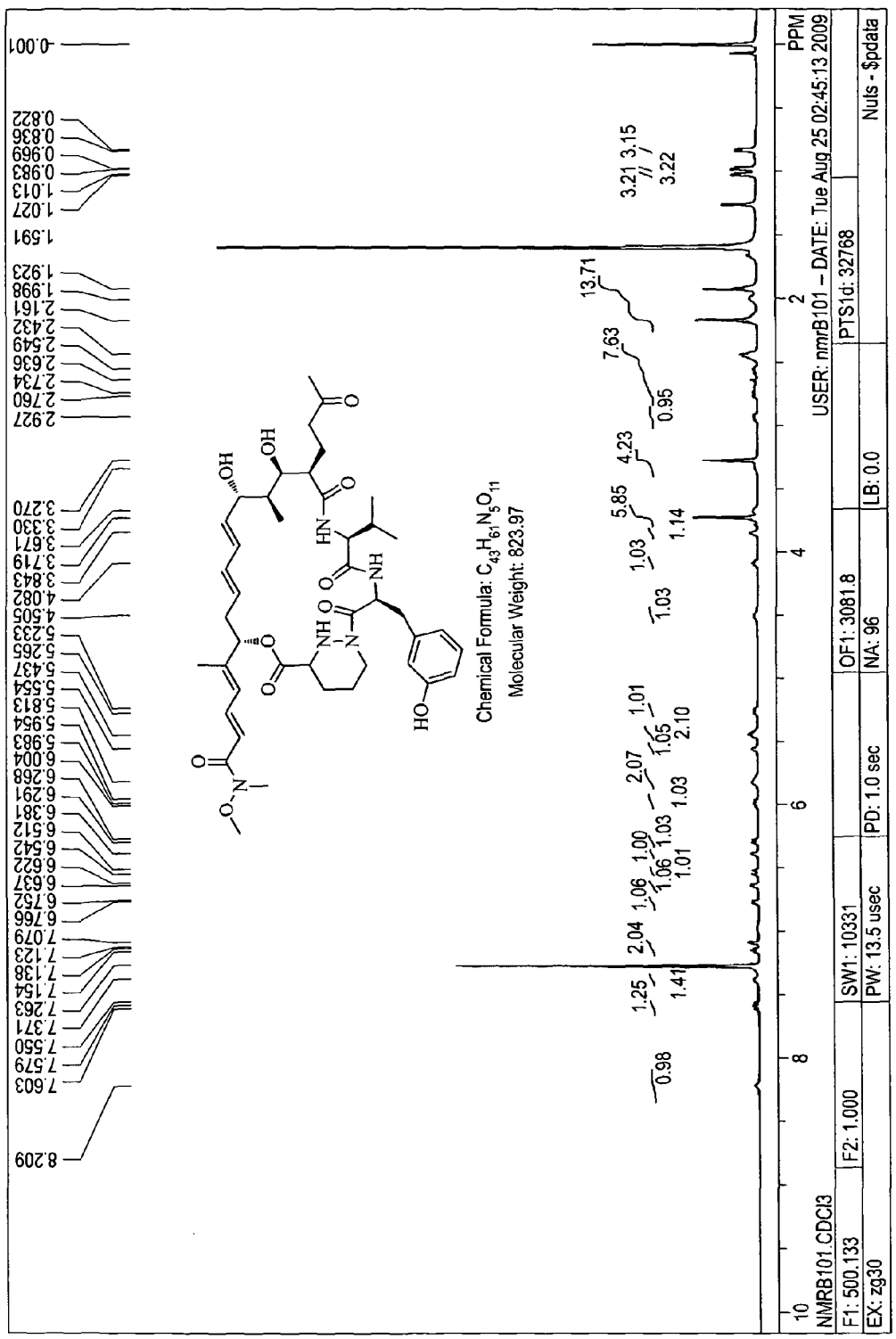
Figure 3:
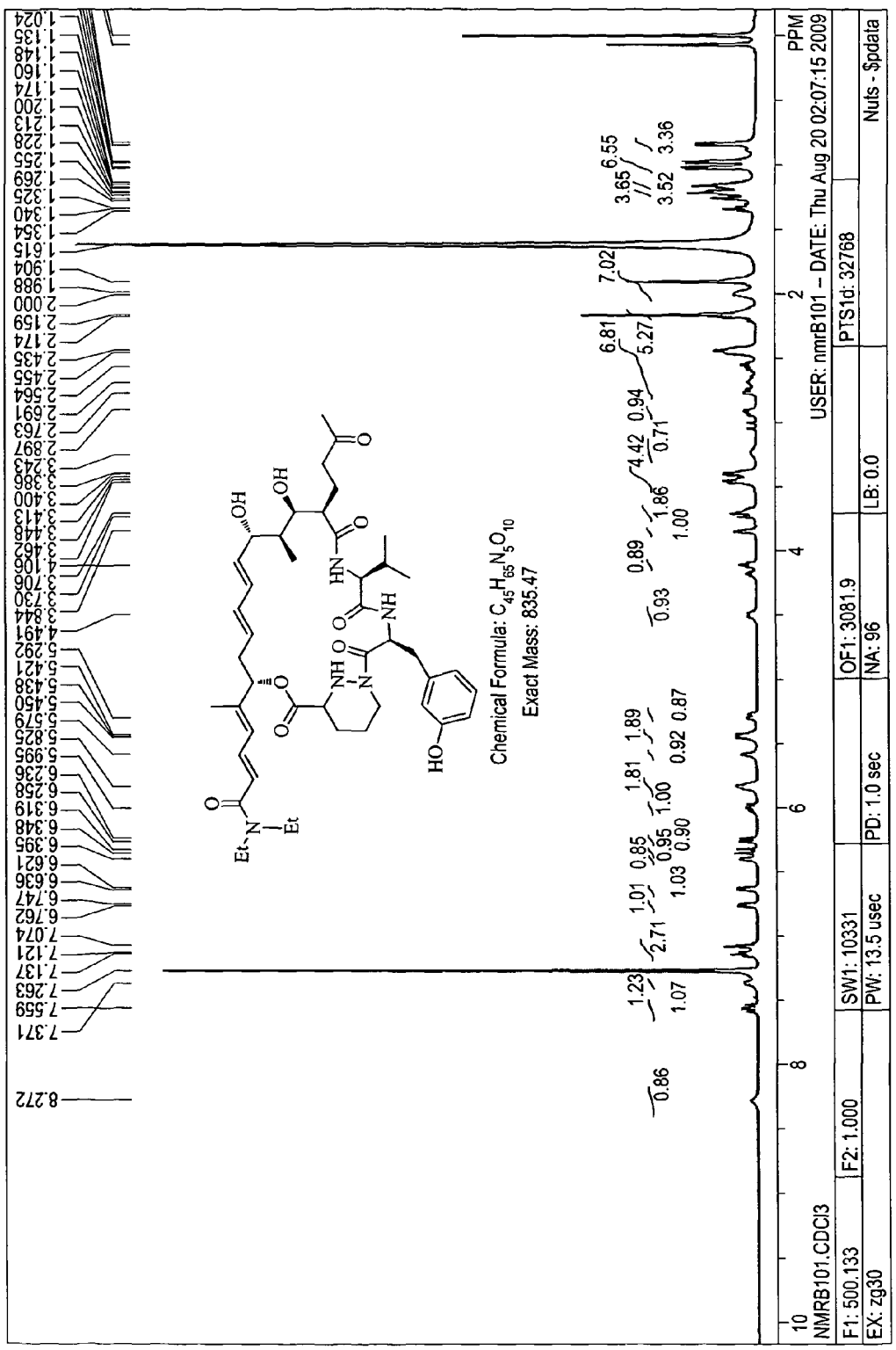
Figure 4:
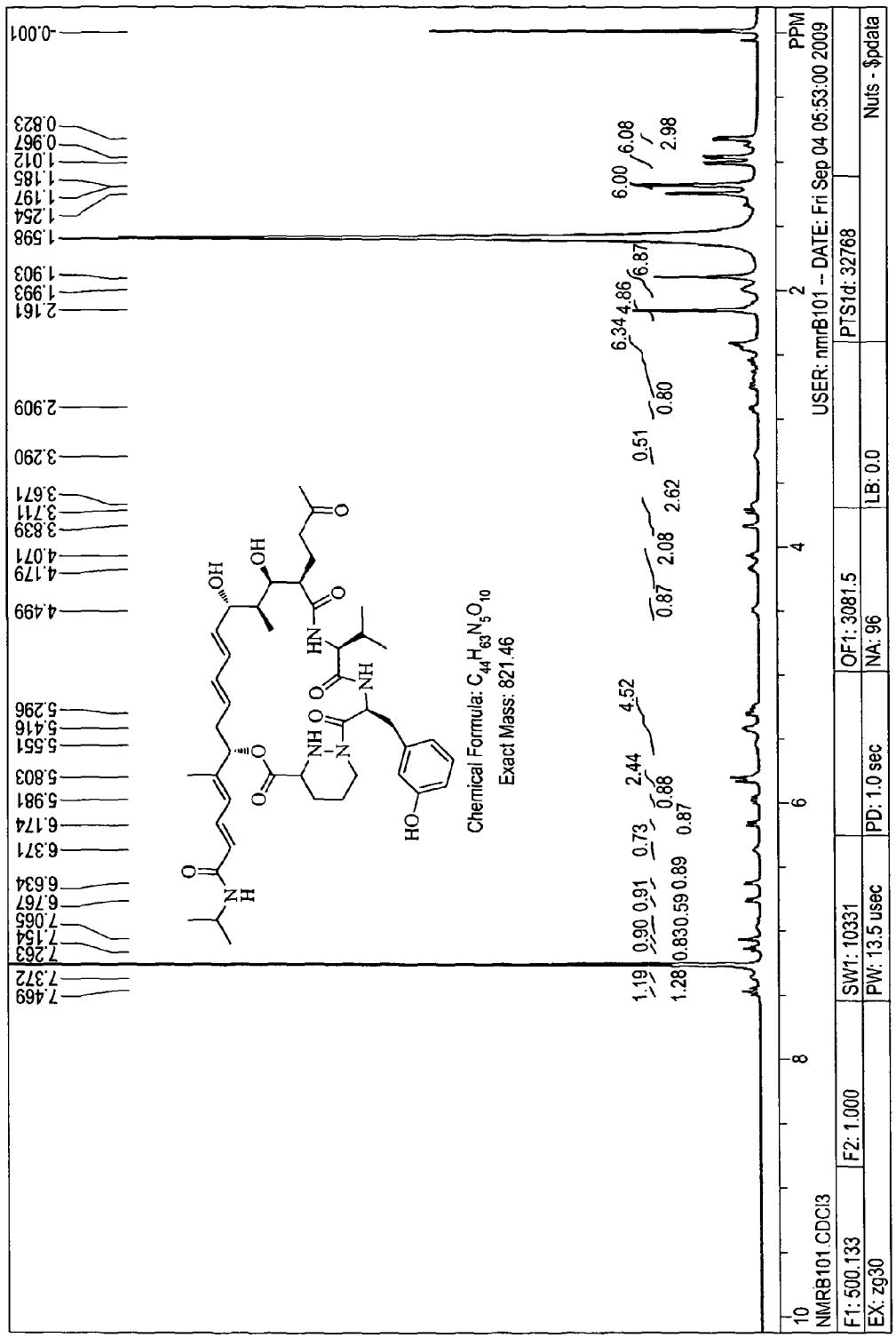
Figure 5:
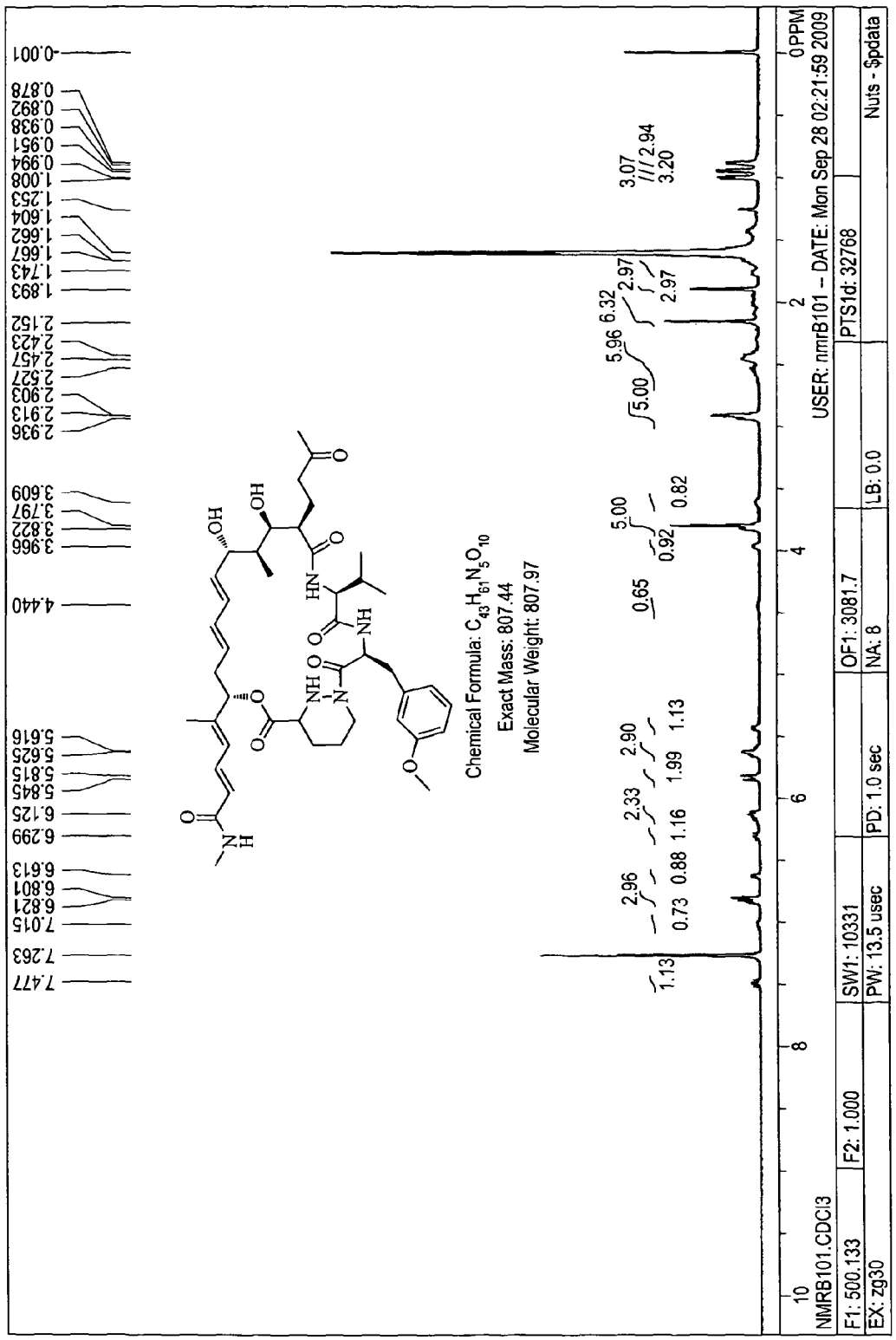
Figure 6:
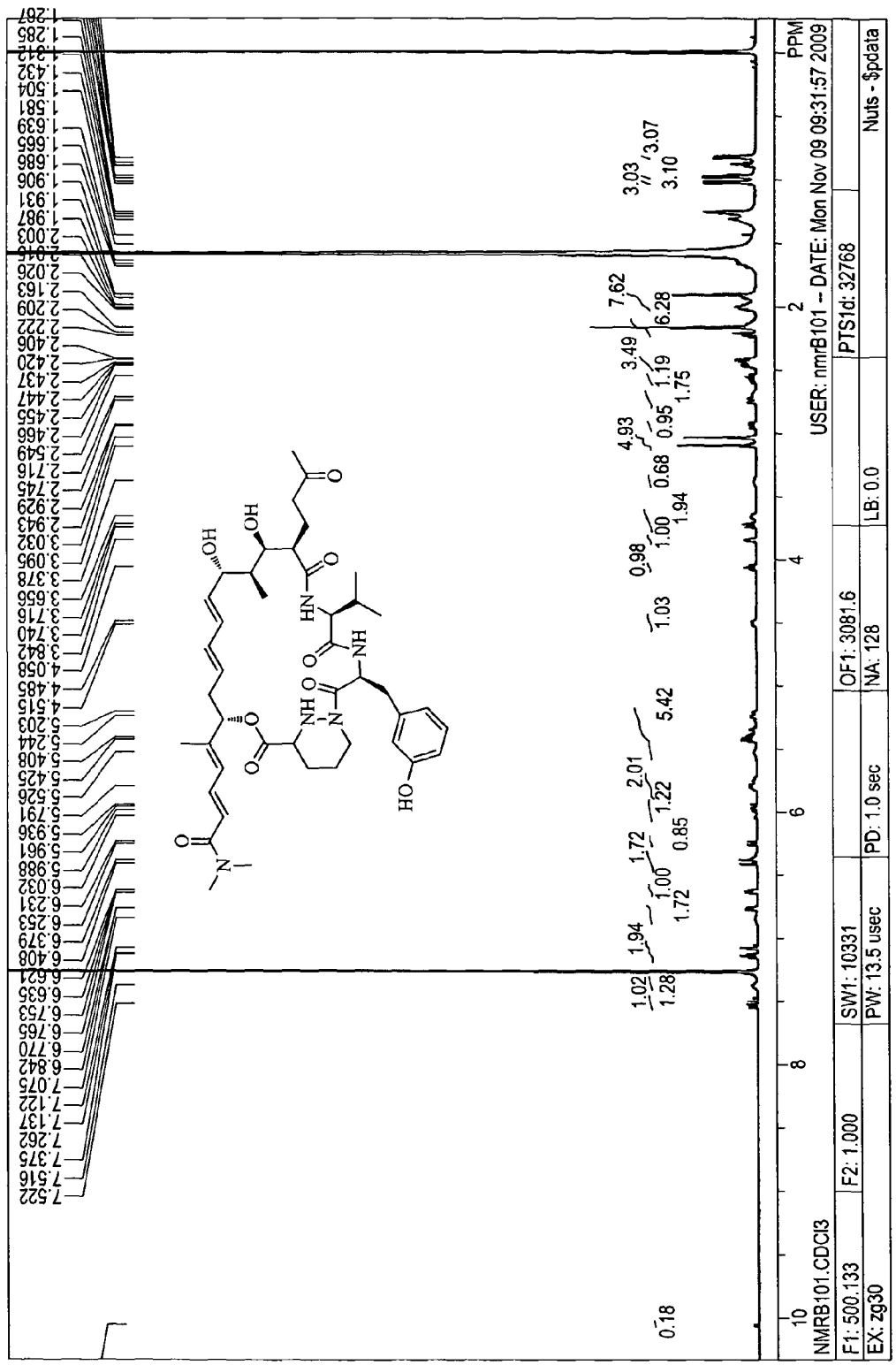
Figure 7:
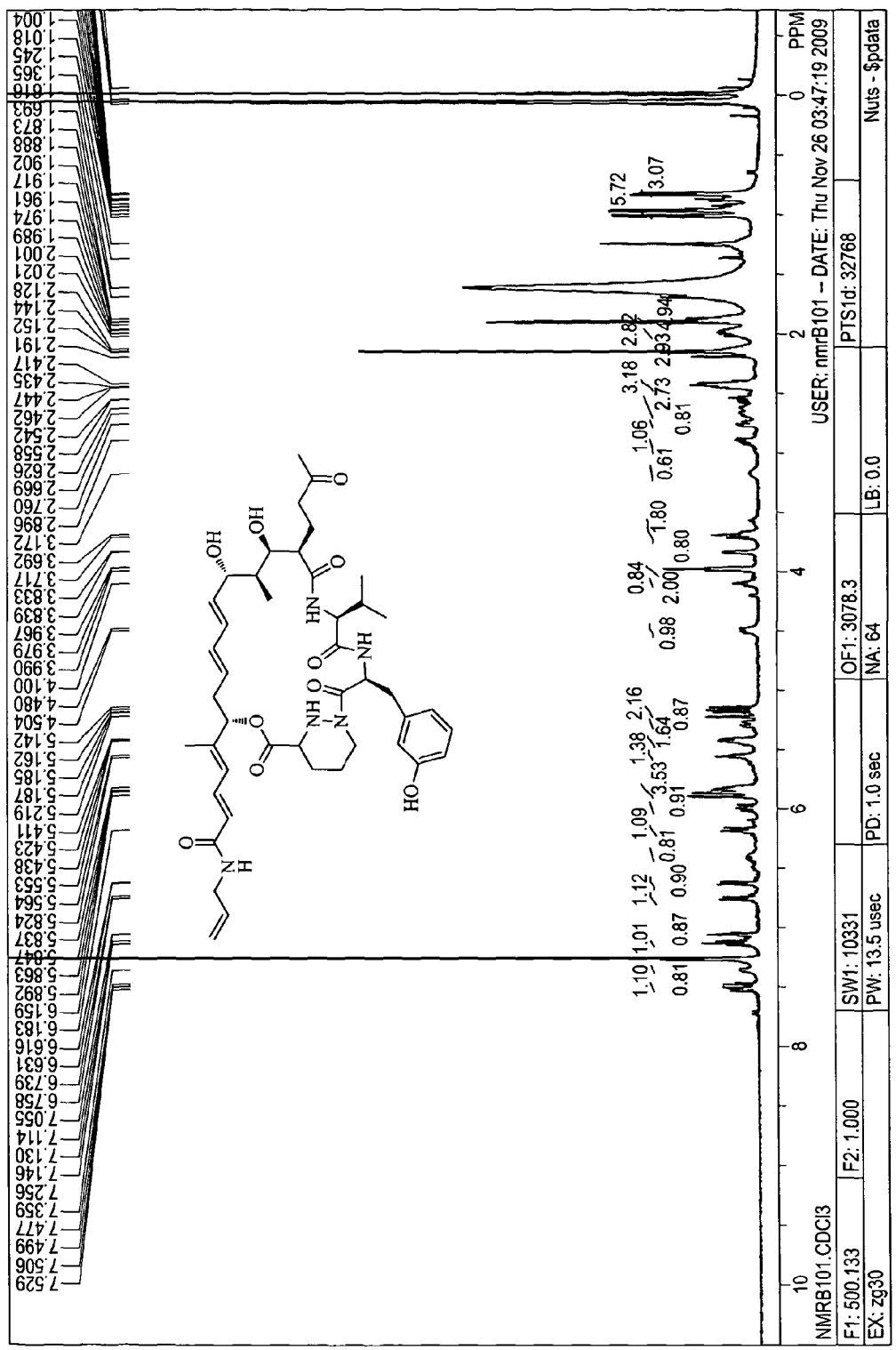
Figure 8:
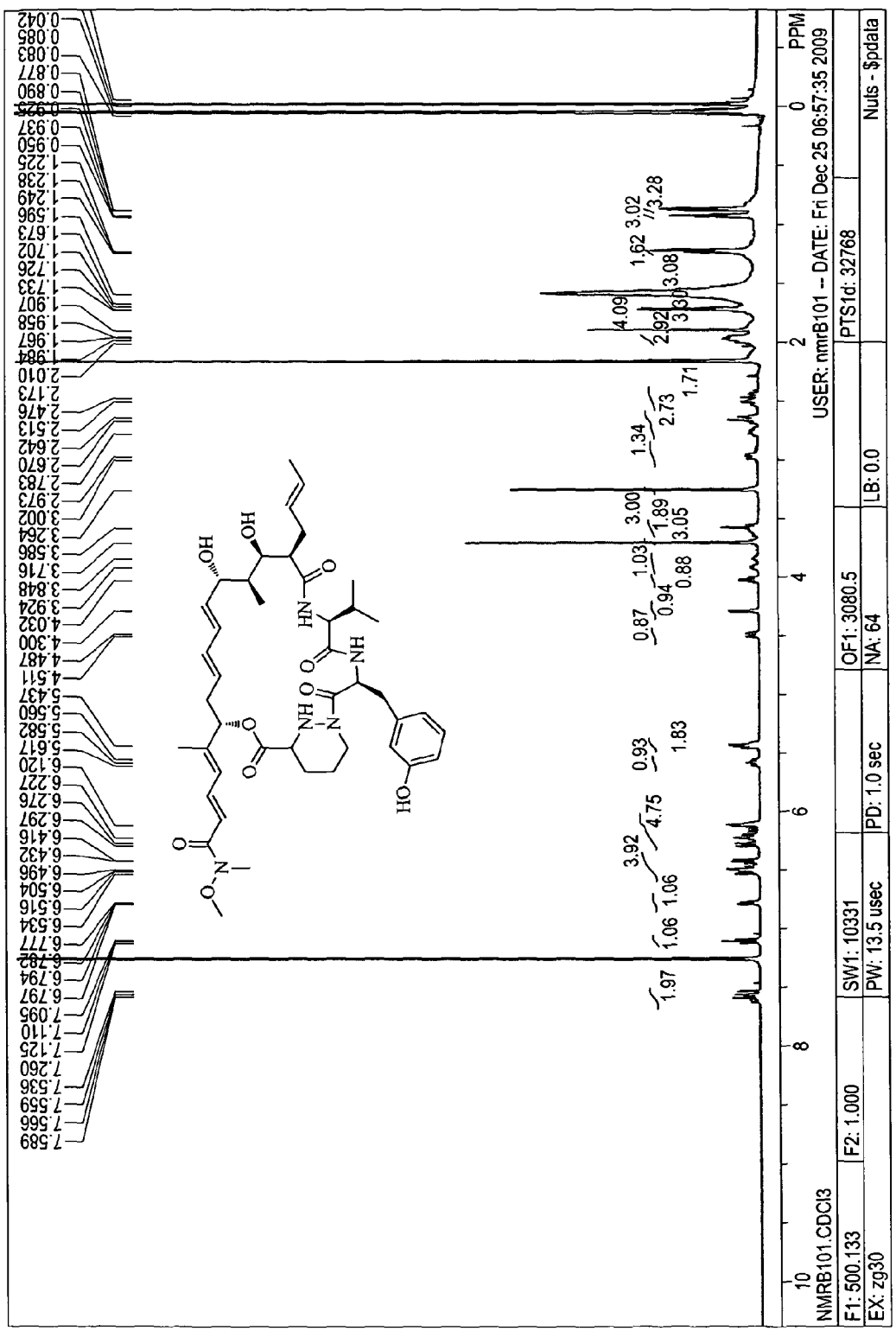
Figure 9:
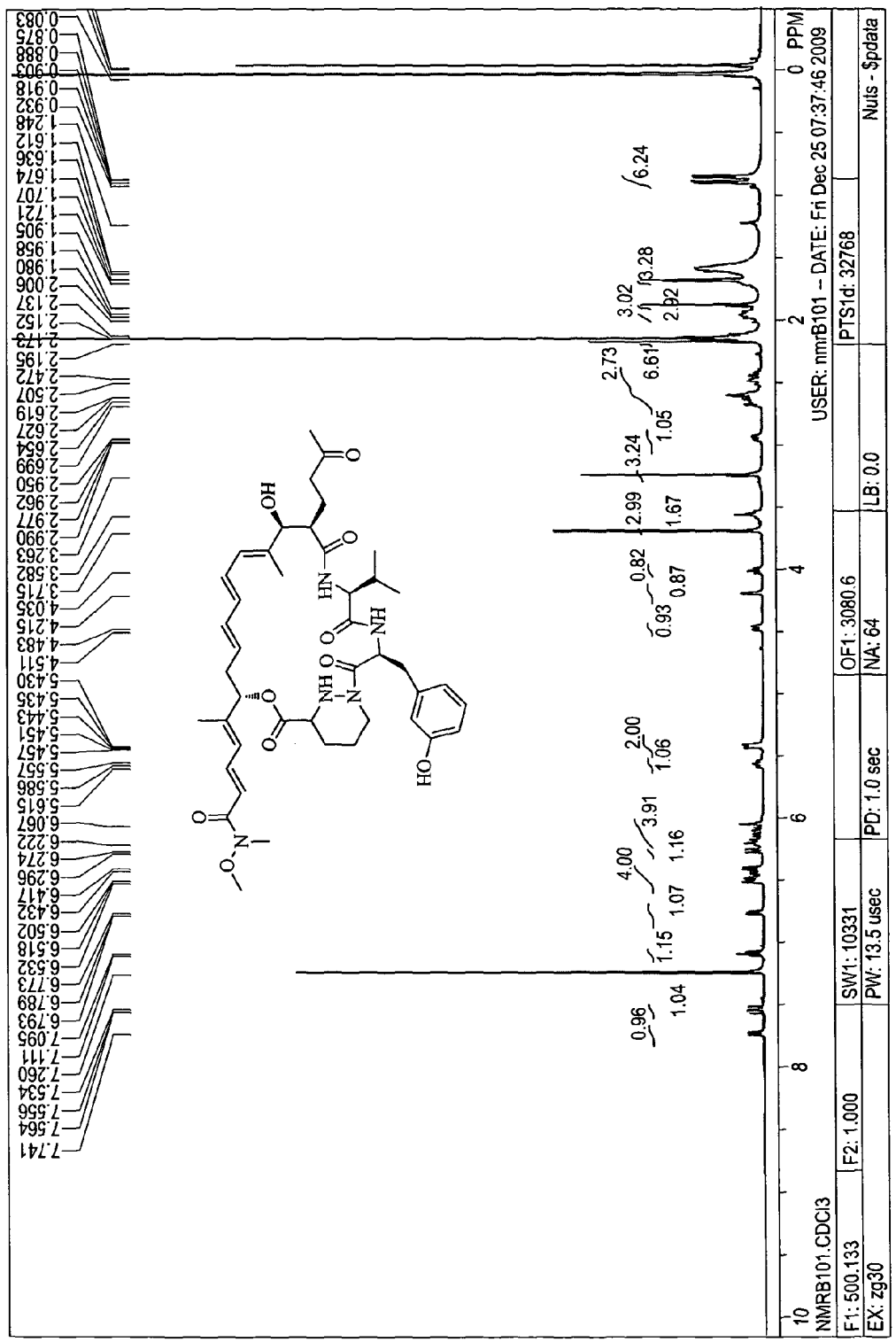
Figure 10:
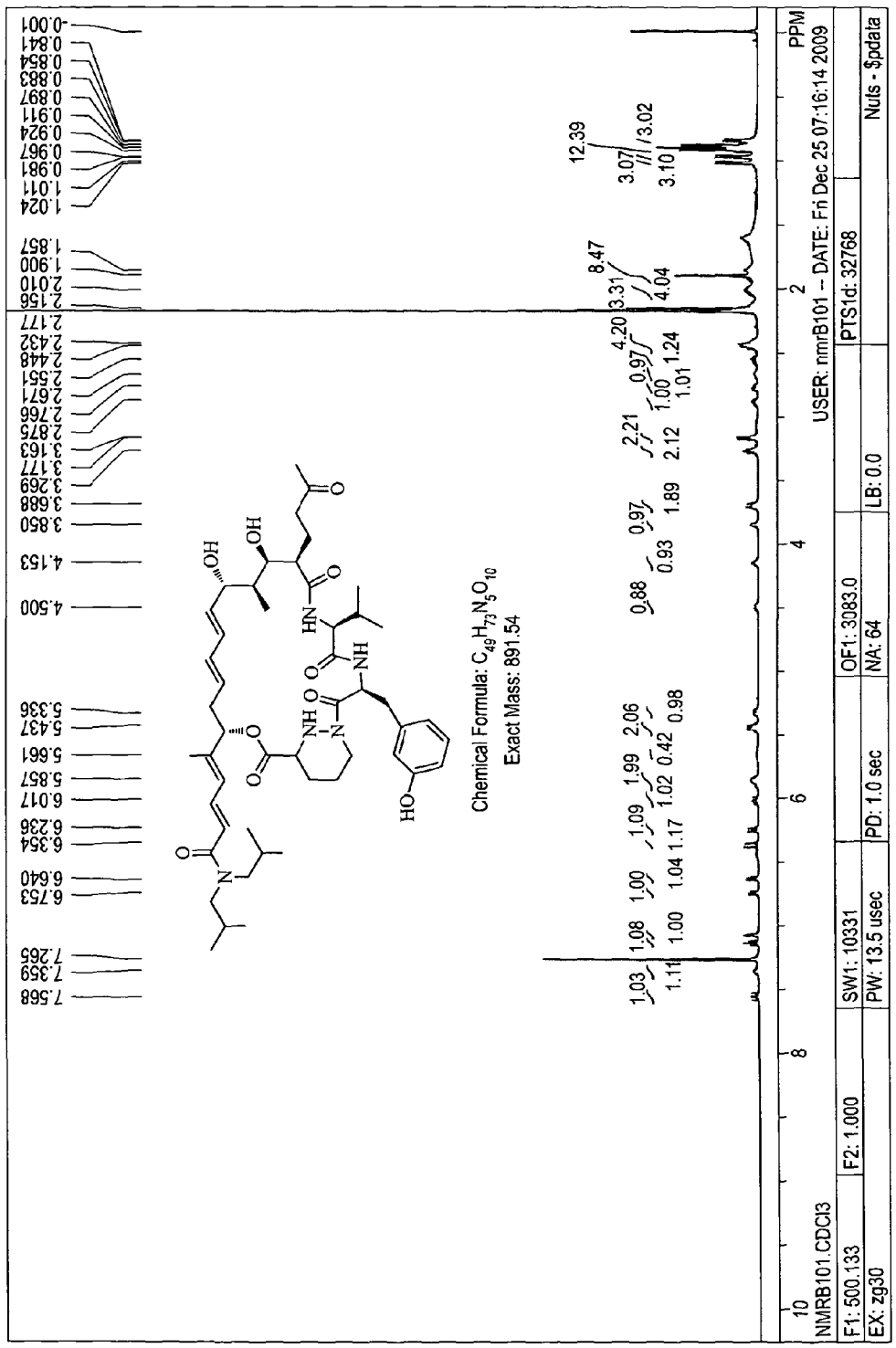
Figure 11:
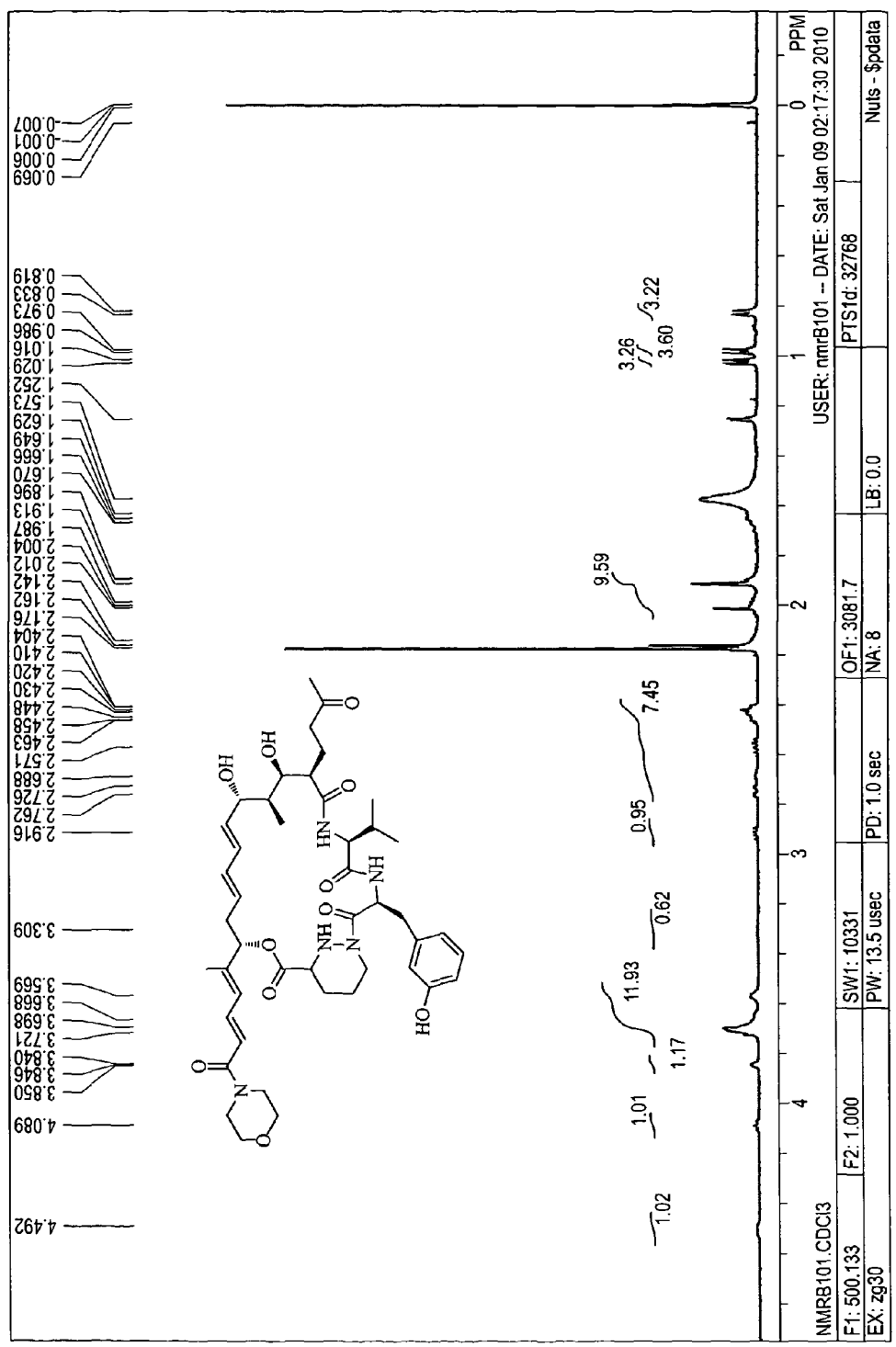
Figure 12:
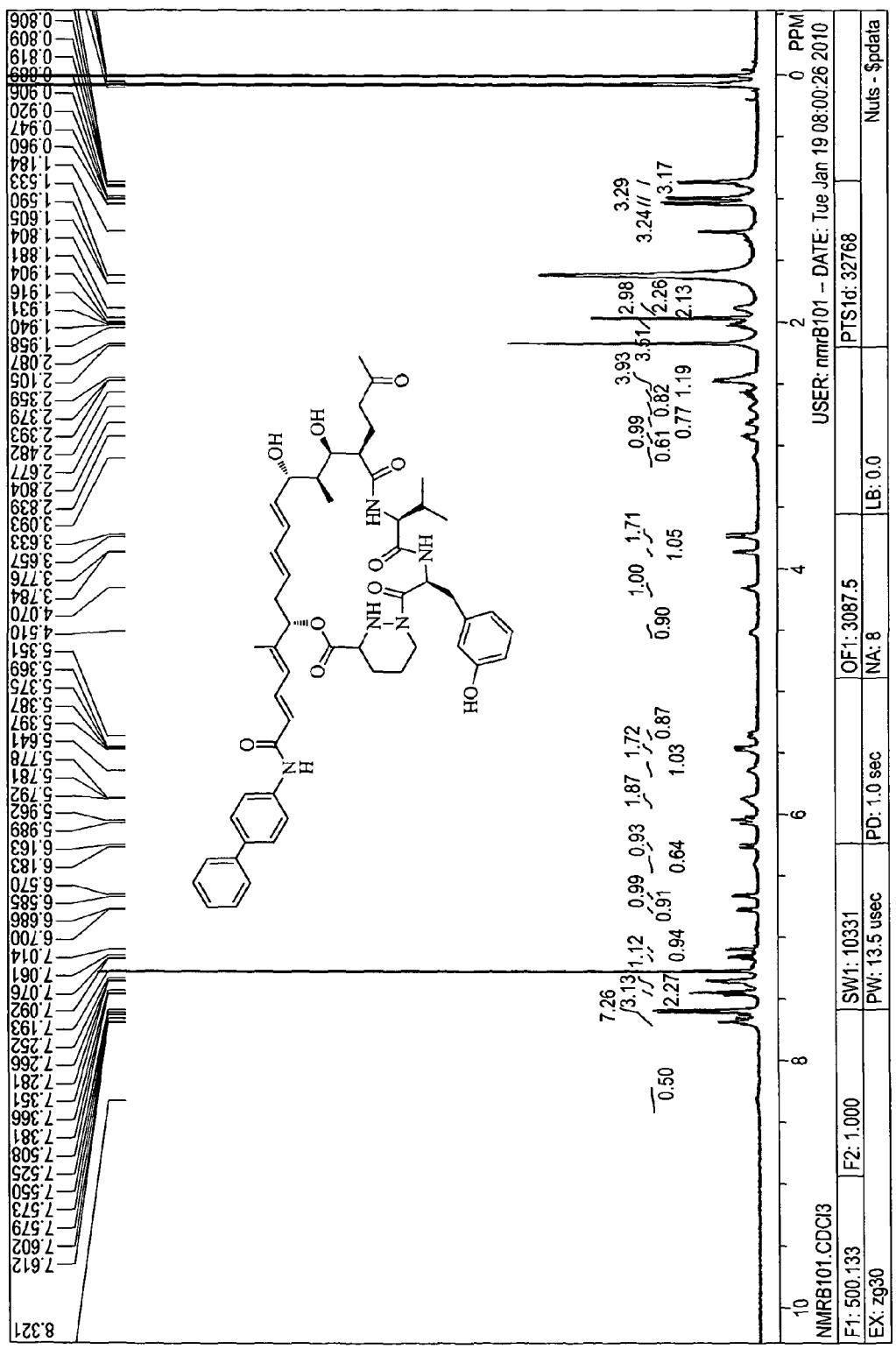
Figure 13:
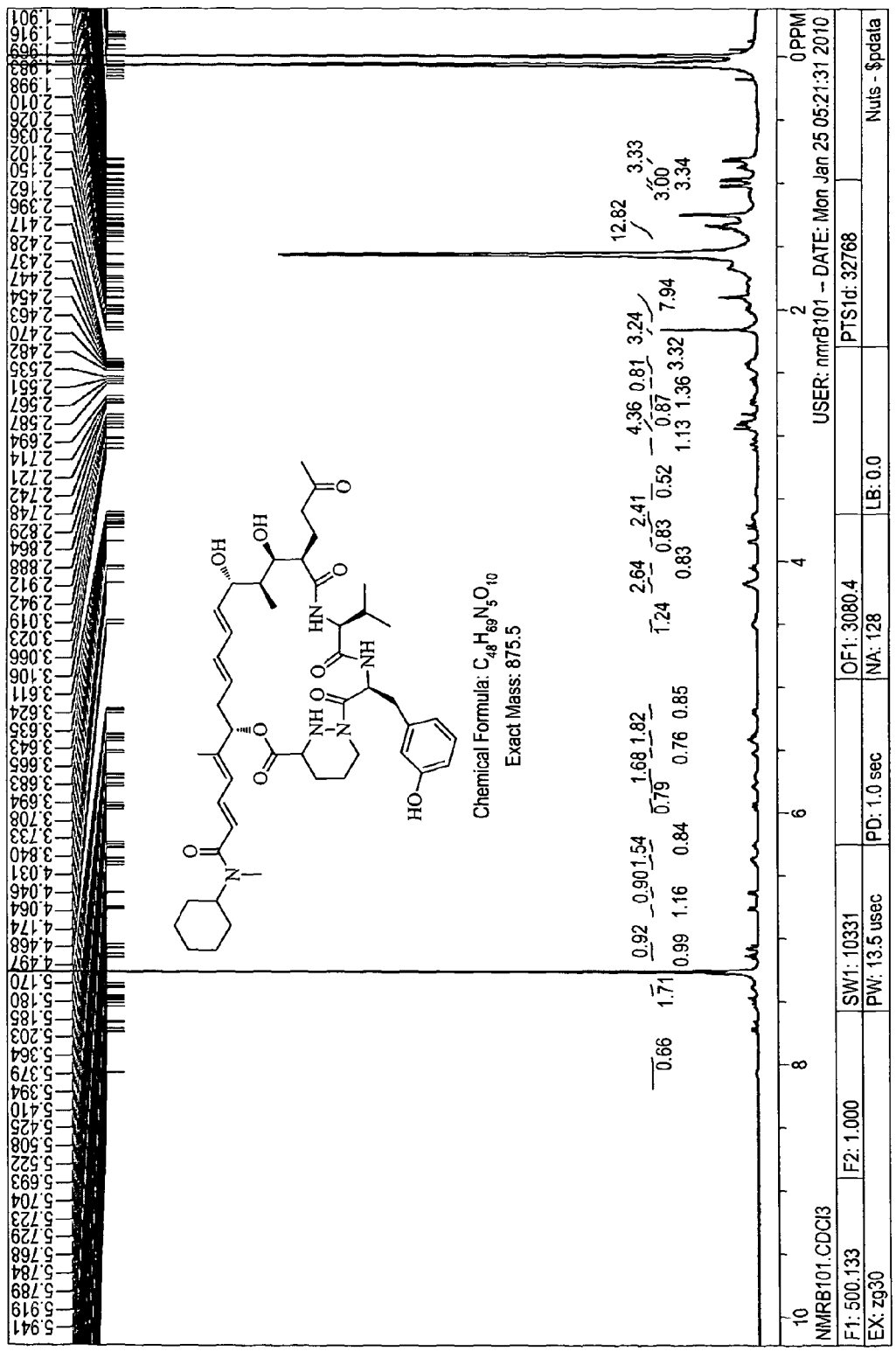
Figure 14:
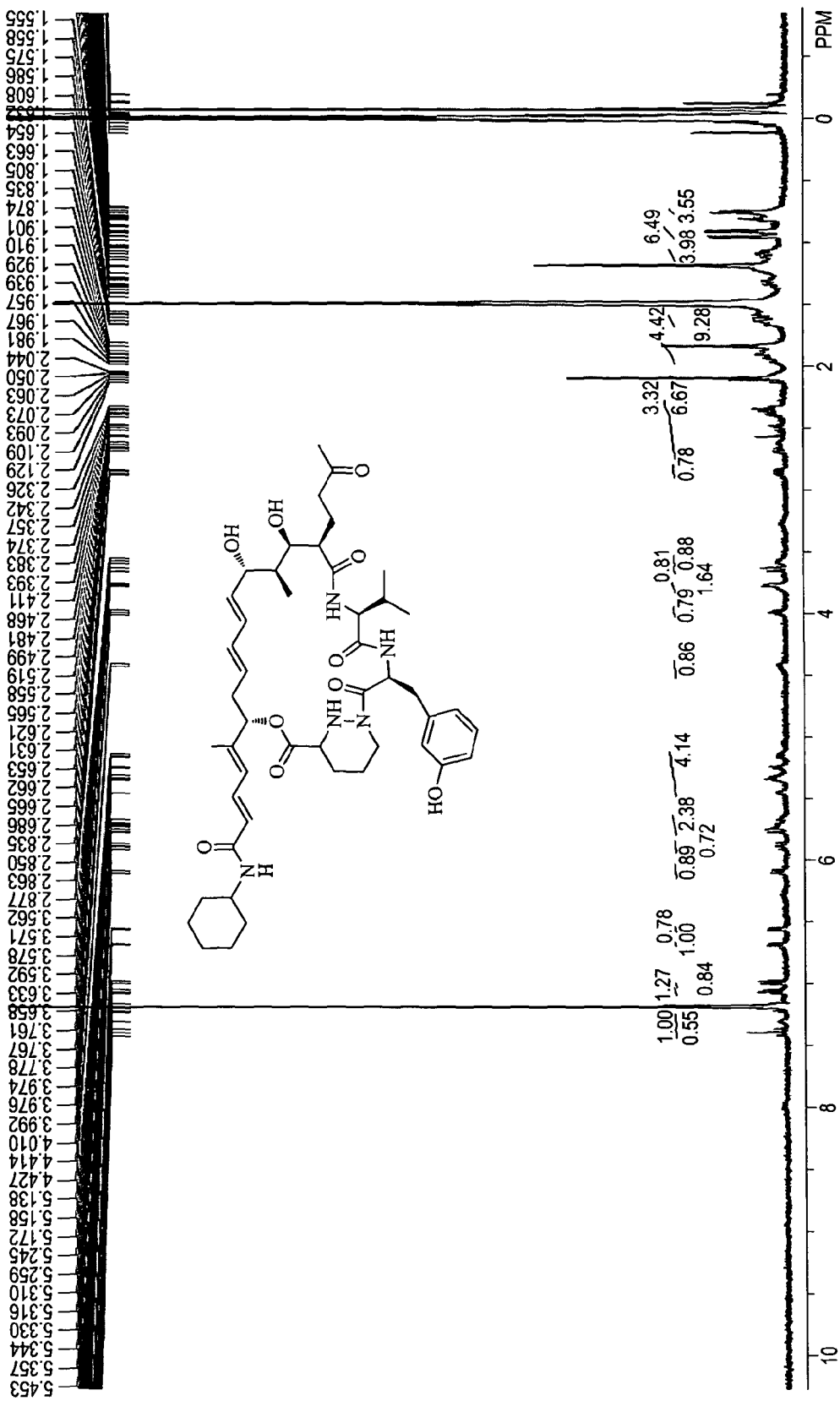
Figure 15:
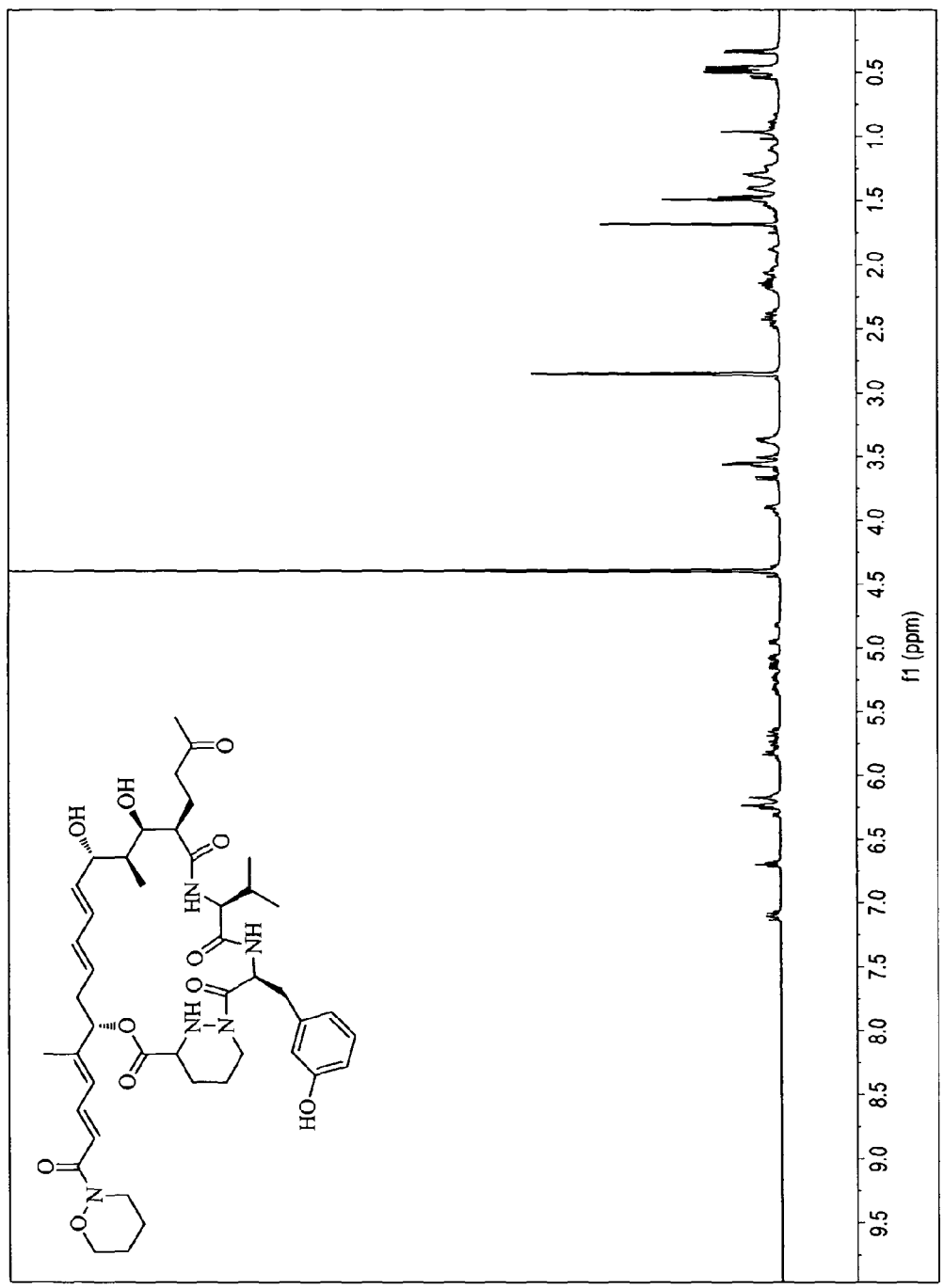
Figure 18:
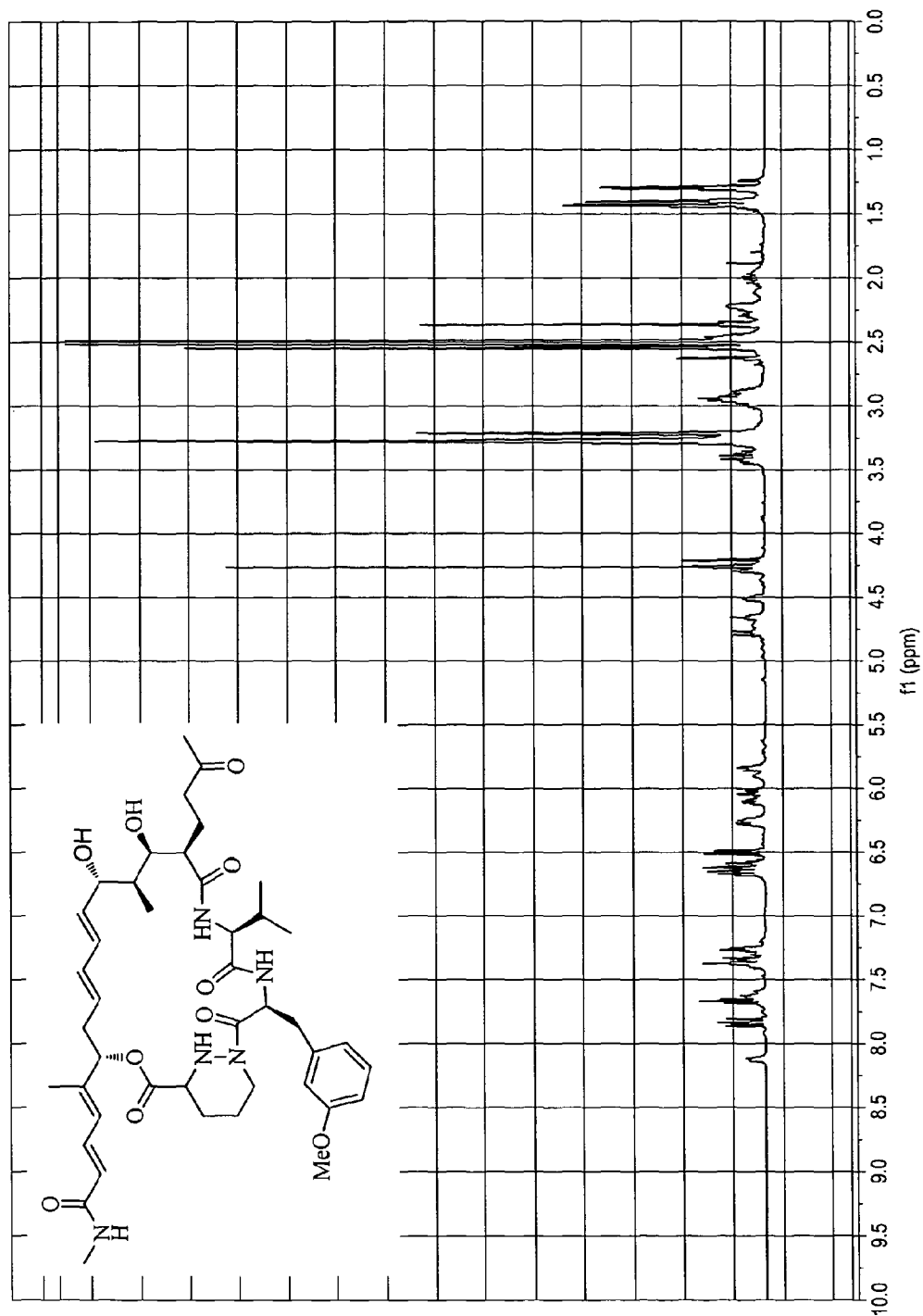

FIG. 2: $^1$H NMR of compound 10
FIG. 3: $^1$H NMR of compound 13
FIG. 4: $^1$H NMR of compound 16
FIG. 5: $^1$H NMR of compound 19
FIG. 6: $^1$H NMR of compound 22
FIG. 7: $^1$H NMR of compound 25
FIG. 8: $^1$H NMR of compound 28
FIG. 9: $^1$H NMR of compound 29
FIG. 10: $^1$H NMR of compound 32
FIG. 11: $^1$H NMR of compound 35
FIG. 12: $^1$H NMR of compound 41
FIG. 13: $^1$H NMR of compound 45
FIG. 14: $^1$H NMR of compound 51
FIG. 15: $^1$H NMR of compound 55
FIG. 16: Synthesised DNA fragment containing a region of homology upstream of the reductive loop of sanglifehrin module 12 (SEQ ID NO: 1).
FIG. 17: MGo013+MGo14 PCR product with inserted G at position 1978 (SEQ ID NO: 4).
FIG. 18: $^1$H NMR of compound 144

DESCRIPTION OF THE INVENTION

The present invention provides sanglifehrin macrocyclic amide analogues, as set out above, methods for preparation of these compounds and methods for the use of these compounds in medicine.

In one embodiment, the compound is a methanol adduct thereof in which a ketal is formed by the combination of the C-53 keto (if present) and the C-15 hydroxyl groups and methanol. In another embodiment it is not.

When $R_1$ and/or $R_2$ contains a group $S(O)_p$, variable p suitably represents 0 or 1. In one embodiment p represents 0 in another embodiment p represents 1. In another embodiment p represents 2.

When $R_1$ and/or $R_2$ represent—alkylaryl, an example includes $C_{1-2}$alkylaryl e.g. benzyl.

When $R_1$ and/or $R_2$ represent—alkenylaryl, an example includes $C_{2-3}$alkenylaryl e.g. —ethenylphenyl.

When $R_1$ and/or $R_2$ represent—alkylheteroaryl, an example includes $C_{1-2}$alkylheteraryl e.g. —methylpyridinyl.

When $R_1$, and/or $R_2$ represent—alkenylheteroaryl, an example includes $C_{2-3}$alkenylheteroaryl e.g. —ethenylpyridinyl.

In one embodiment $R_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl.

In one embodiment $R_2$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl.

In one embodiment $R_1$ represents aryl or heteroaryl optionally substituted by monocyclic aryl or monocyclic heteroaryl. $R_1$ may, for example, represent 4-biphenylyl in which either of the phenyl rings is optionally substituted.

In certain embodiments, a carbon atom of $R_1$ and/or $R_2$ is replaced by a heteroatom, for example one, two or three e.g. one or two e.g. one carbon atom(s) of $R_1$ and/or $R_2$ is (are) replaced by a heteroatom. For example in certain embodiments in the —NR$_1$R$_2$ moiety one, two or three e.g. one or two e.g. one carbon atom(s) is (are) replaced by a heteroatom.

If —CH$_3$ is replaced by N, the group formed is —NH$_2$—. If —CH$_2$— is replaced by N, the group formed is —NH—. If —CHR— is replaced by N the group formed is —NR—. Hence nitrogen atoms within $R_1$ and $R_2$ may be primary, secondary or tertiary nitrogen atoms.

When a carbon atom of $R_1$ and/or $R_2$ is replaced by a heteroatom, it is suitably replaced by O or N, especially O.

In certain embodiments, a carbon atom of $R_1$ and/or $R_2$ is replaced by a heteroatom such that $R_1$ and/or $R_2$ represents heterocyclyl, heterocylenyl, alkylheterocyclyl, alkylheterocyclenyl, alkenylheterocyclyl or alkenylheterocyclenyl.

In an embodiment, $R_1$ may represent aryl or heteroaryl substituted by monocyclic aryl or monocyclic heteroaryl, —C$_{1-4}$alkyl, —OC$_{1-4}$alkyl, —COC$_{1-4}$alkyl or —C$_{2-4}$alkenyl.

Heterocyclic rings formed when $R_1$ and $R_2$ are joined typically contain 4-8 ring atoms, e.g. 5-7 ring atoms, particularly 5 or 6 ring atoms.

Heterocyclic rings formed when $R_1$ and $R_2$ are joined typically contain only the nitrogen atom shown or one or two (e.g. one) additional heteroatom, especially a nitrogen or oxygen atom.

When $R_1$ and/or $R_2$ contain more than one heteroatom, these should typically be separated by two or more carbon atoms.

For example, the ring formed when $R_1$ and $R_2$ are joined may be morpholinyl or 1,2-oxazinane.

When $R_1$ and $R_2$ are joined to form a saturated or unsaturated heterocyclic ring containing the nitrogen atom shown and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring is fused to an aryl or heteroaryl ring, an example is tetrahydroquinolinyl.

When a carbon atom of $R_1$ or $R_2$ is replaced by a carbonyl, the carbonyl is suitably located adjacent to another carbon atom or a nitrogen atom. Suitably carbonyl groups are not located adjacent to sulphur or oxygen atoms.

For example $R_1$ and/or $R_2$ may represent —COC$_{1-4}$alkyl e.g. —COMe.

Suitably a carbon atom of $R_1$ is not replaced by a carbonyl.
Suitably a carbon atom of $R_2$ is not replaced by a carbonyl.
Suitably $R_1$ does not represent hydrogen.
Suitably $R_1$ and $R_2$ do not both represent hydrogen.
Suitably $R_1$ and $R_2$ groups do not comprise a C=C moiety adjacent to a heteroatom. Suitably $R_1$ and $R_2$ groups do not comprise a terminal C=C moiety which is adjacent to the N group shown in formula (I).

Suitably a carbon atom of $R_2$ is not replaced by any heteroatom.

In some embodiments a carbon atom of $R_1$ is not replaced by any heteroatom.

Suitably $R_2$ represents hydrogen, alkyl or alkenyl.
Suitably $R_2$ represents hydrogen, $C_{1-4}$ alkyl or $C_{1-4}$ alkenyl, especially hydrogen, $C_{1-4}$ alkyl. In one embodiment $R_2$ represents hydrogen. In another embodiment $R_2$ represents $C_{1-4}$ alkyl Alternatively, suitably R₁ and R₂ together with the nitrogen to which they are attached represent a 5-7 membered heterocyclic ring, such as a pyrrolidine, piperidine, morpholine or piperazine ring in which the 4-nitrogen of piperazine is optionally substituted by C₁₋₄alkyl.

In another embodiment, suitably R₁ and R₂ together with the nitrogen to which they are attached represent a 5-7 membered heterocyclic ring, such as a pyrrolidine, piperidine, morpholine or piperazine ring in which the 4-nitrogen of piperazine is optionally substituted by C₁₋₄alkyl, and in which a carbon atom adjacent to a nitrogen atom within the ring is replaced with carbonyl. Thus, for example, R₁ and R₂ together with the nitrogen to which they are attached represent piperidinone.

In another embodiment, an oxygen atom is adjacent to the nitrogen atom to which R₁ and R₂ are attached. For example, R₁ may represent alkyl or alkenyl in which the carbon atom adjacent to the nitrogen atom to which R₁ is attached represents O. For example R₁ may represent —OC₁₋₄alkyl e.g. OMe. Alternatively R₁ and R₂ are joined and the carbon atom adjacent to the nitrogen atom to which R₁ is attached represents O e.g. to form a 1,2-oxazinane ring. Suitably x represents O.

When one or more carbon atoms of an R₁ and/or R₂ group are substituted by one or more halogen atoms, exemplary halogen atoms are F, Cl and Br, especially F and Cl particularly F.

For example R₁ and/or R₂ moieties may be substituted by up to 6 halogen atoms (e.g. F atoms) for example up to 3 halogen atoms (e.g. F atoms).

An exemplary halogenated R₁ and/or R₂ moiety is —CF₃.

Suitably carbon atoms of an R₁ and/or R₂ group are not substituted by one or more halogen atoms i.e. R₁ or R₂ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;

or R₁ and/or R₂ represents hydrogen;

and wherein one or more carbon atoms of R₁ and/or R₂ not being part of an aryl or heteroaryl group are optionally replaced by a heteroatom selected from O, N and S(O)ₚ in which p represents 0, 1 or 2 and wherein one or more carbon atoms of R₁ and/or R₂ are optionally replaced by carbonyl;

or R₁ and R₂ are joined to form a saturated or unsaturated heterocyclic ring containing the nitrogen atom shown and wherein one or more carbon atoms of said ring are optionally replaced by a heteroatom selected from O, N and S(O)ₚ in which p represents 0, 1 or 2 and wherein one or more carbon atoms of said ring are optionally replaced by carbonyl and which heterocyclic ring may optionally be fused to an aryl or heteroaryl ring.

Exemplary R₁ groups include methyl, —CF₃, ethyl, propyl (e.g. n-propyl or i-propyl), —CH₂CH=CH or butyl (e.g. n-butyl, t-butyl or i-butyl). The aforementioned exemplary groups may, for example, be taken together with R₂ representing H, Me, ethyl, propyl (e.g. n-propyl or i-propyl) or butyl (e.g. n-butyl, t-butyl or i-butyl).

Further exemplary R₁ groups include cyclopentyl or cyclohexyl. The aforementioned exemplary groups may, for example, be taken together with R₂ representing H, Me, ethyl, propyl (e.g. n-propyl or i-propyl)) or —OMe.

Further exemplary R₁ groups include optionally substituted pyridinyl or optionally substituted phenyl, for example phenyl substituted by phenyl. The aforementioned exemplary groups may, for example, be taken together with R₂ representing H, Me or —OMe.

Further exemplary R₁ groups include —OMe, —OCF₃, —Oethyl, O-i-propyl, —SMe, O-n-propyl, —O-n-butyl, —O-t-butyl, O-i-butyl, O—CH₂C(Me)₃. The aforementioned exemplary groups may, for example, be taken together with R₂ representing H, Me. ethyl, i-propyl or t-butyl.

Further exemplary R₁ groups include —O-(optionally substituted phenyl) or —O-(optionally substituted pyridinyl). The aforementioned exemplary groups may, for example, be taken together with R₂ representing H or Me.

Exemplary moieties that NR₁R₂ may together form include morpholinyl, piperidinyl, pyrrolidinyl, oxazinane (e.g. 1,2-oxazinane) and those moieties disclosed in the following table:

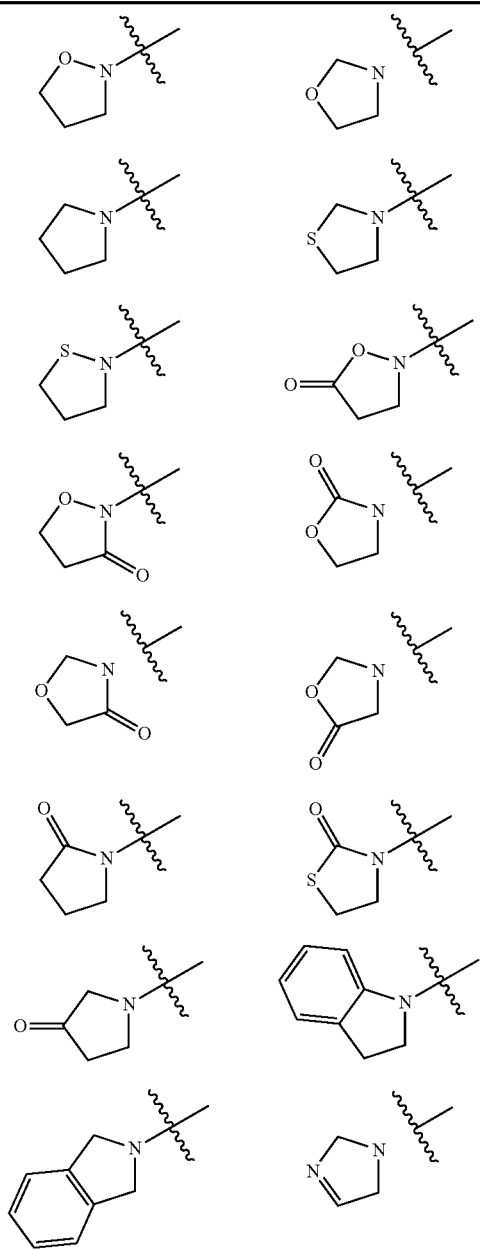

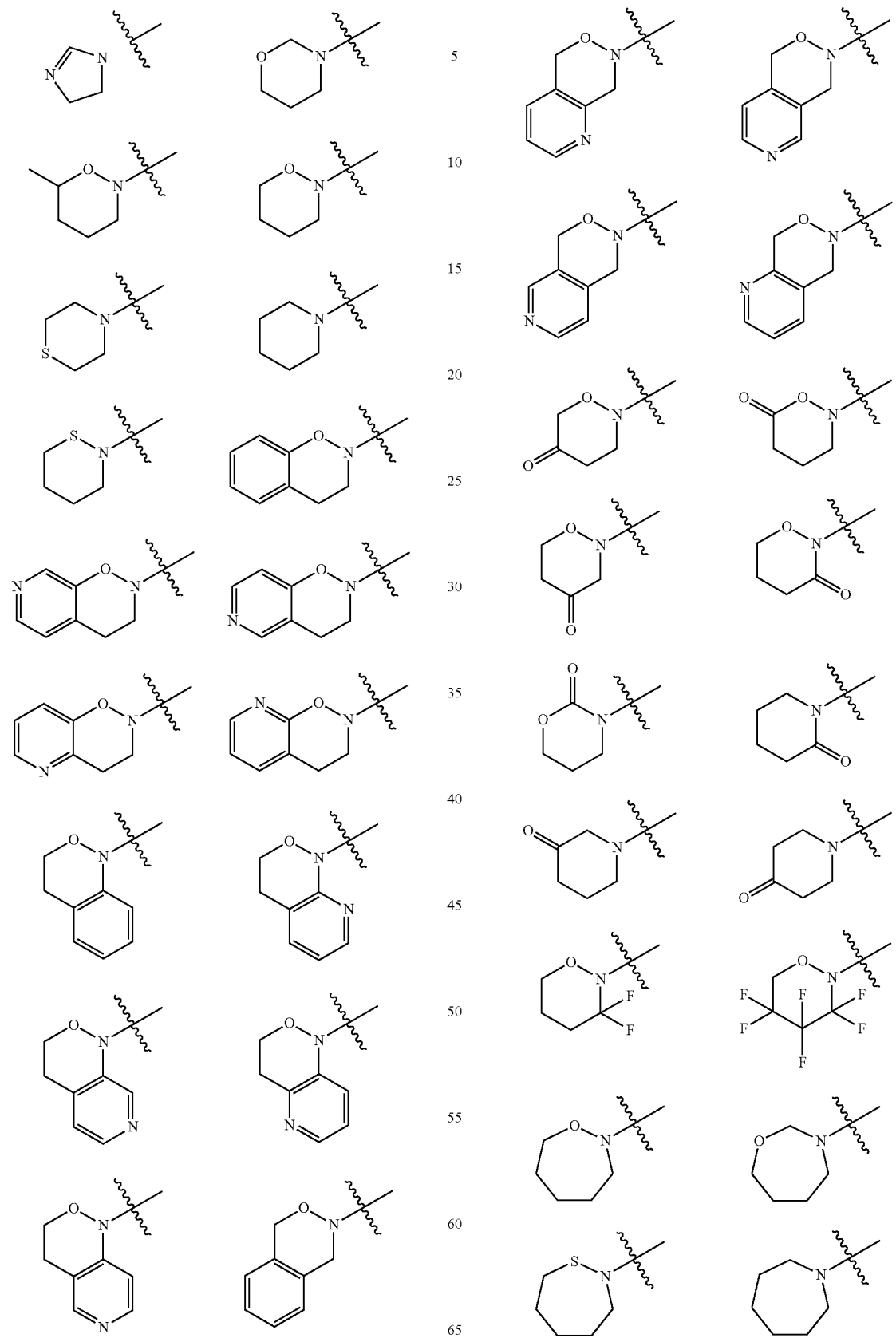

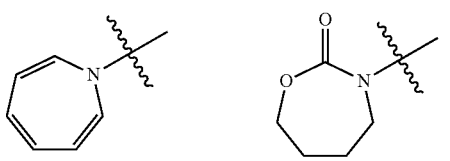
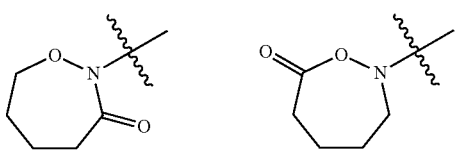
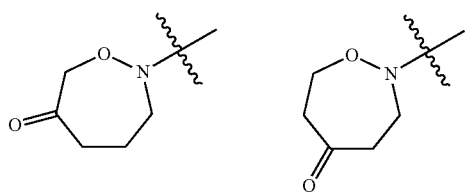
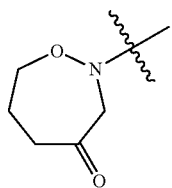 [SMILES: *N1CC(=O)CCCO1]

Suitable $R_3$ represents H or (CO)—$C_{1-4}$alkyl e.g. H or $C_{1-4}$alkyl such as H or methyl, especially H.

Suitably n represents a single bond.

Suitably m represents single bond.

Suitably $R_4$ represents OH.

Suitably $R_5$ represents =O.

In a suitable embodiment of the invention, $R_1$ represents $OCH_3$, $R_2$ represents Me, $R_3$ represents H, $R_4$ represents OH, n represents a single bond, m represents a single bond and $R_5$ represents =O as represented by the following structure:

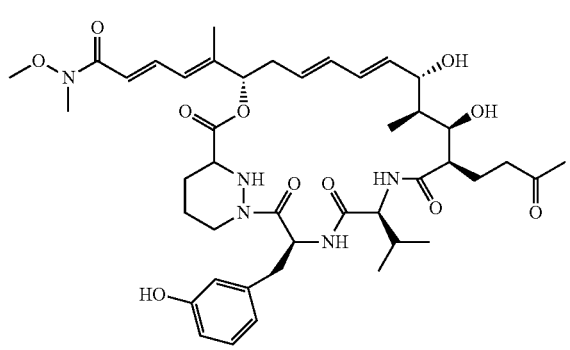 [SMILES: CON(C)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

In another suitable embodiment of the invention, $R_1$ represents ethyl, $R_2$ represents ethyl, $R_3$ represents H, $R_4$ represents OH, n represents a single bond, m represents a single bond and $R_5$ represents =O as represented by the following structure:

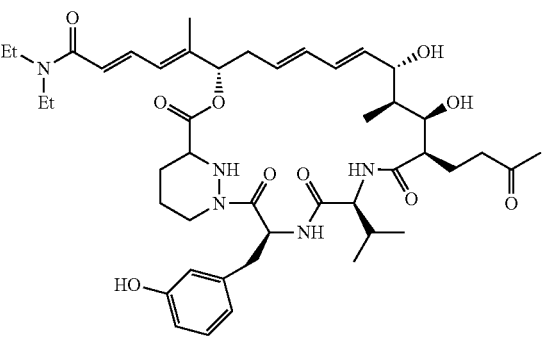 [SMILES: CCN(CC)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

In another suitable embodiment of the invention, $R_1$ represents —$CHMe_2$, $R_2$ represents H, $R_3$ represents H, $R_4$ represents OH, n represents a single bond, m represents a single bond and $R_5$ represents =O as represented by the following structure:

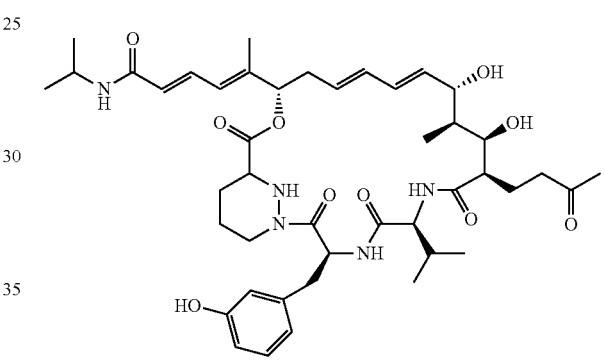

In another suitable embodiment of the invention, $R_1$ represents methyl, $R_2$ represents H, $R_3$ represents H, $R_4$ represents OH, n represents a single bond, m represents a single bond and $R_5$ represents =O as represented by the following structure:

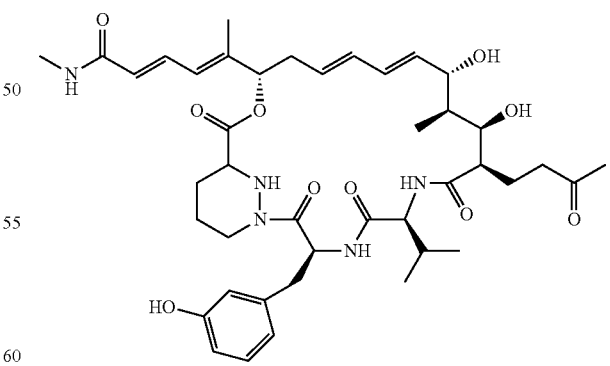

In another suitable embodiment of the invention, $R_1$ represents methyl, $R_2$ represents H, $R_3$ represents Me, $R_4$ represents OH, n represents a single bond, m represents a single bond and $R_5$ represents =O as represented by the following structure:

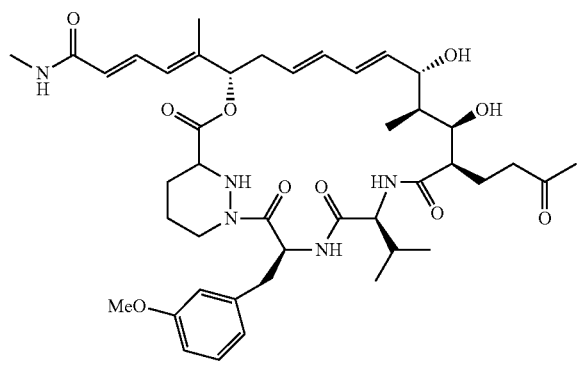 [SMILES: CNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(OC)c2)C(=O)N2CCCC(N2)C(=O)O1]

In another suitable embodiment of the invention, R₁ represents —CH₂CH=CH₂, R₂ represents H, R₃ represents H, R₄ represents OH, n represents a single bond, m represents a single bond and R₅ represents =O as represented by the following structure:

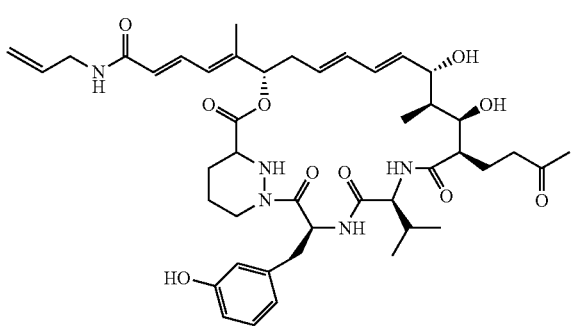 [SMILES: C=CCNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

In another suitable embodiment of the invention, R₁ represents methyl, R₂ represents methyl, R₃ represents H, R₄ represents OH, n represents bond, m represents bond and R₅ represents =O as represented by the following structure:

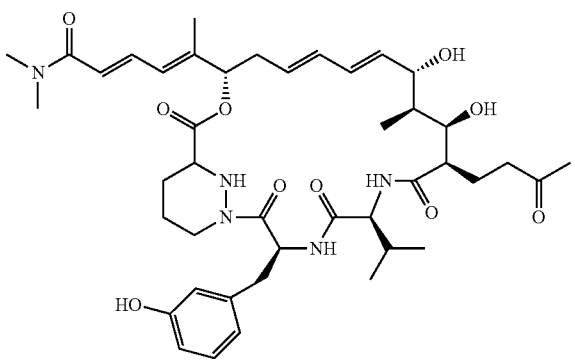 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C)C/C=C/C=C/[C@H](O)[C@H](C)[C@H]1O]

In another suitable embodiment of the invention, R₁ represents —CH₂CHMe₂, R₂ represents —CH₂CHMe₂, R₃ represents H, R₄ represents OH, n represents a single bond, m represents a single bond and R₅ represents =O as represented by the following structure:

In another suitable embodiment of the invention, R₁ represents OCH₃, R₂ represents Me, R₃ represents H, R₄ represents OH, n represents a single bond, m represents a double bond and R₅ represents H as represented by the following structure:

In another suitable embodiment of the invention, R₁ represents OCH₃, R₂ represents Me, R₃ represents H, R₄ represents H, n represents a double bond, m represents a single bond and R₅ represents =O as represented by the following structure:

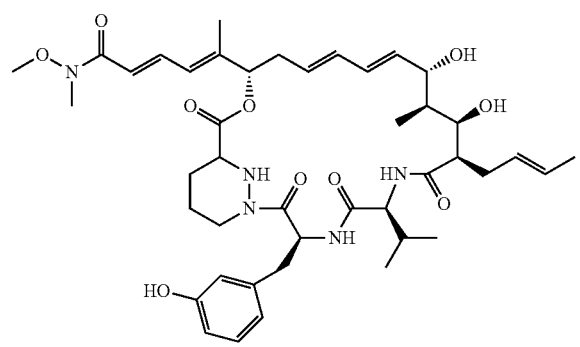 [SMILES: C/C=C/C[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)OC)C/C=C/C=C/[C@H](O)[C@H](C)[C@H]1O]

In another suitable embodiment of the invention, R₁ and R₂ together represent —CH₂CH₂OCH₂CH₂— connected in a 6-membered heterocycle, R₃ represents H, R₄ represents OH, n represents a single bond, m represents a single bond and R₅ represents =O as represented by the following structure:

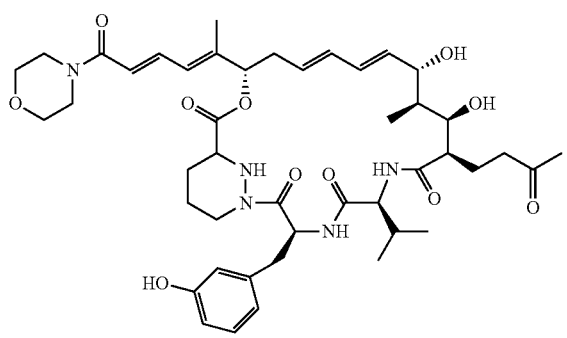 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCOCC2)C/C=C/C=C/[C@H](O)[C@H](C)[C@H]1O]

In another suitable embodiment of the invention, R$_1$ represents 4-biphenylyl, R$_2$ represents H, where, R$_3$ represents H, R$_4$ represents OH, n represents a single bond, m represents a single bond and R$_5$ represents =O as represented by the following structure:

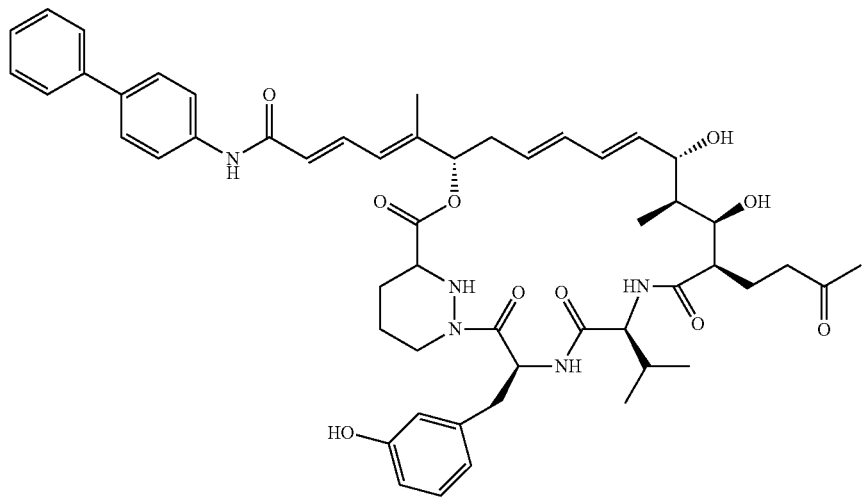 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/[C@H](O)[C@H](C)[C@H]1O]

In another suitable embodiment of the invention, R$_1$ represents cyclohexyl, R$_2$ represents Me, R$_3$ represents H, R$_4$ represents OH, n represents a single bond, m represents a single bond and R$_5$ represents =O as represented by the following structure:

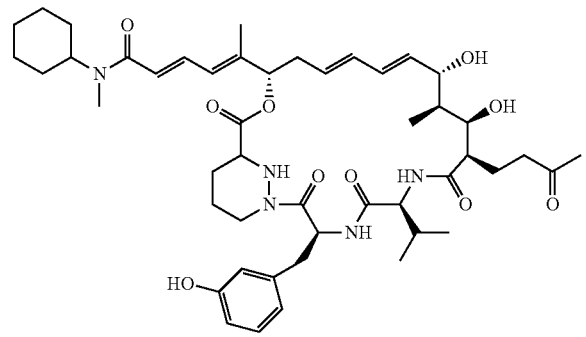 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C2CCCCC2)C/C=C/C=C/[C@H](O)[C@H](C)[C@H]1O]

In another suitable embodiment of the invention, R$_1$ represents cyclohexyl, R$_2$ represents H, R$_3$ represents H, R$_4$ represents OH, n represents a single bond, m represents a single bond and R$_5$ represents =O as represented by the following structure:

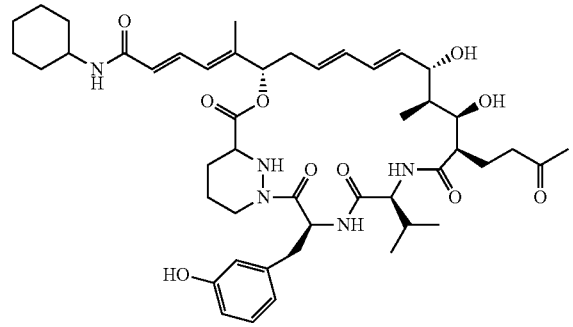 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)NC2CCCCC2)C/C=C/C=C/[C@H](O)[C@H](C)[C@H]1O]

In another suitable embodiment of the invention, R$_1$ and R$_2$ together represent —OCH$_2$CH$_2$CH$_2$CH$_2$— connected in a 6-membered heterocycle. R$_3$ represents H, R$_4$ represents OH, n represents a single bond, m represents a single bond and R$_5$ represents =O as represented by the following structure:

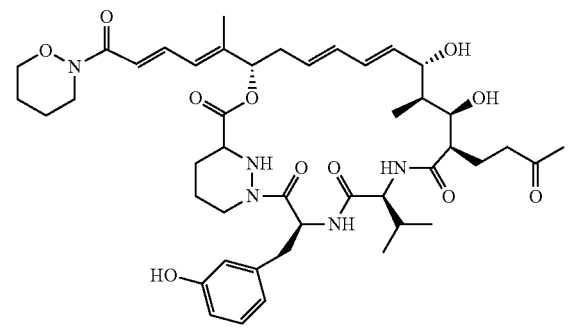 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCCCO2)C/C=C/C=C/[C@H](O)[C@H](C)[C@H]1O]

In another suitable embodiment of the invention, R$_1$ represents 2-pyridinyl, R$_2$ represents H, R$_3$ represents H, R$_4$ represents OH, n represents a single bond, m represents a single bond and R₅ represents =O as represented by the following structure:

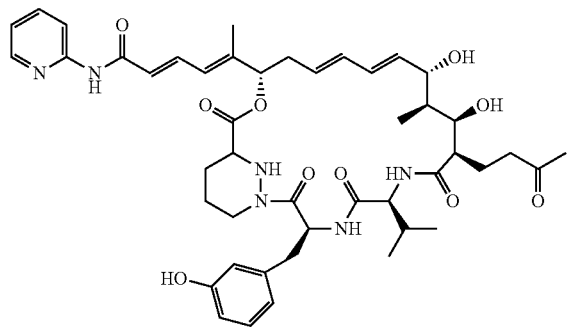 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccccn2)C/C=C/C=C/[C@H](O)[C@H](C)[C@H]1O]

In a suitable embodiment of the invention, R₁ represents OCH₃, R₂ represents Me, R₃ represents H, R₄ represents OH, n represents a single bond, m represents a single bond and R₅ represents OH as represented by the following structure:

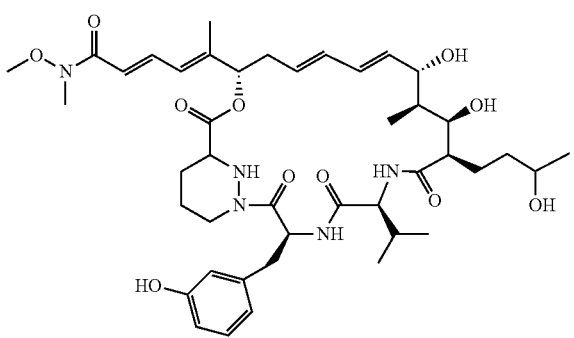 [SMILES: CON(C)C(=O)/C=C/C=C(\C)[C@@H]1C/C=C/C=C/[C@H](O)[C@H](C)[C@@H](O)[C@@H](CCC(C)O)C(=O)N[C@@H](C(C)C)C(=O)N[C@@H](Cc2cccc(O)c2)C(=O)N2CCCC(N2)C(=O)O1]

In another suitable embodiment of the invention, R₁ represents OCH₃, R₂ represents Me, R₃ represents H, R₄ represents H, n represents a single bond, m represents a single bond and R₅ represents =O as represented by the following structure:

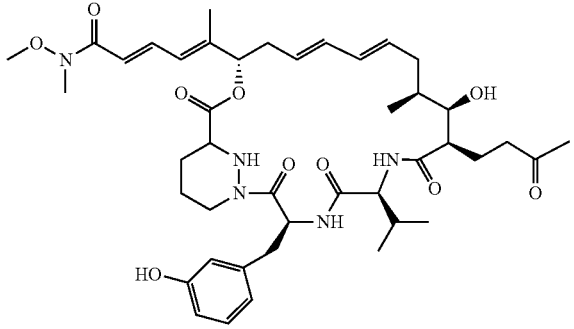 [SMILES: CON(C)C(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

In another suitable embodiment of the invention, R₁ represents ethyl, R₂ represents ethyl, R₃ represents H, R₄ represents H, n represents a single bond, m represents a single bond and R₅ represents =O as represented by the following structure:

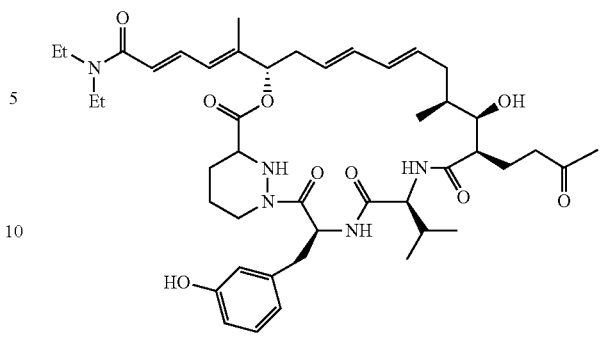

In another suitable embodiment of the invention, R₁ represents —CHMe₂, R₂ represents H, R₃ represents H, R₄ represents H, n represents a single bond, m represents a single bond and R₅ represents =O as represented by the following structure:

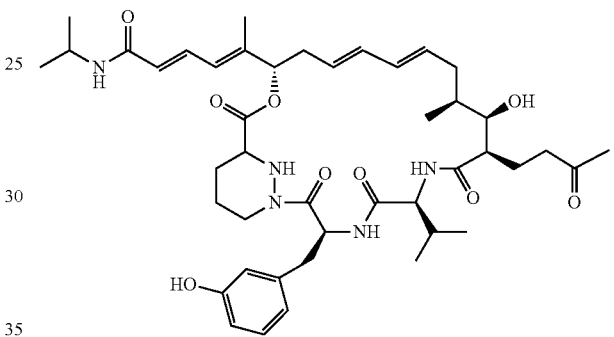

In another suitable embodiment of the invention, R₁ represents methyl, R₂ represents H, R₃ represents H, R₄ represents H, n represents a single bond, m represents a single bond and R₅ represents =O as represented by the following structure:

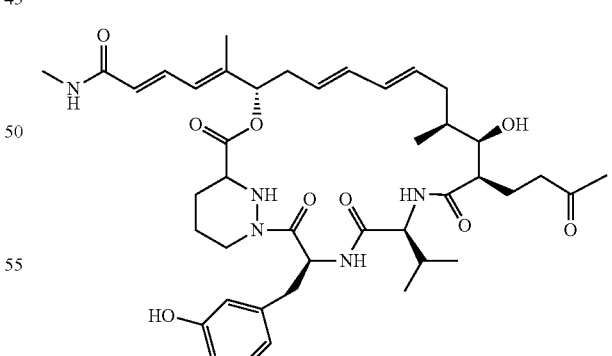

In another suitable embodiment of the invention, R₁ represents methyl, R₂ represents H, R₃ represents Me, R₄ represents H, n represents a single bond, m represents a single bond and R₅ represents =O as represented by the following structure:

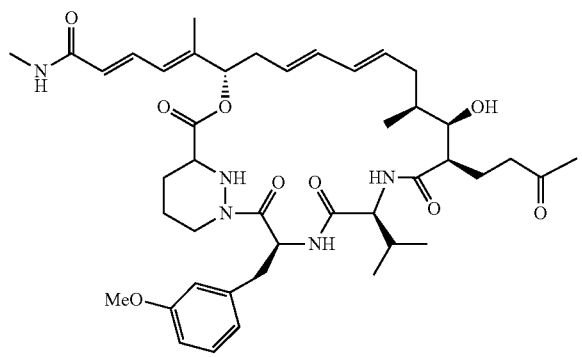 [SMILES: CNC(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

In another suitable embodiment of the invention, $R_1$ represents —$CH_2CH=CH_2$, $R_2$ represents H, $R_3$ represents H, $R_4$ represents H, n represents a single bond, m represents a single bond and $R_5$ represents =O as represented by the following structure:

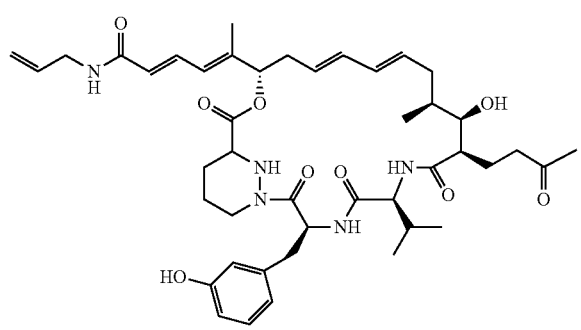 [SMILES: C=CCNC(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

In another suitable embodiment of the invention, $R_1$ represents methyl, $R_2$ represents methyl, $R_3$ represents H, $R_4$ represents H, n represents bond, m represents bond and $R_5$ represents =O as represented by the following structure:

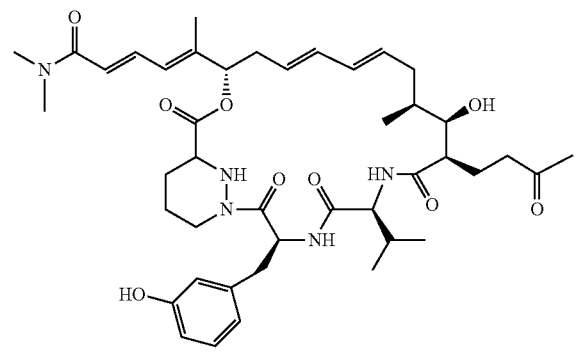 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C)C/C=C/C=C/C[C@H](C)[C@H]1O]

In another suitable embodiment of the invention, $R_1$ represents —$CH_2CHMe_2$, $R_2$ represents —$CH_2CHMe_2$, $R_3$ represents H, $R_4$ represents H, n represents a single bond, m represents a single bond and $R_5$ represents =O as represented by the following structure:

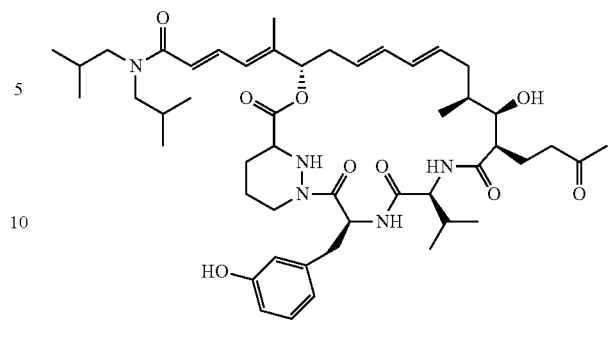

In another suitable embodiment of the invention, $R_1$ represents $OCH_3$, $R_2$ represents Me, $R_3$ represents H, $R_4$ represents H, n represents a single bond, m represents a double bond and $R_5$ represents H as represented by the following structure:

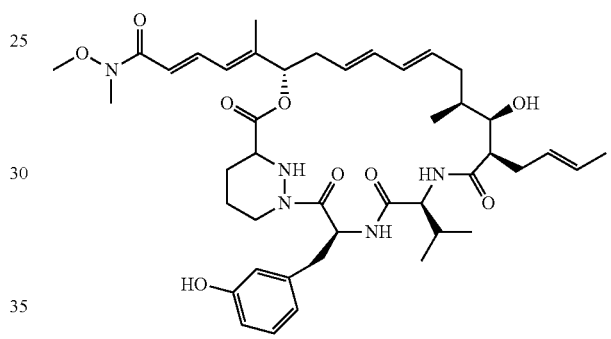

In another suitable embodiment of the invention, $R_1$ and $R_2$ together represent —$CH_2CH_2OCH_2CH_2$— connected in a 6-membered heterocycle, $R_3$ represents H, $R_4$ represents H, n represents a single bond, m represents a single bond and $R_5$ represents =O as represented by the following structure:

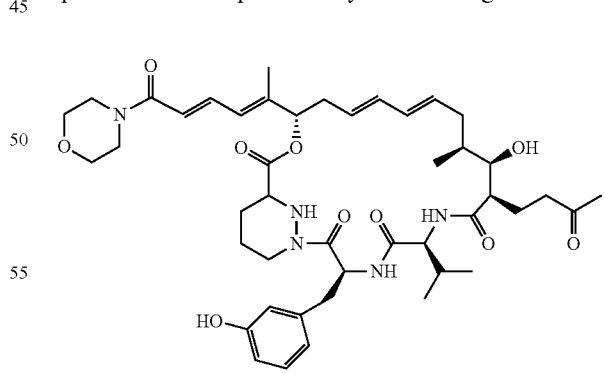

In another suitable embodiment of the invention, $R_1$ represents 4-biphenylyl, $R_2$ represents H, where, $R_3$ represents H, $R_4$ represents H, n represents a single bond, m represents a single bond and $R_5$ represents =O as represented by the following structure:

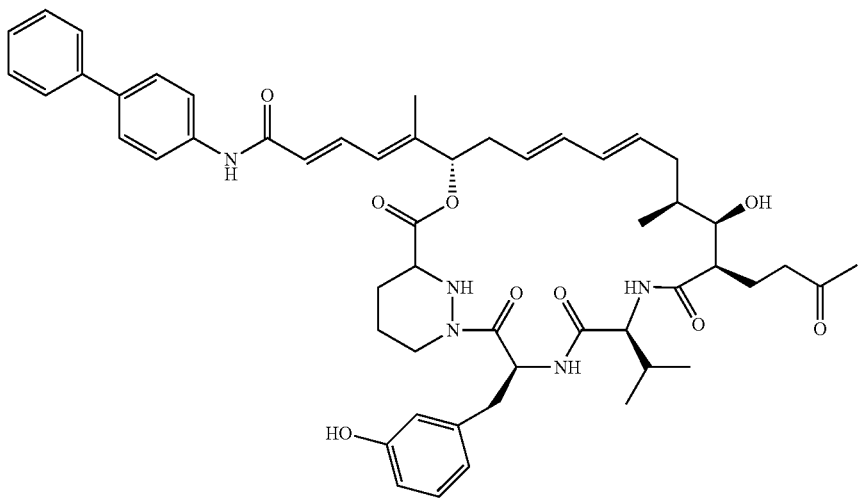 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/C[C@H](C)[C@H]1O]

In another suitable embodiment of the invention, $R_1$ represents cyclohexyl, $R_2$ represents Me, $R_3$ represents H, $R_4$ represents H, n represents a single bond, m represents a single bond and $R_5$ represents =O as represented by the following structure:

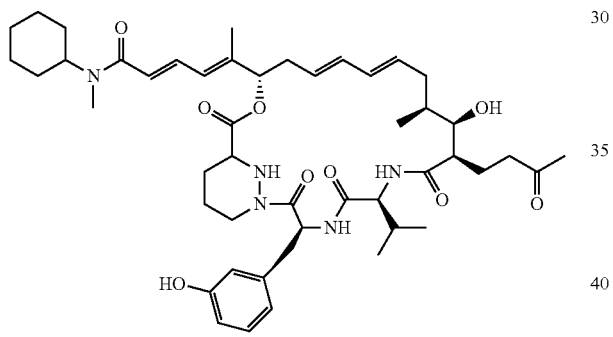

In another suitable embodiment of the invention, $R_1$ represents cyclohexyl, $R_2$ represents H, $R_3$ represents H, $R_4$ represents H, n represents a single bond, m represents a single bond and $R_5$ represents =O as represented by the following structure:

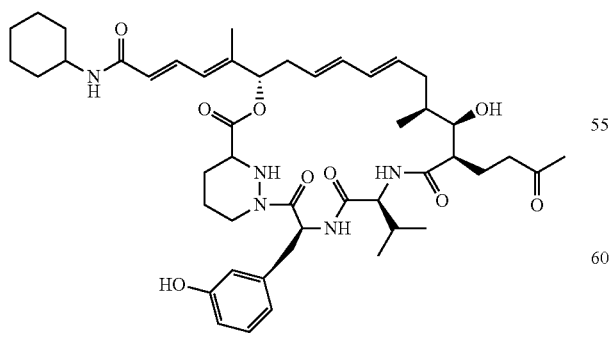

In another suitable embodiment of the invention, $R_1$ and $R_2$ together represent —OCH$_2$CH$_2$CH$_2$CH$_2$— connected in a 6-membered heterocycle. $R_3$ represents H, $R_4$ represents H, n represents a single bond, m represents a single bond and $R_5$ represents =O as represented by the following structure:

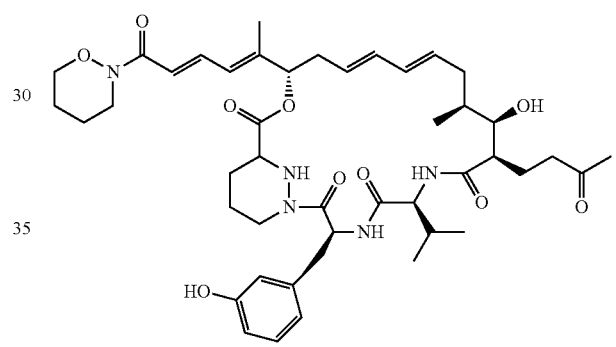

In a suitable embodiment of the invention, $R_1$ represents 2-pyridinyl, $R_2$ represents H, $R_3$ represents H, $R_4$ represents H, n represents a single bond, m represents a single bond and $R_5$ represents =O as represented by the following structure:

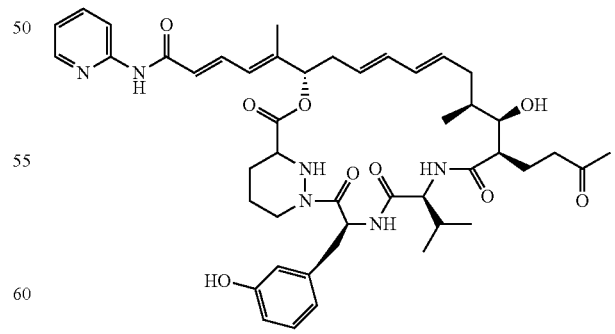

In another series of suitable embodiments, $R_3$ represents H, $R_4$ represents OH, n represents a single bond, m represents a single bond and $R_5$ represents =O as represented by the following structure:

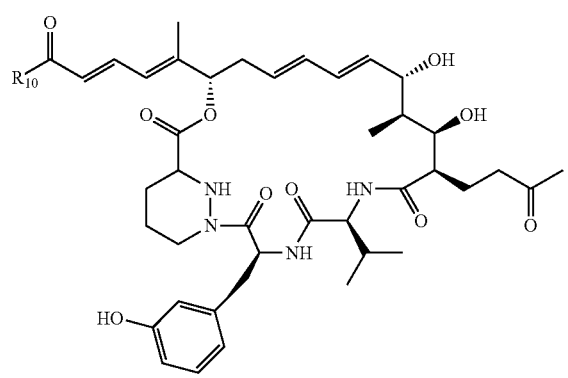
In these embodiments, R$_{10}$ represents one of the following moieties:
| R$_{10}$ | |
|---|---|
| 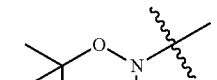 | 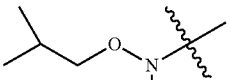 |
| 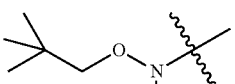 | 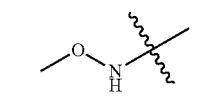 |
| 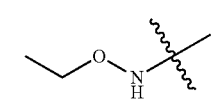 [SMILES: *NOCC] | 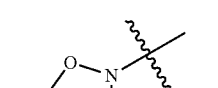 |
| 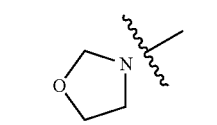 | 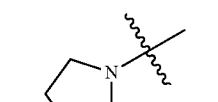 |
| 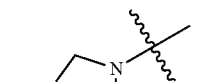 | 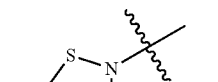 |
| 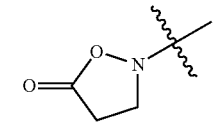 [SMILES: *N1CCC(=O)O1] | 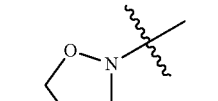 |
-continued
| R$_{10}$ | |
|---|---|
| 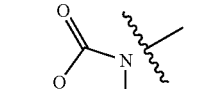 | 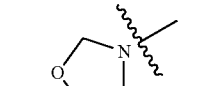 |
| 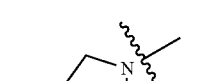 | 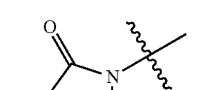 |
|  |  |
|  |  |
| 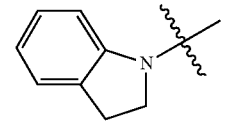 [SMILES: *N1CCc2ccccc21] | 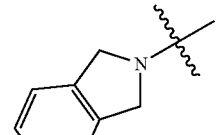 |

| 35 -continued | 36 -continued |
|---|---|
| R_{10} | R_{10} |
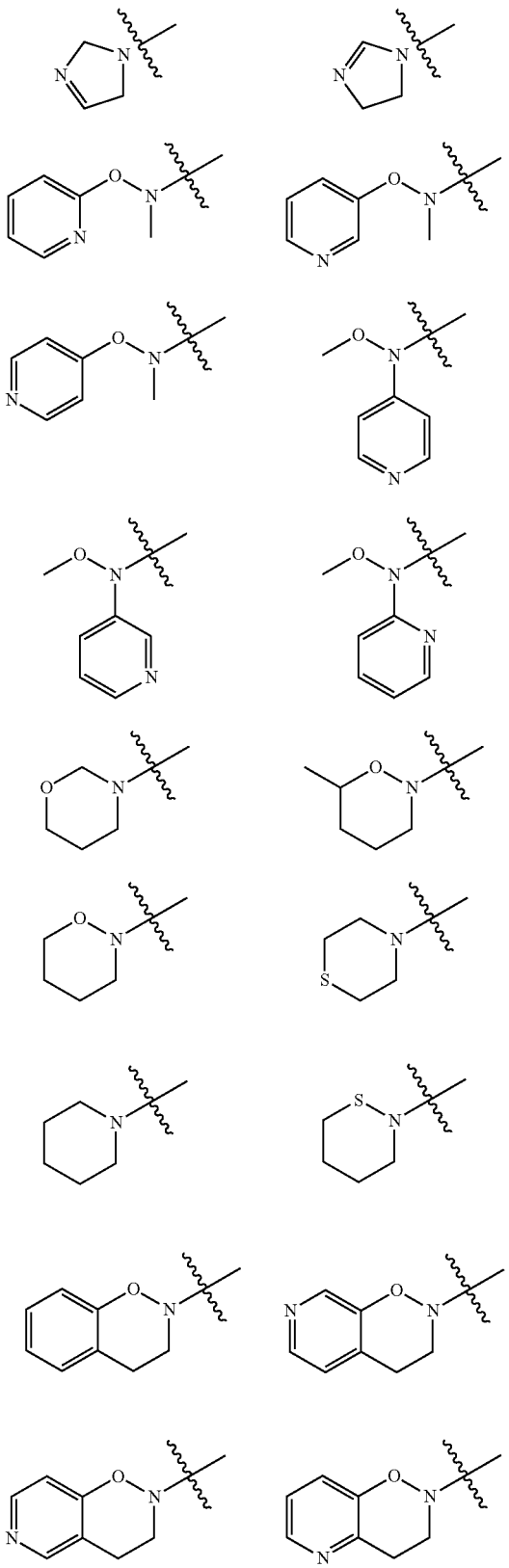
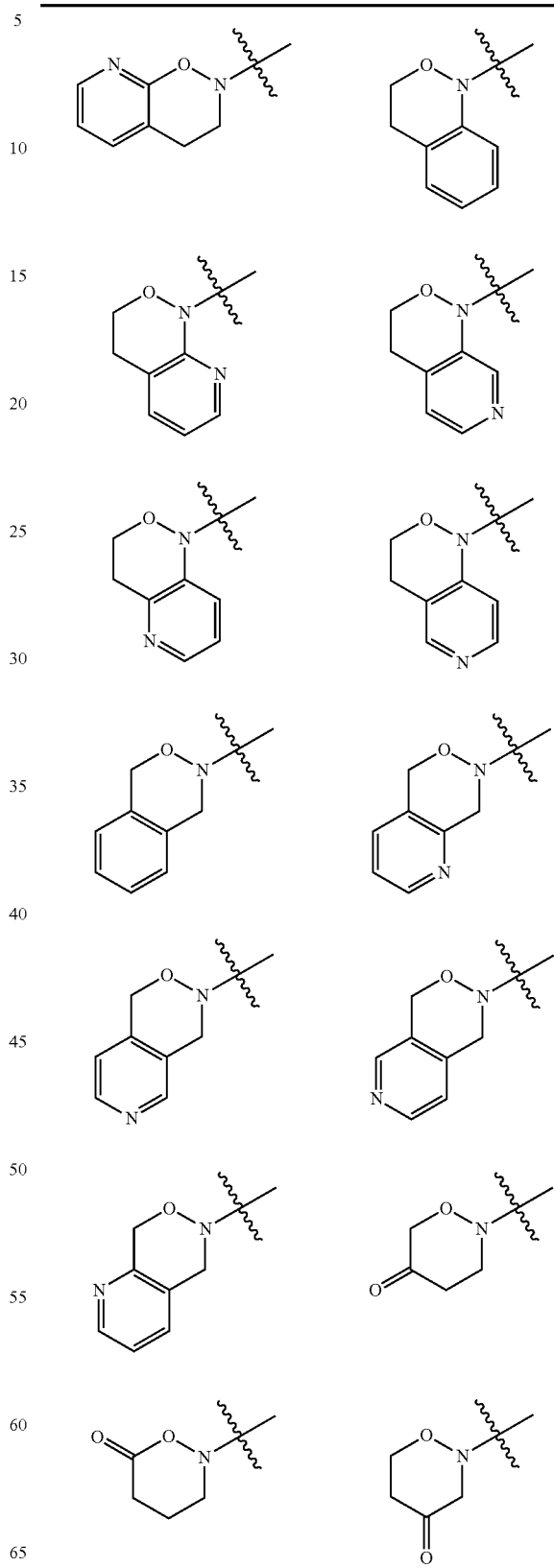

| $R_{10}$ | | $R_{10}$ | |
|---|---|---|---|
| 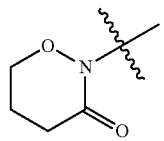 [SMILES: *N1OCCCC1=O] | 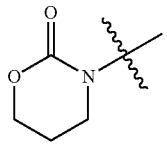 [SMILES: *N1CCCOC1=O] | 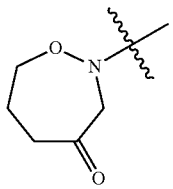 | |
| 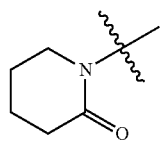 [SMILES: *N1CCCCC1=O] | 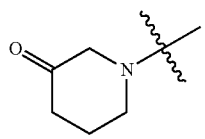 [SMILES: *N1CCCC(=O)C1] | | |
| 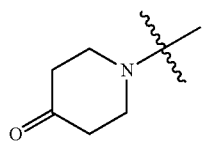 [SMILES: *N1CCC(=O)CC1] | 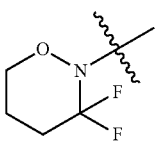 [SMILES: *N1OCCCC1(F)F] | | |
| 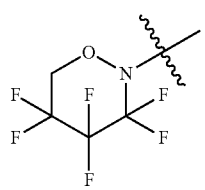 | 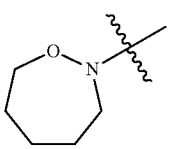 [SMILES: *N1CCCCCO1] | | |
| 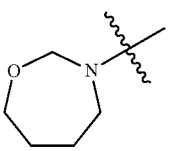 [SMILES: *N1CCCCOC1] | 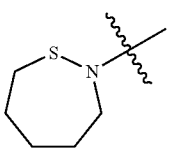 [SMILES: *N1CCCCCS1] | | |
| 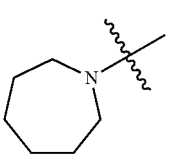 [SMILES: *N1CCCCCC1] | 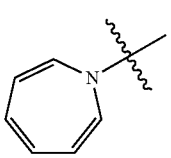 [SMILES: *N1C=CC=CC=C1] | | |
| 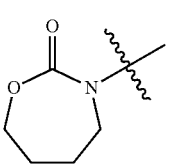 | 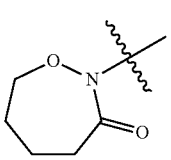 [SMILES: *N1OCCCCC1=O] | | |
| 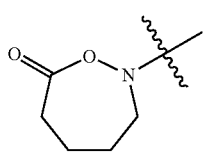 [SMILES: *N1CCCCC(=O)O1] | 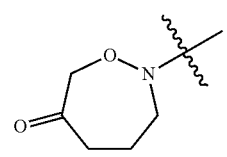 [SMILES: *N1CCCC(=O)CO1] | | |

In some embodiments the double bond at the C26, 27 position (by reference to the structure of sanglifehrin A) may be in the cis form instead of the trans form.

In a suitable embodiment of the invention, the double bond at the C26, 27 position is in the cis form, as represented by the following formula:

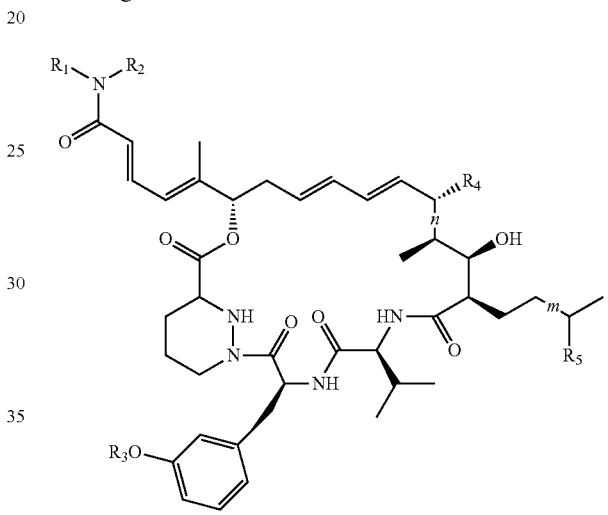

Such compounds may be produced during chemical synthesis.

In general, the compounds of the invention are prepared by semi-synthetic derivatisation of a sanglifehrin. Sanglifehrins may be prepared using methods described in WO97/02285 and WO98/07743, which documents are incorporated in their entirety, or additional methods described herein. Sanglifehrins have also been produced by complex total synthetic chemistry which is capable of producing low amounts of material following extensive laboratory work. Semisynthetic methods for generating the sanglifehrin macrocylic aldehyde are described in U.S. Pat. No. 6,124,453, Metternich et al., 1999, Banteli et al., 2001 and Sedrani et al., 2003.

In general, a process for preparing certain compounds of formula (I) or a pharmaceutically acceptable salt thereof comprises:

(a) dihydroxylation of sanglifehrin A or other naturally occurring analogue of sanglifehrin (e.g. Sanglifehrin B) or an analogue thereof having variation at the positions denoted by variables $R_3$, $R_4$, $R_5$, n and m;

(b) oxidative cleavage of the 1,2-diol to yield an aldehyde; and (c) coupling said aldehyde with a stabilised carbanion (or canonical form thereof), such as a phosphonate carbanion, using a compound of formula II.

This is shown retrosynthetically below:
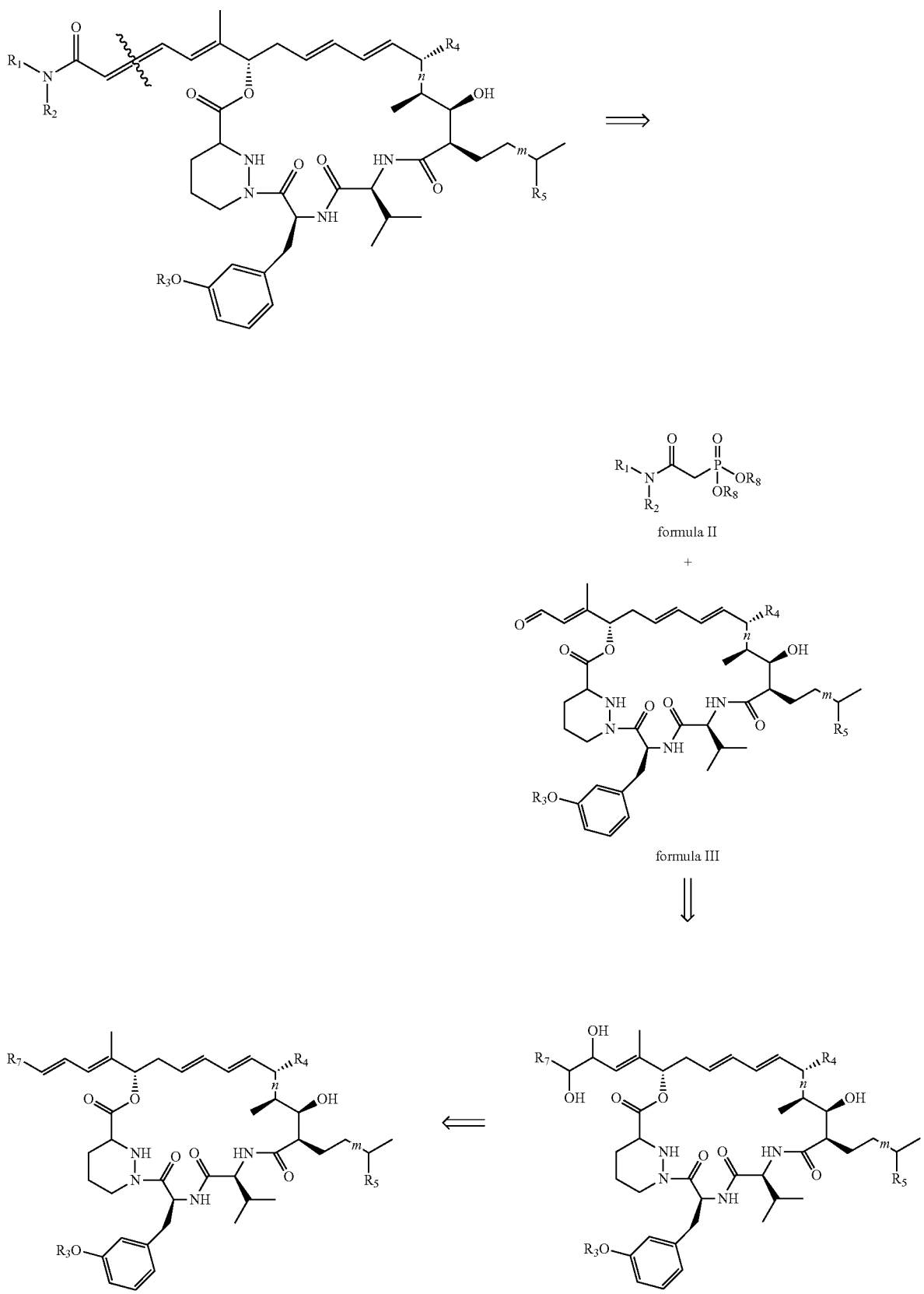

Wherein for sanglifehrin A, $R_7$=

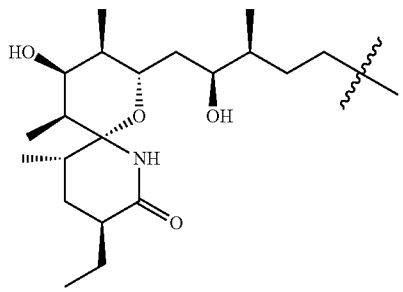 [SMILES: *CC[C@H](C)[C@@H](O)C[C@@H]1O[C@@]2(NC(=O)[C@@H](CC)C[C@@H]2C)[C@@H](C)[C@@H](O)[C@H]1C]

$R_8$ groups, which may be the same or different, independently represent alkyl (e.g. C1-4-alkyl) or benzyl.

Hence, a process for preparing compounds of the invention comprises reacting a compound of formula II with an aldehydic macrocycle (compound of formula III).

The preparation of compounds of formula III has been described previously (Metternich et al. 1999). Briefly, a sanglifehrin, such as SfA, is dihydroxylated using modified Sharpless conditions (catalytic osmium tetroxide). The use of the chiral ligands aids in promoting selectivity. The resultant diol can then be cleaved oxidatively, using for instance sodium periodate. The resultant compound of formula III can then be used as a substrate for derivatisation to an homologated amide. Typically a compound of formula II is dissolved in an aprotic solvent, cooled and the treated with a base, for example sodium hydride. A compound of formula III is then added and the reaction warmed in temperature. After a suitable period of time the reaction is stopped and the compound of formula I is purified by standard conditions (e.g. preparative HPLC, preparative TLC etc).

Derivatisations to introduce changes to groups $R_4$, $R_5$, n and m can be carried out prior to generation of the compound of formula III or after the reaction to form the homologated amide. Briefly, the hydroxyl at $R_4$ can be eliminated by treatment of a suitable substrate in acidic conditions in order to generate a triene. The ketone at $R_5$ can be reduced to a hydroxyl group by treatment with a suitable reducing agent, such as sodium borohydride. The hydroxyl group can be converted to iodo and then eliminated by treatment with a suitable base, such as DBU.

Compounds of formula II may be known or readily synthesised from available amines ($R_1R_2NH$). As shown in scheme 1 (below) the amine may be used to treat chloroacetyl chloride or similar to form an alpha-chloroamide. The alpha-chloroamide is then treated in an Arbuzov reaction to generate the compound of formula II. Other routes to compounds of formula II will be apparent to one skilled in the art.

Scheme 1

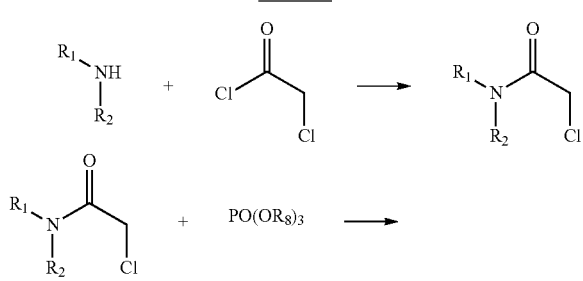

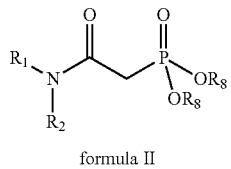

formula II

If desired or necessary, protecting groups may be employed to protect functionality in the aldehydic macrocycle, acid macrocycle or the amine, or in compounds of formula (II) as described in T. W. Green, P. G. M. Wuts, *Protective Groups in Organic Synthesis*, Wiley-Interscience, New York, 1999, 49-54, 708-711.

The methanol adduct may be prepared by fermentation and isolation from broth, or may be prepared from sanglifehrin A (WO97/02285).

In addition to the specific methods and references provided herein a person of skill in the art may also consult standard textbook references for synthetic methods, including, but not limited to Vogel's Textbook of Practical Organic Chemistry (Furniss et al., 1989) and March's Advanced Organic Chemistry (Smith and March, 2001).

Polyketide biosynthetic engineering methods have also been described to enable generation of compounds of formula (I) where $R_4$=H and n=bond (see compounds of formula (III) and (IV) illustrated above). This involves replacing the reductive loop of sanglifehrin module 12 (see WO2010/034243 and Qu et al., 2011), with a reductive loop conferring active dehydratase (DH), enoyl reductase (ER) and ketoreductase (KR) domains (e.g. the reductive loops from rapamycin modules 13, 7 or 1 (Aparicio et al., 1996), erythromycin module 4 (Bevitt et al., 1992) or sanglifehrin module 6 (Qu et al., 2011)). An individual skilled in the art will appreciate that a suitable reductive loop could be identified in a type I polyketide synthase module on the basis of homology to published sequences (eg Aparicio et al 1996), and consequently that this change could be accomplished by the introduction of any such loop containing the three active domains, DH, ER and KR. Methods for polyketide biosynthetic engineering and the concept of a reductive loop are described in WO98/01546 and WO00/01827. It is obvious to someone skilled in the art that these compounds can be synthesised de novo from commercially available compounds, i.e. total synthesis. The synthesis of the tripeptide and subsequent macrocycle formation has been described (Cabrejas et al, 1999). A process such as this could be modified to generate compounds of the invention.

Other compounds of the invention may be prepared by methods known per se or by methods analogous to those described above.

A sanglifehrin macrocycle of the invention may be administered alone or in combination with other therapeutic agents. Co-administration of two (or more) agents allows for lower doses of each to be used, thereby reducing side effect, can lead to improved potency and therefore higher SVR, and a reduction in resistance.

Therefore in one embodiment, the sanglifehrin macrocycle of the invention is co-administered with one or more therapeutic agent/s for the treatment of HCV infection, taken from the standard of care treatments. This could be an interferon (e.g. pIFNa and/or ribavirin).

In an alternative embodiment, a sanglifehrin macrocycle of the invention is co-administered with one or more other antiviral agents, such as a STAT-C (specifically targeted agent for treatment of HCV), which could be one or more of the following: Non-nucleoside Polymerase inhibitors (e.g. ABT-333, ABT-072, BMS 791325, IDX375, VCH-222, BI 207127, ANA598, VCH-916, GS 9190, PF-00868554 (Filibuvir) or VX-759), Nucleoside or nucleotide polymerase inhibitors (e.g. 2'-C-methylcytidine, 2'-C-methyladenosine, R1479, PSI-6130, R7128, R1626, PSI 7977 or IDX 184), Protease inhibitors (e.g. ABT-450, ACH-1625, BI 201355, BILN-2061, BMS-650032, CTS1027, Danoprevir, GS 9256, GS 9451, MK 5172, IDX 320, VX-950 (Telaprevir), SCH503034 (Boceprevir), TMC435350, MK-7009 (Vaneprivir), R7227/ITMN-191, EA-058, EA-063 or VX 985), NS5A inhibitors (e.g. A-831, BMS 790052, BMS 824393, CY-102 or PPI-461), silymarin, NS4b inhibitors, serine C-palmitoyltransferase inhibitors, Nitazoxanide or viral entry inhibitors (e.g. PRO206).

In an alternative embodiment, a sanglifehrin macrocycle of the invention is co-administered with one or more other antiviral agents (such as highly active antiretroviral therapy (HAART)) for the treatment of HIV, which could be one or more of the following: nucleoside reverse transcriptase inhibitors (NRTI) (e.g. Emtricitabine or Tenofovir), non-nucleoside reverse transcriptase inhibitors (NNRTI) (e.g. Rilipivirine or Efavirenz), protease inhibitors (PI) (e.g. Ritonavir or Lopinavir), fusion inhibitors (e.g. Maraviroc or Enfuvirtide), CCR5 inhibitors (e.g. Aplaviroc or Vicriviroc), maturation inhibitors (e.g. Bevirimat), CD4 monoclonal antibodies (e.g. Ibalizumab) and integrase inhibitors (e.g. Eltiegravir).

In an alternative embodiment, a sanglifehrin macrocycle of the invention is co-administered with one or more other antiviral agents for the treatment of HBV, which could be one or more of the following: interferons (e.g. interferon alpha or pegylated interferon alpha), nucleoside or nucleotide analogues (e.g. lamivudine, entecavir, adefovir dipivoxil or telbivudine), other immunomodulators (e.g. Thymosin alpha, CYT107 or DV-601) or HMG CoA reductase inhibitors (e.g. Simvastatin).

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds of the invention will normally be administered orally in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above the formulations of this invention may include other agents conventional in the art having regard to the type of formulation in question, for example those suitable for oral administration may include flavouring agents.

Advantageously, agents such as preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Further aspects of the invention include:

A compound according to the invention for use as a pharmaceutical;

A compound according to the invention for use as a pharmaceutical for the treatment of viral infections (especially RNA virus infections) such as HCV, HBV or HIV infection or other diseases such as muscular dystrophy, Ullrich congenital muscular dystrophy, Bethlem myopathy, multiple sclerosis, diabetes, amyotrophic lateral sclerosis, bipolar disorder, Alzheimer's disease, Huntington's disease, myocardial infarction or chronic alcohol consumption;

A pharmaceutical composition comprising a compound according to the invention together with a pharmaceutically acceptable diluent or carrier;

A pharmaceutical composition comprising a compound according to the invention together with a pharmaceutically acceptable diluent or carrier further comprising a second or subsequent active ingredient, especially an active ingredient indicated for the treatment of viral infections such as HCV, HBV or HIV infection or muscular dystrophy, Ullrich congenital muscular dystrophy, Bethlem myopathy, multiple sclerosis, diabetes, amyotrophic lateral sclerosis, bipolar disorder, Alzheimer's disease, Huntington's disease, myocardial infarction or chronic alcohol consumption;

A method of treatment of viral infections (especially RNA virus infections) such as HCV, HBV or HIV infection or muscular dystrophy, Ullrich congenital muscular dystrophy, Bethlem myopathy, multiple sclerosis, diabetes, amyotrophic lateral sclerosis, bipolar disorder, Alzheimer's disease, Huntington's disease, myocardial infarction or chronic alcohol consumption, which comprises administering to a subject a therapeutically effective amount of a compound according to the invention;

Use of a compound according to the invention for the manufacture of a medicament for the treatment of viral infections such as HCV, HBV or HIV infection or muscular dystrophy, Ullrich congenital muscular dystrophy, Bethlem myopathy, multiple sclerosis, diabetes, amyotrophic lateral sclerosis, bipolar disorder, Alzheimer's disease, Huntington's disease, myocardial infarction or chronic alcohol consumption.

In one embodiment the aforementioned conditions are selected from HCV, HIV infection and muscular dystrophy. In another embodiment the aforementioned condition is HBV infection.

General Methods

Materials and Methods

Bacterial Strains and Growth Conditions

The sanglifehrin producer *Streptomyces* sp. A92-308110 (DSM no 9954, purchased from DSMZ, Braunschweig, Germany) also termed BIOT-4253 and BIOT-4370 is maintained on medium oatmeal agar, MAM, or ISP2 (see below) at 28° C.

*Streptomyces* sp. A92-308110 was grown on oatmeal agar at 28° C. for 7-10 days. Spores from the surface of the agar plate were collected into 20% w/v sterile glycerol in distilled and stored in 0.5-ml aliquots at −80° C. Frozen spore stock was used for inoculating seed media SGS or SM25-3. The inoculated seed medium was incubated with shaking between 200 and 300 rpm at 5.0 or 2.5 cm throw at 27° C. for 24 hours. The fermentation medium SGP-2 or BT6 were inoculated with 2.5%-10% of the seed culture and incubated with shaking between 200 and 300 rpm with a 5 or 2.5 cm throw at 24° C. for 4-5 days. The culture was then harvested for extraction.

Media Recipes

Water used for preparing media was prepared using Millipore Elix Analytical Grade Water Purification System

| SGS Seed Medium | |
| --- | --- |
| Ingredient (and supplier) | Recipe |
| Glucose (Sigma, G7021) | 7.50 g |
| Glycerol (Fisher scientific, G/0650/25) | 7.50 g |
| yeast extract (Becton Dickinson, 212770) | 1.35 g |
| malt extract (Becton Dickinson, 218630) | 3.75 g |
| potato starch (soluble) (Signma, S2004) | 7.50 g |
| NZ-amine A (Sigma, C0626) | 2.50 g |
| toasted soy flour, Nutrisoy (ADM, 063-160) | 2.50 g |
| L-asparagine (Sigma, A0884) | 1.00 g |
| $CaCO_3$ (Calcitec, V/40S) | 0.05 g |
| NaCl (Fisher scientific, S/3160/65) | 0.05 g |
| $KH_2PO_4$ (Sigma, P3786) | 0.25 g |
| $K_2HPO_4$ (Sigma, P5379) | 0.50 g |
| $MgSO_4 \cdot 7H_2O$ (Sigma, M7774) | 0.10 g |
| trace element solution B | 1.00 mL |
| agar | 1.00 g |
| SAG471 Antifoam (GE Silicones, SAG471) | *0.20 mL |
| RO $H_2O$ to final vol. of | **1.00 L | pre-sterilisation pH was adjusted to pH 7.0 with 10M NaOH/10M $H_2SO_4$ sterilised by heating 121° C., 20-30 min (autoclaving)

Notes
*antifoam only used in seed fermenters, NOT seed flasks
**final volume adjusted accordingly to account for seed volume

| Trace Element Solution B | |
| --- | --- |
| Ingredient | Recipe |
| $FeSO_4 \cdot 7H_2O$ (Sigma, F8633) | 5.00 g |
| $ZnSO_4 \cdot 7H_2O$ (Sigma, Z0251) | 4.00 g |
| $MnCl_2 \cdot 4H_2O$ (Sigma, M8530) | 2.00 g |
| $CuSO_4 \cdot 5H_2O$ (Aldrich, 20,919-8) | 0.20 g |
| $(NH_4)_6Mo_7O_{24}$ (Fisher scientific, A/5720/48) | 0.20 g |
| $CoCl_2 \cdot 6H_2O$ (Sigma, C2644) | 0.10 g |
| $H_3BO_3$ (Sigma, B6768) | 0.10 g |
| KI (Alfa Aesar, A12704) | 0.05 g |
| $H_2SO_4$ (95%) (Fluka, 84720) | 1.00 mL |
| RO $H_2O$ to final vol. of | 1.00 L |

| SGP2 Production Medium | |
| --- | --- |
| Ingredient | Recipe |
| toasted soy flour (Nutrisoy) (ADM, 063-160) | 20.00 g |
| Glycerol (Fisher scientific, G/0650/25) | 40.00 g |
| MES buffer (Acros, 172595000) | 19.52 g |
| SAG471 Antifoam (GE Silicones, SAG471) | *0.20 mL |
| RO $H_2O$ to final vol. of | **1.00 L | pre-sterilisation pH adjusted to pH 6.8 with 10M NaOH sterilised by heating 121° C., 20-30 min (autoclaving)

Notes
*final volume adjusted accordingly to account for seed volume
**antifoam was used only in fermentors not flasks Analysis of Culture Broths by LC-UV and LC-UV-MS Culture broth (1 mL) and ethyl acetate (1 mL) is added and mixed for 15-30 min followed by centrifugation for 10 min. 0.4 mL of the organic layer is collected, evaporated to dryness and then re-dissolved in 0.20 mL of acetonitrile.

HPLC Conditions:

C18 Hyperclone BDS C18 Column 3u, 4.6 mm×150 mm

Fitted with a Phenomenex Analytical C18 Security Guard Cartridge (KJO-4282)

Column temp at 50° C.
Flow rate 1 mL/min
Monitor UV at 240 nm
Inject 20 uL aliquot
Solvent Gradient:
0 min: 55% B
1.0 min: 55% B
6.5 min: 100% B
10.0 min: 100% B
10.05 min: 55% B
13.0 min: 55% B
Solvent A is Water+0.1% Formic Acid
Solvent B is Acetonitrile+0.1% Formic Acid
Under these conditions SfA elutes at 5.5 min
Under these conditions SfB elutes at 6.5 min LCMS is performed on an integrated Agilent HP1100 HPLC system in combination with a Bruker Daltonics Esquire 3000+ electrospray mass spectrometer operating in positive ion mode using the chromatography and solvents described above.

Synthesis

All reactions are conducted under anhydrous conditions unless stated otherwise, in oven dried glassware that is cooled under vacuum, using dried solvents. Reactions are monitored by LC-UV-MS, using an appropriate method, for instance the method described above for monitoring culture broths.

QC LC-MS Method
HPLC Conditions:
018 Hyperclone BDS 018 Column 3u, 4.6 mm×150 mm
Fitted with a Phenomenex Analytical C18 Security Guard Cartridge (KJO-4282)
Column temp at 50° C.
Flow rate 1 mL/min
Monitor UV at 210, 240 and 254 nm
Solvent Gradient:
0 min: 10% B
2.0 min: 10% B
15 min: 100% B
17 min: 100% B
17.05 min: 10% B
20 min: 10% B
Solvent A is Water+0.1% Formic Acid
Solvent B is Acetonitrile+0.1% Formic Acid
MS Conditions
MS operates in switching mode (switching between positive and negative), scanning from 150 to 1500 amu.

In vitro analysis LC-MS method (e.g. for solubility assessment)
Using an API-4000 instrument
HPLC Conditions:
Ultimate AQ-C18 (2.1×50 mm, 3 μM)
Column temp at XX° C.
Flow rate 0.4 mL/min
Solvent Gradient A1 (e.g. for cpds 1 and 13):
0.2 min: 10% B
0.7 min: 60% B
1.1 min: 60% B
1.4 min: 98% B
2.3 min: 98% B
2.4 min: 10% B
3.5 min: stop
Solvent Gradient A2 (e.g. for cpds 5 and 10):
0.3 min: 10% B
0.9 min: 95% B
1.9 min: 95% B
2.0 min: 10% B
3.0 min: stop Solvent A is $H_2O$-0.025% FA-1 mM $NH_4OAC$
Solvent B is MeOH-0.025% FA-1 mM $NH_4OAC$
Negative Scan Mode
MRM Setup:

|  | transitions [Da] |
| --- | --- |
| hydroxymacrocycle, 6 (IS): | 741.5 → 294.3 |
| 1 | 602.2 → 156.0 |

Positive Scan Mode,
MRM Setup:

|  | transitions [Da] |
| --- | --- |
| 5 | 1088.8 → 503.2 |
| 7 | 1070.9 → 503.2 |
| 10 | 822.6 → 503.2 |
| 13 | 836.6 → 294.0 |

In vitro Replicon Assay for Assessment of HCV Antiviral Activity

Antiviral efficacy against genotype 1 HCV may be tested as follows: One day before addition of the test article, Huh5.2 cells, containing the HCV genotype 1b l389luc-ubi-neo/NS3-3'/5.1 replicon (Vrolijk et al., 2003) and subcultured in cell growth medium [DMEM (Cat No. 41965039) supplemented with 10% FCS, 1% non-essential amino acids (11140035), 1% penicillin/streptomycin (15140148) and 2% Geneticin (10131027); Invitrogen] at a ratio of 1.3-1.4 and grown for 3-4 days in 75 cm$^2$ tissue culture flasks (Techno Plastic Products), were harvested and seeded in assay medium (DMEM, 10% FCS, 1% non-essential amino acids, 1% penicillin/streptomycin) at a density of 6 500 cells/well (100 μL/well) in 96-well tissue culture microtitre plates (Falcon, Beckton Dickinson for evaluation of the anti-metabolic effect and CulturPlate, Perkin Elmer for evaluation of antiviral effect). The microtitre plates are incubated overnight (37° C., 5% $CO_2$, 95-99% relative humidity), yielding a non-confluent cell monolayer. Dilution series are prepared; each dilution series is performed in at least duplicate. Following assay setup, the microtitre plates are incubated for 72 hours (37° C., 5% $CO_2$, 95-99% relative humidity).

For the evaluation of anti-metabolic effects, the assay medium is aspirated, replaced with 75 μL of a 5% MTS (Promega) solution in phenol red-free medium and incubated for 1.5 hours (37° C., 5% $CO_2$, 95-99% relative humidity). Absorbance is measured at a wavelength of 498 nm (Safire$^2$, Tecan) and optical densities (OD values) are converted to percentage of untreated controls.

For the evaluation of antiviral effects, assay medium is aspirated and the cell monolayers are washed with PBS. The wash buffer is aspirated, 25 μL of Glo Lysis Buffer (Cat. No. E2661, Promega) is added after which lysis is allowed to proceed for 5 min at room temperature. Subsequently, 50 μL of Luciferase Assay System (Cat. No. E1501, Promega) is added and the luciferase luminescence signal is quantified immediately (1000 ms integration time/well, Safire$^2$, Tecan). Relative luminescence units are converted to percentage of untreated controls.

The $EC_{50}$ and $EC_{90}$ (values derived from the dose-response curve) represent the concentrations at which respectively 50% and 90% inhibition of viral replication would be observed. The CC50 (value derived from the dose-response curve) represents the concentration at which the metabolic activity of the cells would be reduced to 50% of the metabolic activity of untreated cells. The selectivity index (SI), indicative of the therapeutic window of the compound, is calculated as $CC_{50}/EC_{50}$.

A concentration of compound is considered to elicit a genuine antiviral effect in the HCV replicon system when, at that particular concentration, the anti-replicon effect is above the 70% threshold and no more than 30% reduction in metabolic activity is observed.

Assessment of Water Solubility

Water solubility may be tested as follows: A 10 mM stock solution of the sanglifehrin analogue is prepared in 100% DMSO at room temperature. Triplicate 0.01 mL aliquots are made up to 0.5 mL with either 0.1 M PBS, pH 7.3 solution or 100% DMSO in amber vials. The resulting 0.2 mM solutions are shaken, at room temperature on an IKA® vibrax VXR shaker for 6 h, followed by transfer of the resulting solutions or suspensions into 2 mL Eppendorf tubes and centrifugation for 30 min at 13200 rpm. Aliquots of the supernatant fluid are then analysed by the LCMS method as described above.

Alternatively, solubility in PBS at pH7.4 may be tested as follows: A calibration curve is generated by diluting the test compounds and control compounds to 40 μM, 16 μM, 4 μM, 1.6 μM, 0.4 μM, 0.16 μM, 0.04 μM and 0.002 μM, with 50% MeOH in $H_2O$. The standard points are then further diluted 1:20 in MeOH:PBS1:1. The final concentrations after 1:20 dilution are 2000 nM, 800 nM, 200 nM, 80 nM, 20 nM, 8 nM, 2 nM and 1 nM. Standards are then mixed with the same volume (1:1) of ACN containing internal standard (hydroxymacrocycle, 6). The samples are centrifuged (5 min, 12000 rpm), then analysed by LC/MS.

applied to the apical surface of Caco-2 cell monolayers and compound permeation into the basolateral compartment is measured. This is performed in the reverse direction (basolateral to apical) to investigate active transport. LC-MS/MS is used to quantify levels of both the test and standard control compounds (such as Propanolol and Acebutolol).

In vivo Assessment of Pharmacokinetics

In vivo assays may also be used to measure the bioavailability of a compound. Generally, a compound is administered to a test animal (e.g. mouse or rat) both intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below. Mice are dosed with 1, 10, or 100 mg/kg of the compound of the invention or the parent compound i.v. or p.o. Blood samples are taken at 5, 10, 15, 30, 45, 60, 90, 120, 180, 240, 360, 420 and 2880 minutes and the concentration of the compound of the invention or parent compound in the sample is determined via HPLC. The time-course of plasma concentrations can then be used to derive key parameters such as the area under the plasma concentration-time curve (AUC—which is directly proportional to the total amount of unchanged drug that reaches the systemic circulation), the maximum (peak) plasma drug concentration, the time at which maximum plasma drug concentration occurs (peak time), additional factors which are used in the accurate determination of bioavailability include: the compound's terminal half life, total body

| Solution(uL) | MeOH/$H_2O$(1:1) (uL) | | Working solution (μM) | Solution(μL) | MeOH/buffer (1:1) (μL) | | Final solution(nM) |
|---|---|---|---|---|---|---|---|
| 10 mM | 10 | 240 | → | 400 | | | |
| 400 μM | 50 | 450 | → | 40 | 20 | 380 | → | 2000 |
| | 20 | 480 | → | 16 | 20 | 380 | → | 800 |
| 40 μM | 50 | 450 | → | 4 | 20 | 380 | → | 200 |
| 16 μM | 50 | 450 | → | 1.6 | 20 | 380 | → | 80 |
| 4 μM | 50 | 450 | → | 0.4 | 20 | 380 | → | 20 |
| 1.6 μM | 50 | 450 | → | 0.16 | 20 | 380 | → | 8 |
| 0.4 μM | 50 | 450 | → | 0.04 | 20 | 380 | → | 2 |
| 0.04 μM | 50 | 950 | → | 0.002 | 20 | 380 | → | 1 |

Test compounds are prepared as stock solutions in DMSO at 10 mM concentration. The stock solutions are diluted in duplicate into PBS, pH7.4 in 1.5 mL Eppendorf tubes to a target concentration of 100 μM with a final DMSO concentration of 1% (e.g. 4 μL of 10 mM DMSO stock solution into 396 μL 100 mM phosphate buffer). Sample tubes are then gently shaken for 4 hours at room temperature. Samples are centrifuged (10 min, 15000 rpm) to precipitate undissolved particles. Supernatants are transferred into new tubes and diluted (the dilution factor for the individual test article is confirmed by the signal level of the compound on the applied analytical instrument) with PBS. Diluted samples are then mixed with the same volume (1:1) of MeOH. Samples are finally mixed with the same volume (1:1) of ACN containing internal standard (hydroxymacrocycle, 6) for LC-MS/MS analysis.

Assessment of Cell Permeability

Cell permeability may be tested as follows: The test compound is dissolved to 10 mM in DMSO and then diluted further in buffer to produce a final 10 μM dosing concentration. The fluorescence marker lucifer yellow is also included to monitor membrane integrity. Test compound is then clearance, steady-state volume of distribution and F %. These parameters are then analysed by non-compartmental or compartmental methods to give a calculated percentage bioavailability, for an example of this type of method see Egorin et al. 2002, and references therein.

In vitro Assessment of Inhibition of MDR1 and MRP2 Transporters

To assess the inhibition and activation of the MDR1 (P-glycoprotein 1) and MRP2 transporters, an in vitro ATPase assay from Solvo Biotechnology Inc. can be used (Glavinas et al., 2003). The compounds (at 0.1, 1, 10 and 100 μM) are incubated with MDR1 or MRP2 membrane vesicles both in the absence and presence of vanadate to study the potential ATPase activation. In addition, similar incubations are conducted in the presence of verapamil/sulfasalazine in order to detect possible inhibition of the transporter ATPase activity. ATPase activity is measured by quantifying inorganic phosphate spectrophotometrically. Activation is calculated from the vanadate sensitive increase in ATPase activity. Inhibition is determined by decrease in verapamil/sulfasalazine mediated ATPase activity.

In vitro Assay for Assessment of HIV Antiviral Activity

Antiviral efficacy against HIV may be tested as follows: Blood derived CD4+ T-lymphocytes and macrophages are isolated as described previously (Bobardt et al., 2008). Briefly, human PBMCs were purified from fresh blood by banding on Ficoll-Hypaque (30 min, 800 g, 25° C.). Primary human CD4+ T cells were purified from PBMCs by positive selection with anti-CD4 Dynabeads and subsequent release using Detachabead. Cells were cultured in RPMI medium 1640 (Invitrogen) supplemented with 10% FCS, MEM amino acids, L-glutamine, MEM vitamins, sodium pyruvate, and penicillin plus streptomycin and were subsequently activated with bacterial superantigen staphylococcal enterotoxin B (SEB; 100 ng/ml) and mitomycin C-killed PBMC from another donor (10:1 PBMC:CD4 cell ratio). Three days after stimulation, cells were split 1:2 in medium containing IL-2 (200 units/ml final concentration). Cultures were then split 1:2 every 2 days in IL-2 medium and infected with HIV at 7 days after stimulation. For generating primary human macrophages, monocytes were purified from human PBMCs by negative selection and activated and cultured at a cell concentration of 106/ml in DMEM, supplemented with 10% FCS, MEM amino acids, L-glutamine, MEM vitamins, sodium pyruvate, and penicillin (100 units/ml), streptomycin (100 mg/ml), and 50 ng/ml recombinant human granulocyte-macrophage colony-stimulating factor (GM-CSF) and maintained at 37° C. in a humidified atmosphere supplemented with 5% $CO_2$. To obtain monocyte-derived macrophages, cells were allowed to adhere to plastic and cultured for 6 days to allow differentiation.

CD4+ HeLa cells, Jurkat cells, activated CD4+ peripheral blood T-lymphocytes and macrophages (500,000 cells/100 µL) were incubated with pNL4.3-GFP(X4 virus) or pNL4.3-BaL-GFP(R5 virus) (100 ng of p24) in the presence of increasing concentrations of test article, Forty-eight hours later, infection was scored by analyzing the percentage of GFP-positive cells by FACS and $EC_{50}$ calculated.

In vitro Assay for Assessment of HBV Antiviral Activity

Antiviral efficacy against HBV may be tested as follows: HepG2 2.2.15 cells are plated in 96-well microtiter plates. After 16-24 hours the confluent monolayer of HepG2 2.2.15 cells is washed and the medium is replaced with complete medium containing various concentrations of a test compound in triplicate (eg six half-log concentrations). Three days later the culture medium is replaced with fresh medium containing the appropriately diluted test compounds. Six days following the initial administration of the test compound, the cell culture supernatant is collected, treated with pronase and then used in a real-time quantitative TaqMan qPCR assay. The PCR-amplified HBV DNA is detected in real-time by monitoring increases in fluorescence signals that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($IC_{50}$). A dye uptake assay is then employed to measure cell viability, which is used to calculate toxicity ($TC_{50}$). The therapeutic index (TI) is calculated as $TC_{50}/IC_{50}$.

In vitro Mixed Lymphocyte Reaction (MLR) Assay for Assessment of Immunosuppressant Activity Immunosuppressant activity was tested as follows: Peripheral blood mononuclear cell (PBMC) populations were purified from the blood of two normal, unrelated volunteer donors (A & B), using centrifugation over histopaque. Cells were counted and plated out at $1 \times 10^5$ cells per well in 96 well plates in RPMI media, with supplements and 2% Human AB serum. Culture conditions included: cell populations A & B alone and a mixed population of cells A&B in the absence or presence of test compounds, each at 6 different concentrations. Compounds were tested at doses ranging from 10 µM to 0.0001 µM in 1-log increments. Control wells contained a comparable concentration of vehicle (0.5% DMSO) to that present in the test compound wells. Cultures were established in triplicate in a 96 well plate and incubated at 37° C. in 5% $CO_2$ in a humidified atmosphere. 3H-thymidine was added on day 6 after assay set up and harvested 24 hrs later. The levels of proliferation between the different culture conditions were then compared.

The ability of each dilution of test compound to inhibit proliferation in the MLR was calculated as percentage inhibition. This allowed estimation of the $IC_{50}$ (concentration of test compound which resulted in a 50% reduction of counts per minute). In order to calculate the $IC_{50}$, the X axis was transformed to a log scale. Non-linear regression was used to fit to the mean data points. A sigmoidal variable slope was selected.

ELISA Analysis of Cyp-NS5A Interaction.

This assay was used to measure the disruption of Cyp-NS5A complexes, which can be used to show the potency of interaction with Cyclophilin D. Briefly, production and purification of recombinant GST, GST-CypD and Con1 NS5A-His proteins was carried out as described previously (Chatterji et al., 2010). Nunc MaxiSorb 8-well strip plates were coated with GST or GST-CypD for 16 h at 4° C. and blocked. Recombinant NS5A-His (1 ng/mL) was added to wells in 50 µL of binding buffer (20 mM Tris pH 7.9, 0.5 M NaCl, 10% glycerol, 10 mM DTT and 1% NP-40) for 16 h at 4° C. Captured NS5A-His was subsequently detected using mouse anti-His antibodies (1 µg/mL) (anti-6×His, Clontech) and rabbit anti-mouse-horseradish peroxidase phosphatase (HRP) antibodies (1:1000 dilution). All experiments were conducted twice using two different batches of recombinant CypD and NS5A proteins.

Anti-PPIAse Analysis of Cyclophilin Inhibition

An alternative methodology for analysing interaction with cyclophilins is described as follows: The PPlase activity of recombinant CypD, produced by thrombin cleavage of GST-CypD, was determined by following the rate of hydrolysis of N-succinyl-Ala-Ala-Pro-Phe-p-nitroanilide by chymotrypsin. Chymotrypsin only hydrolyzes the trans form of the peptide, and hydrolysis of the cis form, the concentration of which is maximized by using a stock dissolved in trifluoroethanol containing 470 mM LiCl, is limited by the rate of cis-trans isomerization. CypD was equilibrated for 1 h at 5° C. with selected test article using a drug concentration range from 0.1 to 20 nM. The reaction was started by addition of the peptide, and the change in absorbance was monitored spectrophotometrically at 10 data points per second. The blank rates of hydrolysis (in the absence of CypD) were subtracted from the rates in the presence of CypD. The initial rates of the enzymatic reaction were analyzed by first-order regression analysis of the time course of the change in absorbance.

EXAMPLES

Example 1

Production of Sanglifehrin A and its Natural Congers in 15-L Stirred Bioreactors with Secondary Seed Vegetative cultures were prepared by inoculating 0.2 mL from a spore stock of *Streptomyces* sp. A92-308110 into 400 mL seed medium SGS in 2-L Erlenmeyer flasks with foam plugs.

The culture flasks were incubated at 27° C., 250 rpm (2.5 cm throw) for 24 h. From the seed culture, 300 mL was transferred into 15 liters of primary seed medium SGS containing 0.02% antifoam SAG 471, in a 15 L Braun fermentor. The fermentation was carried out for 24 hours at 27° C., with starting agitation set at >300 rpm aeration rate at 0.5 V/V/M and dissolved oxygen (DO) level controlled with the agitation cascade at 30% air saturation. From the secondary seed culture prepared in the fermentor, 600 mL was taken under aseptic conditions and transferred into 15 liters of production medium SGP-2 containing 0.02% antifoam SAG 471, in 15 L Braun fermentor. The fermentation was carried out for 5 days at 24° C., with starting agitation set at 300 rpm, aeration rate at 0.5 V/V/M and dissolved oxygen (DO) level controlled with the agitation cascade at 30% air saturation. SfA was seen to be produced at 10-20 mg/L in fermentation broths.

Example 2

Extraction and Purification of Sanglifehrin A

The whole broth (30 L) was clarified by centrifugation. The resulting cell pellet was extracted twice with ethyl acetate (2×10 L), each by stirring for 1 hour with overhead paddle stirrer and leaving to settle before pumping off solvent. The ethyl acetate layers were then combined (~20 L) and the solvent removed under reduced pressure at 40° C. to obtain an oily residue. This oily residue was then suspended in 80:20 methanol:water (total volume of 500 mL), and twice extracted with hexane (2×500 mL). The 80:20 methanol:water fraction was then dried under reduced pressure to yield a crude dry extract which contained SfA and SfB. This extract was dissolved in methanol (100 ml), mixed with 15 g Silica gel and dried to a powder. The powder was loaded into a silica gel column (5×20 cm) packed in 100% $CHCl_3$. For every one litre of elution solvent the methanol concentration was increased stepwise by 1% and 250 ml fractions collected. After three liters of solvent elution the methanol concentration was increased stepwise by 2% up to 8%. Fractions containing SfA and/or SfB were combined and reduced in vacuo to dryness and SfA and SfB purified by preparative HPLC. Preparative HPLC was achieved over a Waters Xterra Prep MS C18 OBD 10 mm (19×250 mm) column running with solvent A (water) and solvent B (acetonitrile) at 20 ml/min with the following timetable:
t=0 mins, 55% B
t=4 mins, 55% B
t=30 mins, 100% B
t=32 mins, 100% B
t=36 mins, 55% B
Fractions containing SfA were combined and taken to dryness.

Example 3

Synthesis of 8 (Aldehydic Macrocycle)

3.1 The Preparation of 26,27-dihydroxysanglifehrin, 9

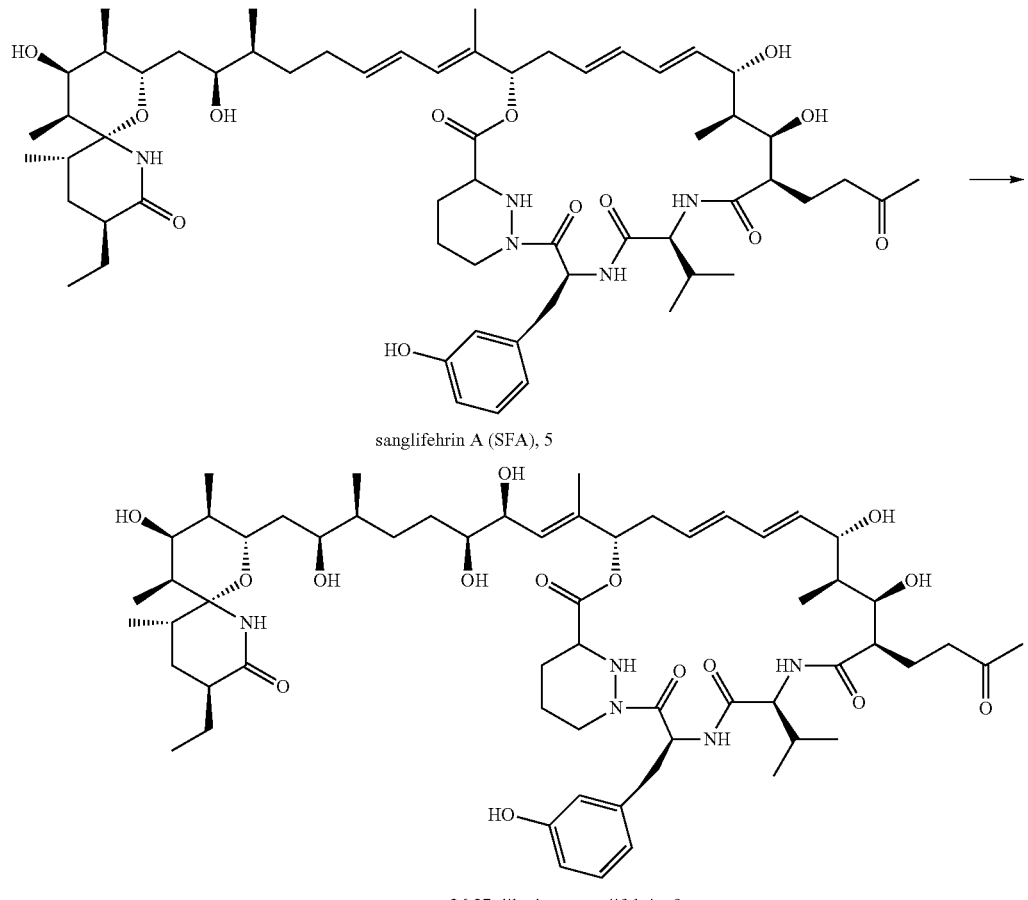

sanglifehrin A (SFA), 5

26,27-dihydroxysanglifehrin, 9

To a stirred solution of sanglifehrin A, 5 (135 mg, 0.1238 mmol), (DHQ)₂PHAL (5.76 mg, 0.0074 mmol), 2.5 wt % solution of osmium tetroxide in tert-butyl alcohol (47 uL, 0.0037 mmol), and methanesulfonamide (23.6 mg, 0.2476 mmol) in tert-butyl alcohol (4 mL) were added at room temperature together with a solution of potassium ferricyanide (122.3 mg, 0.3714 mmol) and potassium carbonate (51.3 mg, 0.3714 mmol) in 4 mL of water. After stirring for 1 h, a solution of saturated aqueous sodium sulfite (187.3 mg, 1.4857 mmol) was added. The resulting mixture was stirred for 30 min and then extracted with three portions of ethyl acetate. The organic layers were washed with brine, dried over anhydrous sodium sulfate, filtered, and concentrated under reduced pressure. The residue was purified by Combiflash using reverse phase column (C18 column, A=H₂O, B=acetonitrile, t=2 min, B=0%; t=4 min, B=30%, t=9 min, B=35%; t=12 min, B=45%; t=16 min, B=70%) to afford 26,27-dihydroxysanglifehrin, 9 (102 mg, 70%) as a white solid. QC LC-MS, $R_T$=5.3 mins, m/z=1124.8 [M+H]⁺, 1122.7 [M−H]⁻

3.2 The Preparation of the Aldehydic Macrocycle, 8

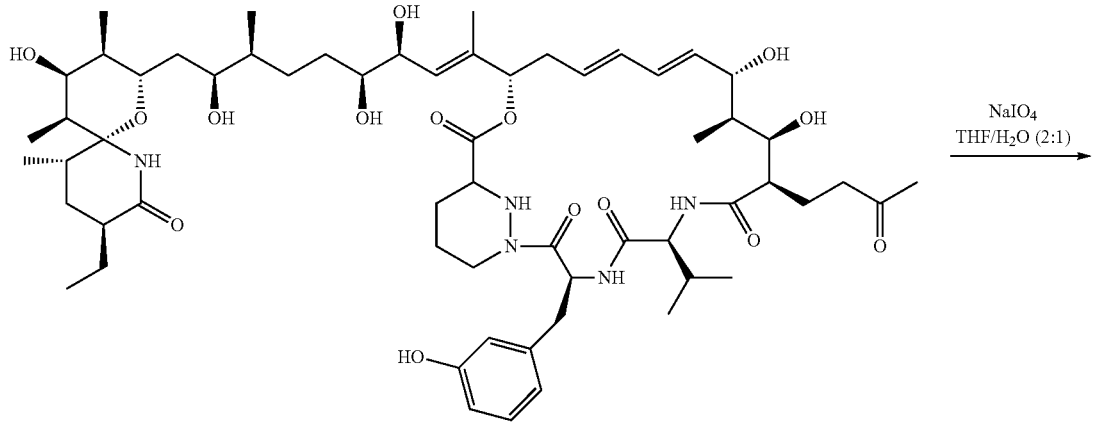

26,27-dihydroxysanglifehrin, 9

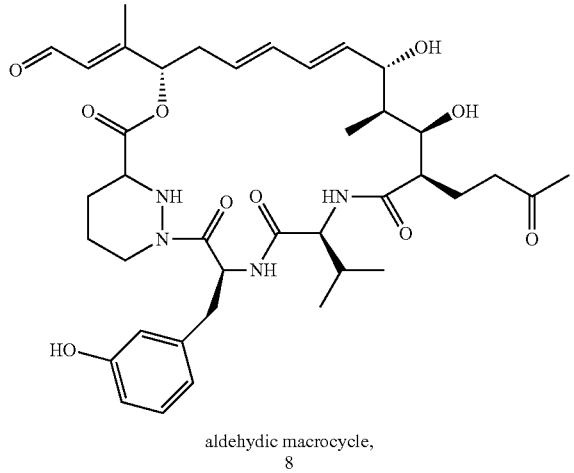

aldehydic macrocycle, 8

To a solution of 26,27-dihydroxysanglifehrin, 9 (60.0 mg, 0.053 mmol) in THF and water (2:1, 5 mL) was added sodium periodate (22.8 mg, 0.107 mmol). The resulting mixture was stirred at room temperature for 2 h, and saturated aqueous sodium bicarbonate was added. This mixture was extracted with three portions of ethyl acetate. The combined organic layers were washed with brine, dried over anhydrous sodium sulfate, filtered, and concentrated under reduced pressure. The residue was purified by Combiflash using reverse phase column (018 column, A=water, B=CH₃CN, t=3 min, B=0%; t=12 min, B=40%; t=17 min, B=40%, t=21 min, B=70%) to afford the aldehydic macrocycle, 8 (35 mg, 90%) as a white solid. QC LC-MS, RT=4.0 mins, m/z=761.4 [M+Na]⁺, 737.3 [M−H]⁻

Example 4

Synthesis of 10

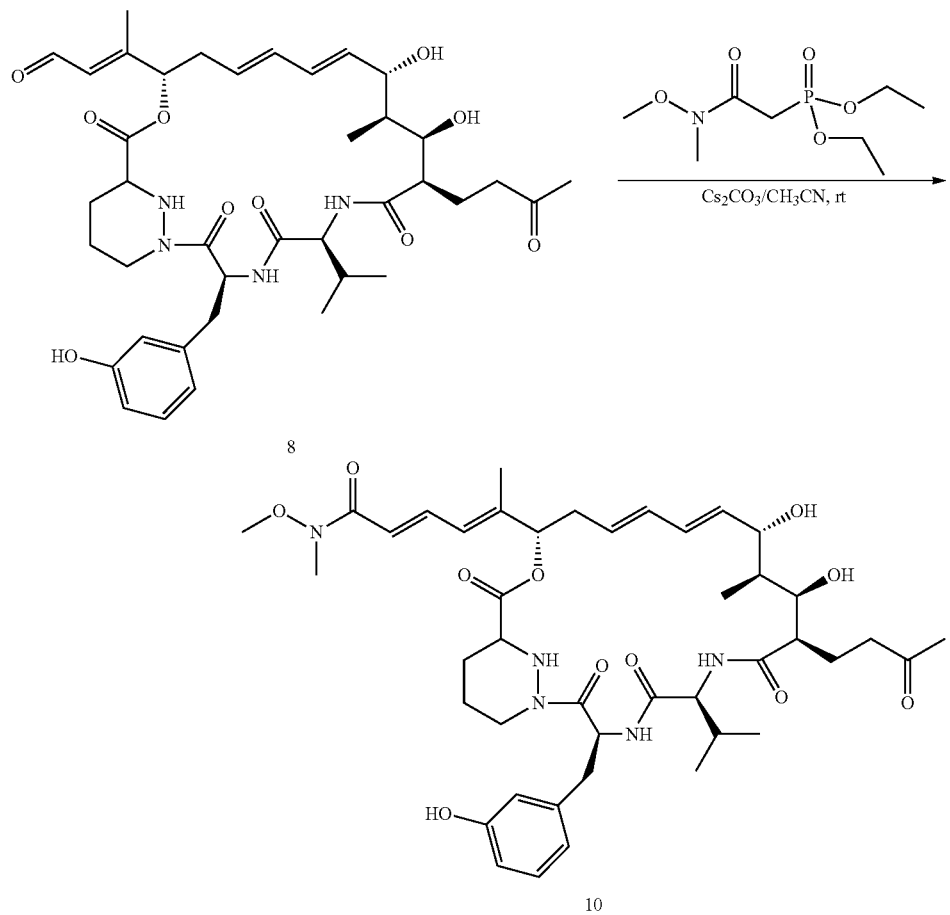

To a suspension of NaH (0.974 mg, 0.041 mmol) in anhydrous THF (1.0 ml) was added dropwise a solution of diethyl 2-(methoxy(methyl)amino)-2-oxoethylphosphonate (25.8 mg, 0.108 mmol) in anhydrous THF (0.2 ml) under $N_2$ atmosphere at −3° C. with stirring. The solution was then stirred at room temperature until it became clear. A solution of 8 (20 mg, 0.027 mmol) in anhydrous THF (0.2 ml) was added dropwise to the clear solution and the mixture stirred at room temperature for 30 min. The mixture was quenched with water and the THF was removed under reduced pressure. The residue was extracted with ethyl acetate. The organic layer was washed with brine then dried. The solvent was removed under reduced pressure to yield a residue of 14 mg. The crude compound (dissolved in acetone) was loaded on TLC plate (1 mm, 20*20 cm) and developed with acetone/petroleum ether=3:2. The target band (visualized by UV) was collected and mixed with acetone, then filtered through a pad of silica gel (2-3 cm height, pre-rinsed with acetone to remove impurities). The filtration was concentrated under vacuo. Finally, adding acetonitrile and water to the obtained sample, the solution was freeze-dried to give the desired product as white solid powder (8.2 mg, 37%). LC-MS: 824 $[M+1]^+$. See FIG. 2 for $^1H$ NMR.

Example 5

Synthesis of 13

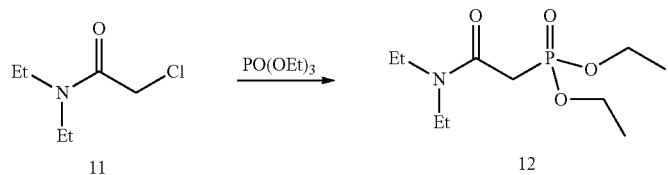

-continued
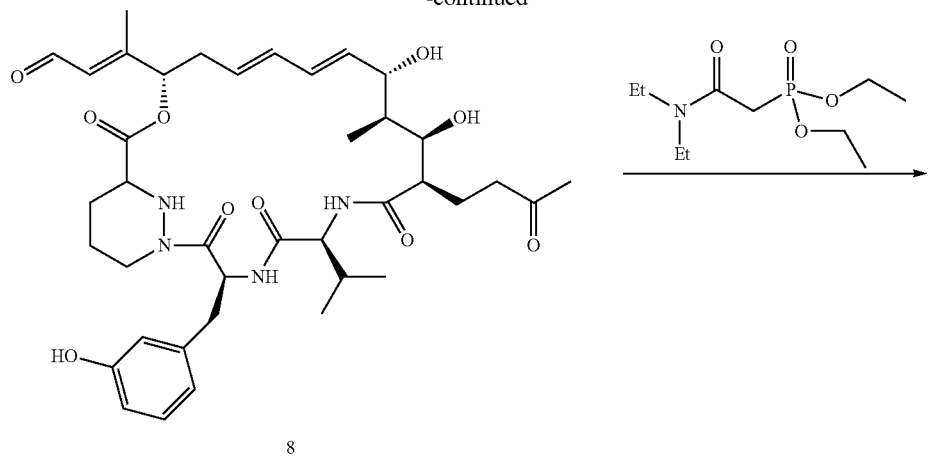
8
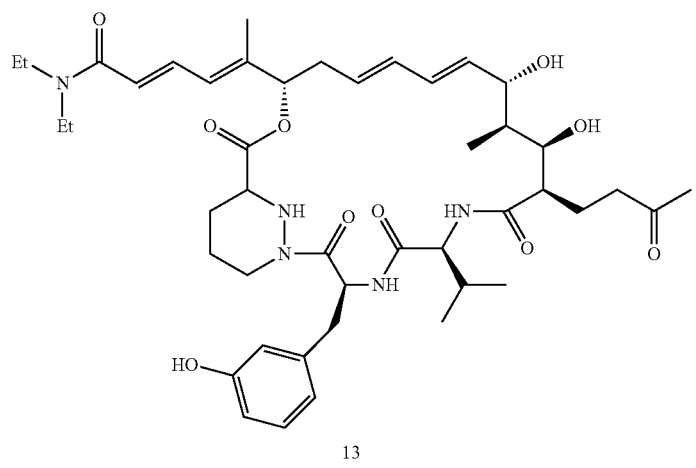
13
5.1 Synthesis of Intermediate 12
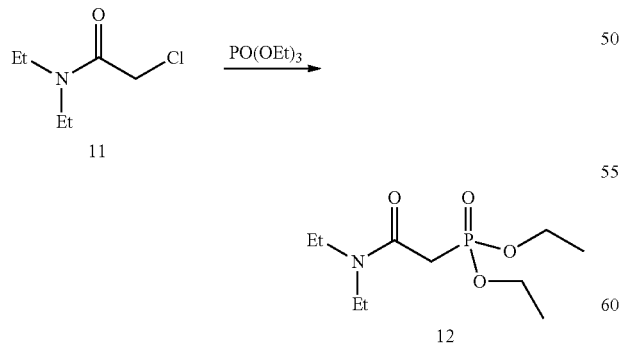
A mixture of N,N-diethylchloroacetamide (17.5 mL, 0.127 mmol) and triethyl phosphite 22 mL, 0.1309 mmol) was stirred at 180° C. for 8 h. The reaction mixture was cooled to room temperature and distilled to give intermediate 12 (15g, 47%) as a colorless oil.

5.2 Synthesis of 13

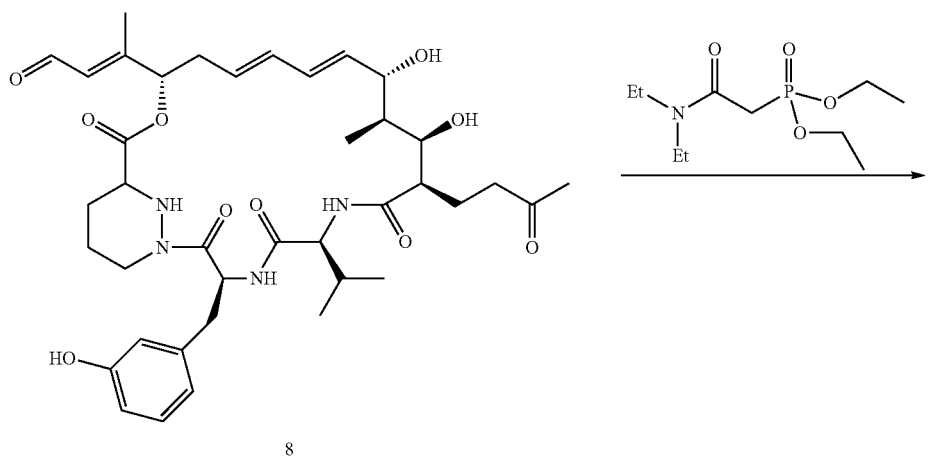

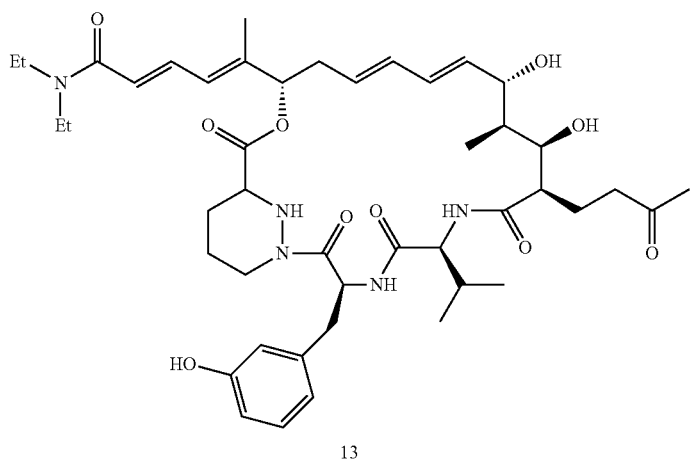

To a suspension of NaH (0.776 mg, 0.0324 mmol) in anhydrous THF (1.0 mL) was added dropwise a solution of diethyl 2-(diethylamino)-2-oxoethylphosphonate (28.5 mg, 0.1134 mol) in anhydrous THF (0.2 mL) under $N_2$ atmosphere at −3° C. with stirring. The solution was then stirred at room temperature until it became clear. A solution of 8 (20 mg, 0.027 mmol) in anhydrous THF (0.2 mL) was added dropwise to the clear solution and the mixture stirred at rt for 30 min. The mixture was quenched with water and THF was evaporated under reduced pressure. The residue was extracted with EA. The organic layer was washed with brine then dried. The solvent was evaporated off, giving a residue of 17 mg which was purified with Prep TLC. The crude compound (dissolved in acetone) was loaded on TLC plate (1 mm, 20*20 cm) and developed with acetone/petroleum ether=3:2. The target band (visualized by UV) was collected and mixed with acetone, then filtered through a pad of silica gel (2-3 cm height, pre-rinsed with acetone to remove impurities). The filtration was concentrated under vacuo. Finally, adding acetonitrile and water to the obtained sample, the solution was freeze-dried to give the desired product as white solid powder. (9.0 mg, 40%). LC-MS: 836 $[M+1]^+$. See FIG. 3 for $^1H$ NMR.

Example 6

Synthesis of 16

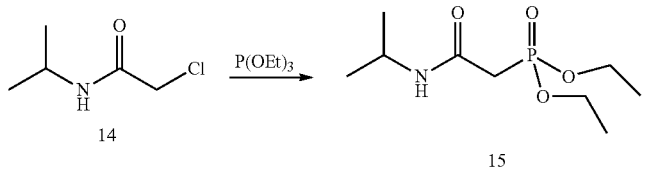

-continued
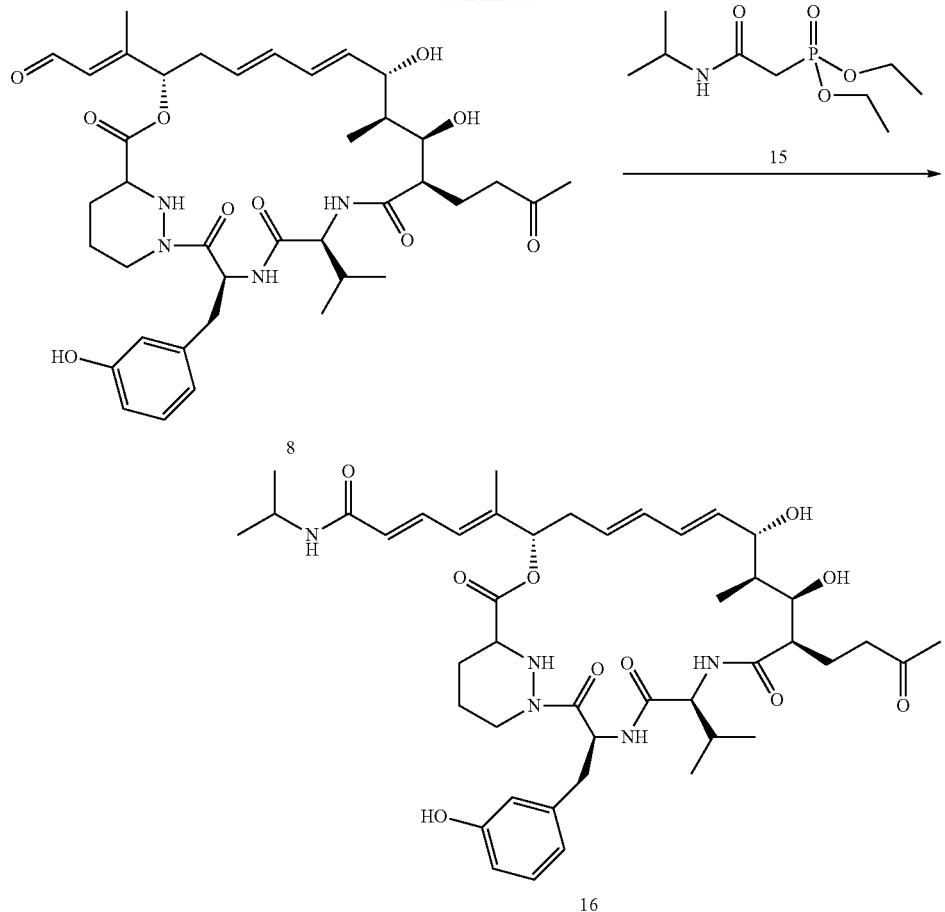
6.1 Synthesis of Intermediate 15
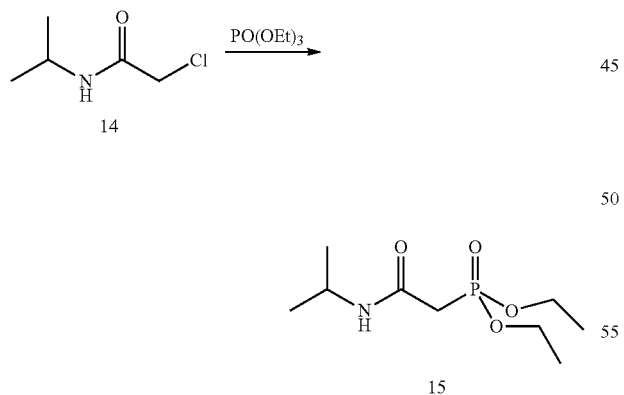
A mixture of N,-isopropylchloroacetamide (1 g, 7.41 mmol) and triethyl phosphite1.6 mL, 9.09 mmol) was stirred at 140° C. for 8 h. The reaction mixture was cooled to room temperature and 200 mg sample was use to be purified by Prep HPLC to give intermediate 15 (60 mg, 34%) as a colorless oil.

6.2 Synthesis of 16

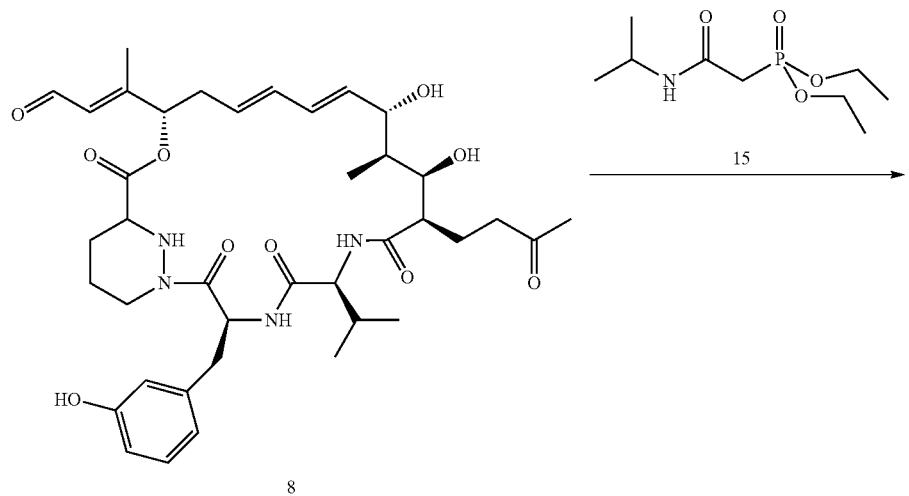

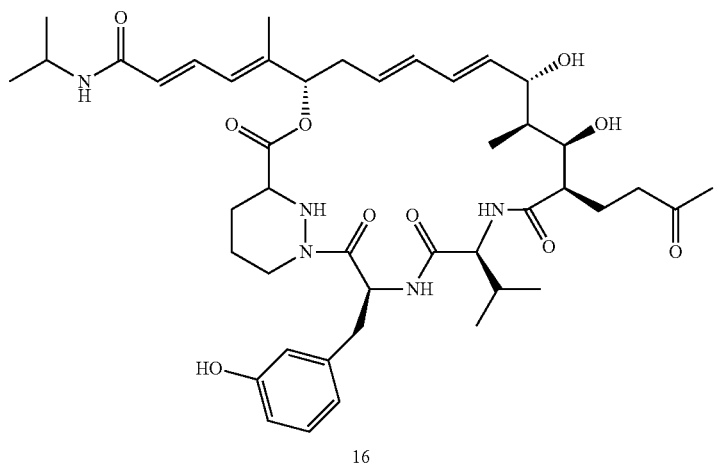

To a suspension of NaH (0.972 mg, 0.0405 mmol) in anhydrous THF (1.0 mL) was added dropwise a solution of diethyl 2-(isopropylamino)-2-oxoethylphosphonate (26 mg, 0.108 mmol) in anhydrous THF (0.2 mL) under $N_2$ atmosphere at −3° C. with stirring. The solution was then stirred at room temperature until it became clear. A solution of 8 (20 mg, 0.027 mmol) in anhydrous THF (0.2 ml) was added dropwise to the clear solution and the mixture stirred at rt for 30 min. The mixture was quenched with water and THF was evaporated under reduced pressure. The residue was extracted with EA. The organic layer was washed with brine then dried. The solvent was evaporated off, giving a residue of 18 mg which was purified with Prep TLC. The crude compound (dissolved in acetone) was loaded on TLC plate (1 mm, 20*20 cm) and developed with acetone/petroleum ether=3:2. The target band (visualized by UV) was collected and mixed with acetone, then filtered through a pad of silica gel (2-3 cm height, pre-rinsed with acetone to remove impurities). The filtration was concentrated under vacuo. Finally, adding acetonitrile and water to the obtained sample, the solution was freeze-dried to give the desired product as white solid powder (8.5 mg, 38%). LC-MS: 822 [M+1]$^+$. See FIG. 4 for $^1$H NMR.

Example 7

Synthesis of 19

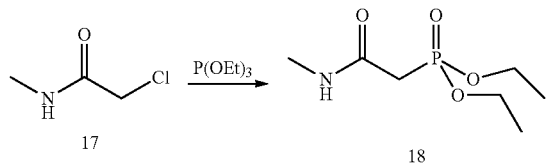

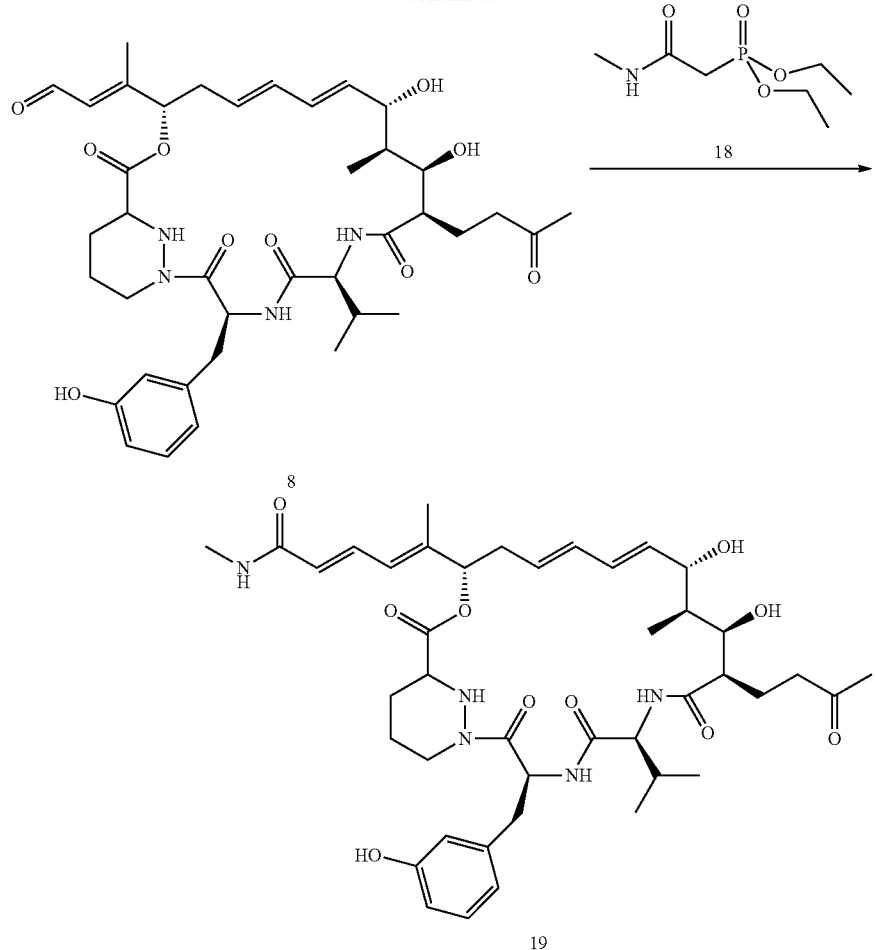
7.1 Synthesis of Intermediate 18
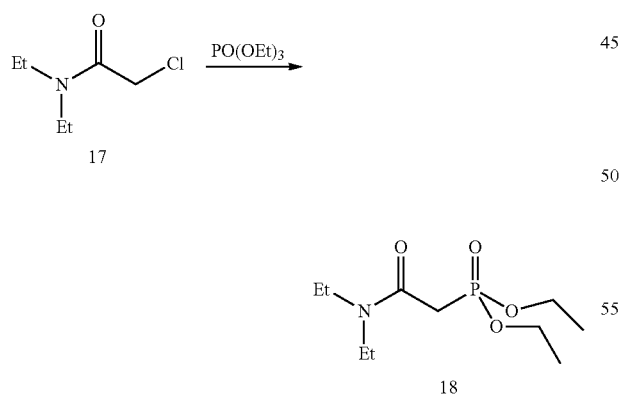
A mixture of N-methylchloroacetamide (200 mg, 1.87 mmol) and triethyl phosphite (0.67 mL, 3.74 mmol) was stirred at 130° C. for 8 h. The reaction mixture was cooled to room temperature and was purified by Prep HPLC to give intermediate 18 (60 mg, 15%) as a colorless oil.

7.2 Synthesis of 19

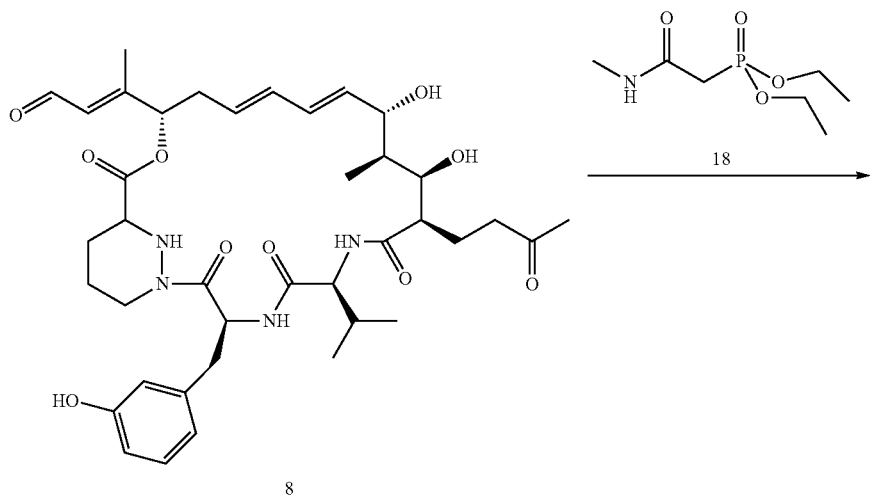

8

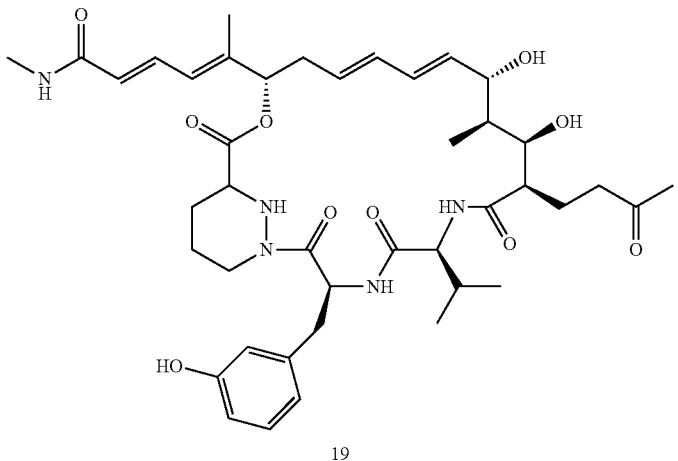

19

To a suspension of NaH (0.972 mg, 0.0405 mmol) in anhydrous THF (1.0 ml) was added dropwise a solution of diethyl 2-(methylamino)-2-oxoethylphosphonate (23 mg, 0.108 mmol) in anhydrous THF (0.2 ml) under $N_2$ atmosphere at −3° C. with stirring. The solution was then stirred at room temperature until it became clear. A solution of 8 (20 mg, 0.027 mmol) in anhydrous THF (0.2 ml) was added dropwise to the clear solution and the mixture stirred at rt for 30 min. The mixture was quenched with water and THF was evaporated under reduced pressure. The residue was extracted with EA. The organic layer was washed with brine then dried. The solvent was evaporated off, giving a residue of 14 mg which was purified with Prep TLC. The crude compound (dissolved in acetone) was loaded on TLC plate (1 mm, 20*20 cm) and developed with acetone/petroleum ether=3:2. The target band (visualized by UV) was collected and mixed with acetone, then filtered through a pad of silica gel (2-3 cm height, pre-rinsed with acetone to remove impurities). The filtration was concentrated under vacuo. Finally, adding acetonitrile and water to the obtained sample, the solution was freeze-dried to give the desired product as white solid powder (7.0 mg, 37%). LC-MS: 794 [M+1]$^+$. See FIG. 5 for $^1$H NMR.

Example 8

Synthesis of 22

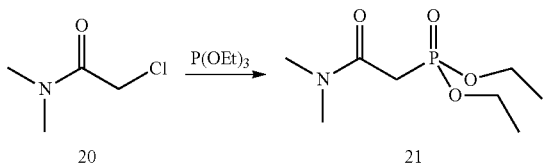

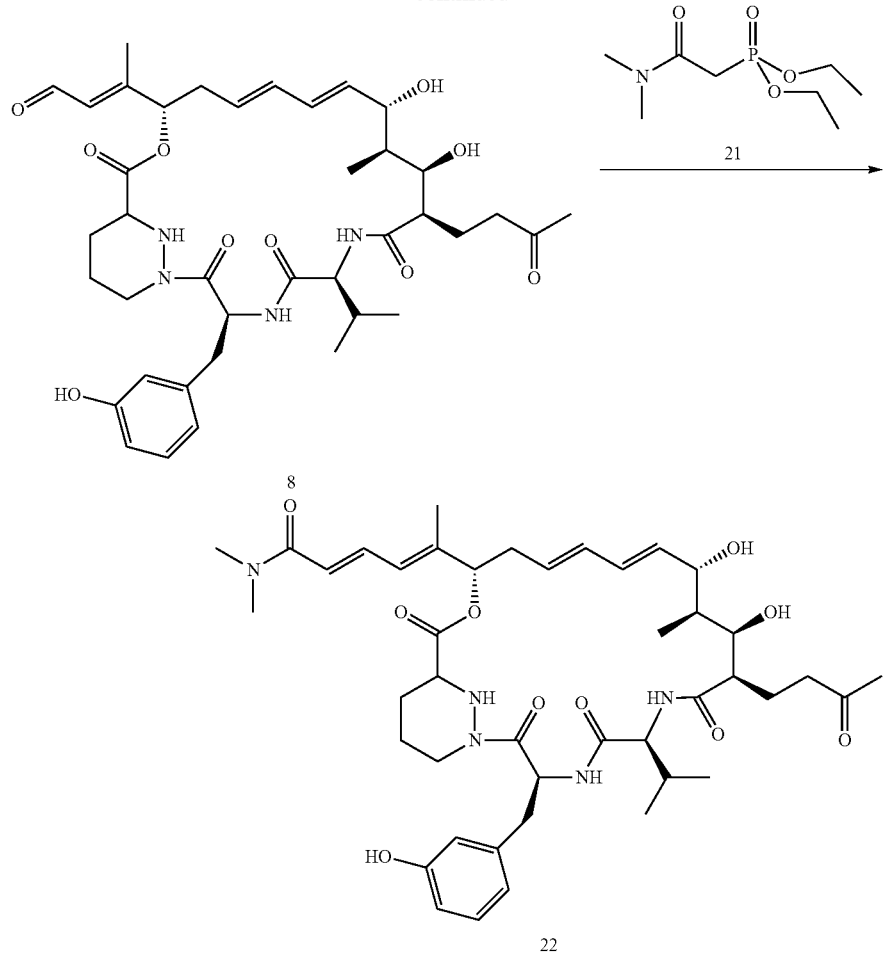
8.1 Synthesis of Intermediate 21
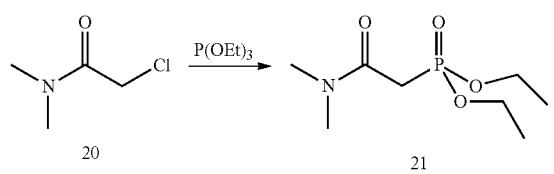
A mixture of 2-chloro-N,N-dimethylacetamide (300 mg, 2.47 mmol) and triethyl phosphite (820 mg, 4.94 mmol) was stirred at 150° C. overnight. The reaction mixture was cooled to room temperature and was purified by Prep HPLC to give intermediate 21 (105 mg, 20%).
8.2 Synthesis of 22
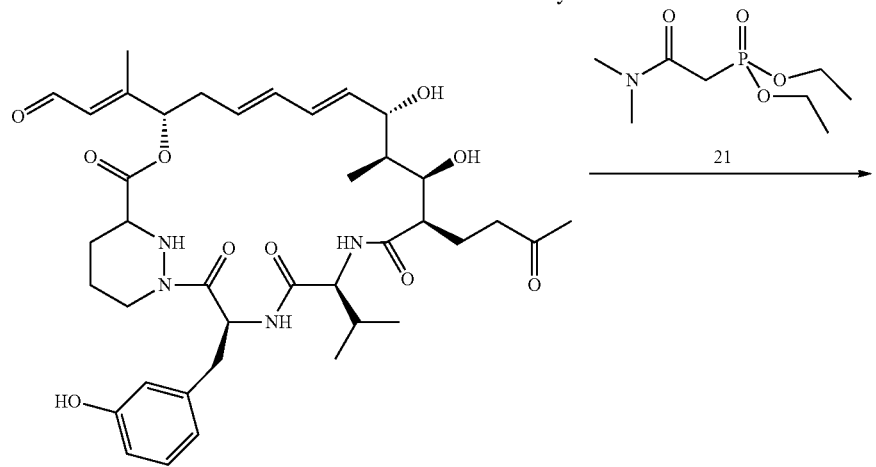

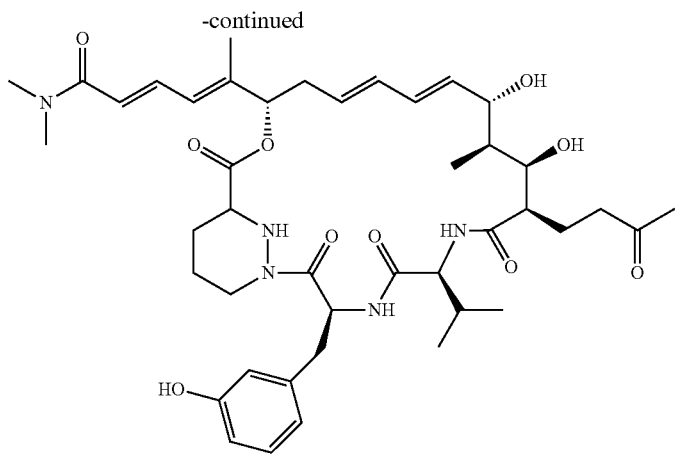

22

To a solution of 21 (50 mg, 0.224 mmol) in THF (1.0 mL) was added NaH (1.6 mg, 0.068 mmol) in anhydrous THF (0.2 mL) at 0° C. with stirring. The solution was then stirred at room temperature until it became clear. Then 8 (40 mg, 0.054 mmol) was added to the clear solution and the mixture stirred at room temperature for 1 h. The mixture was quenched with water (10 mL) and extracted with EA (3×20 mL). The organic layer was washed with brine and dried over $Na_2SO_4$, filtered, evaporated. The residue was purified by Prep HPLC [Column: Spring C18(25*250 mm, 10 μm), Mobile phase: A:$H_2O$ B:Acetonitrile, Gradient: B from 30% to 40% over 10 min] to obtained 22 as a white solid (12.4 mg, 28%). LC-MS: 808 $[M+1]^+$. See FIG. 6 for $^1H$ NMR.

Example 9

Synthesis of 25

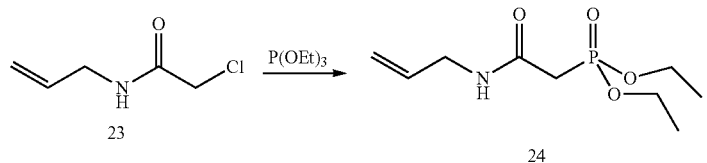

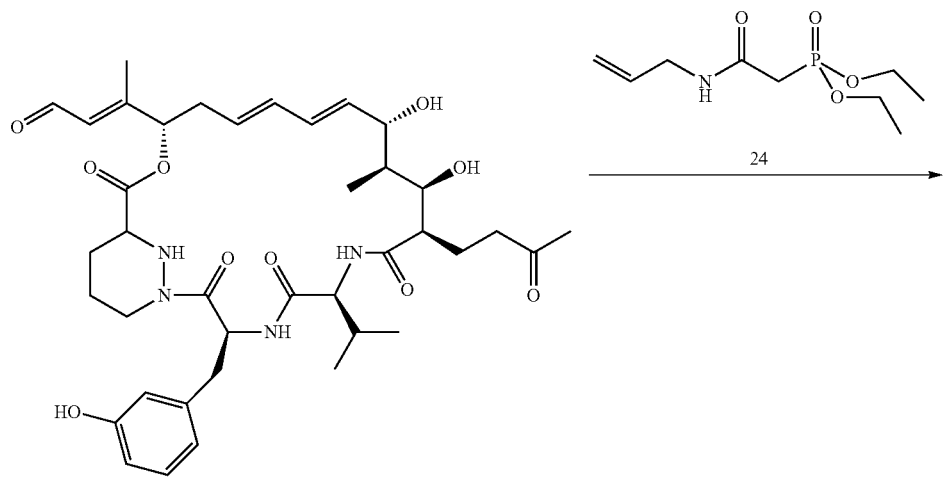

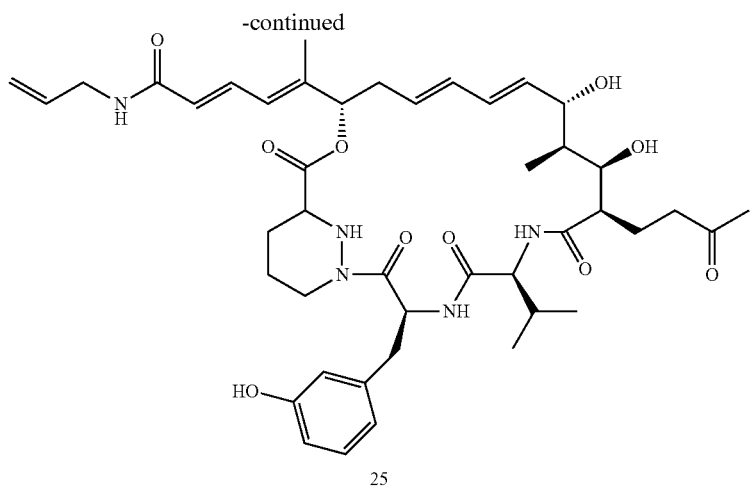
25
9.1 Synthesis of Intermediate 24
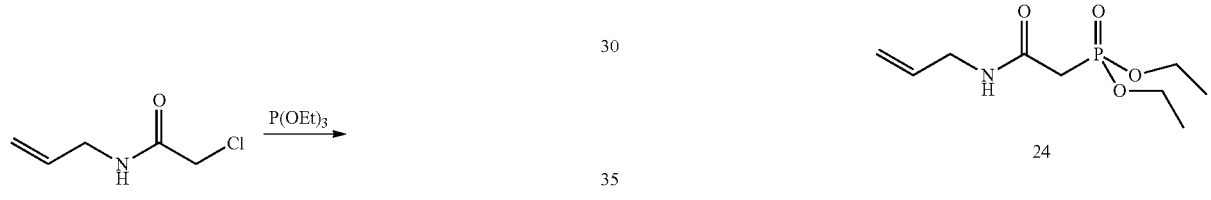
A mixture of P(Oet)$_3$ (0.63 ml, 3.75 mmol) and 23 (500 mg, 3.74 mmol) were stirred at 180° C. for 6 h. The reaction was cooled and purified by prep-HPLC to obtain intermediate 24 as colorless oil (100 mg, 11%).
9.2 Synthesis of 25
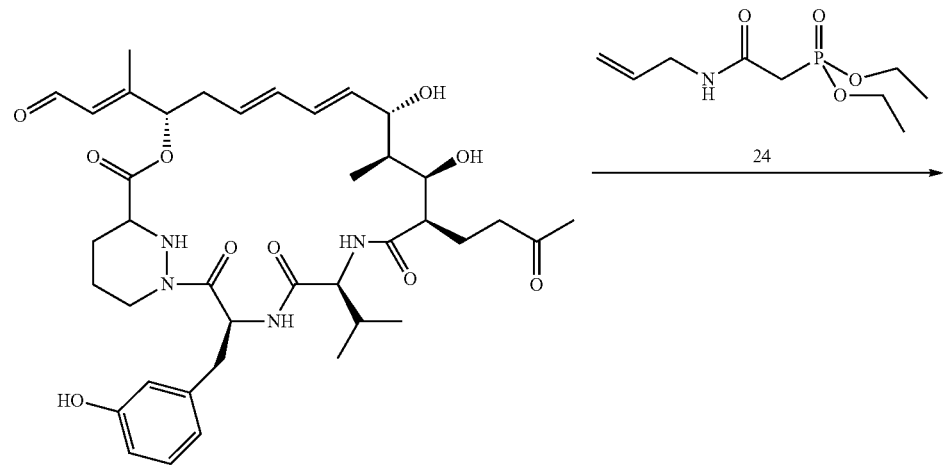

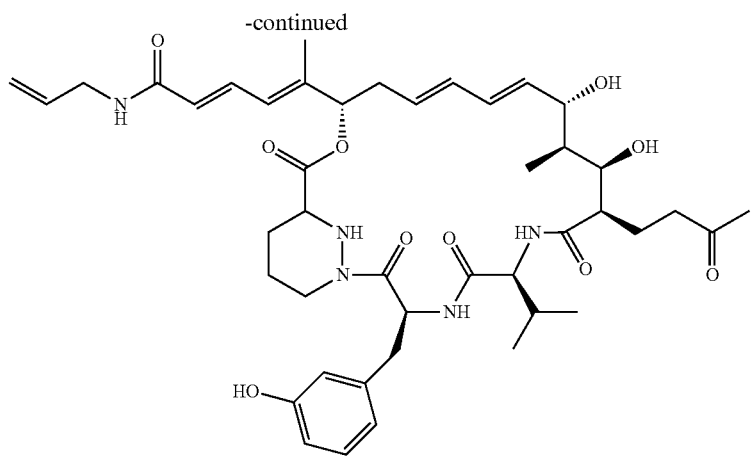

25

To a solution of 24 (38 mg, 0.1624 mmol) dissolved in THF (1 mL) was added NaH (1.5 mg, 0.0625 mmol) at 0° C. and stirred for 10 min. Then the solution was stirred at room temperature and compound 8 (30 mg, 0.0406 mmol) was added. The reaction was stirred for 30 min at room temperature and quenched with water (5 mL). The reaction was extracted with ethyl acetate (3×20 mL). The combined organic phase was washed with brine, dried over sodium sulfate and reduced in vacuo. The residue was purified by Pre-HPLC to obtain 25 as white solid (7.4 mg, 22%). See FIG. 7 for $^1$H NMR.

Example 10

Synthesis of 26 and 28

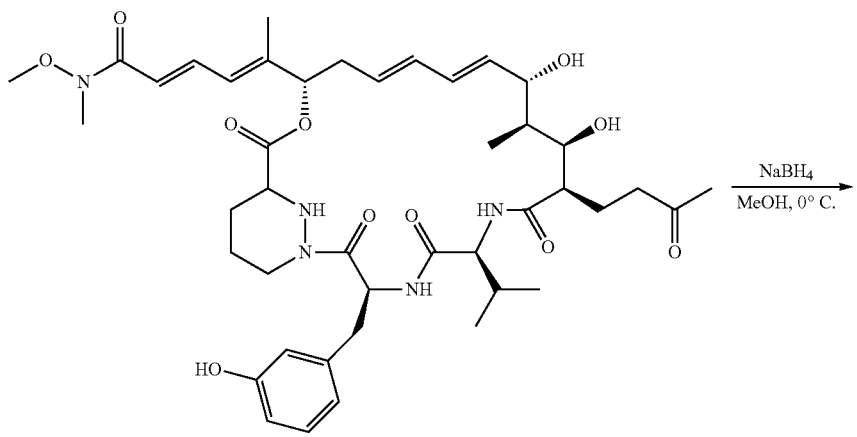

10

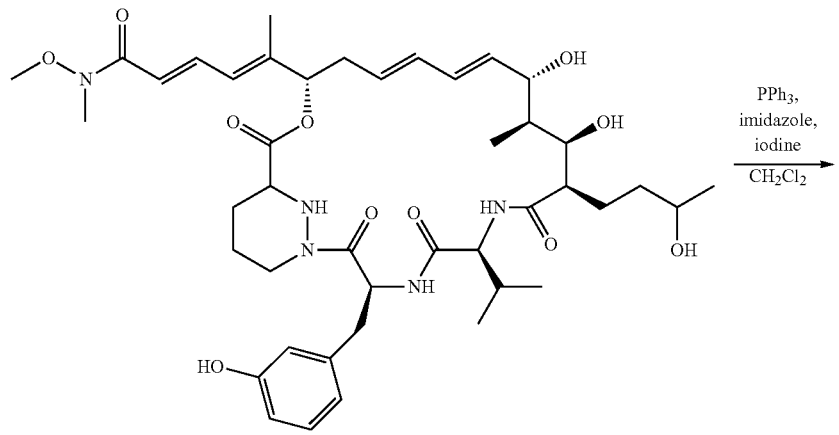

26

-continued
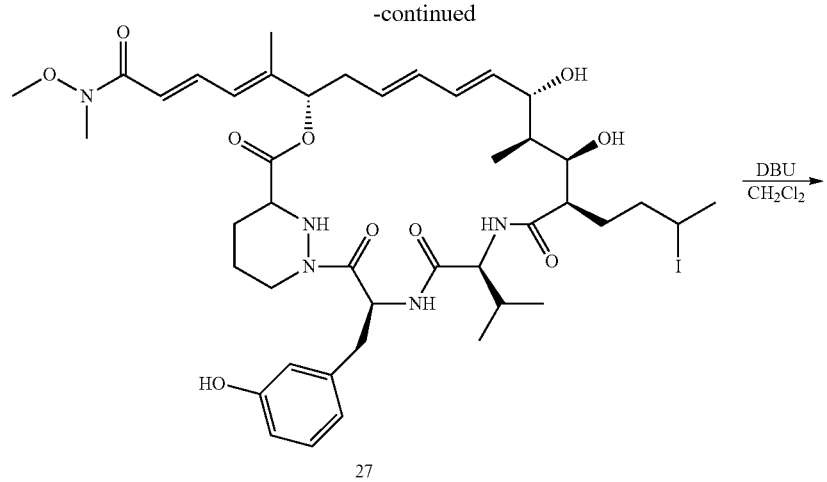
27
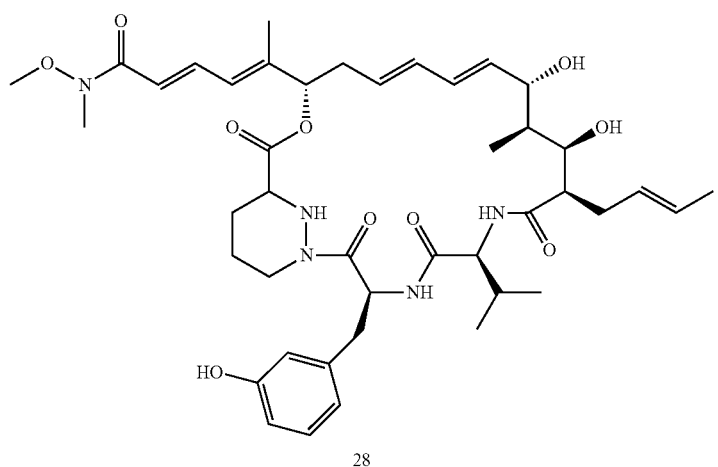
28
10.1 Synthesis of 26
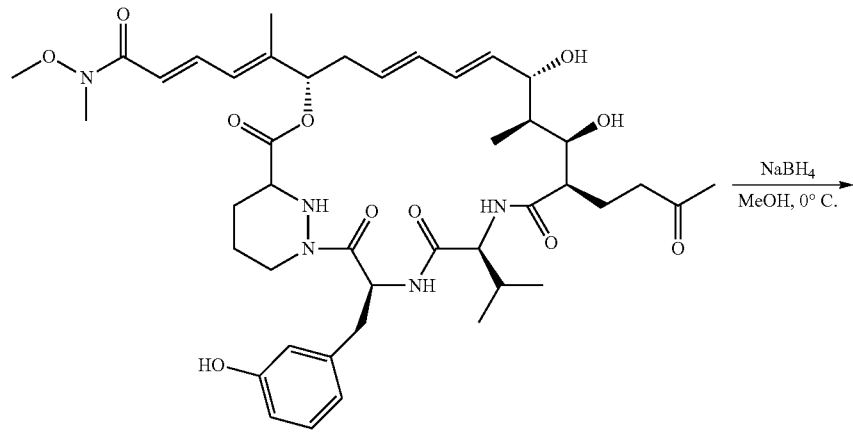
10

-continued

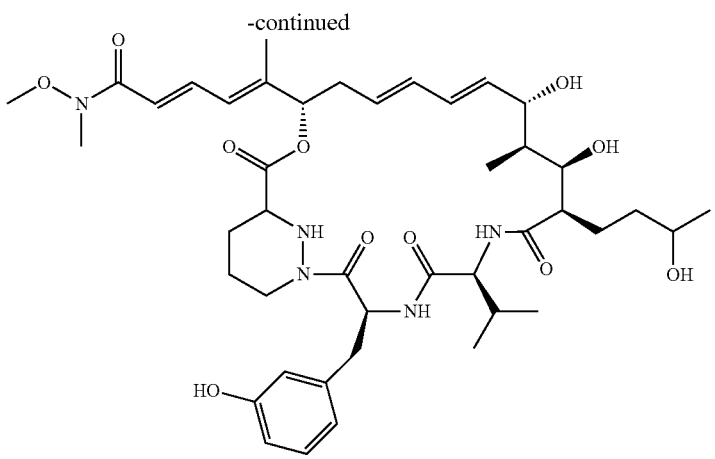

26

To a solution of 10 (25 mg, 0.0304 mmol, 1 eq) dissolved in methanol (2 mL) at 0° C. was added sodium borohydride (2.3 mg, 0.0608 mmol, 2 eq). The reaction mixture was stirred 3 h at 0° C. The reaction was added sodium bicarbonate solution and extracted with ethyl acetate (3×20 mL). The combined organic layers were washed with brine, dried over sodium sulfate and removed in vacuo. The residue was used directly to the next step.

10.2 Synthesis of Intermediate 27

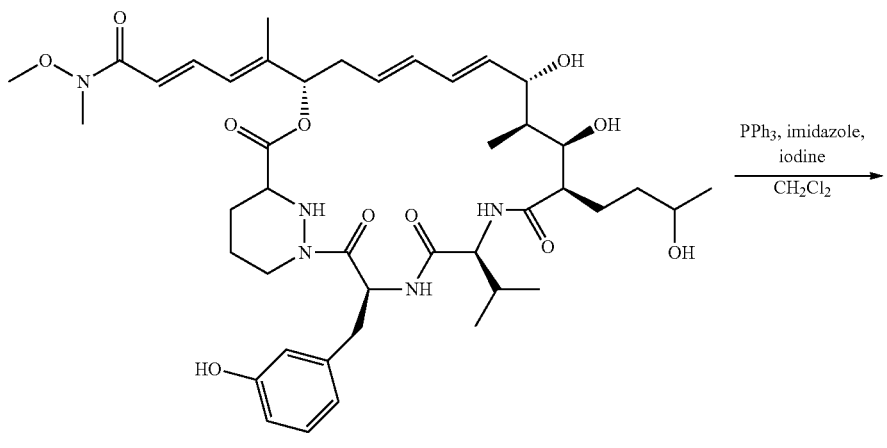

26

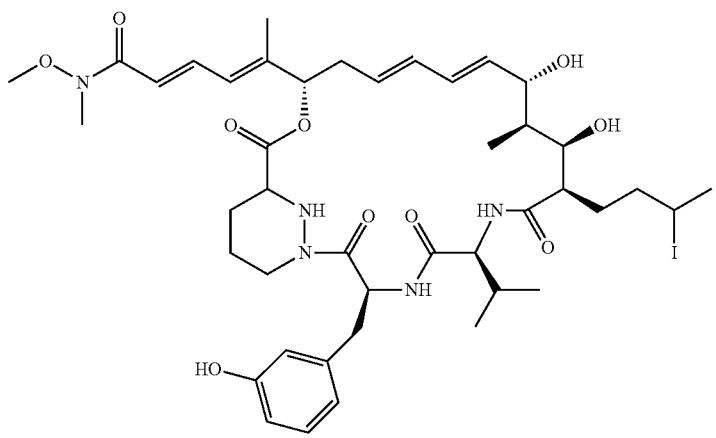

27

To a solution of triphenylphosphine (24 mg, 0.0915 mmol, 3 eq) dissolved in $CH_2Cl_2$ (1.5 ml) were added imidazole (8.2 mg, 0.1206 mmol, 4 eq) and iodine (23 mg, 0.0914 mmol, 3 eq). The reaction mixture was stirred 30 min and cooled to 0° C. The compound 27 (crude 25 mg, 0.0303 mmol, 1 eq) was added and the reaction stirred for 4.5 h at room temperature. The reaction was quenched with saturated aqueous sodium bicarbonate solution (2 mL) and extracted with ethyl acetate (3×10 mL). The combined organic layers were washed with saturated aqueous $Na_2S_2O_3$ (10 mL) and brine, dried over sodium sulfate and evaporated. The residue was used directly in the next step.

10.3 Synthesis of 28

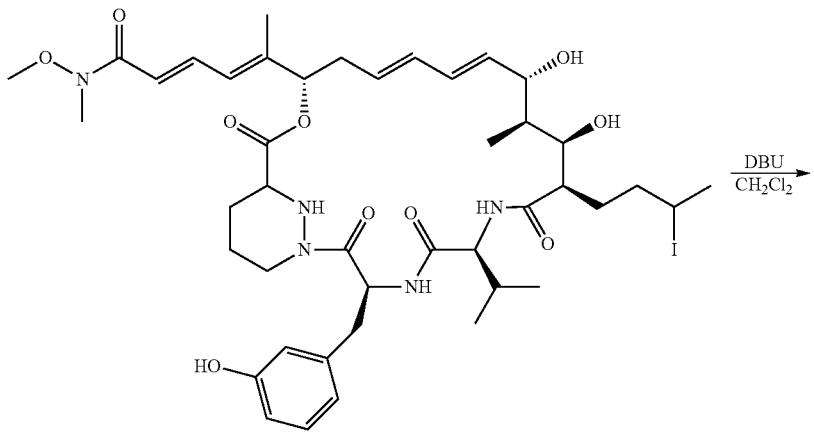

27

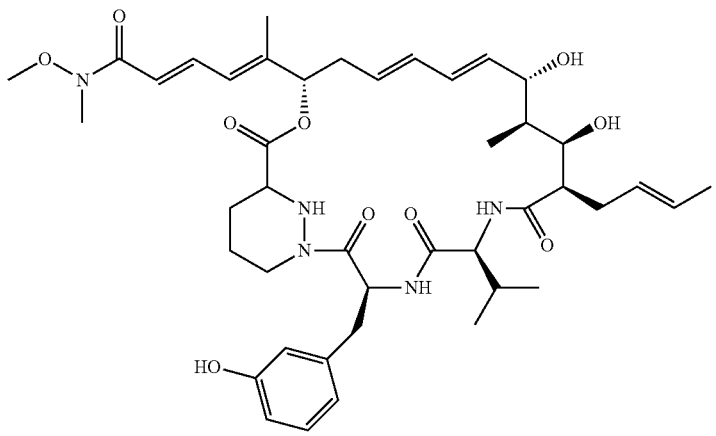

28

To a solution of 27 (25 mg, 0.02673 mmol, 1 eq) dissolved in $CH_2Cl_2$ (1.5 mL) was added DBU (8.2 mg, 0.1206 mmol, 4 eq) at 0° C. The reaction mixture was stirred 2 h at room temperature. The reaction was quenched with saturated aqueous sodium bicarbonate solution (4 mL) and extracted with ethyl acetate (3×20 mL). The combined organic layers were washed with brine, dried over sodium sulfate and evaporated. The residue was purified by Pre-HPLC to give 28 as a white solid. (7 mg, 29%). See FIG. 8 for $^1H$ NMR.

Example 11

Synthesis of 29

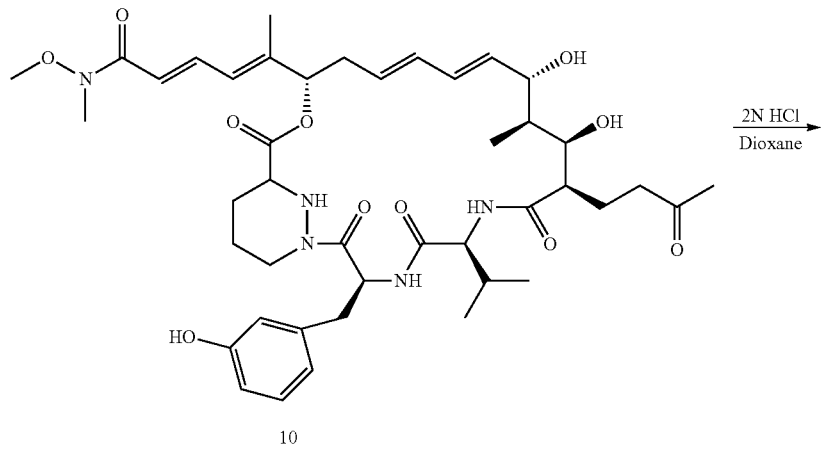

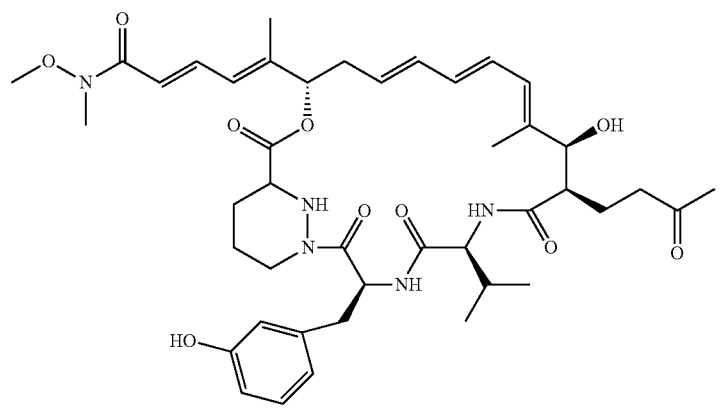

To a solution of 10 (30 mg, 0.0365 mmol) dissolved in dioxane (2 mL) was added aqueous HCl solution (2 M, 0.18 ml, 0.36 mmol). The reaction was stirred at room temperature for 4 days and the reaction was quenched with water and extracted with ethyl acetate (3×10 mL). The organic phase was dried over sodium sulfate and evaporated. The residue was purified by prep-HPLC to give 29 as a white solid (11 mg, 38%). See FIG. 9 for $^1$H NMR.

Example 12

Synthesis of 32

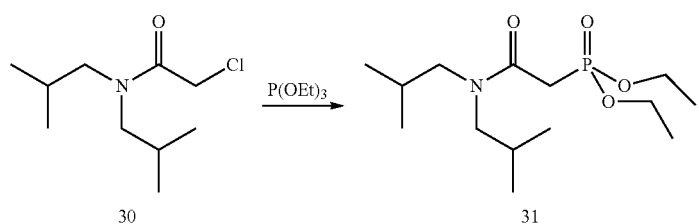

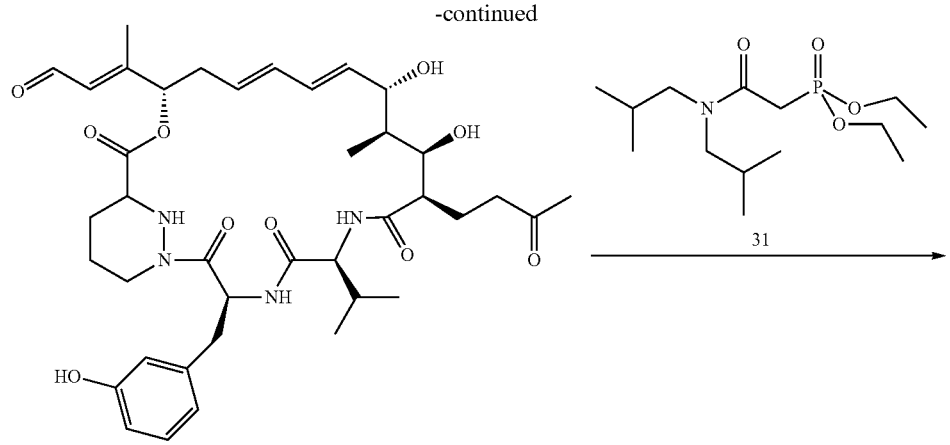
8
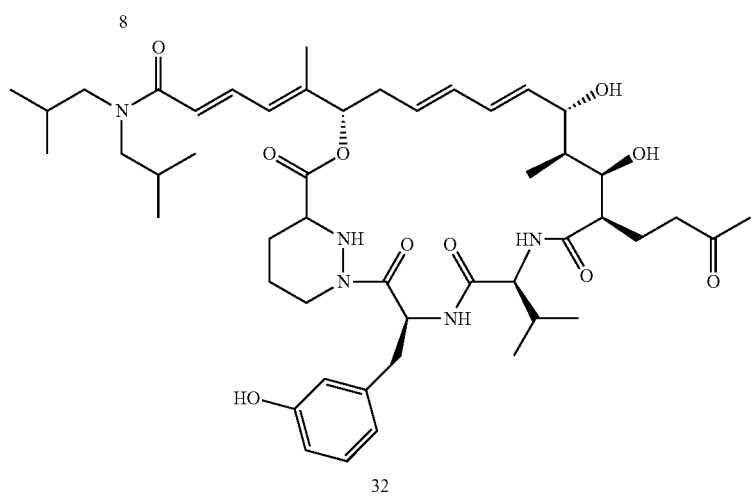
32
12.1 Synthesis of Intermediate 31
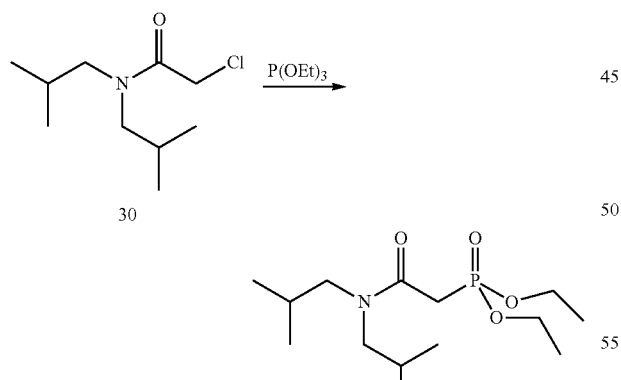
A mixture of 2-chloro-N,N-diisobutylacetamide, 31 (206 mg, 1.00 mmol) and triethyl phosphite (332 mg, 2.00 mmol) was stirred at 140° C. for 6 h. The reaction mixture was cooled to room temperature and was purified by combiflash to give intermediate 31 (222 mg, 20%).

12.2 Synthesis of 32

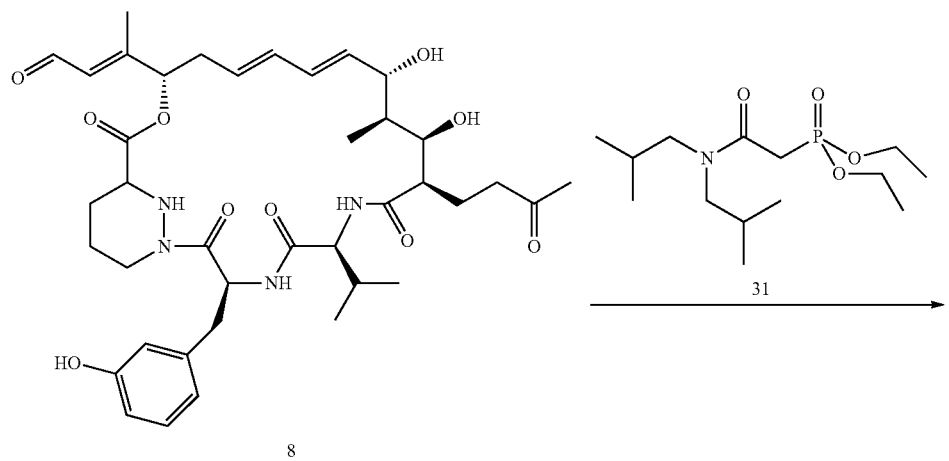

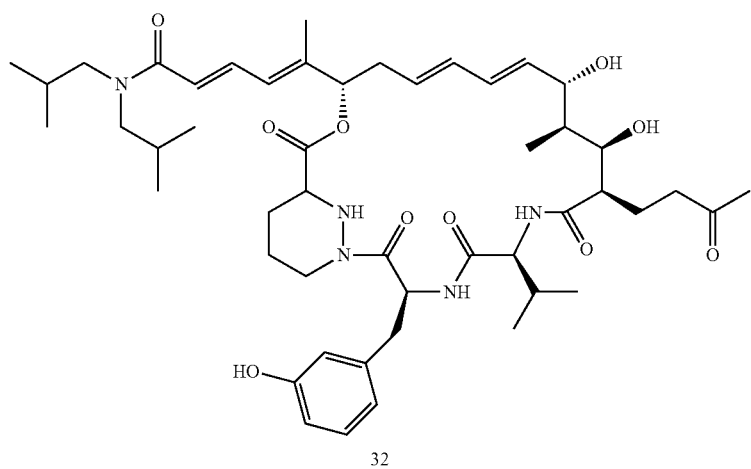

To a solution of 31 (58 mg, 0.188 mmol) in THF (1.0 mL) was added NaH (1.4 mg, 0.0564 mmol) in anhydrous THF (0.2 mL) at room temperature with stirring. Then 8 (35 mg, 0.047 mmol) was added to the clear solution and the mixture stirred at room temperature for 3 h. The mixture was quenched with water (10 mL) and extracted with EA (3×30 mL). The organic layer was washed with brine and dried over $Na_2SO_4$, filtered and evaporated. The residue was purified by Prep HPLC to obtained 32 as a white solid (16.2 mg 38%). LC-MS: 892 [M+1]$^+$. See FIG. 10 for $^1$H NMR.

Example 13

Synthesis of 35

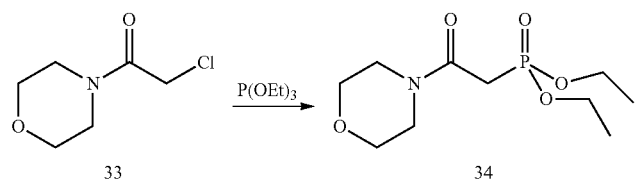

-continued
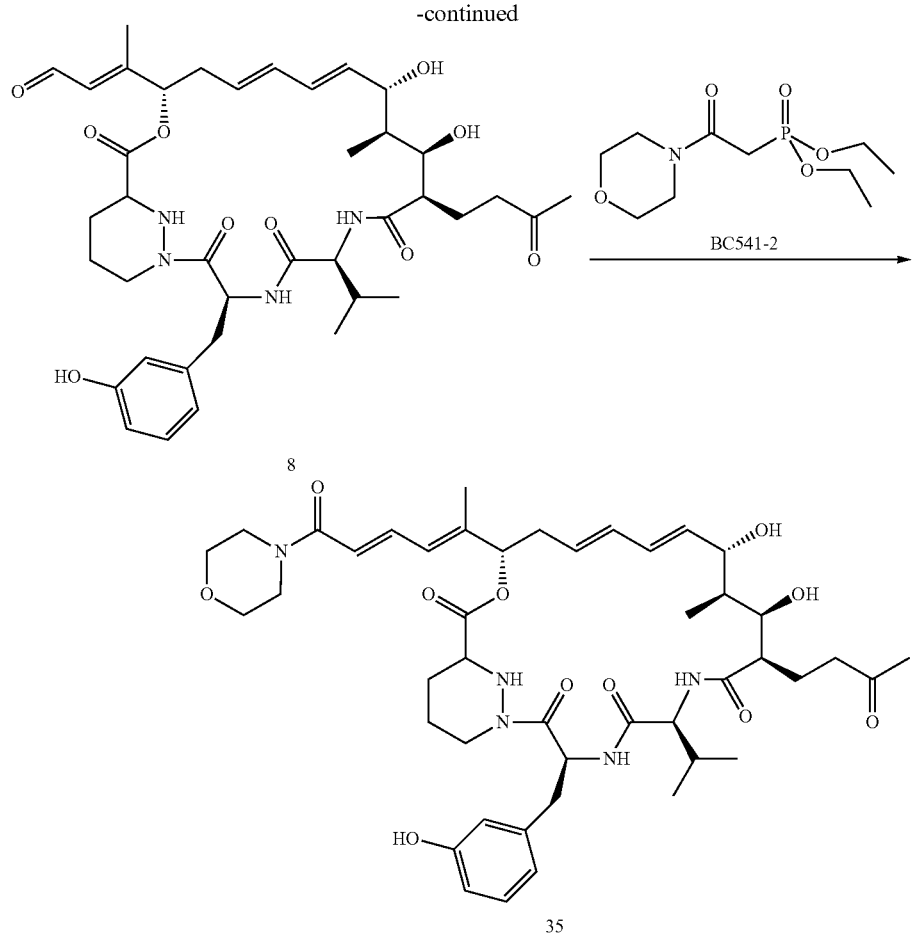
13.1 Synthesis of Intermediate 34
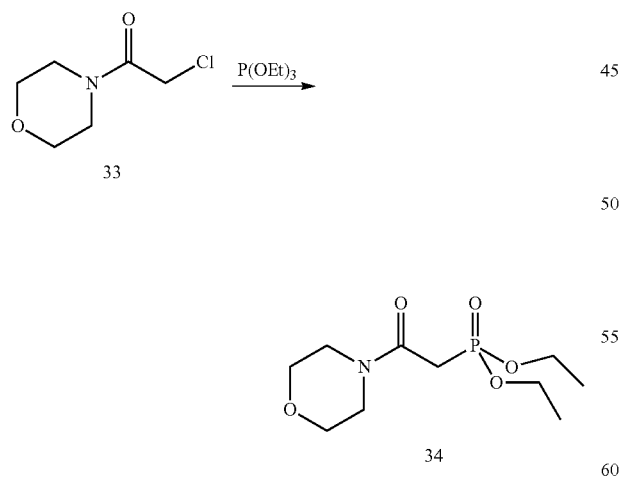
A mixture of 2-chloro-1-morpholinoethanone 33 (327 mg, 2 mmol) and triethyl phosphite (665 mg, 4 mmol) was stirred at 140° C. overnight. The reaction mixture was cooled to room temperature and was purified by combiflash to give intermediate 34 as a colourless oil (190 mg, 36%).

13.2 Synthesis of 35

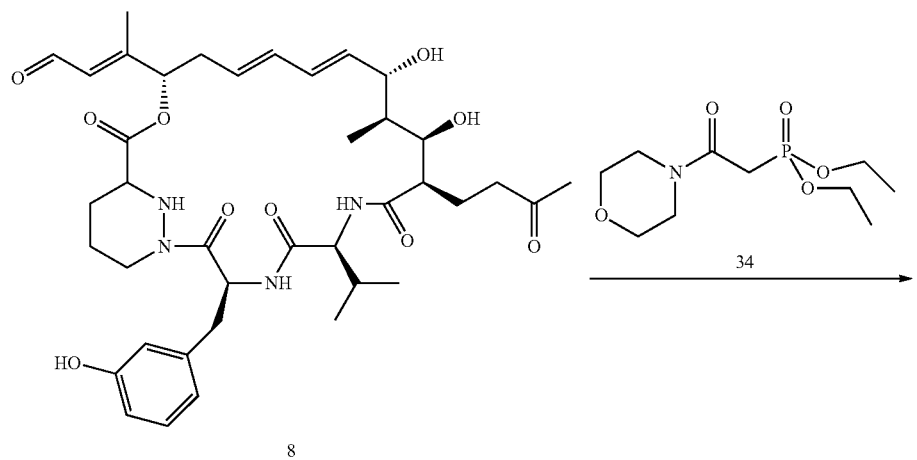

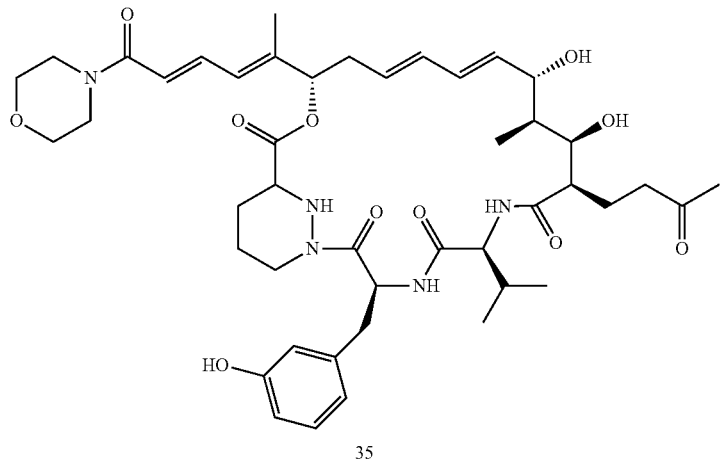

To a solution of 34 (50 mg, 0.188 mmol) in THF (1.0 mL) was added NaH (1.4 mg, 0.056 mmol) in anhydrous THF (0.2 mL) at 0° C. with stirring. The solution was then stirred at room temperature until it became clear. Then 8 (35 mg, 0.047 mmol) was added to the clear solution and the mixture stirred at rt for 3 h. The mixture was quenched with water (10 mL) and extracted with EA (20 mL*3). The organic layer was washed with brine and dried over $Na_2SO_4$, filtered, evaporated. The residue was purified by pre-HPLC to obtained 14 mg pure product 35 as a white solid (yield, 35%). LC-MS: 850 $[M+1]^+$. See FIG. 11 for $^1H$ NMR.

Example 14

Synthesis of 41

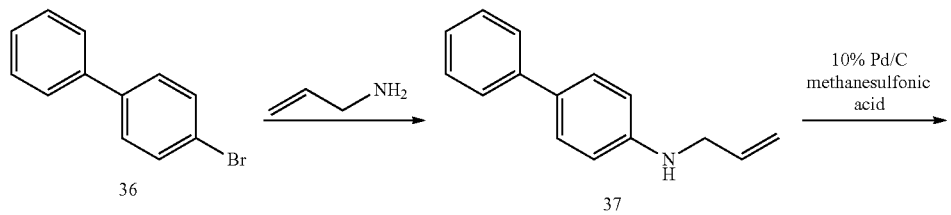

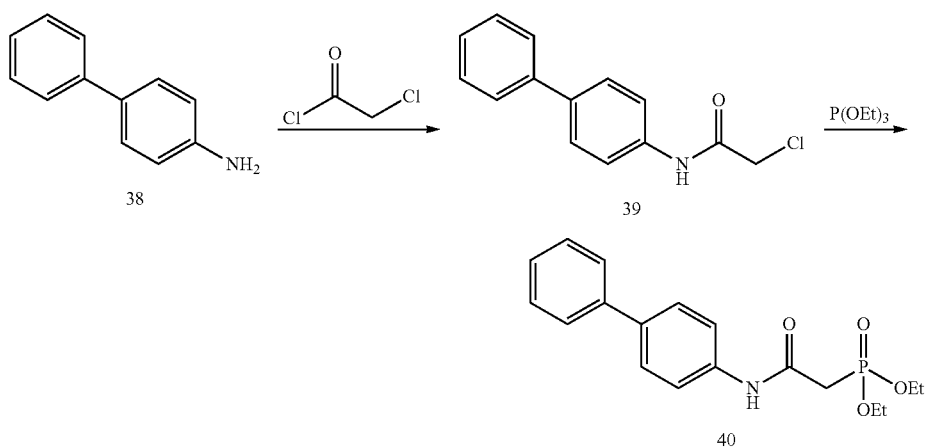
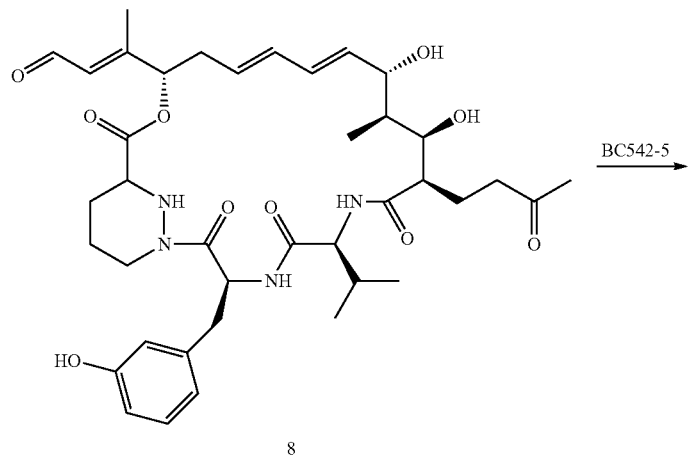
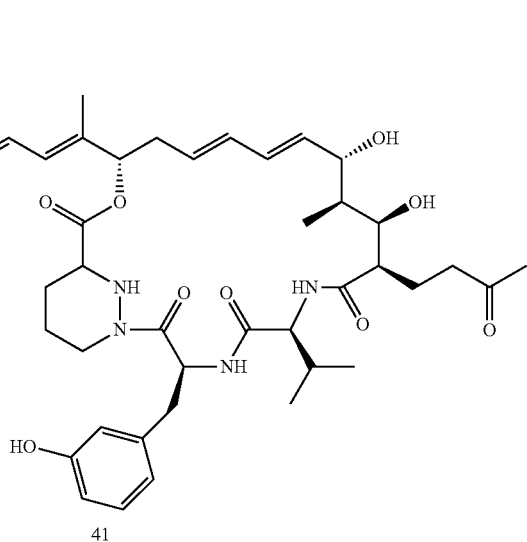

14.1 Synthesis of Intermediate 37

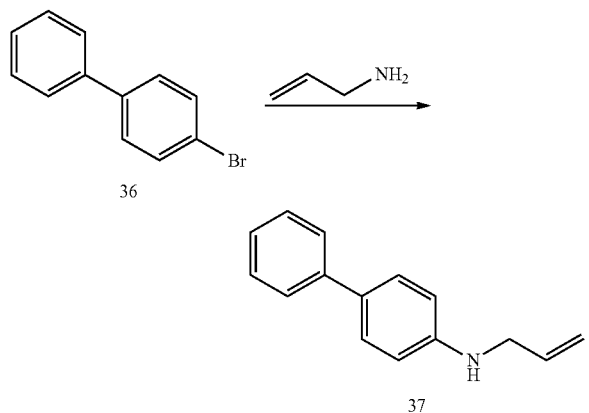

A mixture of 4-bromobiphenyl 36 (5 g, 21.55 mmol), allylamine (2.4 mL, 32.33 mmol), sodium tert-butoxide (3.11 g, 32.33 mmol), Pd(DPPF)Cl$_2$ (0.79 g, 1.08 mmol) and DPPF (1.79 g, 3.23 mmol) in 20 mL anhydrous THF was heated to 80° C. for 4 h. TLC indicated the complete disappearance of the starting 4-bromobiphenyl. The dark red reaction mixture was filtered through Celite and concentrated in vacuo leaving a dark colored oil. The oil was chromatographed on silica gel using PE/EA (5:1) to give 37 (3.5 g, 60% yield) as a yellow solid.

14.2 Synthesis of Intermediate 38

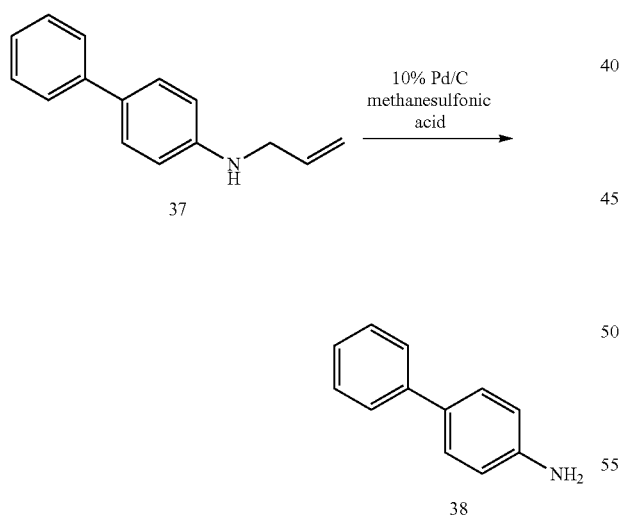

A mixture of N-allylbiphenyl-4-amine 37 (3 g, 14.35 mmol), 10% Pd/C (0.3 g) and methanesulfonic acid (922 uL, 14.35 mmol, 1 eq.) in 50 mL of absolute ethanol was refluxed for 2 h. TLC indicated the disappearance of starting N-allylbiphenyl-4-amine. The reaction mixture was filtered through a Celite pad and wash with aq.NaOH (10%), and extracted with ethyl acetate. The organic layer was washed with brine and dried over Na$_2$SO$_4$, filtered, concentrated in vacuo to give 1.6 g of the crude product 38 which was used to the next step without any further purification.

14.3 Synthesis of Intermediate 39

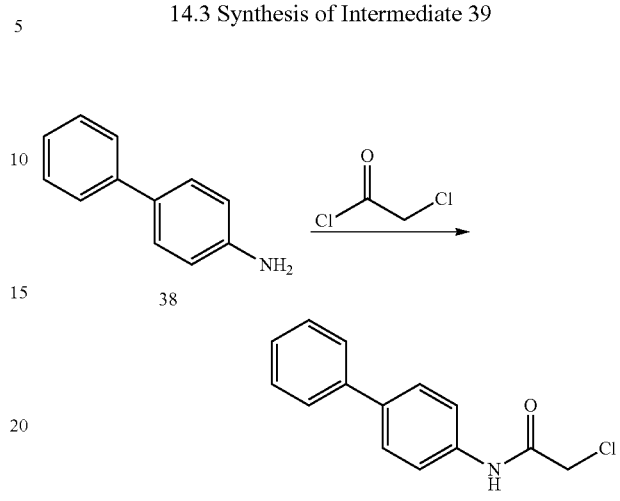

To a solution of crude 38 (1.6 g, 9.462 mmol), Et$_3$N (1.052 g, 10.408 mmol) in dry DCM (50 mL) was added dropwise chloroacetyl chloride (1.165 g, 10.408 mmol). The reaction mixture was stirred at 0-10° C. for 3 h, poured into ice water, and extracted with ethyl acetate. The organic layer was washed with brine and dried over Na$_2$SO$_4$, filtered, concentrated in vacuo to give a light yellow solid. The solid was purified by pre-TLC with PE/EA (4:1), and give the desired compound 39 (200 mg, 6% yield for two steps).

14.4 Synthesis of Intermediate 40

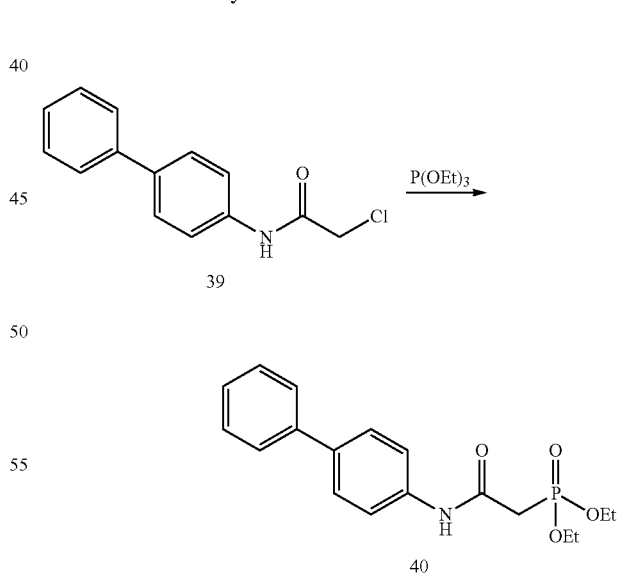

A mixture of N-(biphenyl-4-yl)-2-chloroacetamide 39 (200 mg, 0.8161 mmol) and triethyl phosphite 271 mg, 1.6323 mmol) was stirred at 140□ overnight. The reaction mixture was cooled to room temperature and was purified by combiflash to give intermediate 40 (77 mg, 27%) as a light yellow solid.

14.5 Synthesis of 41

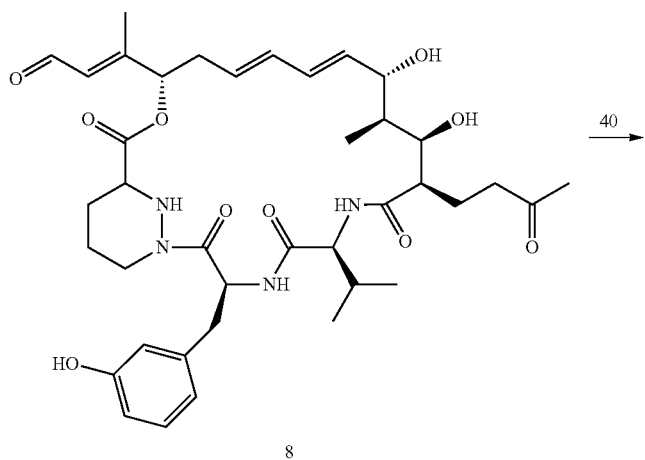

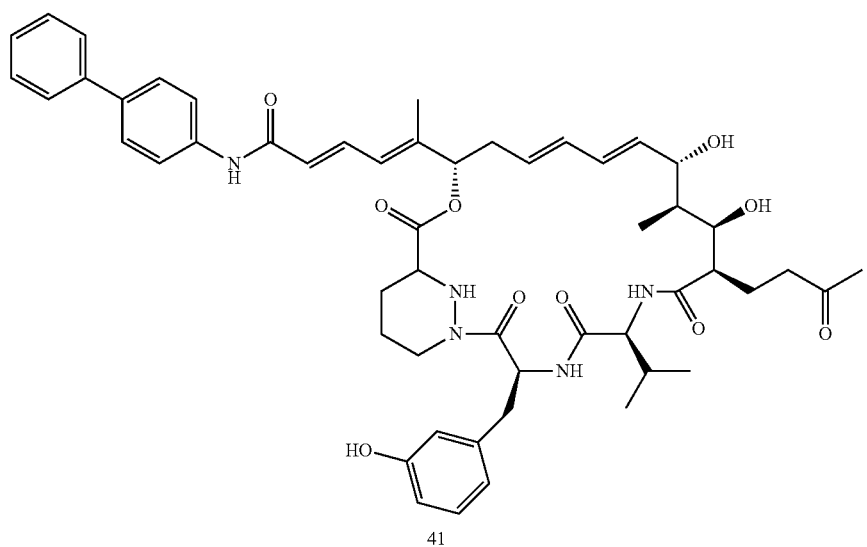

To a solution of 40 (65 mg, 0.188 mmol) in THF (1.0 mL) was added NaH (1.4 mg, 0.056 mmol) in anhydrous THF (0.2 mL) at 0° C. with stirring. The solution was then stirred at room temperature until it became clear. Then 8 (35 mg, 0.047 mmol) was added to the clear solution and the mixture stirred at rt for 3 h. The mixture was quenched with water (10 mL) and extracted with EA (20 mL*3). The organic layer was washed with brine and dried over $Na_2SO_4$, filtered, evaporated. The residue was purified by pre-HPLC to obtained 9.4 mg pure product 41 as a white solid (yield, 21%). LC-MS: 932 $[M+1]^+$. See FIG. 12 for $^1H$ NMR.

Example 15

Synthesis of 45

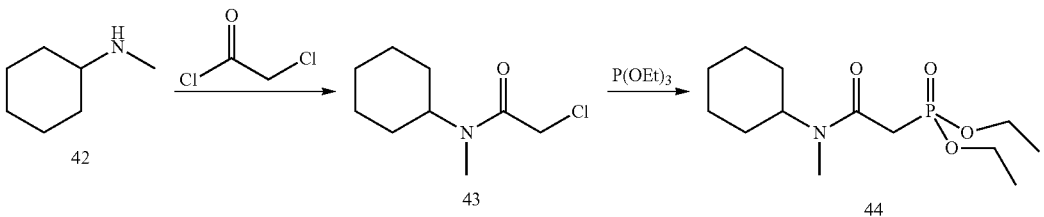

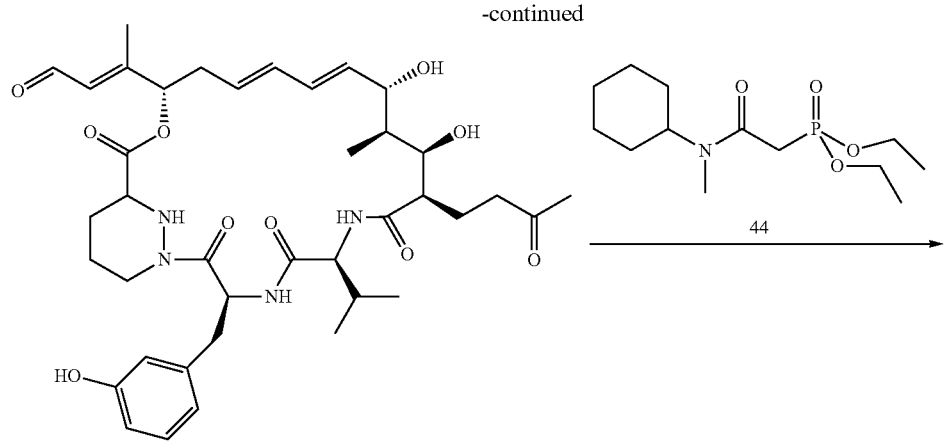

8

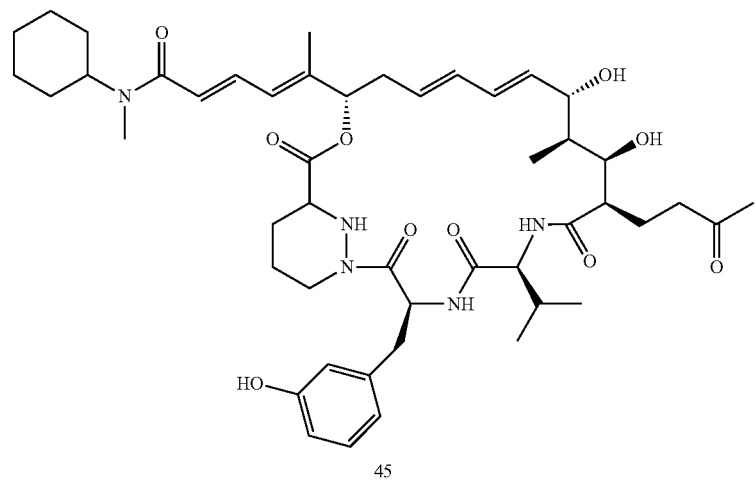

45

15.1 Synthesis of Intermediate 43

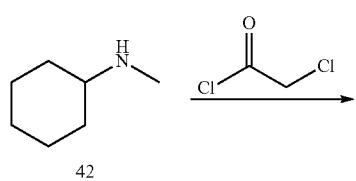

To a solution of 42 (1 g, 8.834 mmol), Et₃N (0.983 g, 9.724 mmol) in dry DCM (10 mL) was added dropwise chloroacetyl chloride (1.088 g, 9.724 mmol). The reaction mixture was stirred at 0-10° C. for 3 h, poured into ice water, and extracted with ethyl acetate. The organic layer was washed with brine and dried over Na₂SO₄, filtered, concentrated in vacuo to give a light yellow liquid (1.95 g) which was used to the next step without any further purification.

15.2 Synthesis of Intermediate 44

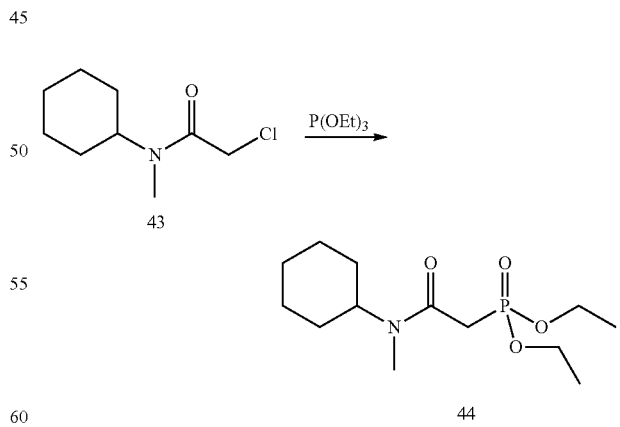

A mixture of 43 (crude, 400 mg, 2.11 mmol) and triethyl phosphite 701 mg, 4.22 mmol) was stirred at 140° C. overnight. The reaction mixture was cooled to room temperature and purified by combiflash to give intermediate 44 (265 mg, 43%) as a light yellow liquid.

15.3 Synthesis of 45

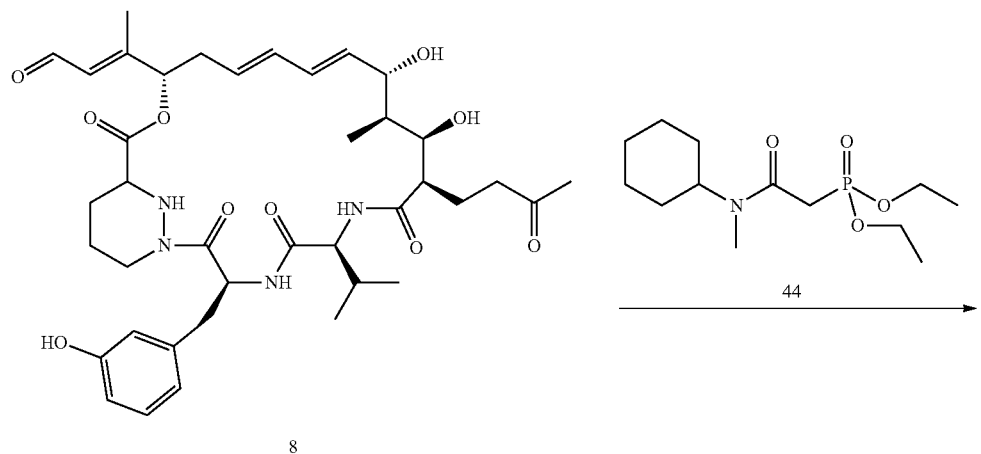

8

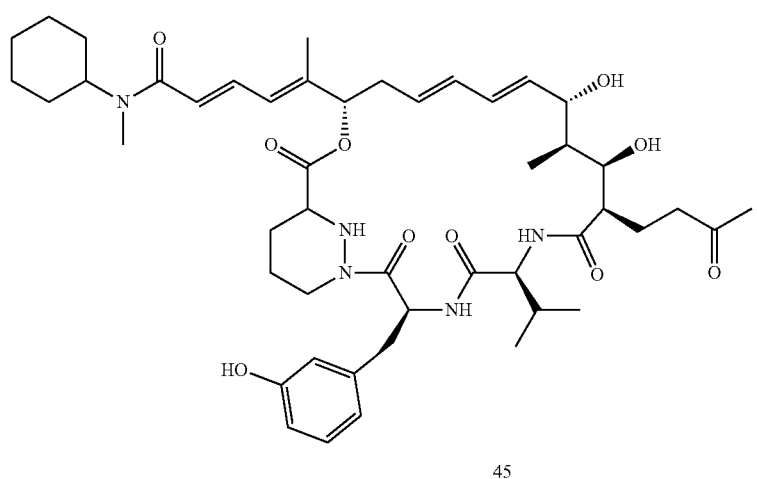

45

To a solution of 44 (55 mg, 0.188 mmol) in THF (1.0 mL) was added NaH (1.4 mg, 0.056 mmol) in anhydrous THF (0.2 mL) at 0° C. with stirring. The solution was then stirred at room temperature until it became clear. Then 8 (35 mg, 0.047 mmol) was added to the clear solution and the mixture stirred at rt for 3 h. The mixture was quenched with water (10 mL) and extracted with EA (20 mL*3). The organic layer was washed with brine and dried over $Na_2SO_4$, filtered, evaporated. The residue was purified by pre-HPLC to obtained 2.5 mg pure product 45 as a white solid (yield, 6%). LC-MS: 876 $[M+1]^+$. See FIG. 13 for $^1H$ NMR.

Example 16

Synthesis of 48

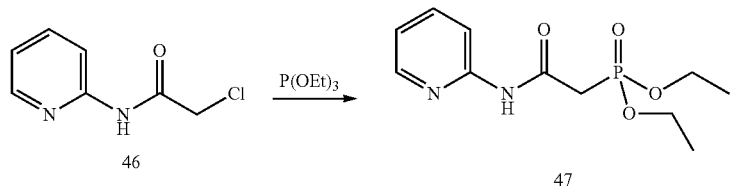

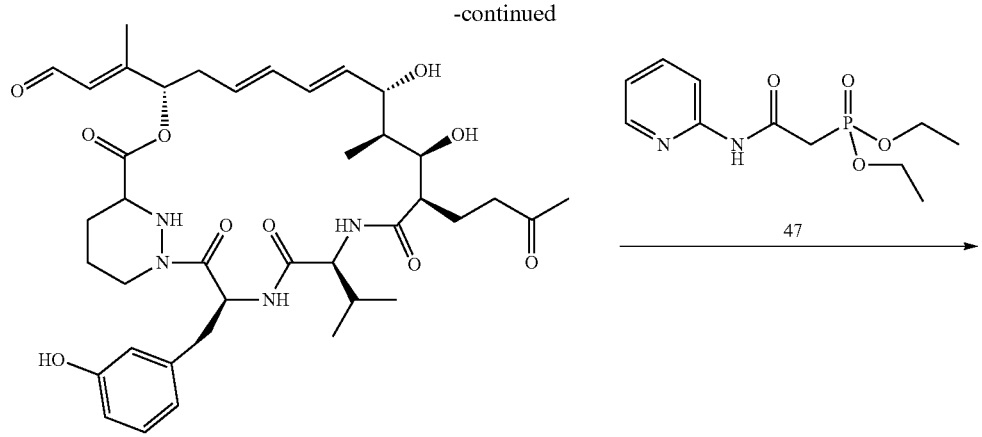
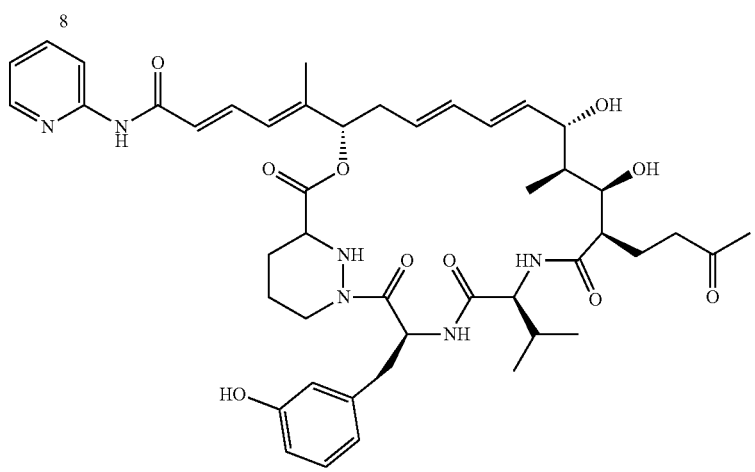
16.1 Synthesis of Intermediate 47
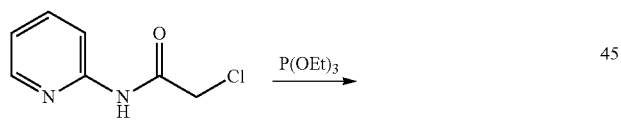
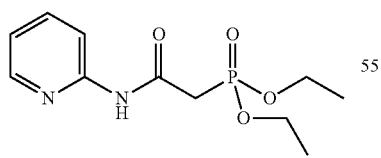
A mixture of 2-chloro-N-(pyridin-2-yl)acetamide (170 mg, 1.00 mmol) and triethyl phosphite (332 mg, 2.00 mmol) was stirred at 140° C. fpr 6 h. The reaction mixture was cooled to room temperature and was purified by combiflash to give intermediate 47 (48 mg, 18%).

16.2 Synthesis of 48

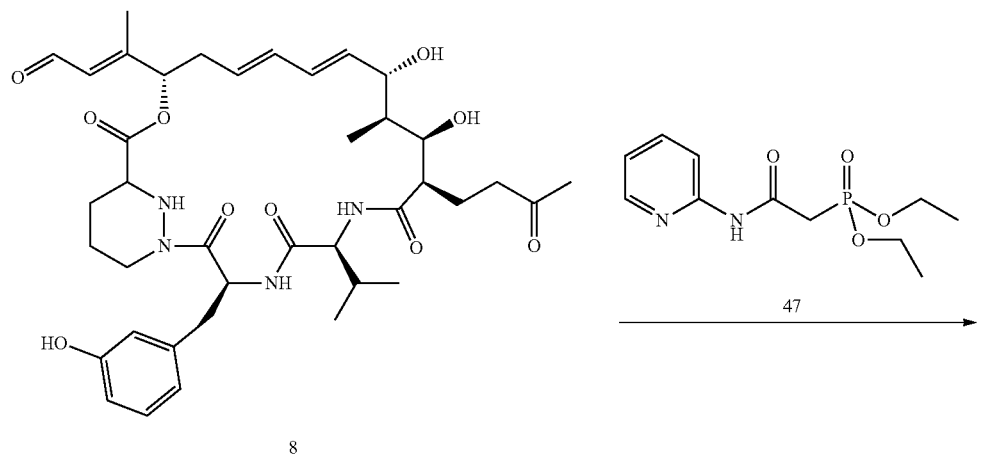

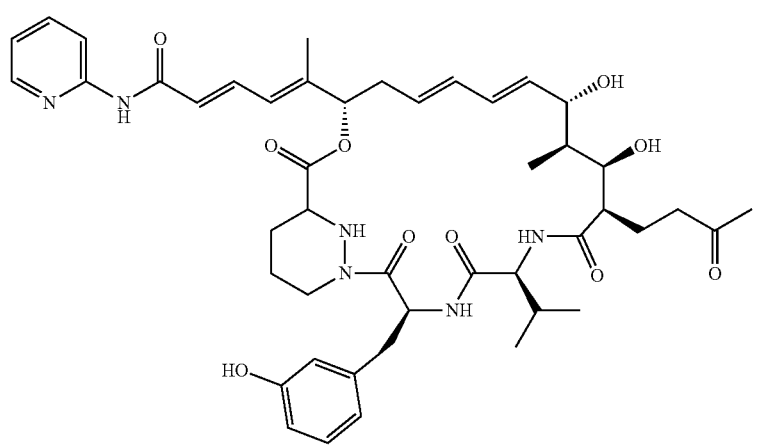

To a solution of 47 (51 mg, 0.188 mmol) in THF (1.0 mL) was added NaH (1.4 mg, 0.0564 mmol) in anhydrous THF (0.2 mL) at rt with stirring. Then 8 (35 mg, 0.047 mmol) was added to the clear solution and the mixture was stirred at rt for 3 h. The mixture was quenched with water (10 mL) and extracted with EA (30 mL*3). The organic layer was washed with brine and dried over $Na_2SO_4$, filtered, evaporated. The residue was purified by Prep HPLC to obtained 19.7 mg pure product 48 as a white solid (yield, 48.5%). LC-MS: 857 $[M+1]^+$.

Example 17

Synthesis of 51

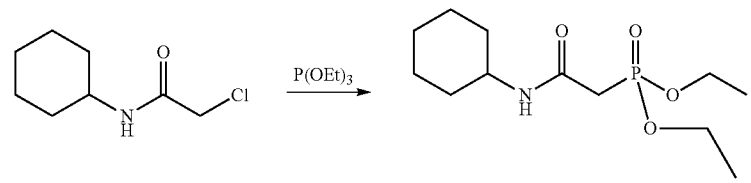

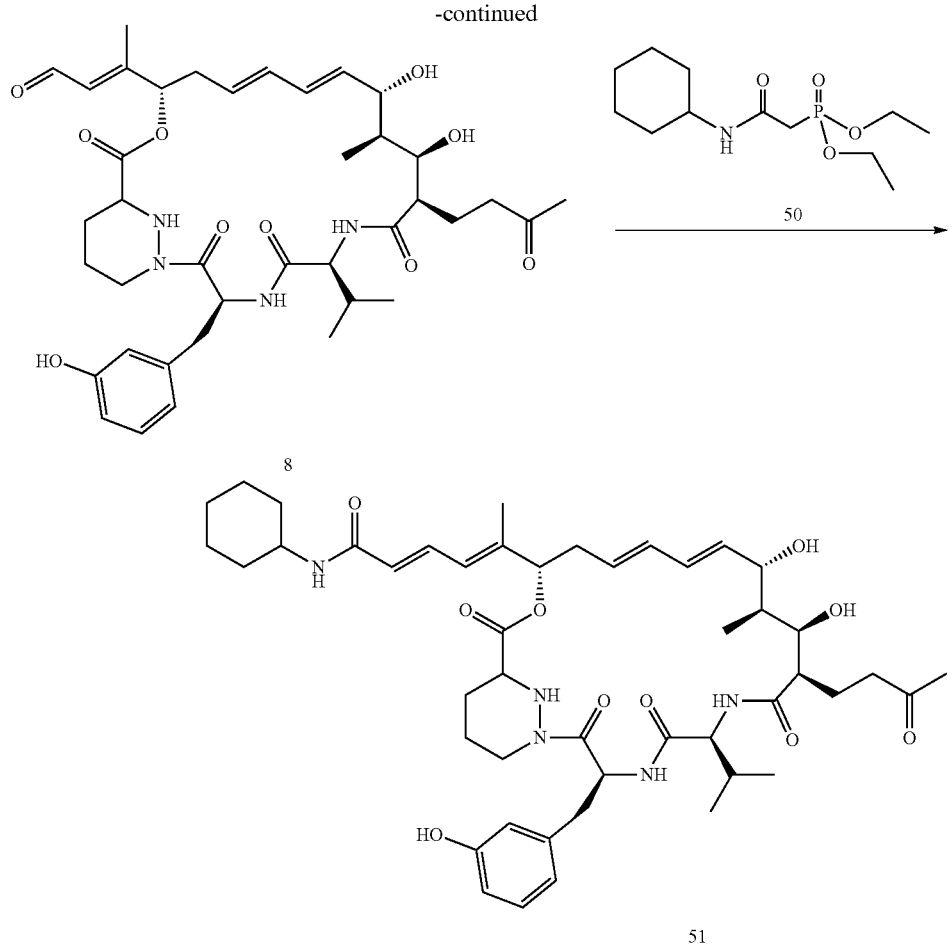
8
51
17.1 Synthesis of Intermediate 49
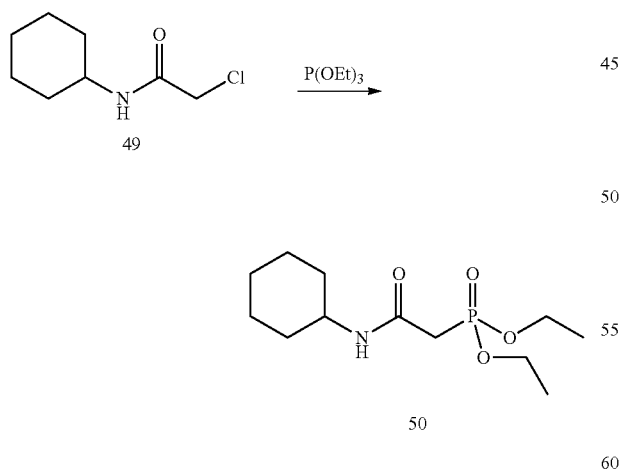
49 and 2 equivalents of triethyl phosphite were stirred at 120° C. overnight. The reaction mixture was cooled to room temperature and purified by crystalisation to give intermediate 50.

17.2 Synthesis of 51

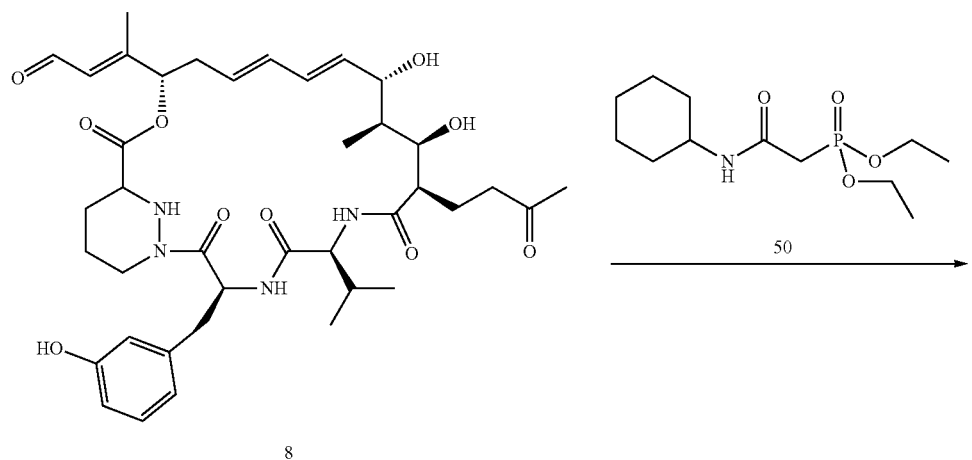

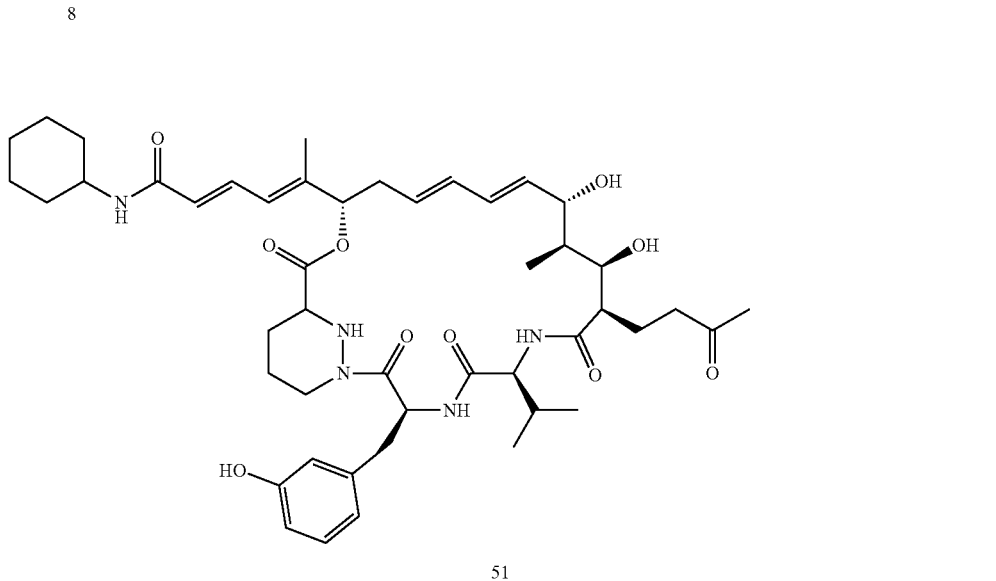

To a solution of 50 in THF was added NaH in anhydrous THF at 0° C. with stirring. The solution was then stirred at room temperature until it became clear. Then 8 (30 mg) was added to the clear solution and the mixture stirred at rt for 3 h. The mixture was quenched with water and extracted with ethyl acetate. The organic layer was washed with brine and dried over Na$_2$SO$_4$, filtered, evaporated. The residue was purified by prep-TLC and prep-HPLC to obtained 2.4 mg pure product 51 as a white solid. LC-MS: 862 [M+1]$^+$. See FIG. 14 for $^1$H NMR.

Example 18

Synthesis of 55

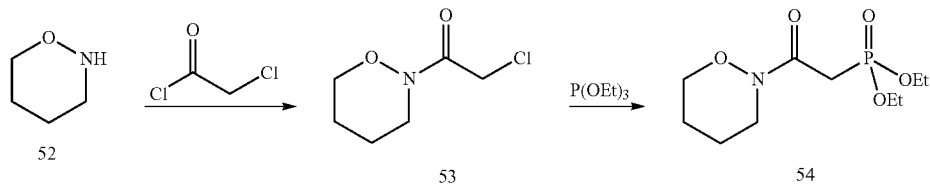

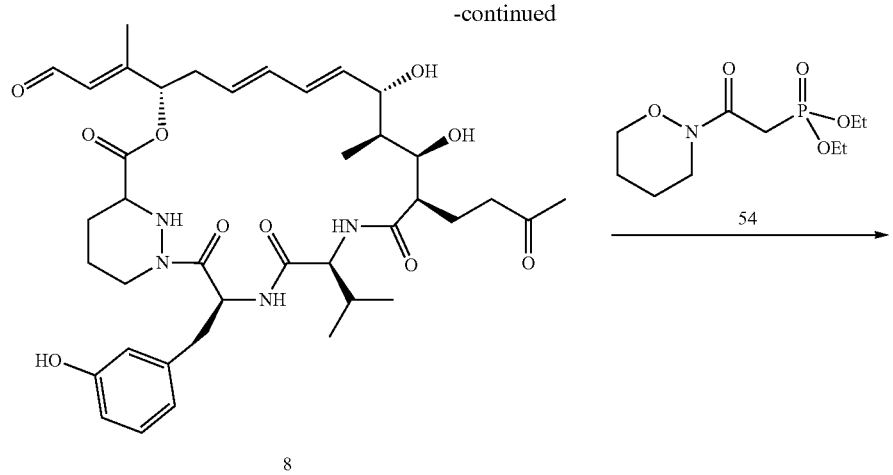

8

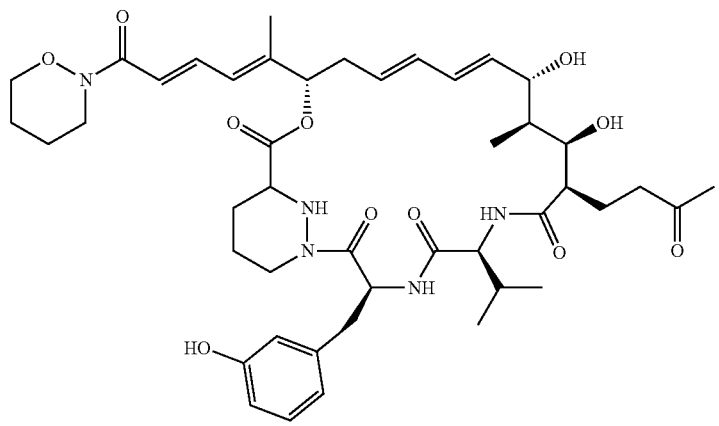

55

18.1 Synthesis of Intermediate 53

18.2 Synthesis of Intermediate 54

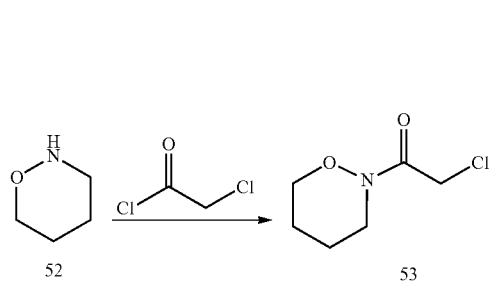

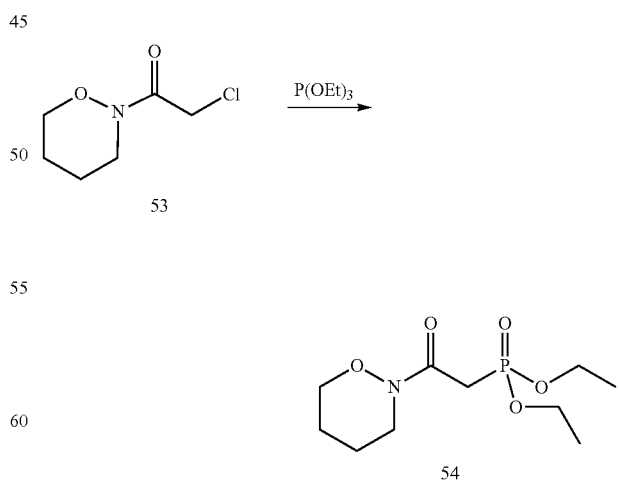

To a solution of 52, Et$_3$N in dry DCM was added dropwise chloroacetyl chloride. The reaction mixture was stirred at 0-10° C. for 30 minutes, and extracted with ethyl acetate. The organic layer was washed and to give a liquid which was used to the next step without any further purification.

A mixture of 53 and triethyl phosphite were stirred at 120° C. overnight. The reaction mixture was cooled to room temperature and was purified by combiflash to give intermediate 54.

18.3 Synthesis of 55

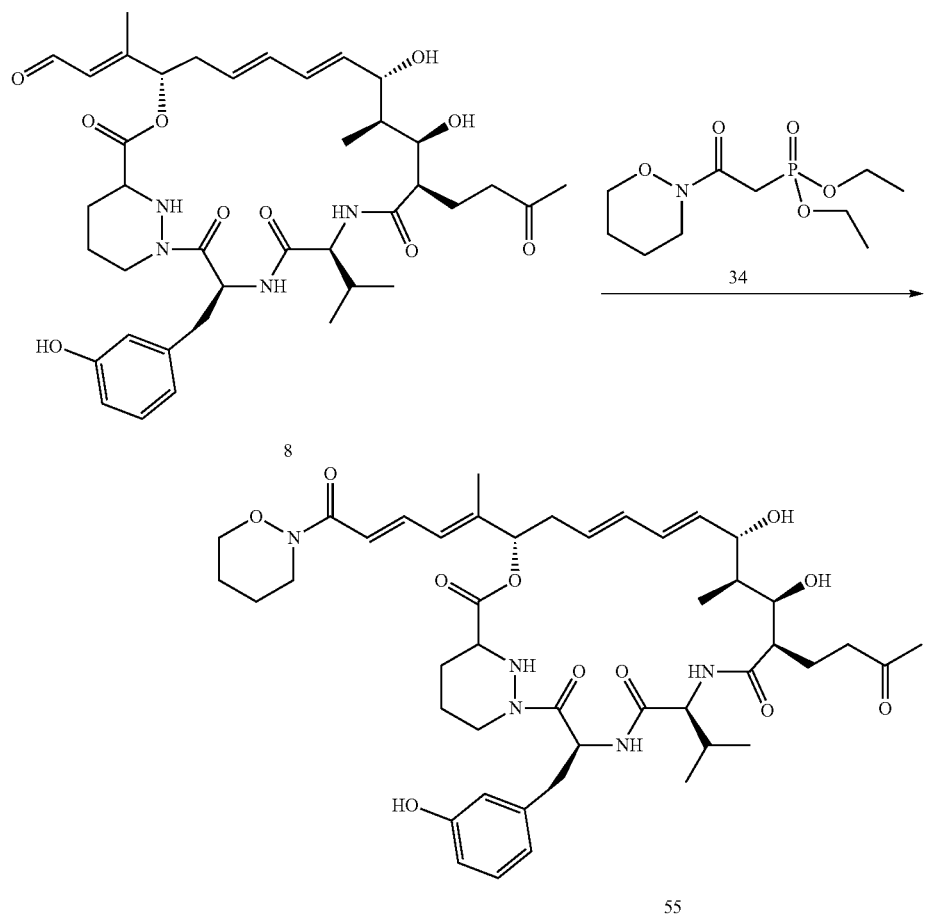

To a solution of 54 in THF was added NaH in anhydrous THF at 0° C. with stirring. The solution was then stirred at room temperature until it became clear. Then 8 was added to the clear solution and the mixture stirred at room temperature. The mixture was quenched with water and extracted with ethyl acetate. The organic layer was washed with brine and dried over $Na_2SO_4$, filtered, evaporated. The residue was purified by prep-HPLC to obtained 55 as a white solid. LC-MS: 850 $[M+1]^+$.

Example 19

Biological Data—In vitro Evaluation of HCV Antiviral Activity in the Replicon System Compounds were analysed in the replicon assay as described in the General Methods. Cyclosporine A, 1, sanglifehrin A, 5, and the hydroxymacrocycle, 6 were included as a comparison.

| Name | $EC_{50}$ | $EC_{90}$ | $CC_{50}$ | Selectivity index ($CC_{50}/EC_{50}$) |
|---|---|---|---|---|
| Cyclosporine A, 1 | 0.2 | 0.678 | 4.3 | 21.5 |
| Sanglifehrin A, 5 | 0.318 | 5.5 | 9.1 | 28.7 |

-continued

| Name | $EC_{50}$ | $EC_{90}$ | $CC_{50}$ | Selectivity index ($CC_{50}/EC_{50}$) |
|---|---|---|---|---|
| 6 | 8.4 | 39.7 | 83.6 | 9.9 |
| 10 | 0.162 | 0.921 | >100 | >617 |
| 13 | 0.204 | 1.2 | >100 | >490 |
| 16 | 0.56 | 4.6 | >100 | >179 |
| 19 | 8 | 60.2 | >100 | >80 |
| 22 | 0.349 | 6.2 | >100 | >287 |
| 25 | 1.6 | 8.5 | 48.4 | 30 |
| 28 | 0.628 | 4 | 17.7 | 28.2 |
| 29 | 0.293 | 1.5 | 20.2 | 68.4 |
| 32 | 0.309 | 1.1 | 2.1 | 6.9 |
| 35 | 1.66 | 0.737 | 39.7 | 238.1 |
| 41 | 0.208 | 1.1 | >100 | >481 |
| 45 | 0.148 | 1.9 | 66.4 | 449 |
| 48 | 0.167 | 0.737 | 39.7 | 238.1 |
| 51 | 0.336 | 4.2 | >100 | >298 |
| 55 | 0.125 | 0.691 | >100 | >800 |

As can be seen, 10, 13, 16, 22, 28, 29, 32, 41, 45, 48, 51 and 55 are all very potent in the Huh5.2 replicon assay (as shown by the low $EC_{50}$), with the majority of them also showing low cytotoxicity against the cell line (as shown by a high $CC_{50}$). The previously described macrocylic sanglifehrin hydroxymacrocycle, 6, is less potent at HCV inhibition, and cyclosporine A, 1 and sanglifehrin A, 5 both show more cytotoxicity.

Example 20

Solubility in PBS

Solubility of the compounds in PBS pH 7.4 was analysed as described in the General Methods. Cyclosporine A, 1 and sanglifehrin A, 5 were included as a comparison.

| Name | Solubility (μM) |
| --- | --- |
| Cyclosporine A, 1 | 51.3 |
| Sanglifehrin A, 5 | 9.4 |
| 10 | >100 |
| 13 | >100 |
| 19 | >100 |
| 22 | >100 |
| 25 | 96 |
| 28 | 78 |
| 29 | 66 |
| 32 | 33 |
| 48 | 61 |
| 55 | >100 |

As can be seen, the compounds of the invention, 10, 13, 19, 22, 25, 28, 29, 48 and 55 all have increased solubility when compared to sanglifehrin A (5) and over cyclosporine A (1).

Example 21

Biological Data—Activity Against HIV

Compounds were analysed in an HIV antiviral assay using immortalized and primary target cells as described in the General Methods. Cyclosporine A, 1, and sanglifehrin B, 7, were included as a comparison.

| Name | HeLa cells $EC_{50}$ (μM) | T cells $EC_{50}$ (μM) | CD4+ T-lymphocytes $EC_{50}$ (μM) | Macrophages $EC_{50}$ (μM) |
| --- | --- | --- | --- | --- |
| Cyclosporine A, 1 | 5.3 | 3.5 | 3.3 | 9.4 |
| 29 | 0.4 | 0.2 | 0.21 | 0.31 |
| 48 | 0.25 | 0.11 | 0.14 | 0.21 |
| 55 | 0.31 | 0.22 | 0.15 | 0.23 |

As can be seen, the compounds of the invention 29, 48, 55 are all significantly more potent than cyclosporine A, 1 at inhibiting HIV infection of four cell types.

Example 22

Biological Data—Activity Against HBV

Compounds were analysed in the replicon assay as described in the General Methods. Cyclosporine A, 1, and sanglifehrin A, 7, were included as a comparison.

| Name | HBV $EC_{50}$ (μM) | $TC_{50}$ (μM) | Therapeutic index ($TI_{50}$) |
| --- | --- | --- | --- |
| Cyclosporine A, 1 | 5.22 | 7.53 | 1.44 |
| 29 | <0.1 | >32 | >320 |
| 48 | >32 | >32 | 1 |

As can be seen, the compound of the invention, 29, is remarkably potent at inhibiting replication of HBV, and shows no cytotoxicity at concentrations up to 32 μM, leading to a large therapeutic index.

Example 23

Biological Data—Assessment of Immunosuppressive Activity in a mixed Lymphocyte Reaction (MLR)

Immunosuppressive activity is an unwanted side effect for use as an antiviral therapy. Therefore the compounds were tested in a mixed lymphocyte reaction (MLR) as described in the general methods. Cyclosporine A, 1, and sanglifehrin A, 5, were included as a

| Name | Human MLR $IC_{50}$ (μM) |
| --- | --- |
| Cyclosporine A, 1 | 0.003 |
| Sanglifehrin A, 5 | 0.215 |
| 48 | 1.06 |
| 55 | 1.45 |

As can be seen, the compounds of the invention, 48 and 55, both show very low levels of immunosuppressive activity, and are all less immunosuppressive than CsA, 1, and SfA, 5.

Example 23

Biological Data—Inhibition of Cyclophilin D

To investigate the interaction of test compounds with cyclophilin D, the CypD-NS5A disruption system was used, as described in the general methods.

| Name | CypD-NS5A disruption $IC_{50}$ (μM) |
| --- | --- |
| Cyclosporine A, 1 | 0.91 |
| Sanglifehrin A, 5 | 0.37 |
| 29 | 0.25 |
| 48 | 0.38 |
| 55 | 0.23 |

As can be seen, the compounds of the invention, 29, 48 and 55, all show potent disruption of the CypD-NS5A complex, at a more potent level than CsA, 1, and SfA, 5. It was also confirmed that these assays gave comparable data (and similar rank orders) to a PPIase assay measuring direct inhibition of CypD isomerase activity (data not shown—see general methods for details of methodology).

Example 24

Generation of bio-engineered *Streptomyces* sp. A92-308110 (DSM9954) (BIOT-4370) strains in which the reductive loop of module 12 of the biosynthetic cluster for sanglifehrin biosynthesis is replaced by the reductive loop from rapamycin module 13 or sanglifehrin module 6 using a reductive loop swap strategy.

The reductive loop of sanglifehrin module 12 contains a ketoreductase which is responsible for the hydroxyl group at C17 of the sanglifehrin molecule. The reductive loops from both rapamycin module 13 and sanglifehrin module 6 contain all of the functional domains to result in full processing of the beta-keto group to result in a methylene; specifically they contain a keto reductase to reduce the keto to a hydroxyl group, a dehydratase to remove water and result in a double bond, and an enoyl reductase to reduce the double bond to a methylene. Vectors pMGo136 and pMGo137 are vectors to engineer the replacement of the reductive loop of module 12 of the biosynthetic cluster for sanglifehrin biosynthesis with the reductive loop from rapamycin module 13 or sanglifehrin module 6, respectively.

Positions of DNA fragments used in this example are given according to the sequence available in January 2011 but reported as approximate because Genbank DNA sequences can be updated.

The vectors are constructed as follows:

24.1 The DNA Homologous to the Upstream Flanking Region of the Reductive Loop of Sanglifehrin Module 12.

This 2072 bp DNA fragment (SEQ ID NO: 1) shown in FIG. 16 contains a region of homology upstream of the reductive loop of sanglifehrin module 12 (approximately from 86654 bp-88798 bp in the published sequence Genbank accession number FJ809786.1) along with additional sequences both 5' and 3' to incorporate restriction enzyme sequences to aid cloning. This fragment (SEQ ID NO:1) was synthesised by GenScript (860 Centennial Ave., Piscataway, N.J. 08854, USA) and provided, according to the GenScript protocol with 12 protective flanking bases on each side which do not participate in the cloning beyond this point, in pUC57 resulting in plasmid pMGo128.

24.2 Cloning of DNA Homologous to the Downstream Flanking Region of the Reductive Loop of Sanglifehrin Module 12.

Oligos MGo013 (SEQ ID NO: 2) and MGo014 (SEQ ID NO: 3) were used to amplify a 1994 bp DNA fragment (SEQ ID NO: 4) in a standard PCR reaction using cosmid pTL3102 (Qu et al. 2011) DNA as the template and KOD Hot Start DNA polymerase. A 5' extension was designed in each oligo to introduce restriction sites to facilitate cloning of the amplified fragment. Alternatively, genomic DNA from *Streptomyces* sp. A92-308110 (DSM9954) (BIOT-4370) could have been used as the template for this PCR reaction to give the same DNA fragment, or the DNA fragment could be obtained by DNA synthesis for example using GenScript (860 Centennial Ave., Piscataway, N.J. 08854, USA). The resulting 1995 bp PCR product (SEQ ID NO: 4) contains a region of homology downstream of the reductive loop of sanglifehrin module 12 (approximately from 90415 bp-92381 bp in the published sequence genbank accession number FJ809786.1) with an undesired insertion, G at position 1978 (see FIG. 17; inserted G is bold and underlined). The 1995 bp PCR product (SEQ ID NO: 4) was cloned into pUC19 (New England Biolabs) that had been linearised with SmaI and dephosphorylated, resulting in plasmid pMGo123.

```
                                              (SEQ ID NO: 2)
MGo013 5' GCTCTCGAGGCGGCTAGCCTCCCTGCCCGAGGCCG
             XhoI     NheI (SEQ ID NO: 3)
MGo014 5' AGAAAGCTTCGGCCCGGTCGGCGCCCTGGGCC
             HindIII
```

The orientation of the 1995 bp PCR product (SEQ ID NO: 4) in pUC19 was such that the HindIII site on the insert was adjacent to the HindIII site of the pUC19 polylinker. The sequence of the insert in pMGo123 was confirmed by sequencing.

In order to avoid the region containing the additional base, a shorter downstream region was targeted as follows: Oligos MGo037 (SEQ ID NO: 5) and MGo038 (SEQ ID NO: 6) were used to amplify a 1956 bp DNA fragment (SEQ ID NO: 7) in a standard PCR reaction using plasmid pMGo123 DNA as the template and KOD Hot Start DNA polymerase. A 5' extension was designed in each oligo to introduce restriction sites to facilitate cloning of the amplified fragment. The 1956 bp PCR product (SEQ ID NO: 7) contains a region of homology downstream of the reductive loop of sanglifehrin module 12 (approximately from 90415 bp-92343 bp in the published sequence Genbank accession number FJ809786.1). The 1956 bp PCR product (SEQ ID NO: 7) was cloned into pUC19 (New England Biolabs) that had been linearised with SmaI and dephosphorylated, resulting in plasmid pMGo125.

```
                                              (SEQ ID NO: 5)
MGo037 5' GCTCTCGAGGCGGCTAGCCTCCCTG
             XhoI     NheI (SEQ ID NO: 6)
MGo038 5' AAAAAGCTTGCGGGGTCGGGGGTGCCGGCGGCGAC
             HindIII
```

The orientation of the 1956 bp PCR product (SEQ ID NO: 7) in pUC19 was such that the HindIII site on the insert was adjacent to the HindIII site of the pUC19 polylinker. The sequence of the insert in pMGo125 was confirmed by sequencing.

24.3 Cloning Strategy for Generating pMGo136 and pMGo137.

The upstream and downstream regions of homology of the sanglifehrin reductive loop of module 12 are cloned together as follows: The 2065 bp upstream region is excised from pMGo128 by digestion with EcoRI and XhoI and the 1944 bp downstream region is excised from pMGo125 bp digestion with XhoI and HindIII. Both fragments are cloned together into the large backbone fragment generated when pUC19 (New England Biolabs) is digested with EcoRI and HindIII in a three part ligation. Plasmids containing both inserts correctly cloned are identified by restriction enzyme analysis, one correct plasmid is designated pMGo130.

pMGo130 is designed such that a reductive loop on a suitable NheI/BglII fragment, can be cloned into the NheI and BglII sites to yield a portion of a type I PKS module in which the DNA sequence is in frame and can be translated to give an amino acid sequence. The exact positioning of these sites in the in-coming loop is crucial in maintaining the frame of the sequence and this translation into a functional amino acid sequence.

Source of Rapamycin Module 13 Reductive Loop: Rapamycin module 13 reductive loop has been used previously as a donor loop in other systems (eg. Gaisser et al., 2003). Rapamycin module 13 loop, flanked by appropriate regions of homology from avermectin module 2 is present in pPF137 (Gaisser et al., 2003). pPF137 is constructed from pJLK137 as described in Gaisser et al 2003. The full description of the construction of pJLK137 is contained within International patent application WO00/01827/1998 and references therein. A brief summary follows: The rapamycin module 13 loop was isolated bp PCR amplification using the following oligos.

```
                                              (SEQ ID NO: 8)
5' TAAGATCTTCCGACCTACGCCTTCCAAC
      BglII
```

-continued (SEQ ID NO: 9)
5' TA<u>ATGCAT</u>CGACCTCGTTGCGTGCCGCGGT
      NsiI which contain introduced restriction enzyme sites, and using the template rapamycin cos 31 (Schwecke et al. 1995). This fragment was cloned into pUC18 previously digested with SmaI and dephoshorylated to give pJLK120. This loop was then introduced into pJLK133, which was constructed as follows: The linker was removed from pJLK117 on a BglII/NheI fragment and cloned between 2 regions of homology to avermectin module 2 to give pJLK133. The rapamycin module 13 reductive loop was cloned from pJLK120 as a BglII/NsiI fragment into BglII/NsiI digested pJLK133.

pJLK117 (refer to International patent application WO00/01827/1998 and references therein) is an expression plasmid containing a PKS gene comprising the erythromycin loading module, the first and the second extension modules of the erythromycin PKS and the erythromycin chain terminating thioesterase, except the DNA segment between the end of the acyltransferase (AT) and the beginning of the acyl carrier protein (ACP) has been substituted by a synthetic oligonucleotide linker containing the recognition sites of the following restriction enzymes; AvrII, BglII, SnaBI, PstI, SpeI, NsiI, Bsu361, and NheI and was made in multiple steps as described in the patent application. These restriction enzyme sites were selected because they can be incorporated with minimal disruption to the original protein sequence in module 2 of the erythromycin PKS. The first linker containing vector, pJLK114 contains the generated by annealing the oligos PIf (SEQ ID NO: 10) and PIb (SEQ ID NO: 11).

P1f
(SEQ ID NO: 10)
5' CTAGGCCGGGCCGGACTGGTAGATCTGCCTACGTATCCTTTCCAGG

GCAAGCGGTTCTGGCTGCAGCCGGACCGCACTAGTCCTCGTGACGAGGG

AGATGCATCGAGCCTGAGGGACCGGTT

P1b
(SEQ ID NO: 11)
5' AACCGGTCCCTCAGGCTCGATGCATCTCCCTCGTCACGAGGACTAG

TGCGGTCCGGCTGCAGCCAGAACCGCTTGCCCTGGAAAGGATACGTAGG

CAGATCTACCAGTCCGGCCCGGC

The plasmid pJLK117 was constructed by replacing the 5' end of the linker of pJLK114 with a fragment in which the only difference is that the HpaI site, GTTAAC is replaced by an NheI site, GCTAGC.

The source of the rapamycin module 13 reductive loop in this example is pPF137. One skilled in the art will appreciate that it is not necessary to follow this complex series of steps in order to obtain this fragment. The same fragment may be obtained as follows: First the multiple cloning region of pUC18, or pUC19 may be replaced by a synthetic linker containing the sites BglII, NsiI and NheI for example this could be achieved by digesting the pUC vector with EcoRI and HindIII and using two oligonucleotides to make a synthetic linker with the sites listed above, which, when annealed, leave the appropriate overhangs to ligate into the digested backbone. Incorporating the sequence of the linker of pJLK117 between the NsiI and NheI sites will provide part of the required sequence and the remainder can be obtained bp PCR amplification from a cosmid such as rapamycin cos 31 or genomic DNA of *Streptomyces hygroscopicus* NRRL 5491 and the oligos shown as SEQ ID NO: 08 and SEQ IP NO: 09. This provide the rapamycin module 13 loop on a BglII/NsiI fragment which can be cloned into the BglII/NsiI sites of the modified pUC vector and then the desired loop cloned out as a BglII/NheI fragment.

Alternatively, the rapamycin module 13 loop could be amplified directly as a BglII/NheI fragment for example using the oligos SEQ ID NO: 8 as shown above and SEQ ID NO:12

(SEQ ID NO: 12)
5' TAGCTAGCCGGGCGCTCAGGGGCTGCGAGCCGACCT

The rapamycin module 13 reductive loop was cloned from pPF137 into pKC1139WMB02 as a BglII/NheI fragment to give pKC1139WMB02-137. pKC1139WMB02 is a pKC1139-based plasmid and contains a 7.8 kb DNA fragment containing the rapamycin module 11 reductive loop and flanking regions. It has been engineered such that the reductive loop can be excised as a BglII/NheI fragment and replaced with other loops. pKC1139WMB02-137 was constructed to effect a loop swap in rapamycin and contains the rapamycin module 13 reductive loop with flanking regions from rapamycin module 11. In this example, rapamycin module 13 loop is cloned from pKC1139WMB02-137 as a BglII/NheI fragment. This is the identical fragment that can be obtained from pPF137, or pJLK120 or by carrying out an equivalent PCR reaction using the oligo sequences provided and genomic DNA and cloning it into a suitable vector such as pUC18 or pUC19.

The sanglifehrin reductive loop of module 6 is obtained as follows: Oligos MGo019 (SEQ ID NO: 13) and MGo020 (SEQ ID NO: 14) are used to amplify a 3176 bp DNA fragment (SEQ ID NO: 15) in a standard PCR reaction using KOD Hot Start DNA polymerase and the 5 kb-6 kb fraction of AlwNI digested genomic DNA from *Streptomyces* sp. A92-308110 (DSM9954) (BIOT-4370) as the template. This fraction contains the 5402 bp AlwNI fragment of the sanglifehrin gene cluster (approximately from 56578 bp-61979 bp in the published sequence genbank accession number FJ809786.1). Alternatively, undigested genomic DNA from *Streptomyces* sp. A92-308110 (DSM9954) (BIOT-4370) is used as the template. Genomic DNA is obtained using the Edge BioSystems bacterial genomic DNA purification kit (Edge BioSystems, 201 Perry Parkway, Suite 5, Gaithersburg, Md. 20877, USA). A 5' extension is designed in each oligo to introduce restriction sites to facilitate cloning of the amplified fragment in-frame with the flanking regions. The 3176 bp PCR product (SEQ ID NO: 15) contains the reductive loop of sanglifehrin module 6 (approximately from 57166 bp-60326 bp in the published sequence genbank accession number FJ809786.1). The 3176 bp PCR product (SEQ ID NO: 15) is cloned into pUC19 (New England Biolabs) that has been linearised with SmaI and dephosphorylated, resulting in plasmid pMGo127.

(SEQ ID NO: 13)
MGo019 5' CCGT<u>AGATCT</u>GCCCACCTACGCCTTCCAGCGCG
              BglII (SEQ ID NO: 14)
MGo020 5' TCCG<u>GCTAGC</u>CGTTGGGGCAGCGCGG
              NheI pKC1139WMB02-137 and pMGo127 are each digested with NheI and BglII to isolate the rapamycin module 13 reductive loop and the sanglifehrin module 6 reductive loop. Each loop is cloned into pMGo130 digested with NheI and BglII. Insert-containing plasmids are analysed by restriction enzyme analysis, one correct plasmid containing rapamycin module 13 reductive loop is designated pMGo132 and one correct plasmid containing sanglifehrin module 6 reductive loop is designated pMGo133.

pMGo132 and pMGo133 each contain an appropriate DNA insert to effect a reductive loop swap in sanglifehrin module 12 by double recombination. Each insert is cloned as an EcoRI/HindIII fragment into pKC1139 digested with EcoRI and HindIII to provide suitable plasmid functions for transformation of *Streptomyces* sp. and selection of transformants as well as a temperature sensitive origin. Insert-containing plasmids are analysed by restriction enzyme analysis, one correct plasmid containing the fragment with rapamycin module 13 reductive loop is designated pMGo136 and one correct plasmid containing the fragment with sanglifehrin module 6 reductive loop is designated pMGo137.

23.4 Conjugation of *Streptomyces* sp. A92-308110 (DSM9954) (BIOT-4370) and Engineering of a Reductive Loop Swap in Sanglifehrin Module 12.

Plasmids pMGo136 and pMGo137 are transformed into *E. coli* ET12567 pUZ8002 using standard techniques and selected on 2TY plates containing apramycin (50 μg/mL), kanamycin (25 μg/mL) and chloramphenicol (12.5 μg/mL). The resulting strains are used to inoculate 3 mL of liquid 2TY containing apramycin (50 μg/ml), kanamycin (25 μg/mL) and chloramphenicol (12.5 μg/mL) and incubated overnight at 37° C., 250 rpm. 0.8 mL of each culture is used to inoculate 10 mL liquid 2TY containing apramycin (50 μg/mL), kanamycin (25 μg/mL) and chloramphenicol (12.5 μg/mL) in a 50 mL Falcon tube and incubated at 37° C. 250 rpm until $OD_{600nm}$ ~0.5 is reached. The resulting cultures are centrifuged at 3500 rpm for 10 min at 4° C., washed twice with 10 mL 2TY medium using centrifugation to pellet the cells after each wash. The resulting pellets are resuspended in 0.5 mL 2TY and kept on ice ready for use. This process is timed to coincide with the completion of preparation of *Streptomyces* spores described below.

Spores of *Streptomyces* sp. A92-308110 (DSM9954) (BIOT-4370) are harvested from a 1-2 week old confluent plate by resuspending in ~3 mL 20% glycerol and splitting equally between 2 Eppendorf tubes. Alternatively, ~1.5 mL of a cryopreserved spore suspension prepared in the same way is used. Spores are centrifuged (6000 rpm, 5 min room temperature) and washed twice with 1 mL 50 mM TES buffer before resuspending in 0.5 mL 50 mM TES buffer. This tube is heat shocked at 50° C. for 10 min in a water bath before adding 0.5 mL of TSB medium and incubating in an Eppendorf Thermomixer compact at 37° C. for 4-5 hours.

The prepared *E. coli* ET12567 pUZ8002 pMGo136 and *E. coli* ET12567 pUZ8002 pMGo137 are each mixed with BIOT-4370 at ratios 1:1 (100 μL each strain) and 1:3 (100 μL *E. coli*+300 μL BIOT-4370) and immediately spread on R6 plates and transferred to a 37° C. incubator. After approximately 2 hours incubation these plates are overlaid with 2 mL of sterile water containing nalidixic acid to give a final in-plate concentration of 50 μg/L. Plates are returned to the 37° C. incubator overnight before overlaying with 2 mL of sterile water containing apramycin to give a final in-plate concentration of 20-25 μg/L. Alternatively, the plates are initially incubated for 16-18 hours, then overlaid with the nalidixic acid solution and allowed to dry for 1-2 hours before being overlaid with the apramycin solution. Ex-conjugant colonies appear after ~4-7 days and are patched onto ISP4 media containing apramycin (25 μg/L) and nalidixic acid (50 mg/L) and incubated at 37° C. Incubation at 37° C. in the presence of apramycin should ensure that integration of the plasmid occurs, since the temperature sensitive origin does not function at this temperature. Integration should occur in one of the flanking regions where there is homology between the genome and the plasmid insert. Once adequate mycelial growth is observed strains are repatched to ISP4 media containing apramycin (25 μg/L) at 37° C. and allowed to sporulate. Strains are then subcultured three times (to promote removal of the temperature sensitive plasmid) by patching to ISP4 (without antibiotic) and incubating at 37° C. for 3-4 days each time. Strains are finally patched onto ISP4 and incubated at 28° C. to allow for sporulation (5-7 days). Spores are harvested and serially diluted onto ISP4 plates at 28° C. to allow selection of single colonies. Sporulated single colonies are doubly patched to ISP4 plates with and without apramycin (25 μg/L) to identify colonies which loose the plasmid and allowed to grow ~7 days before testing for production of sanglifehrins and sanglifehrin analogues. Strains selected for analysis are those that do not grow in the presence of apramycin, indicating loss of the resistance marker desirably by secondary recombination.

24.5 Screening Strains for Production of Sanglifehrins and Sanglifehrin Analogues in Falcon Tubes A single ~7 mm agar plug of each well sporulated patch is used to inoculate 7 mL of sterile SM25-3 media and incubated at 27° C. 200 rpm in a 2 inch throw shaker. After 48 hours of growth 0.7 mL of each culture is transferred to a sterilised falcon tube containing 7 mL of SGP6 media (30 g/L Nutrisoy (Toasted Soy Flour), 60 g/L glycerol, 21 g/L MOPS; pH 6.8) with 5% HP20 resin. Cultures are grown at 24° C. 300 rpm on a 1 inch throw shaking incubator for 5 days before harvest. 0.8 mL of each bacterial culture is removed and aliquoted into a 2 mL Eppendorf tube ensuring adequate dispersal of the resin in throughout the culture prior to aliquoting. 0.8 mL acetonitrile and 15 μL of formic acid are added and the tube mixed for 30 min. The mixture is cleared by centrifugation and 150 μL of the extract removed into a HPLC vial and analysed by HPLC.

24.6 Analysis of Strains for Reversion to Wild Type or Module 12 Loop Swap.

Extracts of strains are analysed by HPLC. Strains that produced sanglifehrin A and B are not analysed further as this result indicates reversion to wild type. Strains lacking sanglifehrin A and B production and showing peaks consistent with the production of 17-deoxy-sanglifehrin A and 17-deoxy-sanglifehrin B are taken forward.

Example 25

Isolation of 17-Deoxysanglifehrin A and Generation of Semisynthetic Derivatives

A strain producing 17-deoxy sanglifehrin A and/or B is then grown using a similar method to that described in Example 1, the compound isolated using a similar method to that described in Example 2, and the aldehyde generated using a similar method to that described in example 3. This is then used as a template for semisynthesis as described to generate compounds of formula 1.

Example 26

Synthesis of 144

Synthesis of Intermediate 146

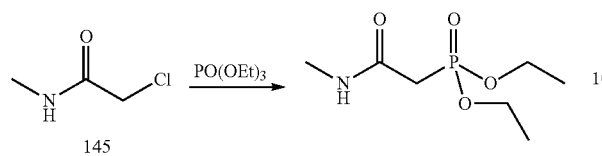

A mixture of N-methylchloroacetamide (145, 200 mg, 1.87 mmol) and triethyl phosphite (0.67 mL, 3.74 mmol) was stirred at 130° C. for 8 h. The reaction mixture was cooled to room temperature and was purified by Prep HPLC to give intermediate 146 (60 mg, 15%) as colourless oil.

Synthesis of 147

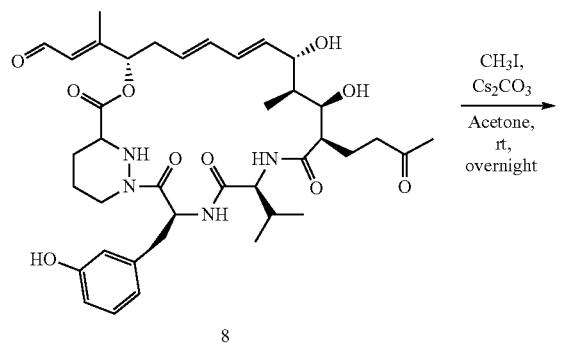

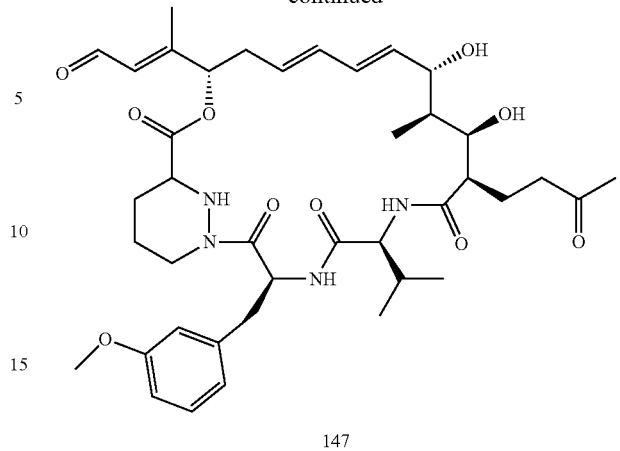

CH$_3$I (13.5 uL, 0.203 mmol) was added to a stirred acetone (4.0 mL) solution of 8 (50 mg, 0.068 mmol) and Cs$_2$CO$_3$ (75 mg, 0.203 mmol) at room temperature. The mixture was stirred at room temperature overnight and concentrated in vacuo. The residue was extracted with ethyl acetate and washed with water. The organic layers was dried with Na$_2$SO$_4$, filtered and evaporated, the residue was purified by Prep TLC (Acetone/Petroleum=1.2/1) to get 22 mg 147 (86% pure) which was used directly for the next step.

Synthesis of 144

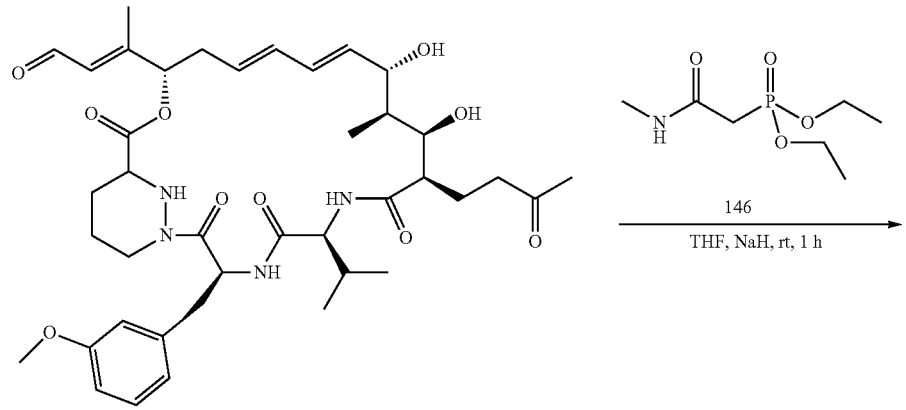

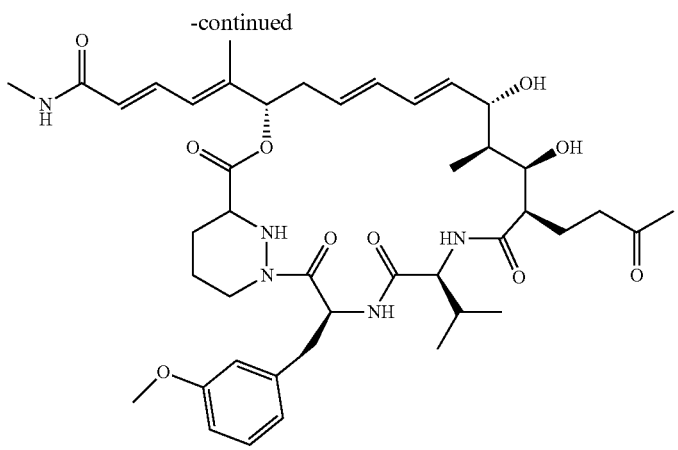

144

To a suspension of NaH (1.052 mg, 0.044 mmol) in anhydrous THF (0.2 mL) was added dropwise a solution of 146 (24.5 mg, 0.117 mmol) in anhydrous THF (0.2 mL) under $N_2$ atmosphere at −3° C. with stirring. The solution was then stirred at room temperature until it became clear. A solution of 147 (22 mg) in anhydrous THF (0.6 mL) was added dropwise to the clear solution and the mixture stirred at room temperature for 30 minutes. The mixture was quenched with water and THF was evaporated under reduced pressure. The residue was extracted with ethyl acetate. The organic layer was washed with brine then dried. The solvent was removed in vacuo and the residue was purified by preparative TLC (Acetone/Petroleum=1.3/1) to obtained 12 mg crude 144 which was purified again by preparative HPLC to yield the product as a white solid (5 mg, 20%). LC-MS: 808 [M+H]$^+$.

References

Aparicio J F, Molnar, I, et al. (1996) "Organisation of the biosynthetic gene cluster for rapamycin in *Streptomyces hygroscopicus* analysis of the enzymatic domains in the modular polyketide synthase." *Gene* 169:9-16

Appel, N., T. Schaller, et al. (2006). "From structure to function: new insights into hepatitis C virus RNA replication." *J Biol Chem* 281(15): 9833-6.

Ayoub, W. S, and Keefe, E. B. (2008). "Review article: current antiviral therapy of chronic hepatitis B". *Aliment Pharmacol Ther* 28:167-177

Banteli, R., J. Wagner, et al. (2001). "Synthesis of derivatives of the novel cyclophilin-binding immunosuppressant sanglifehrin A with reduced numbers of polar functions." *Bioorg Med Chem Lett* 11(12): 1609-12.

Bevitt, D. J., Cortes, J. et al. (1992). "6-deoxyerythronolide D synthase 2 from Saccharopolyspora erythraea. Cloning of the structural gene, sequence analysis and inferred domain structure of the multifunctional enzyme." *J. Biochem.* 204: 39-49

Bobardt, M. D., Cheng, G. et al., (2008). "Hepatitis C virus NS5A anchor peptide disrupts human immunodeficiency virus". *Proc. Natl. Acad. Sci. USA* 105(14):5525-5530.

Castro, A. P., Carvalho, T. M., et al., (2003). "Redisribution of cyclophilin A to viral factories during vaccinia virus infection and its incorporation into mature particles." *J. Virol.* 77:9052-9068

Chatterji, U., M. Bobardt, et al. (2009). "The isomerase active site of cyclophilin A is critical for HCV replication." *J Biol. Chem.* 284:16998-17005

Chatterji, U., et al., (2010) HCV resistance to cyclosporin A does not correlate with a resistance of the NS5A-cyclophilin A interaction to cyclophilin inhibitors. *J Hepatol.* 53(1): p. 50-6.

Chen, Z., Mi, L. et al., (2005). "Function of HAb18G/CD147 in invasion of host cells by severe acute respiratory syndrome coronavirus". *J. Infect. Dis.* 191:755-760

Colgan, J., M. Asmal, et al. (2000). "Isolation, characterization and targeted disruption of mouse ppia: cyclophilin A is not essential for mammalian cell viability." *Genomics* 68(2): 167-78.

Crabbe, R., G. Vuagniaux, et al. (2009). "An evaluation of the cyclophilin inhibitor Debio 025 and its potential as a treatment for chronic hepatitis C." *Expert Opin Investig Drugs* 18(2): 211-20. Dolinski, K., S. Muir, et al. (1997). "All cyclophilins and FK506 binding proteins are, individually and collectively, dispensable for viability in *Saccharomyces cerevisiae*." *Proc Natl Acad Sci USA* 94(24): 13093-8.

Du, H., and Yan, S. S. (2010). "Unlocking the Door to Neuronal Woes in Alzheimer's Disease: Aβ and Mitochondrial Permeability Transition Pore". *Pharmaceuticals* 3:1936-1948

E. Lawitz, R. R., T. Nguyen, M. Huang, J. Ke, J. Praestgaard, D. Serra, M. Koziel, T. Evans (2009). "Safety And Antiviral Efficacy Of 14 Days Of The Cyclophilin Inhibitor Nim811 In Combination With Pegylated Interferon 0.2a In Relapsed Genotype 1 Hcv Infected Patients." *Journal of Hepatology* 50(S1): S379.

Egorin, M. J., T. F. Lagattuta, et al. (2002). "Pharmacokinetics, tissue distribution, and metabolism of 17-(dimethylaminoethylamino)-17-demethoxygeldanamycin (NSC 707545) in CD2F1 mice and Fischer 344 rats." *Cancer Chemother Pharmacol* 49(1): 7-19.

Fehr, T., J. Kallen, et al. (1999). "Sanglifehrins A, B, C and D, novel cyclophilin-binding compounds isolated from *Streptomyces* sp. A92-308110. II. Structure elucidation, stereochemistry and physico-chemical properties." *J Antibiot* (Tokyo) 52(5): 474-9.

Ferir, G., Kaptein, S. et al., (2008). "Antiviral treatment of chronic hepatitis B virus infections: the past, the present and the future". *Rev. Med. Virol.* 18:19-34.

Flisiak, R., A. Horban, et al. (2008). "The cyclophilin inhibitor Debio-025 shows potent anti-hepatitis C effect in patients coinfected with hepatitis C and human immunodeficiency virus." *Hepatology* 47(3): 817-26.

Forte, M., Gold, B. G. et al., (2007). "Cyclophilin D inactivation protects axons in experimental autoimmune encephalomyelitis, an animal model of multiple sclerosis. *Proc. Natl. Acad. Sci. USA* 104:7558-7563.

Fujimoto, K., Chen, Y. et al. (2010). "Targeting cyclophilin D and the mitochondrial permeability transition enhances β-cell survival and prevents diabetes in Pdx1 deficiency". *Proc. Natl. Acad. Sci. USA* 107: 10214-10219

Furniss, B. S., Furniss, A. I., Vogel, A. I., Ed. (1989). *Vogel's Textbook of Practical Organic Chemistry*, Prentice Hall.

Gaither, L. A., Borawski, J., Anderson, L. J., Balabanis, K. A. et al., (2010). "Multiple cyclophilins involved in different cellular pathways mediate HCV replication" *Virology* 397: 43-55.

Glavinas, H., Krajcsi, P., Cserepes, J., Sarkadi, B. (2004). "The role of ABC transporters in drug resistance, metabolism and toxicity." *Curr. Drug. Deliv.* 1(1): 27-42.

Gomez, L., H. Thibault, et al. (2007). "Inhibition of mitochondrial permeability transition improves functional recovery and reduces mortality following acute myocardial infarction in mice."*Am J Physiol Heart Circ Physiol* 293 (3): H1654-61.

Goto, K., Watashi, K., Inoue, D., Hijikata, M., Shimotohno, K. (2009) "Identification of cellular and viral factors related to anti-hepatitis C virus activity of cyclophilin inhibitor" *Cancer Science* 100(10): 1943-1950

Hanoulle, X., Badillo A, Wieruszeski J M, Verdegem D, Landrieu I, Bartenschlager R, Penin F, Lippens G (2009). "Hepatitis C virus NS5A protein is a substrate for the Peptidyl-Prolyl cis/trans isomerase activity of Cyclophilins A and B." *J Biol. Chem.* 284:13589-13601

Han, X., Yoon, S. H. et al., "Cyclosporin A and sanglifehrin A enhance chemotherapeutic effect of cisplatin in C6 glioma cells" *Oncology Reports* 23:1053-1062

Hartel, C., P. Iblher, et al. (2006). "Immunosuppressive activity of the immunophilin-binding drug Sanglifehrin A in human whole blood: potent inhibition of interleukin-6 produced by lymphocytes and monocytes." Scand J Immunol 63(1): 26-34.

Herrler, M., H. Bang, et al. (1994). "Cloning and characterization of ppiB, a *Bacillus subtilis* gene which encodes a cyclosporine A-sensitive peptidyl-prolyl cis-trans isomerase." *Mol Microbiol* 11(6): 1073-83.

Hite, M., Turner, S., Federici, C. (2003). "Part 1: Oral delivery of poorly soluble drugs". *Pharmaceutical Manufacturing and Packing Sourcer*. Summer 2003 issue.

Hopkins, S. Gavis, D. et al., (2009). "Safety, plasma pharmacokinetics, and anti-viral activity of SCY-635 in adult patients with chronic hepatitis C virus infection." *Journal of Hepatology* 50(S1): S36.

Inoue, K., K. Sekiyama, et al. (2003). "Combined interferon alpha2b and cyclosporine A in the treatment of chronic hepatitis C: controlled trial." *J Gastroenterol* 38(6): 567-72.

Inoue, K., T. Umehara, et al. (2007). "Evaluation of a cyclophilin inhibitor in hepatitis C virus-infected chimeric mice in vivo." *Hepatology* 45(4): 921-8.

Ishii, N., K. Watashi, et al. (2006). "Diverse effects of cyclosporine on hepatitis C virus strain replication." *J Virol* 80(9): 4510-20.

Ke, J., Rozier, R. et al., (2009). "Safety, And Tolerability Of Nim811, A Novel Cyclophilin Inhibitor For HCV, Following Single And Multiple Ascending Doses In Healthy Volunteers And Hcv-Infected Patients." *Journal of Hepatology* 50(S1): S229.

Jacobson, I., McHutchison, JG, Sulkowski, M. (2007). *Gastroenterol & Hepatol* 3(S34): 1-10.

Kallen, J., R. Sedrani, et al. (2005). "Structure of human cyclophilin A in complex with the novel immunosuppressant sanglifehrin A at 1.6 A resolution." *J Biol Chem* 280 (23): 21965-71.

Kaul, A., Stauffer, S. et al., (2009). "Essential Role of Cyclophilin A for Hepatitis C Virus Replication and Virus Production and Possible Link to Polyprotein Cleavage Kinetics". PLOS Pathogens 5(8): e1000546

Kawasaki, H., E. S. Mocarski, et al. (2007). "Cyclosporine inhibits mouse cytomegalovirus infection via a cyclophilin-dependent pathway specifically in neural stem/progenitor cells." *J Virol* 81(17): 9013-23.

King, A. L., Swain, T. M. et al., (2010) "Chronic ethanol consumption enhances sensitivity to $Ca^{2+}$-mediated opening of the mitochondrial permeability transition pore and increases cyclophilin D in liver" *Am J Physiol Gastrointest Liver Physiol* 299(4):G954-966

Kubota, M., Kasahara, T. et al., (2010). "Therapeutic implications of down-regulation of cyclophilin D in bipolar disorder". *International Journal of Neuropsychopharmacology* 13(10):1355-1368

Liu, X., Sun, L. et al., (2009). "Cyclophilin A interacts with influenza A virus M1 protein and impairs the early stage of the viral replication". *Cell Microbiol.* 11:730-741.

Malouitre, S., Dube, H. et al., (2010). "Mitochondrial targeting of cyclosporin A enables selective inhibition of cyclophilin-D and enhanced cytoprotection after glucose and oxygen deprivation" *Biochem. J.* 425:137-148

Manns, M. P., G. R. Foster, et al. (2007). "The way forward in HCV treatment—finding the right path." *Nat Rev Drug Discov* 6(12): 991-1000.

Martin Cabrejas, L. M., S. Rohrbach, et al. (1999). "Macrolide Analogues of the Novel Immunosuppressant Sanglifehrin: New Application of the Ring-Closing Metathesis Reaction." *Angew Chem Int Ed Engl* 38(16): 2443-2446.

Martin, L. J. (2010). "The mitochondrial permeability transition pore: A molecular target for amyotrophic lateral sclerosis therapy". *Biochimica et Biophysica Acta* 1802: 186-197

Mathy, J. E., S. Ma, et al. (2008). "Combinations of cyclophilin inhibitor NIM811 with hepatitis C Virus NS3-4A Protease or NS5B polymerase inhibitors enhance antiviral activity and suppress the emergence of resistance." *Antimicrob Agents Chemother* 52(9): 3267-75.

Melnikova, I. (2008). "Hepatitis C therapies." *Nature Rev Drug Disc* 7: 799-800.

Metternich, R., Denni, D., That, B, Sedrani, R. (1999). "Toward a Total Synthesis of the Immunosuppressant Sanglifehrin A. Preparation of Two Relay Compounds by Degradation and Their Use in the Reassembly of the Natural Product." *J. Org. Chem.* 64: 9632-9639.

Millay, D. P., M. A. Sargent, et al. (2008). "Genetic and pharmacologic inhibition of mitochondrial-dependent necrosis attenuates muscular dystrophy." *Nat Med* 14(4): 442-7.

Nelson, D. R., Ghalib, R. H., Sulkowski, M., Schiff, E., Rustgi, V., Pockros, P. J., Wang, C., Decosterd Kerhuel, D., and P. Grosgurin, Porchet, H., Crabbe, R. (2009). "Efficacy And Safety Of The Cyclophilin Inhibitor Debio 025 In Combination With Pegylated Interferon Alpha-2a And Ribavirin In Previously Null-Responder Genotype 1 Hcv Patients." *Journal of Hepatology* 50(S1): S40.

Niwa, T., Yamamoto, S, Saito, M, Shiraga, T, Takagi, A. (2007). "Effect of Cyclosporine and Tacrolimus on Cytochrome P450 Activities in Human Liver Microsomes." *Yakugaku Zasshi* 127(1): 209-216.

Paeshuyse, J., A. Kaul, et al. (2006). "The non-immunosuppressive cyclosporine DEBIO-025 is a potent inhibitor of hepatitis C virus replication in vitro." *Hepatology* 43(4): 761-70.

Palma, E., Tiepolo, T. et al., (2009). "Genetic ablation of cyclophilin D rescues mitochondrial defects and prevents muscle apoptosis in collagen VI myopathic mice" *Human Molecular Genetics* 18:2024-2031

Parfieniuk, A., J. Jaroszewicz, et al. (2007). "Specifically targeted antiviral therapy for hepatitis C virus." *World J Gastroenterol* 13(43): 5673-81.

Pawlotsky, J. M. (2000). "Hepatitis C virus resistance to antiviral therapy." *Hepatology* 32(5): 889-96.

Pawlotsky, J. M. (2005). "Current and future concepts in hepatitis C therapy." *Semin Liver Dis* 25(1): 72-83.

Pawlotsky, J. M. (2006). "Virology of hepatitis B and C viruses and antiviral targets." *J Hepatol* 44(1 Suppl): S10-3.

Pemberton, T. J. and J. E. Kay (2003). "Cyclophilin sensitivity to sanglifehrin A can be correlated to the same specific tryptophan residue as cyclosporine A." *FEBS Lett* 555(2): 335-40.

Perry, G. M., Tallaksen-Greene, S. et al., (2010). "Mitochondrial calcium uptake capacity as a therapeutic target in the R6/2 mouse model of Huntington's disease". *Human Molecular Genetics* 19(17):3354-3371

Pockros, P. (2008). "Emerging Therapies for Chronic Hepatitis C Virus." *Gastroenterol and Hepatology* 4(10): 729-734.

Ptak, R. G., P. A. Galley, et al. (2008). "Inhibition of human immunodeficiency virus type 1 replication in human cells by Debio-025, a novel cyclophilin binding agent." *Antimicrob Agents Chemother* 52(4): 1302-17.

Qing, M., Yang, F. (2009). "Cyclosporine Inhibits Flavivirus Replication through Blocking the Interaction between Host Cyclophilins and Viral NS5 Protein" *Antimicrob Agents Chemother* 53(8):3226-3235

Qu, X., Jiang, N et al., (2011) "Cloning, sequencing and characterization of the biosynthetic gene cluster of sanglifehrin A, a potent cyclophilin inhibitor". Molecular Biosystems DOI: 10.1039/COMB00234H Robida, J. M., H. B. Nelson, et al. (2007). "Characterization of hepatitis C virus subgenomic replicon resistance to cyclosporine in vitro." *J Virol* 81(11): 5829-40.

Sanglier, J. J., V. Quesniaux, et al. (1999). "Sanglifehrins A, B, C and D, novel cyclophilin-binding compounds isolated from *Streptomyces* sp. A92-308110.1. Taxonomy, fermentation, isolation and biological activity." *J Antibiot* (Tokyo) 52(5): 466-73.

Schneider, M. D. (2005). "Cyclophilin D: knocking on death's door." *Sci STKE* 2005(287): pe26.

Schopman, N. C. T., ter Brake, O. and Berkhout, B. (2010). "Anticipating and blocking HIV-1 escape by second generation antiviral shRNAs" *Retroviroloqy* 7:52

Sedrani, R., J. Kallen, et al. (2003). "Sanglifehrin-cyclophilin interaction: degradation work, synthetic macrocyclic analogues, X-ray crystal structure, and binding data." *J Am Chem Soc* 125(13): 3849-59.

Shafer, R. W., and Schapiro, J. M. (2008). "HIV-1 Drug Resistance Mutations: an Updated Framework for the Second Decade of HAART". *AIDS Rev.* 10(2):67-84

Smith, M. B. a. M., J., Ed. (2001). *March's advanced organic chemistry*, John Wiley and Sons Inc., UK.

Steinschulte, C., T. Taner, et al. (2003). "Cutting edge: sanglifehrin A, a novel cyclophilin-binding immunosuppressant blocks bioactive IL-12 production by human dendritic cells." *J Immunol* 171(2): 542-6.

Steyn, D., Richman, D. et al., (2006). "A double-blind placebo-controlled study in HIV-1-infected subjects on the safety, pharmacokinetics, and antiviral effect of cyclophilin A targeting Debio-025". *Int. Conf. Retroviruses Opportunistic Infec.* 13:Abs 516

Strader, D. B., T. Wright, et al. (2004). "Diagnosis, management, and treatment of hepatitis C." *Hepatology* 39(4): 1147-71.

Tropschug, M., I. B. Barthelmess, et al. (1989). "Sensitivity to cyclosporine A is mediated by cyclophilin in *Neurospora crassa* and *Saccharomyces cerevisiae*." *Nature* 342 (6252): 953-5.

Vrolijk, J. M., A. Kaul, et al. (2003). "A replicon-based bioassay for the measurement of interferons in patients with chronic hepatitis C." *J Virol Methods* 110(2): 201-9.

Watashi, K. (2010). "Alisporivir, a cyclosporine derivative that selectively inhibits cyclophilin, for the treatment of HCV infection". *Curr. Opp. Invest. Drugs* 11(2):213-224

Xie, H., Xia, W. et al., (2007). "Evaluation of hepatitis B virus replication and proteomic analysis of HepG2.2.15 cell line after cyclosporine A treatment". *Acta Pharmacol. Sin.* 7:975-984

Yang, F., J. M. Robotham, et al. (2008). "Cyclophilin A is an essential cofactor for hepatitis C virus infection and the principal mediator of cyclosporine resistance in vitro." *J Virol* 82(11): 5269-78.

Zenke, G., U. Strittmatter, et al. (2001). "Sanglifehrin A, a novel cyclophilin-binding compound showing immunosuppressive activity with a new mechanism of action." *J Immunol* 166(12): 7165-71.

Zeuzem, S, and E. Herrmann (2002). "Dynamics of hepatitis C virus infection." *Ann Hepatol* 1(2): 56-63.

Zhang, L. H. and J. O. Liu (2001). "Sanglifehrin A, a novel cyclophilin-binding immunosuppressant, inhibits IL-2-dependent T cell proliferation at the G1 phase of the cell cycle." *J Immunol* 166(9): 5611-8.

All references including patent and patent applications referred to in this application are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A compound according to formula (I) below, or a pharmaceutically acceptable salt thereof:

(I)

wherein:
- $R_1$ and $R_2$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
- or $R_1$ represents hydrogen; and wherein one or more carbon atoms of $R_1$ and/or $R_2$ not being part of an aryl or heteroaryl group are optionally replaced by a heteroatom selected from O, N and $S(O)_p$ in which p represents 0, 1 or 2 and wherein one or more carbon atoms of $R_1$ and/or $R_2$ are optionally replaced by carbonyl;
- or $R_1$ and $R_2$ are joined to form a saturated or unsaturated heterocyclic ring containing the nitrogen atom shown and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;
- and wherein one or more carbon atoms of an $R_1$ and/or $R_2$ group may optionally be substituted by one or more halogen atoms;
- $R_3$ represents H, $—(CO)_x$alkyl;
- $R_4$ represents H or OH;
- $R_5$ represents H, OH or =O;
- n represents a single or double bond save that when n represents a double bond $R_4$ represents H; and
- m represents a single or double bond save that when m represents a double bond $R_5$ represents H;
- x represents 0 or 1;
- including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl groups and methanol.

2. A compound according to claim 1 wherein $R_1$ and $R_2$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
- or $R_1$ represents hydrogen; and wherein one or more carbon atoms of $R_1$ and/or $R_2$ not being part of an aryl or heteroaryl group are optionally replaced by a heteroatom selected from O, N and $S(O)_p$ in which p represents 0, 1 or 2 and wherein one or more carbon atoms of $R_1$ and/or $R_2$ are optionally replaced by carbonyl;
- or $R_1$ and $R_2$ are joined to form a saturated or unsaturated heterocyclic ring containing the nitrogen atom shown and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring.

3. A compound according to claim 2 wherein $R_1$ represents aryl or heteroaryl substituted by monocyclic aryl or monocyclic heteroaryl, $—C_{1-4}$alkyl, $—OC_{1-4}$alkyl, $—COC_{1-4}$alkyl or $—C_{2-4}$alkenyl.

4. A compound according to claim 1, wherein $R_2$ represents hydrogen, $C_{1-4}$ alkyl or $C_{1-4}$ alkenyl.

5. A compound according to claim 4 wherein $R_2$ represents hydrogen or $C_{1-4}$ alkyl.

6. A compound according to claim 2 wherein $R_1$ and $R_2$ together with the nitrogen to which they are attached represent a 5-7 membered heterocyclic ring.

7. A compound according to claim 1 wherein, independently or in any combination:
- $R_3$ represents H or $(CO)_xC_{1-4}$alkyl;
- n represents a single bond;
- m represents single bond;
- $R_4$ represents OH;
- $R_5$ represents =O.

8. A compound according to claim 1, wherein x represents 0.

9. A compound according to claim 1 wherein:
$R_1$ represents $OCH_3$, $R_2$ represents Me, $R_3$ represents H, $R_4$ represents OH, n represents a single bond, m represents a single bond and $R_5$ represents =O as represented by the following structure:

or $R_1$ represents ethyl, $R_2$ represents ethyl, $R_3$ represents H, $R_4$ represents OH, n represents a single bond, m represents a single bond and $R_5$ represents =O as represented by the following structure:

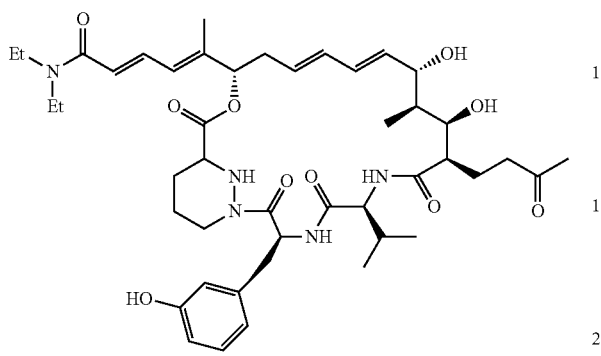

or $R_1$ represents —CHMe$_2$, $R_2$ represents H, $R_3$ represents H, $R_4$ represents OH, n represents a single bond, m represents a single bond and $R_5$ represents =O as represented by the following structure:

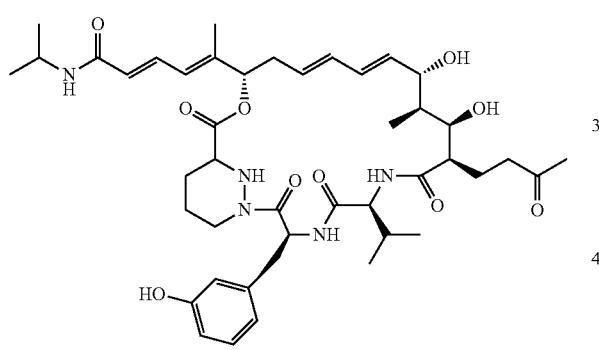

or $R_1$ represents methyl, $R_2$ represents H, $R_3$ represents H, $R_4$ represents OH, n represents a single bond, m represents a single bond and $R_5$ represents =O as represented by the following structure:

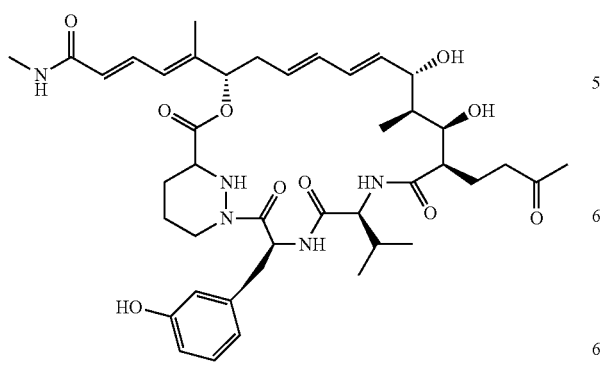

or $R_1$ represents methyl, $R_2$ represents H, $R_3$ represents Me, $R_4$ represents OH, n represents a single bond, m represents a single bond and $R_5$ represents =O as represented by the following structure:

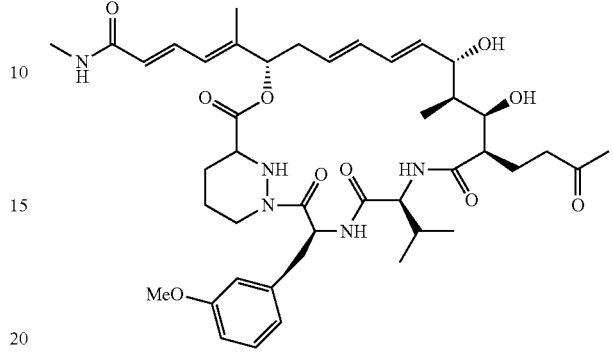

or $R_1$ represents —CH$_2$CH=CH$_2$, $R_2$ represents H, $R_3$ represents H, $R_4$ represents OH, n represents a single bond, m represents a single bond and $R_5$ represents =O as represented by the following structure:

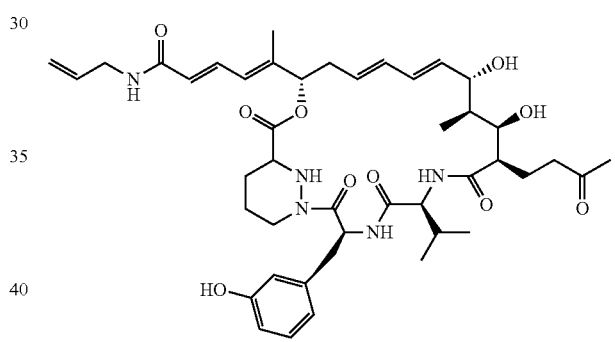

or $R_1$ represents methyl, $R_2$ represents methyl, $R_3$ represents H, $R_4$ represents OH, n represents bond, m represents bond and $R_5$ represents =O as represented by the following structure:

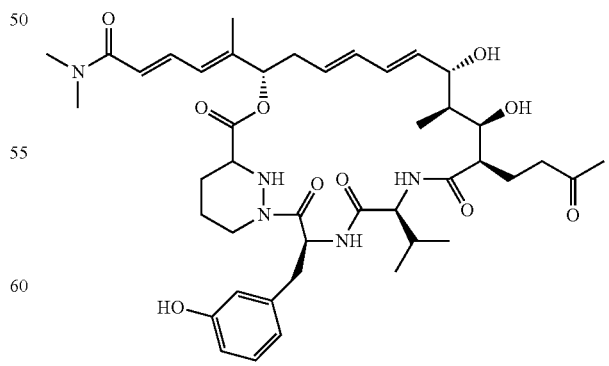

or $R_1$ represents —CH$_2$CHMe$_2$, $R_2$ represents —CH$_2$CHMe$_2$, $R_3$ represents H, $R_4$ represents OH, n represents a single bond, m represents a single bond and $R_5$ represents =O as represented by the following structure:

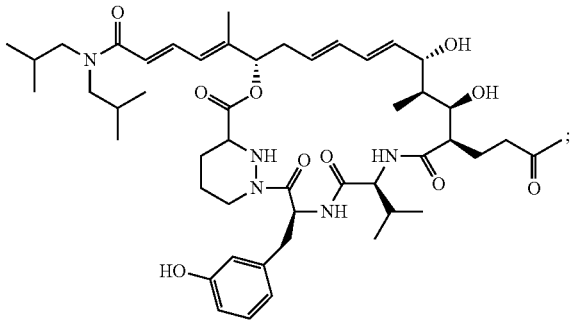 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(CC(C)C)CC(C)C)C/C=C/C=C/[C@H](O)[C@H](C)[C@H]1O]

or $R_1$ represents $OCH_3$, $R_2$ represents Me, $R_3$ represents H, $R_4$ represents OH, n represents a single bond, m represents a double bond and $R_5$ represents H as represented by the following structure:

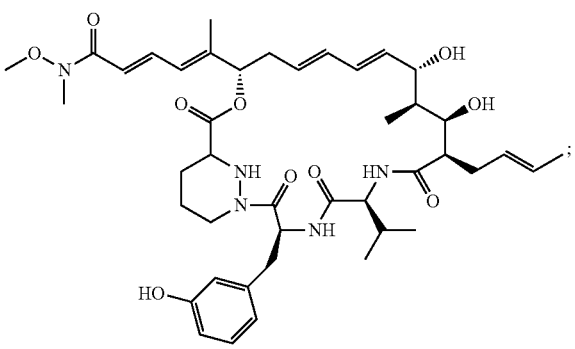 [SMILES: C/C=C/C[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)OC)C/C=C/C=C/[C@H](O)[C@H](C)[C@H]1O]

or $R_1$ represents $OCH_3$, $R_2$ represents Me, $R_3$ represents H, $R_4$ represents H, n represents a double bond, m represents a single bond and $R_5$ represents =O as represented by the following structure:

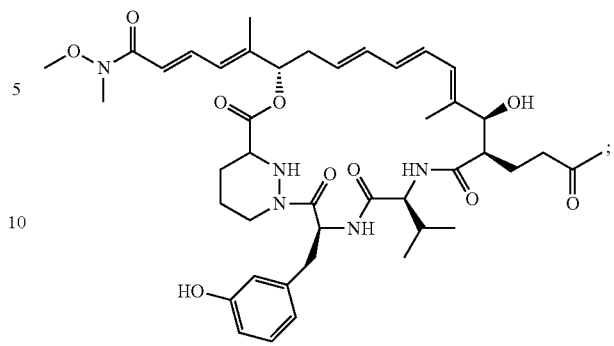

or $R_1$ and $R_2$ together represent —$CH_2CH_2OCH_2CH_2$— connected in a 6-membered heterocycle, $R_3$ represents H, $R_4$ represents OH, n represents a single bond, m represents a single bond and $R_5$ represents =O as represented by the following structure:

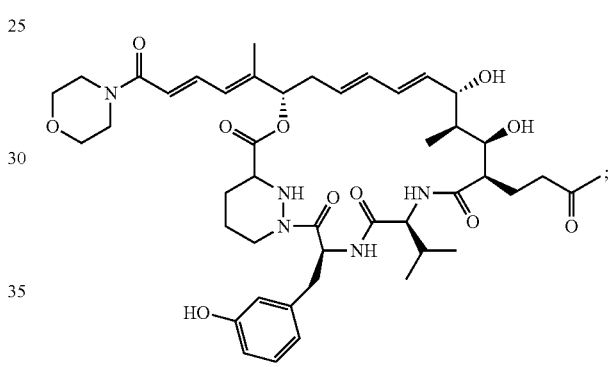

$R_1$ represents 4-biphenylyl, $R_2$ represents H, where, $R_3$ represents H, $R_4$ represents OH, n represents a single bond, m represents a single bond and $R_5$ represents =O as represented by the following structure:

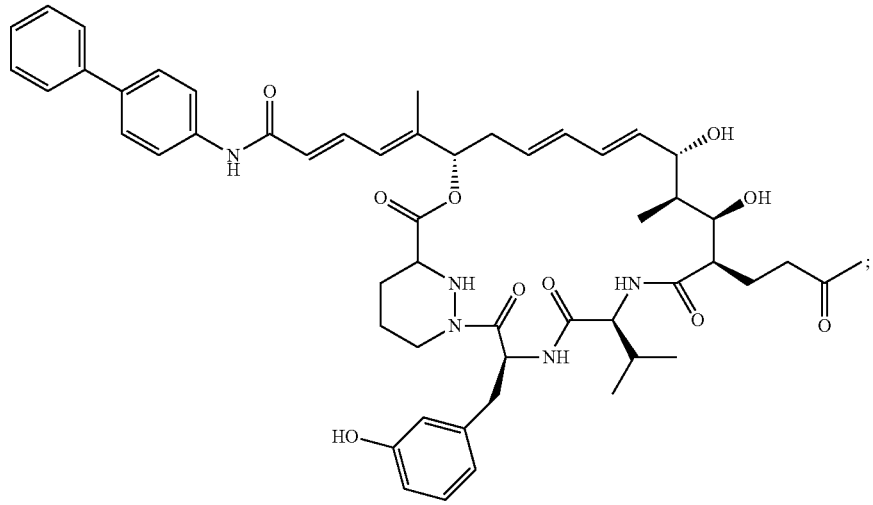 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/[C@H](O)[C@H](C)[C@H]1O]

or

R₁ represents cyclohexyl, R₂ represents Me, R₃ represents H, R₄ represents OH, n represents a single bond, m represents a single bond and R₅ represents =O as represented by the following structure:

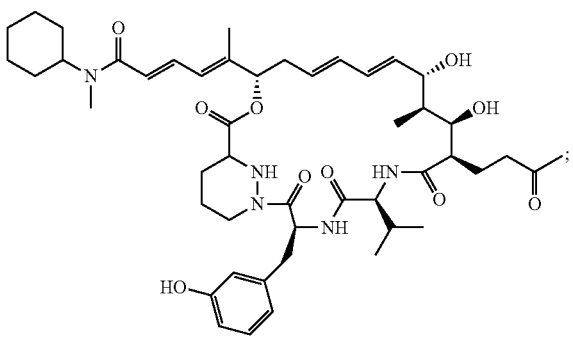 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C2CCCCC2)C/C=C/C=C/[C@H](O)[C@H](C)[C@H]1O]

or

R₁ and R₂ together represent —OCH₂CH₂CH₂CH₂— connected in a 6-membered heterocycle, R₃ represents H, R₄ represents H, n represents a single bond, m represents a single bond and R₅ represents =O as represented by the following structure:

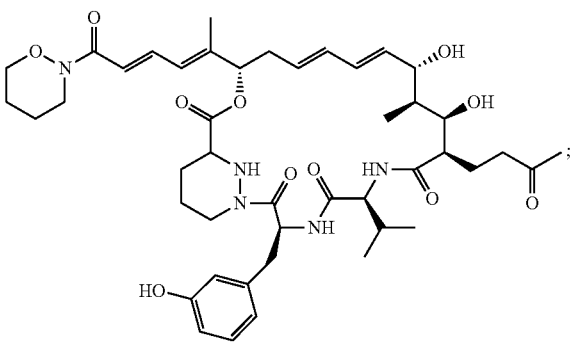 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCCCO2)C/C=C/C=C/[C@H](O)[C@H](C)[C@H]1O]

or

R₁ represents 2-pyridinyl, R₂ represents H, R₃ represents H, R₄ represents OH, n represents a single bond, m represents a single bond and R₅ represents =O as represented by the following structure:

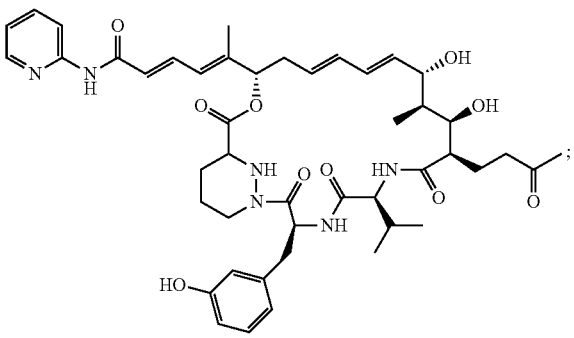 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccccn2)C/C=C/C=C/[C@H](O)[C@H](C)[C@H]1O]

or

R₁ represents cyclohexyl, R₂ represents H, R₃ represents H, R₄ represents OH, n represents a single bond, m represents a single bond and R₅ represents =O as represented by the following structure:

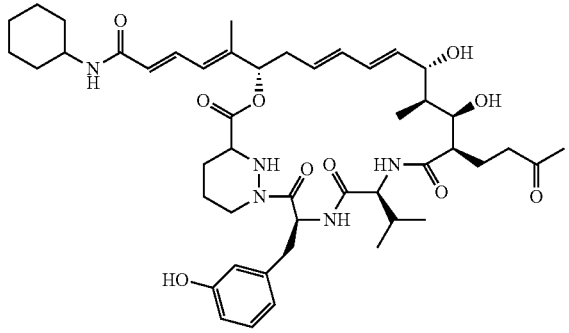 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)NC2CCCCC2)C/C=C/C=C/[C@H](O)[C@H](C)[C@H]1O]

or

R₁ represents OCH₃, R₂ represents Me, R₃ represents H, R₄ represents OH, n represents a single bond, m represents a single bond and R₅ represents OH as represented by the following structure:

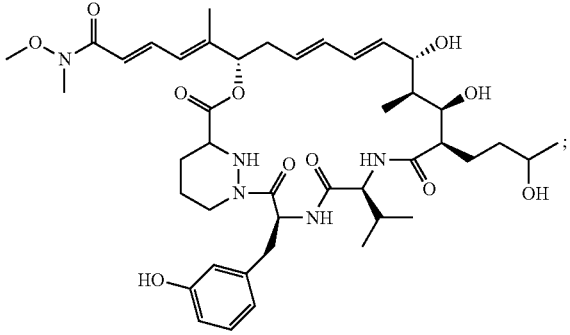 [SMILES: CON(C)C(=O)/C=C/C=C(\C)[C@@H]1C/C=C/C=C/[C@H](O)[C@H](C)[C@@H](O)[C@@H](CCC(C)O)C(=O)N[C@@H](C(C)C)C(=O)N[C@@H](Cc2cccc(O)c2)C(=O)N2CCCC(N2)C(=O)O1]

or a pharmaceutically acceptable salt of any one thereof; including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl groups and methanol.

10. A compound according to claim 1 wherein:

R₁ represents OCH₃, R₂ represents Me, R₃ represents H, R₄ represents H, n represents a single bond, m represents a single bond and R₅ represents =O as represented by the following structure:

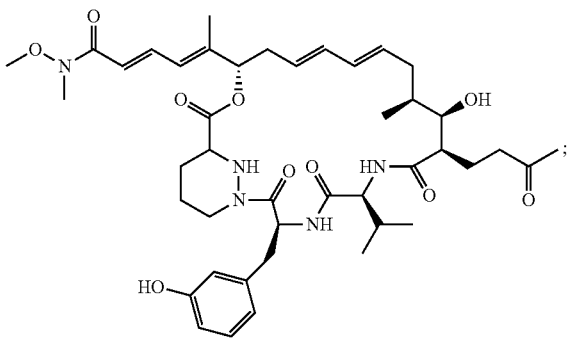 [SMILES: CON(C)C(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or

R₁ represents ethyl, R₂ represents ethyl, R₃ represents H, R₄ represents H, n represents a single bond, m represents a single bond and R₅ represents =O as represented by the following structure:

153

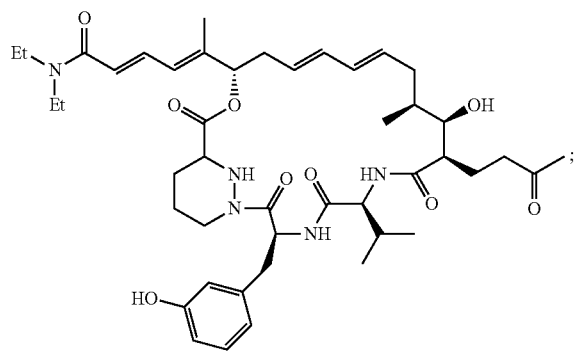 [SMILES: CCN(CC)C(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or
R₁ represents —CHMe₂, R₂ represents H, R₃ represents H, R₄ represents H, n represents a single bond, m represents a single bond and R₅ represents ═O as represented by the following structure:

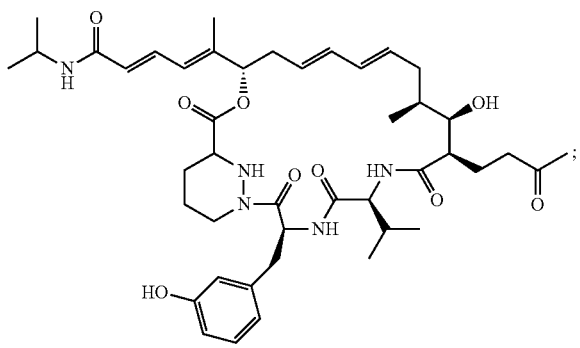 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)NC(C)C)C/C=C/C=C/C[C@H](C)[C@H]1O]

or
R₁ represents methyl, R₂ represents H, R₃ represents H, R₄ represents H, n represents a single bond, m represents a single bond and R₅ represents ═O as represented by the following structure:

154

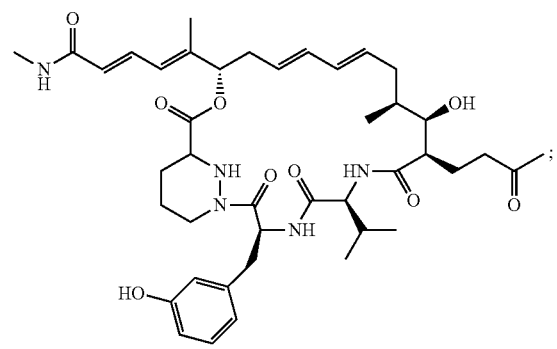 [SMILES: CNC(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

10 or
R₁ represents methyl, R₂ represents H, R₃ represents Me, R₄ represents H, n represents a single bond, m represents a single bond and R₅ represents ═O as represented by the following structure:

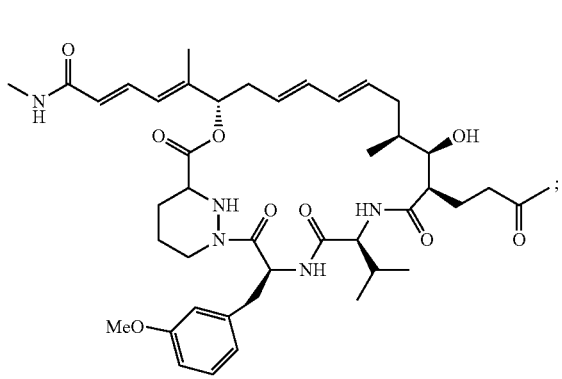 [SMILES: CNC(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(OC)c2)C(=O)N2CCCC(N2)C(=O)O1]

or
R₁ represents —CH₂CH═CH₂, R₂ represents H, R₃ represents H, R₄ represents H, n represents a single bond, m represents a single bond and R₅ represents ═O as represented by the following structure:

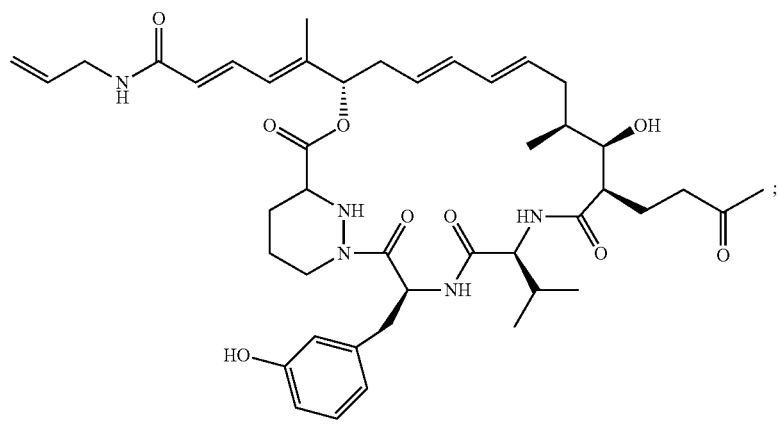 [SMILES: C=CCNC(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or $R_1$ represents methyl, $R_2$ represents methyl, $R_3$ represents H, $R_4$ represents H, n represents bond, m represents bond and $R_5$ represents =O as represented by the following structure:

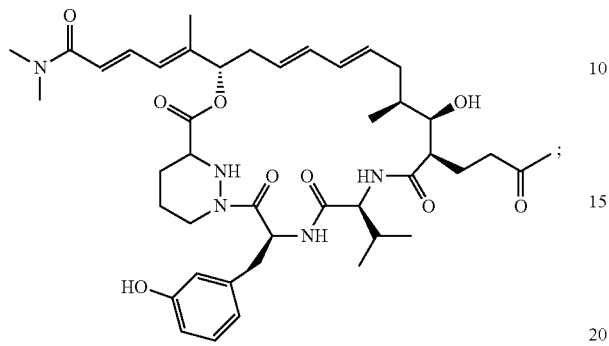

or $R_1$ represents —CH$_2$CHMe$_2$, $R_2$ represents —CH$_2$CHMe$_2$, $R_3$ represents H, $R_4$ represents H, n represents a single bond, m represents a single bond and $R_5$ represents =O as represented by the following structure:

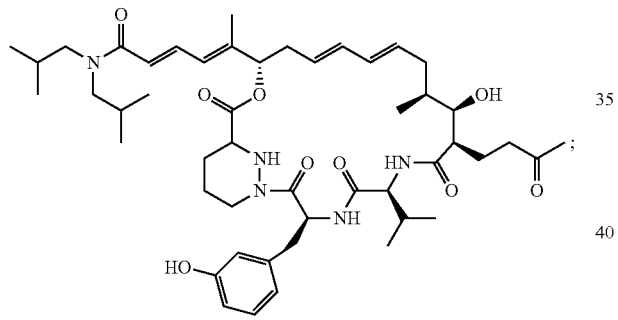

or $R_1$ represents OCH$_3$, $R_2$ represents Me, $R_3$ represents H, $R_4$ represents H, n represents a single bond, m represents a double bond and $R_5$ represents H as represented by the following structure:

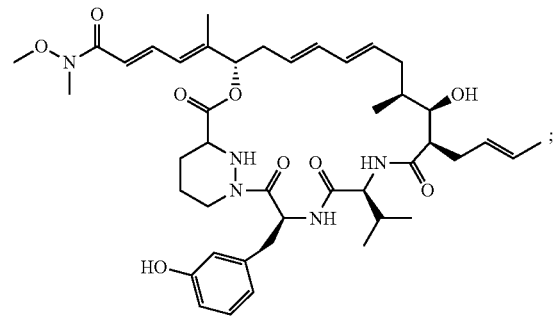 [SMILES: C/C=C/C[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)OC)C/C=C/C=C/C[C@H](C)[C@H]1O]

or $R_1$ and $R_2$ together represent —CH$_2$CH$_2$OCH$_2$CH$_2$— connected in a 6-membered heterocycle, $R_3$ represents H, $R_4$ represents H, n represents a single bond, m represents a single bond and $R_5$ represents =O as represented by the following structure:

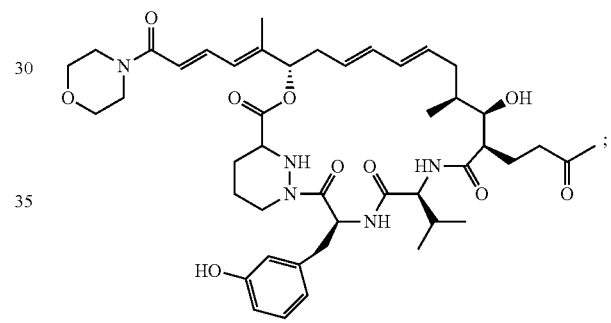

or $R_1$ represents 4-biphenylyl, $R_2$ represents H, where, $R_3$ represents H, $R_4$ represents H, n represents a single bond, m represents a single bond and $R_5$ represents =O as represented by the following structure:

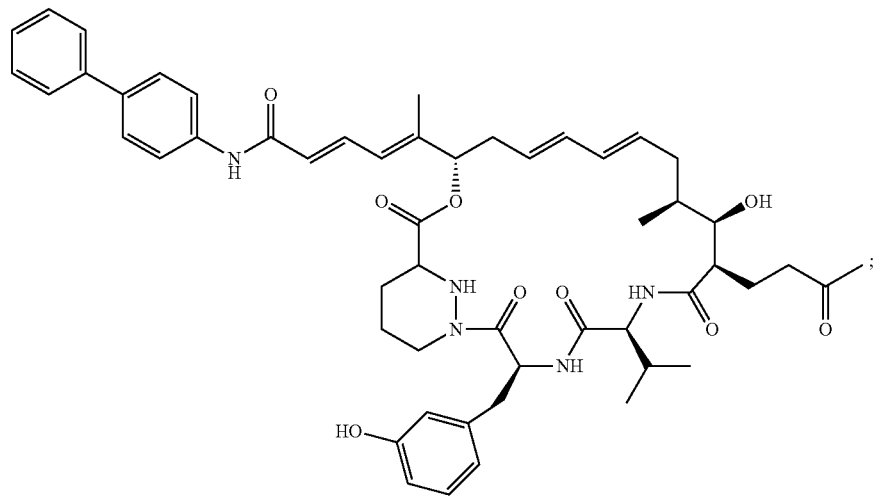 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/C[C@H](C)[C@H]1O]

or $R_1$ represents cyclohexyl, $R_2$ represents Me, $R_3$ represents H, $R_4$ represents H, n represents a single bond, m represents a single bond and $R_5$ represents =O as represented by the following structure:

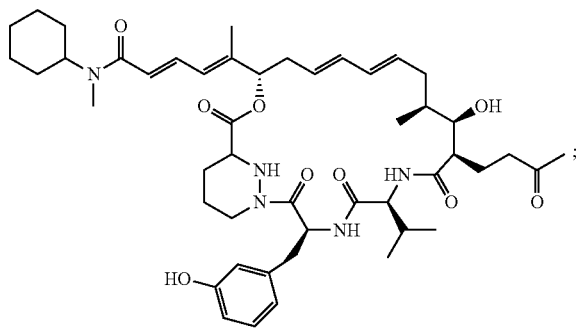 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C2CCCCC2)C/C=C/C=C/C[C@H](C)[C@H]1O]

or $R_1$ represents cyclohexyl, $R_2$ represents H, $R_3$ represents H, $R_4$ represents H, n represents a single bond, m represents a single bond and $R_5$ represents =O as represented by the following structure:

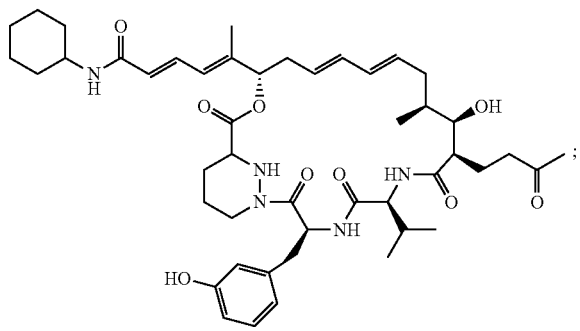 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)NC2CCCCC2)C/C=C/C=C/C[C@H](C)[C@H]1O]

or $R_1$ and $R_2$ together represent —OCH$_2$CH$_2$CH$_2$CH$_2$— connected in a 6-membered heterocycle. $R_3$ represents H, $R_4$ represents H, n represents a single bond, m represents a single bond and $R_5$ represents =O as represented by the following structure:

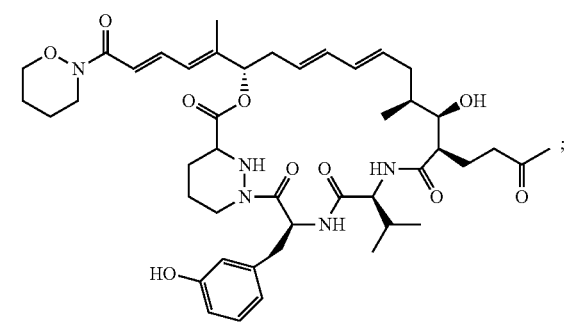 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCCCO2)C/C=C/C=C/C[C@H](C)[C@H]1O]

or $R_1$ represents 2-pyridinyl, $R_2$ represents H, $R_3$ represents H, $R_4$ represents H, n represents a single bond, m represents a single bond and $R_5$ represents =O as represented by the following structure:

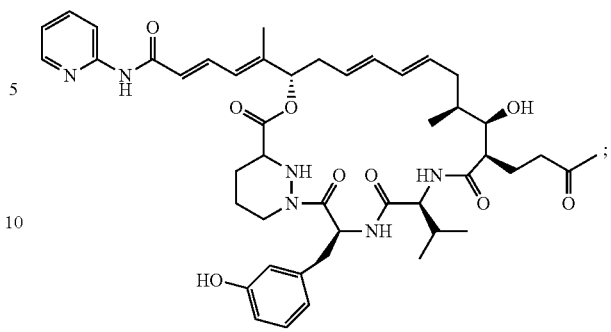

or a pharmaceutically acceptable salt of any one thereof; including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl groups and methanol.

11. A compound according to claim 1 wherein:

$R_3$ represents H, $R_4$ represents OH, n represents a single bond, m represents a single bond and $R_5$ represents =O as represented by the following structure:

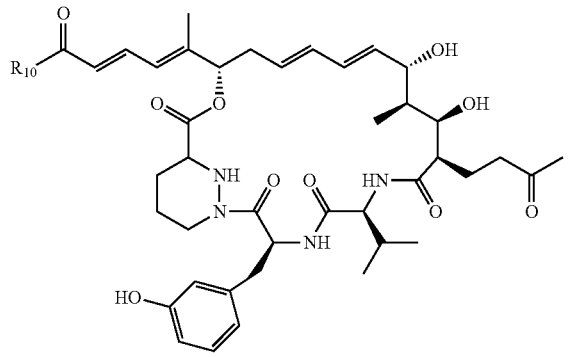

wherein $R_{10}$ represents a group as shown in the following table:

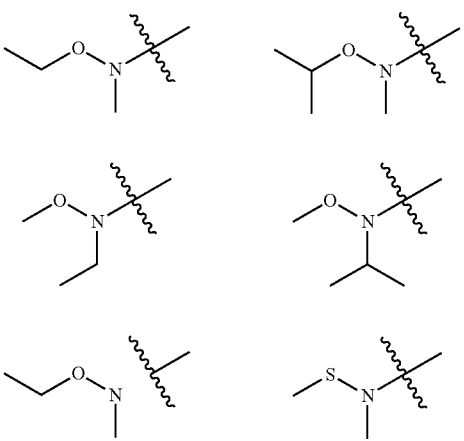

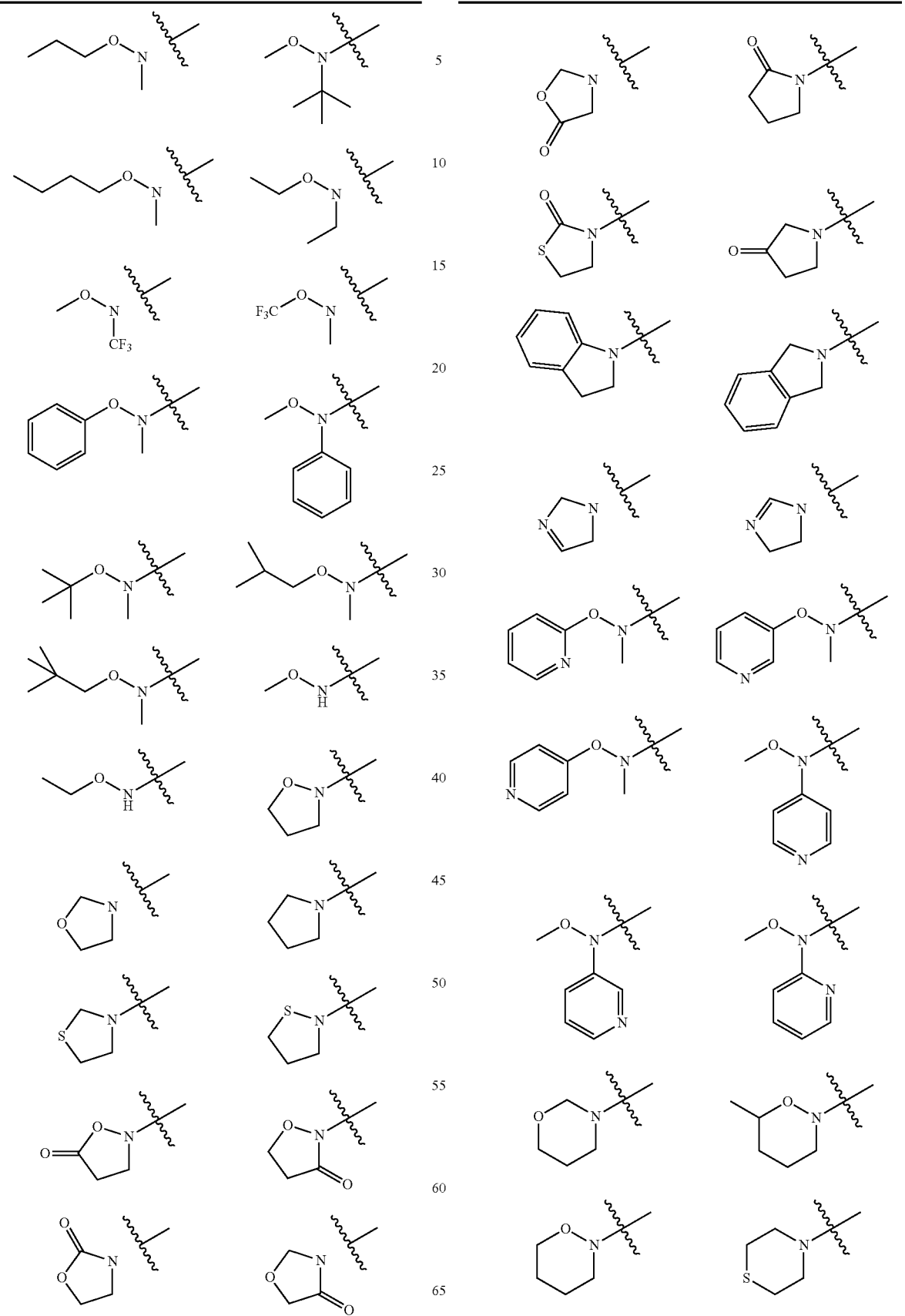

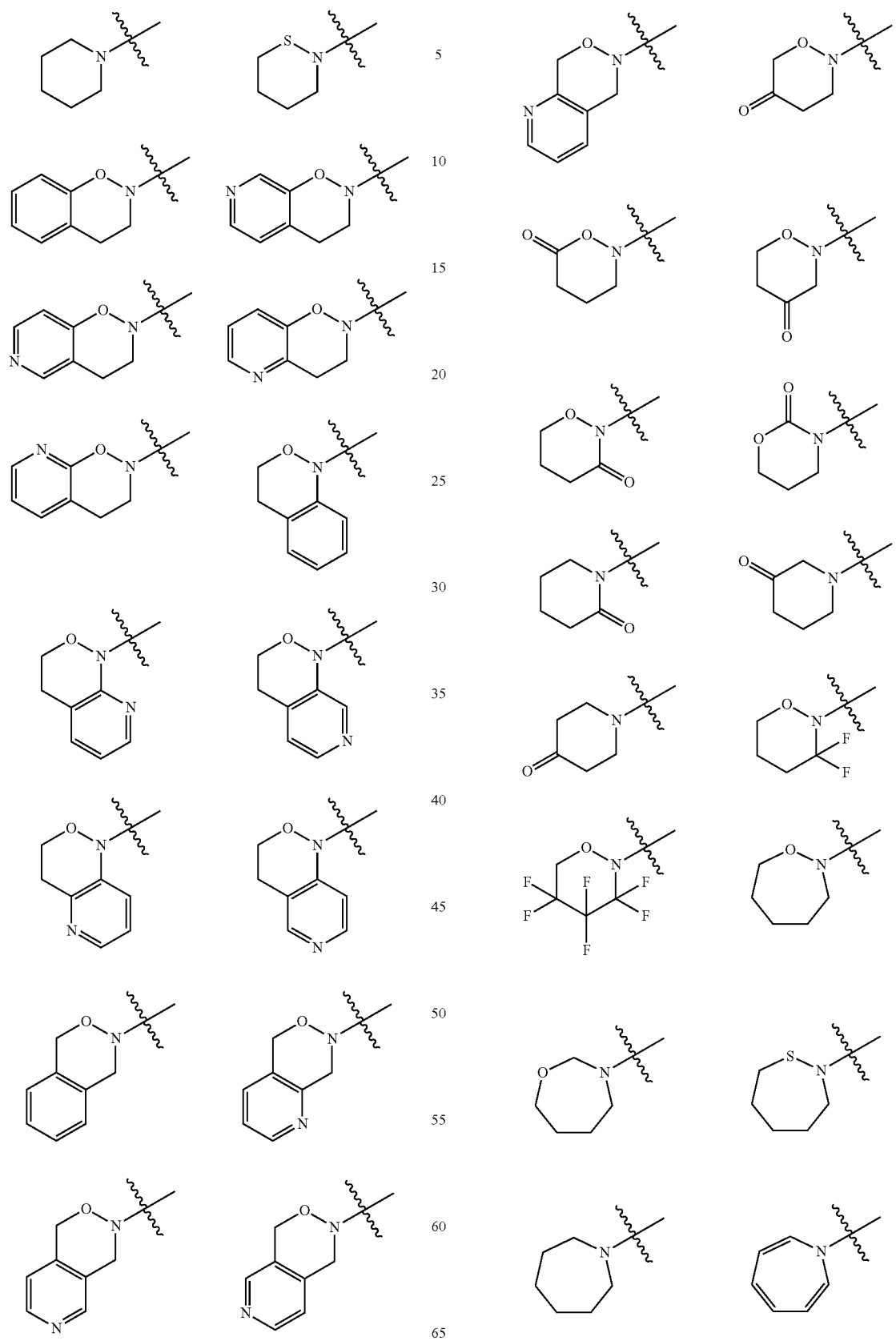

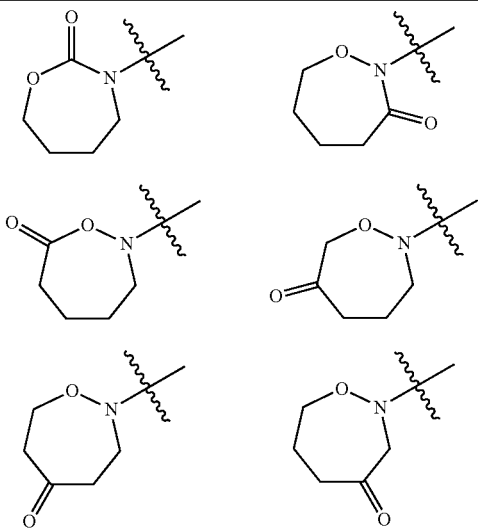

or a pharmaceutically acceptable salt of any one thereof; including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl groups and methanol.

12. A pharmaceutical composition comprising a compound according to claim 1 together with a pharmaceutically acceptable diluent or carrier.

13. A pharmaceutical composition comprising a compound according to claim 1 together with a pharmaceutically acceptable diluent or carrier further comprising a second or subsequent active ingredient.

14. A method of treating a HCV, HBV, or HIV infection comprising administering to a subject a therapeutically effective amount of a compound according to claim 1.

15. A process for preparing a compound according to claim 1 which comprises reacting a compound of formula II:

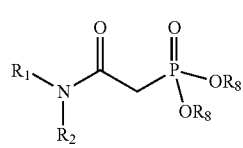

formula II wherein $R_8$ represents $C_{1-4}$ alkyl or benzyl;
with an aldehydic macrocycle (compound of formula III):

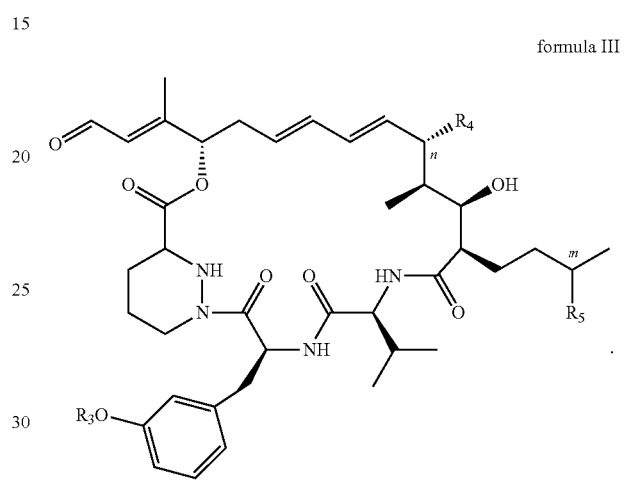

formula III

16. A compound according to claim 6, wherein said 5-7 membered heterocyclic ring is a pyrrolidine, piperidine, morpholine or piperazine ring, where the 4-nitrogen of the priperazine is optionally substituted by $C_{1-4}$alkyl and wherein a carbon atom adjacent to a nitrogen atom within the piperazine ring is optionally replaced with carbonyl.

* * * * *

SEQUENCE LISTING

```
<160> NUMBER OF SEQ ID NOS: 15

<210> SEQ ID NO 1
<211> LENGTH: 2072
<212> TYPE: DNA
<213> ORGANISM: Artificial Sequence
<220> FEATURE:
```

<223> OTHER INFORMATION: Synthetic Sequence

<400> SEQUENCE: 1

| | | | | | |
|---|---|---|---|---|---|
| gccgaattcc | gctgcaagtc | ctactccgcc | gaggccgacg | gcaccggctg | gtccgagggc | 60 |
| gtcggcatgc | tcctcgtcga | acggctcggc | gacgccgaac | ggctcggcca | ccccgtcctc | 120 |
| gccgtgctgc | gcggctcagc | ggtcaaccag | gacggtgcca | gcagcggcct | caccacccc | 180 |
| aacgggccgg | cccagcagcg | cgtcatccgg | caggcgctcg | ccgacgcccg | gctcaccccc | 240 |
| gccgacctgg | acctcgtgga | gggccacggc | accggcaccc | cgctcggcga | cccgatcgag | 300 |
| gtgcaggccc | tgctcgccac | ctacggccag | gaccgcgccg | aaccgctctg | gctgggctcg | 360 |
| gtgaagtcca | acatcggcca | cacccaggcc | gccgccggcg | tcgccggagt | catcaaggcc | 420 |
| gtcctggccc | tccggcacgg | tgtactgccc | ggcaccgccc | acctgaccga | gccgaccccg | 480 |
| caggtcgact | ggaccgccgg | cgccgtggaa | ccgctgcggg | agacgcgcgc | ctggcccgag | 540 |
| accggcaggc | cgccgccgcc | ggccgtgtcc | tcgttcggca | tcagcggcac | caacgcccac | 600 |
| atcgtcctgg | aacaggcccc | cgccccgcg | gcgccgcagg | cggccggagc | ccaggcgccc | 660 |
| gcggcgccgc | ggcccgtcgg | gaaccaggcc | accgccgcgc | cgaggtccat | ggaggaccgg | 720 |
| accgccgccg | cgcctagcgc | cggcggagac | ccgaccctca | ccgcgccggc | cccctccgcg | 780 |
| ccccgcccg | ccccgccgc | cctccccgtc | ccgctgtccg | ccgcgaccga | gcccggtgtc | 840 |
| cgtgcccagg | ccctccggct | ggccgcccac | ctcaccgagc | ccccgaact | cgccccgcag | 900 |
| gacatcgcgt | tcagcgccgc | caccacgcgc | gccgcgctgg | cgtcccgggc | cgtcgtgctc | 960 |
| gccgacgacc | gggccgggct | gctggacgcc | ctcaccgcgc | tggccgaggg | acggccggc | 1020 |
| cccgccgtcg | tcaccggcgc | cgccgcggcc | ggcgcgcgcc | ggatcaccTT | cgtcttcccc | 1080 |
| ggccagggcg | cccagtgggc | cggcatggcc | gtacccctgc | tggagacctc | gccggtgttc | 1140 |
| gcggcgaagt | gggccgaatg | cgcccgcgtg | ctcgccccct | gggtggactg | gtcgcccgac | 1200 |
| gaggcgctgc | gctcaccgca | ggcactggaa | cgggtcgacg | tcgtccagcc | cgtgctgtgg | 1260 |
| gccgtcatgg | tcagcctcgc | cgagctgtgg | cgggcggcgg | gcgtacggcc | cgacgccgta | 1320 |
| ctcggccatt | cgcagggcga | gatcgccgcc | gcctgcgtcg | ccggcgccct | gtccctggag | 1380 |
| gacggcgcca | aggtcgtcgc | gctgcgcgcc | aaggccctgc | tcgcgctcgc | cggccgcggc | 1440 |
| ggcatgctct | ccgtcccgct | gccgaggcg | gaggtccgcg | cccggctcga | cagcggccc | 1500 |
| ggcctcggca | tcgccgccgt | caacgggccc | gccaccgtgg | tggtctccgg | cgagacggcc | 1560 |
| gcccctcgacg | aggcccaggc | cgcctgggag | gccgagggcg | tccgggtgcg | ccgcatcccc | 1620 |
| gtcgactacg | cctcccactc | cccgcacgtc | gccgaggtgc | aggaccgcct | cgccgccgac | 1680 |
| ctcgccggca | tcgccccgcg | cccggccgag | gtgaccttcc | tgtccacgct | caccggggaa | 1740 |
| cccttcgaca | ccaccggact | cgacgccggc | tactggtacc | gcaacctgcg | cgagcaggtc | 1800 |
| cgcttcgagg | cggccacccg | gcgcgcccctg | gagcagggcc | accgcgtgtt | catcgaggtc | 1860 |
| ggcccgcacc | ccgtgctcac | gctcggcgtc | cagcagaccg | ccgaggccat | ggacgtgccc | 1920 |
| gccgaggcga | tcgccaccct | ccgccgcgac | cagggcgacc | tgctccgctt | ccgcaccgcg | 1980 |
| ctcgccgagg | ccgccgtcct | cggcgccccc | gtcgactggg | ccgccgaact | cgccccgtac | 2040 |
| gcgccccgcc | gggtagatct | gccctcgagc | gc | | | 2072 |

<210> SEQ ID NO 2
<211> LENGTH: 35
<212> TYPE: DNA
<213> ORGANISM: Artificial Sequence

```
<220> FEATURE:
<223> OTHER INFORMATION: Primer

<400> SEQUENCE: 2
gctctcgagg cggctagcct ccctgcccga ggccg                               35

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
agaaagcttc ggcccggtcg gcgccctggg cc                                  32

<210> SEQ ID NO 4
<211> LENGTH: 1995
<212> TYPE: DNA
<213> ORGANISM: Streptomyces sp.

<400> SEQUENCE: 4
gctctcgagg cggctagcct ccctgcccga ggccggccgc cggcgggccg tcaccgaact    60
ggtccgcgag cacgccgccg ccgtcctcgg ccacgactcg cccgccgcgc tccccgccga   120
ccgcgccttc cgggacgtcg gcttcgactc catcaccgcg gtcgagctgc gcaaccggct   180
ccgctcggcc accggcctgg ccctgcccgc caccctcgtc ttcgaccacc cgtcgcccac   240
cgcgctggcc ggccacctgc tcgcgctcgc cttcgacacc gccgcggcgg acctcgccgc   300
gcccgccgcc cgcgccgccg acgatgacga cgacccgatc gccgtcgtcg gcctcagctg   360
ccgctacgcc ggcggcgtcg cctccccgga cgagctgtgg cggctcgtcg tggccggtca   420
ggacgcggtg ggcgccctgc ccaccgaccg tggctgggac ctcgactcgc tctacgactc   480
cgaccccgac gcccgcggtc gcagctacgt ccgccaaggg gccttcctca ccgacccgc    540 cggcttcgac gccgccttct tcggcatcgc cccggcggag gccggggcca ccgacccgca   600
gcagcggctg ctcctggaag ccgcctggga ggcgttcgag cacgccggca tcgacgccac   660
cggcctgcgc ggctcgcgcg tcggcgtctt cgccggcgcc aacgtcggcg actacgcctc   720
cagccgcggc cctggcgccg gcggctccga cggacagctg ctcaccggca acgtccccag   780
tgtgatctcc ggccggatct cctacacctt cggtttcgag gggccggccg tcaccgtgga   840
caccgcctgc tcgtccgccc tggtcgccct ccacctggcc tgccggtcgg tgcgcggcgg   900
cgagagcgac atggccctgg ccggcggcgt cgcgctcatg tccagcccgg ccgccctgat   960
cggcttctcc gcgcagcgcg gcctgtccgg cgacggccgc tgcaaggcct tcgccgacgc  1020
cgccgacggc accggtctcg ccgagggcgt cggactgctg ctggtggaac gcctctcccg  1080
ggcccgcgcc cagggccacc gcgtcctcgc cctcgtacgc ggctcggcga tcaaccagga  1140
cggcgcctcc aacggactca ccgccccag cggacccgcc cagcagcgcg tcatcaccgc  1200 ccgcgctcgcc gacgccgggc tgcggcccgc cgacgtcgac gccgtggagg cccatggcac  1260 cggcaccgc ctcggcgacc cgatcgaggc ccaggccctg ctcgccacct acggacagga  1320
ccgcgccgaa ccgctctggc tcggctcggt gaagtccaac atcggccact cccaggccgc  1380
gtccggcgcg gccggcgtga tcaagaccgt gcaggcgctg cggcacggcc tgctgcccgc  1440
cacgctccac gtggaccggc ccaccaccca ggtcgactgg accgccggcg ccgtcgaggt  1500
gctgaccgag gcccggggact ggccggccgt ggaccggcct cggcgggccg ccgtgtcggc  1560
```

```
gttcggcctg tccggcacca acgcgcacgt gatcctcgaa caggcccccg ccgaagacgc    1620
ccacccggcc cccgaaccgg ccccgggcga ggactccac  ccgaccccg  aaacggcccc    1680 aggcgaggac gccccgcgga ccgcgcccga gcccgcgcgg cccgtggtgt ggccggtgca    1740
cggccgtacc cgggacgccc tgcgcgccca ggcggcgcgg ctgcgcaccc acctggagac    1800
ccgccccgac gcccgcccgg ccgacgtcgg ctggaccctc gcggccggtc gggccgtgtt    1860
cgaccaccgc gccgtggtgc tcggcgccga ccgcgccgag ctgctgcgcg gactcgacgc    1920
cgtcgccgcc ggcacccccg acccgcggt  cgccgacggc gcggcccagg gcgccgagcc    1980
gggccgaagc tttct                                                     1995

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
gctctcgagg cggctagcct ccctg                                            25

<210> SEQ ID NO 6
<211> LENGTH: 35
<212> TYPE: DNA
<213> ORGANISM: Artificial Sequence
<220> FEATURE:
<223> OTHER INFORMATION: Primer

<400> SEQUENCE: 6
aaaaagcttg cggggtcggg ggtgccggcg gcgac                                 35

<210> SEQ ID NO 7
<211> LENGTH: 1956
<212> TYPE: DNA
<213> ORGANISM: Streptomyces sp.

<400> SEQUENCE: 7
gctctcgagg cggctagcct ccctgcccga ggccggccgc cggcgggccg tcaccgaact      60
ggtccgcgag cacgccgccg ccgtcctcgg ccacgactcg cccgccgcgc tccccgccga     120
ccgcgccttc cgggacgtcg gcttcgactc catcaccgcg gtcgagctgc gcaaccggct     180
ccgctcggcc accggcctgg ccctgcccgc caccctcgtc ttcgaccacc cgtcgcccac     240
cgcgctggcc ggccacctgc tcgcgctcgc cttcgacacc gccgcggcgg acctcgccgc     300
gcccgccgcc cgcgccgccg acgatgacga cgacccgatc gccgtcgtcg gcctcagctg     360
ccgctacgcc ggcggcgtcg cctccccgga cgagctgtgg cggctcgtcg tggccggtca     420
ggacgcggtg ggcgccctgc ccaccgaccg tggctgggac ctcgactcgc tctacgactc     480
cgaccccgac gcccgcggtc gcagctacgt ccgccaaggg gccttcctca ccgacccgc      540 cggcttcgac gccgccttct tcggcatcgc ccgcgcggag gccgggcca  ccgacccgca     600 gcagcggctg ctcctggaag ccgcctggga ggcgttcgag cacgccggca tcgacgccac     660
cggcctgcgc ggctcgcgcg tcggcgtctt cgccggcgcc aacgtcggcg actacgcctc     720
cagccgcggc cctggcgccg gcggctccga cggacagctg ctcaccggca acgtccccag     780
tgtgatctcc ggccggatct cctacacctt cggtttcgag gggccggccg tcaccgtgga     840
caccgcctgc tcgtccgccc tggtcgccct ccacctggcc tgccgtcgg  tgcgcggcg      900 cgagagcgac atggccctgg ccggcgcgt  cgcgctcatg tccagcccgg ccgccctgat     960
```

```
cggcttctcc gcgcagcgcg gcctgtccgg cgacggccgc tgcaaggcct tcgccgacgc    1020
cgccgacggc accggtctcg ccgagggcgt cggactgctg ctggtggaac gcctctcccg    1080
ggcccgcgcc cagggccacc gcgtcctcgc cctcgtacgc ggctcggcga tcaaccagga    1140
cggcgcctcc aacggactca ccgccccag cggacccgcc cagcagcgcg tcatcaccgc     1200
cgcgctcgcc gacgccgggc tgcggcccgc cgacgtcgac gccgtggagg cccatggcac    1260
cggcacccgc ctcggcgacc cgatcgaggc ccaggccctg ctcgccacct acggacagga    1320
ccgcgccgaa ccgctctggc tcggctcggt gaagtccaac atcggccact cccaggccgc    1380
gtccggcgcg gccggcgtga tcaagaccgt gcaggcgctg cggcacggcc tgctgccccgc   1440 cacgctccac gtggaccggc ccaccaccca ggtcgactgg accgccggcg ccgtcgaggt    1500
gctgaccgag gccgggact ggccggccgt ggaccggcct cggcgggccg ccgtgtcggc     1560
gttcggcctg tccggcacca acgcgcacgt gatcctcgaa caggccccg ccgaagacgc     1620 ccacccggcc cccgaaccgg ccccgggcga ggactccac ccgaccccg aaacggcccc      1680 aggcgaggac gccccgcgga ccgcgcccga gcccgcgcgg cccgtggtgt ggccggtgca    1740
cggccgtacc cgggacgccc tgcgcgccca ggcggcgcgg ctgcgcaccc acctggagac    1800
ccgccccgac gcccgcccgg ccgacgtcgg ctggacccctc gcggccggtc gggccgtgtt   1860
cgaccaccgc gccgtggtgc tcggcgccga ccgcgccgag ctgctgcgcg gactcgacgc    1920
cgtcgccgcc ggcaccccg accccgcaag ctttt                                 1956

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
taagatcttc cgacctacgc cttccaac                                          28

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
taatgcatcg acctcgttgc gtgccgcggt                                        30

<210> SEQ ID NO 10
<211> LENGTH: 122
<212> TYPE: DNA
<213> ORGANISM: Artificial Sequence
<220> FEATURE:
<223> OTHER INFORMATION: Primer

<400> SEQUENCE: 10
ctaggccggg ccggactggt agatctgcct acgtatcctt tccagggcaa gcggttctgg      60
ctgcagccgg accgcactag tcctcgtgac gagggagatg catcgagcct gagggaccgg     120
tt                                                                    122

<210> SEQ ID NO 11
<211> LENGTH: 118
<212> TYPE: DNA
```

```
<213> ORGANISM: Artificial Sequence
<220> FEATURE:
<223> OTHER INFORMATION: Primer

<400> SEQUENCE: 11
aaccggtccc tcaggctcga tgcatctccc tcgtcacgag gactagtgcg gtccggctgc    60
agccagaacc gcttgccctg gaaaggatac gtaggcagat ctaccagtcc ggcccggc    118

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
tagctagccg ggcgctcagg ggctgcgagc cgacct    36

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
ccgtagatct gcccacctac gccttccagc gcg    33

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
tccggctagc cgttggggca gcgcgg    26

<210> SEQ ID NO 15
<211> LENGTH: 3176
<212> TYPE: DNA
<213> ORGANISM: Streptomyces sp.

<400> SEQUENCE: 15
ccgtagatct gcccacctac gccttccagc gcgagcacta ctggctgccc gtcgactccg    60
gcgccggcac ggccccggcc gggcaccccc tgctgtccgc cgcggtcgac ctgcggacg    120 gcggcctcgt actcaccggg cggctctcgc ccgccgcgcg ccctggctc gcccagcaca    180 ccgtgcgcgg cagcgccctg ctgcccggca ccgccctgct ggacctggcc ctcgccgcgg    240
ccggccaggc ggccgcgccc ggcgtcgccg aactgatcct cgaagccccc ctcgtgctgc    300
ccgccgaggg cgccgtggag gtgcgcgtca ccgtcggcgc cgccgggacc gacggccgcc    360
gcgcgatcgc cctgcacacc cgcgccggcg acggcgactg gacccggcac gccaccggag    420
ccctgggcga ggtgcccggc gagcccacgg ccgcggcgc ctggccgccc ccggatgccc    480
gccccgccga cctcgccgcc ctgtacgcg ggctggccga cgccggcttc ggctacgggc    540
ccgcctacca gggcctccgt gccgcctggc ggcgcggcga aggcccggcg gccgaggtgt    600
tcgccgaggc cgaactgccc gcggccgtcc ccgacgccga ccgtgccccc gtacacccgg    660
cgctgctgga cgccgtcctg cacgccatcg gcgtgggcgg gctgatcacc gacccggcgc    720
acggcggact cccgttcgcc tggaccgggg tacgggtctt cgcccccggc gcccgggcgg    780
```

```
tccgcgcccg gctctcccgg gccggcgccg aaggcgccct cgccgtcgac ctgttcgacg   840
ccgacgggct gccagtggcc gccatcggct ccctgcggct gcgcccgccc gccgctcccg   900
cggtgcccga cgccctcttc gagaccgcct ggacgcctgt cgagcagggc acggccccgg   960
cccgccgcct cgccgctgctc ggcgccgaca ccgccctcgc ggccggcctc accgcggccg  1020 gcgccgcccct cgccgacgcc acggaccgct ccgccgaggt gctcgtcctg ccgatcgtca  1080
ccgaccccgg cgcggccccc gtcaccgaga cccaccgggc gaccgccgcc gtcctgacgg  1140
ccctccgtga cgtcctggcc gacgaggaga gcaccgcccg cctcgccgtg gtcacccgcg  1200
gcgccctcgc gctgtccgcc gaggagtccc cggaccggc cgcccgcgcc gtctggggtc   1260
tggtgcggtc cgcccagacc gagcaccccg accggatcgt cctcgccgac ctggacgccg  1320
ccgacgcctc ggcccgcgcc ctgcccgccg cgctgacctg cggggaaccg cagctcgccg  1380
tgcggtccgg cgcggtcagc gcaccccggc tcaccgcgc cggcgccgac gcgctggtcc   1440
tgcccgacgg cggctggcgc ctgcggcccg gcgccaccgg caccgtcgac ggcatgacgg  1500
ccgtgccgca ccccgacgcg ccgctcgccg acggcgaggt acgggtcgcc gtccgcgcgg  1560
tcggcgtcac cttccgggac gtcctcagcg tgctcggcct ctaccccggg gcaccccagc  1620
cgctcggcat cgaggcggcg ggcgtggtga ccggaccgg ccccggcgtg agcgacctcg   1680
cccccggcga ccgggtgttc ggactgctgc ccggctccat gggctcctcc gccgtcgccg  1740
accggcgcgt gctcgcgccc gtccccgacg gctggggctt caccgggcc gcctcggtgc   1800 cctccgcgtt cctcaccgcc tggttcgcgc tgcgcgatgt ggccggggtg cgggcggggg  1860
agcgggtgct ggtgcacgcg gcggccggtg gtgtgggcat ggccgcggtg cgggtggcgc  1920
ggctgctggg cgccgaggtg tatgcgacgg cgagtcccgg caagcatggg gtgctgcggg  1980
cggccggtct ggacgaggcg cgtgtggcgt cgtcgcggga cacggagttc gcgcagcggt  2040
tcccggagat ggacgtcgtg ctgaactccc tcacgggtga gttcgtggac gcgtcgctgc  2100
gactgctccg tcccggcgga cggttcgtgg aactcggcaa gaccgacctg cgcaccgaca  2160
ccgccggcat cacctaccgg gccgtcgacc tcgcggacgc cggccccgac cgcatccagg  2220
agatgctcac cgaactcctg gaccgcctcg cggccggcga cctcgcccac ctgcccgtcc  2280
gcagcatgcc catgggccgc gcccgcgagg cgttccgctt catggcccag gcccggcaca  2340
ccgggaagct cgtcctcacc accgcccgt acggcgacgg caccgtcctc gtcaccggcg   2400
gcaccggcgc cctcggcggc ctcgtggccc ggcacctcgt caccgaacac ggcatccgcg  2460
acctggtgct cgtcggacga cagggcgccg agcccccgt caccgccgaa ctgcgcgccg   2520
ccggcgcccg ggtccgcgtg gcggcctgcg acgtgtccga ccgggccgcg ctcgccgcgc  2580
tgctcgcgga catcgagccg cccctgaccg cggtggtgca cgcggccggc gtcctcgacg  2640
acggcacgct cacctcgctg acccccgaac ggctcgccgc cgtactgcgc ccgaaggccg  2700
acgccgcctg gcacctgcac gaactcaccg aggacaggga cctgtccgcc ttcgtgctgt  2760
tctcctcggc ggccggcacg ttcggcgccc ccggccaggg caactacgcc gccgccaacg  2820
ccgccctgga cgcgctcgcc gagcaccgcc gctcccgcgg cctgcccgcc gtctccctcg  2880
cctgggggcc gtgggccgcc gagagcgcca tgaccggcgg cctcagcagc ggcgaccgcg  2940
```

| | | | | | |
|---|---|---|---|---|---|
| ccaggatgac | ccgggccggc | gtccggcccc | tggccgccac | cgaggcactc | gccgtgctcg | 3000 |
| acgccgcctg | ccgcaccgga | gccggcgccc | tcgccgcgct | ccgtctcgac | accgcggcgc | 3060 |
| tcaccgcccg | caccggcgcc | ccgcacccgc | tgctgcgcga | cctggtccgc | cgtccggccg | 3120 |
| gccccgcccg | cgacgacgcc | gacacccagc | ccgcgctgcc | ccaacggcta | gccgga | 3176 |